US007091227B2

(12) United States Patent
Scott et al.

(10) Patent No.: US 7,091,227 B2
(45) Date of Patent: Aug. 15, 2006

(54) BENZOTHIAZOLE DERIVATIVES

(75) Inventors: Barbara Scott, Spencer, MA (US); Lee D. Arnold, Westboro, MA (US); Anna M. Ericsson, Shrewsbury, MA (US); Kevin P. Cusack, Holden, MA (US)

(73) Assignee: Abbott GmbH & Co. KG, Wiesbaden (DE)

( * ) Notice: Subject to any disclaimer, the term of this patent is extended or adjusted under 35 U.S.C. 154(b) by 0 days.

(21) Appl. No.: 09/777,554

(22) Filed: Feb. 6, 2001

(65) Prior Publication Data

US 2003/0153568 A1    Aug. 14, 2003

Related U.S. Application Data

(60) Provisional application No. 60/180,841, filed on Feb. 7, 2000.

(51) Int. Cl.
*A61K 31/425* (2006.01)
*C07D 277/82* (2006.01)

(52) U.S. Cl. ............... 514/367; 548/103; 548/161
(58) Field of Classification Search ............... 548/163, 548/161; 514/367, 371
See application file for complete search history.

(56) References Cited

U.S. PATENT DOCUMENTS

| | | | | |
|---|---|---|---|---|
| 3,810,988 A | * | 5/1974 | Janiak ................... | 514/371 |
| 4,966,849 A | | 10/1990 | Vallee et al. ............ | 435/199 |
| 5,217,999 A | | 6/1993 | Levitzki et al. ......... | 514/613 |
| 5,302,606 A | | 4/1994 | Spada et al. ............ | 514/357 |
| 5,330,992 A | | 7/1994 | Eissenstat et al. ...... | 514/312 |
| 2002/0123484 A1 | * | 9/2002 | Das et al. ............... | 514/80 |

FOREIGN PATENT DOCUMENTS

| | | |
|---|---|---|
| EP | 566 226 B1 | 11/1995 |
| GB | 1580876 | 12/1980 |
| JP | 57-175189 | 10/1982 |
| JP | 62-187842 | 8/1987 |
| JP | 11-130761 | 5/1999 |
| JP | 11-222431 | 8/1999 |
| WO | WO 91/15495 A1 | 10/1991 |
| WO | WO 92/20642 A1 | 11/1992 |
| WO | WO 92/21660 A1 | 12/1992 |
| WO | WO 94/03427 A1 | 2/1994 |
| WO | WO 94/10202 A1 | 5/1994 |
| WO | WO 94/14808 A1 | 7/1994 |
| WO | WO 97/22596 A1 | 6/1997 |
| WO | WO 97/34876 A1 | 9/1997 |
| WO | WO97/40830 A1 | 11/1997 |
| WO | WO 97/40831 A1 | 11/1997 |
| WO | WO 97/42187 A1 | 11/1997 |
| WO | WO 98/04536 A1 | 2/1998 |
| WO | WO 98/07832 A1 | 2/1998 |
| WO | WO 99/00357 A1 | 1/1999 |
| WO | WO 99/24035 A1 | 5/1999 |
| WO | WO 01/07411 A1 | 2/2001 |

OTHER PUBLICATIONS

Duncia et al., 2000, CAS: 133:252423.*
Sawhney et al., 1984, CAS:100:139014.*
Bhattacharya et al., CAS:113:100536.*
Nakrani, A.D. et al., "Manganese(II) complexes of N-phenyl-N'-(6-substituted)benzothiazolylthiocarbamide," *J. Ind. Chem. Soc.* 68(9):517-18 (1991).
Sarkis, G.Y. et al., "Cobalt(II), Nickel(II) and copper(II) complexes of some N-benzoyl N'-aryl or heterocyclic substituted thioureas," *J. Iraqi Chem. Soc.*, 13(1):103-115 (1988).
Singh, G.C., "Studies on N-methyl-N'-2-benzothlazolyl guanidines," *Indian J. Appl. Chem.* 31(3-4):117-120 (1968).
Sutoris, V. et al., "Benzothiazole compounds. III. Synthesis and biological activity of substituted N-(2- benzothiazolyl)ureas and benzothiazolyldihydrouracils," *Chem. Zvesti*, 27(6):829-33 (1973).
Weiss, B. et al., "Effects of various amides on a rat brain puromycin-sensitive aminopeptidase and on induced convulsions in mice," *Res. Commun. Psychol.*, 17(3-4):153-9 (1992).
Bell, F.W. "Phenethylthiazolethiourea (PETT) compounds, a new class of HIV-1 reverse transcriptase inhibitors. Synthesis and basic structure-activity relationship studies of PETT analogs," *J. Med. Chem.* 38(25):4929-36 (1995).
Bhargava, P.N. et al., "Substituted benzothiazolyl guanidines," *Curr. Sci.* 40(6):430-32 (1971).

(Continued)

*Primary Examiner*—Joseph K. McKane
*Assistant Examiner*—Robert Shiao
(74) *Attorney, Agent, or Firm*—John D. Conway; Gayle B. O'Brien

(57) ABSTRACT

The present invention is directed to a compound of formula (I),

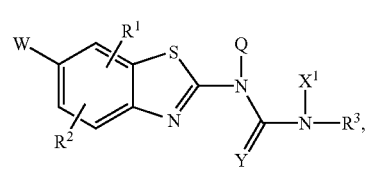

racemic-diastereomeric mixtures thereof, optical isomers thereof, prodrugs thereof, isotopes thereof or pharmaceutically-acceptable salts of said compound, isomers, prodrugs and isotopes, wherein the variables are defined herein.

The compounds of this invention are useful as inhibitors of serine/threonine and tyrosine kinases. In particular, compounds of this invention are useful as inhibitors of tyrosine kinases that are important in hyperproliferative diseases, especially in cancer and in the process of angiogenesis.

40 Claims, No Drawings

OTHER PUBLICATIONS

Bhargava, P.N. et al., "Synthesis of some new substituted benzothiazolyl thiazolidones as potential gungicides," *Curr. Sci.* 42(20):717-18 (1973).

Bhargava, P.N. et al., "Synthesis and spectral behaviour of some new (substituted) benzothiazolyl guanidines," *Curr. Sci.* 43(2):33-36 (1974).

Bhargava, P.N. et al., "Synthesis of some new benzothiazolylguanidines and their activities," *J. Ind. Chem. Soc.* 56(4):377-80 (1979).

Chaudhari, B.R. et al., "Synthesis of some 2-imino-N(6'-substituted benzothiazo-2'-yl)-4-thiazolidinones and their bis-derivatives as antibacterial agents," *Asian. J. Chem.* 7(4):832-36 (1995).

Kamala, K. et al., "Synthesis of 2-aroyliminobenzothiazolo[3,2-*b*]-1,2,4-thiadiazolines," *J. Ind. Chem.*, 29B(8):778-80 (1990).

*Expert Opin. Ther. Pat.* 8(4): 475-478 (1998).

Achen et al, "Vascular endothetial growth factor D (VEGF-D) is a ligant for the tyrosine kinases VEGF receptor 2 (Flk1) and VEGF receptor 3 (Flt4)." *PNAS USA* 95(2): 548-553 (1998).

Aplin et al., "In vitro phosphorylation of the cytoplasmic domain ot the amyloid precursor protein by blycogen synthase kinase-3β," *Journal of Neurochemistry*, 67:699-707 (1996).

Armstrong, "Treatment of opportunistic fungal infections," *Clinical Infectious Diseases*, 16:1-7 (1993).

Badger et al., "Pharmacological profile of SB 203580, a selective inhibitor of cytokine suppressive binding protein/p38 kinase, in animal models of arthritis, bone resorption, endotoxin shock and immune function," *The Journal of Pharmacology and Experimental Therapeutics*, 279:1453-1461 (1996).

Baeuerie et al., "Function and activation of NF-kappa B in the immune system," *Annual Review of Immunology*, 12:141-179 (1994).

Beg et al., "An essential role for NF-kappaB in prreventing TNF-alpha-induced cell death," *Science*, 274:782-784 (1996).

Bolen, "Nonreceptor tyrosina protein kinases," *Oncogene* 8:2025-2931 (1993).

Borthwick et al., "Inhibition of glycogen synthase kinase-3 by insulin cultured human skeletal muscle myoblasts," *Biochemical & Biophysical Research Communications*, 210:738-745 (1995).

Brickell, "The p60c-src family of protein-tyrosine kinases: structure, regulation, and function," *Critical Reviews in Oncogenesis*, 3:401-406 (1992).

Brown et al., *Regulation of Angiogenesis* (ed. L.D. Goldberg and E.M. Rosen), 233-269 (1997).

Buchdunger et al., "Selective inhibition of the platelet-derived growth factor signal transduction pathway by a protein-tyrosine kinase inhibitor of the 2-phenylaminopyrimidine class," *PNAS USA*, 92:2258-2262 (1995).

Courtneidge, "Protein tyrosine kinases, with emphasis on the Src family," *Seminars in Cancer Biology*, 5:236-246 (1994).

Cowburn, "Peptide recognition by PTB and PDZ domains," *Curr. Opin. Struct. Biol*, 7(6):835-838 (1997).

De Vries et al. "The fms-like tyrosine kinase, a receptor for vascular endothelial growth factor," *Science* 255:989-991 (1992).

Draetta, "Cdc2 activation: The interplay of cyclin binding and Thr161 phosphorylation," *Trends in Cell Biology*, 3:287-289 (1993).

Ducommun et al., "cdc2 phosphorylation is required for its interaction with cyclin," *EMBO Jornal*, 10:3311-1119 (1991).

Fanti et al., "Distinct phosphotyrosines on a growth factor receptor bind to specific molecules that mediate different signaling pathways," *Cell* 69:413-423 (1992).

Ferrara et al. "The vascular endothelial growth factor family of polypeptides," *J. Cell. Biochem.* 47:211-218 (1991).

Ferrara et al., "Vascular endothelial growth factor. Basic biology and clinical implications," in Regulation of Angiogenesis (ed. L. D. Goldberg and E.M. Rosen), 209-232 (1997).

Ferrara et al., "The biology of vascular entothelial growth factor," *Endocrine Reviews* 18(1): 4-25 (1997).

Gautier et al., "Dephosphorylation and activation of Xenopus p34cdc2 protein kinase during the cell cycle," *Nature* 339:626-629 (1989).

Gilbert, "Horizontal integration and cortical dynamics," *Neuron* 9:1-13 (1992).

Girard et al., "Cyclin A is required for the onset of DNA replication in mammalian fibroblasts,." *Cell*, 67:1169-1179 (1991).

Kim et al., "Inhibition of vascular endothelial growth factor-induced angiogenesis suppresses tumour growth in vivo," *Nature* 362:841-844 (1993).

He et al., "The human cytomegalovirus UL97 protein is a protein kinase that autophosphorylates on serines and threonines," *Journal of Virology*, 71:405-411 (1997).

Hosoi et al., "Evidence for cdk5 as a major activity phosphorylating tau proteinin porcine brain extract," *Journal of Biochemistry (Tokyo)*, 117:741-749 (1995).

Hunter et al., "Cyclins and cancer. II: Cyclin D and CDK inhibitors come of age," *Cell*, 79:573-582 (1994).

Jakeman et al., "Developmental expression of binding sites and messenger ribonucleic acid for vascular entothelial growth factor suggests a role for this protein in vasculogenisis and angiogenesis," *Endocrinology* 133:848-859 (1993).

Jellinek et al., "Inhibition of receptor binding by high-affinity RNA ligands to vascular endothelial growth factor," *Biochemistry* 33:10450-56 (1994).

Kendall et al., "Inhibition of vascular endothelial cell factor activity by an endogenously encoded soluble receptor," *Proc. Natl. Acad. Scl* 90:10705-09 (1994).

Kinsella, et al. "Protein Kinase C regulates endothelial celll tube formation on basement membrane matrix, Matrigel," *Exp. Cell Res.* 199:56-62 (1992).

Klagsburn et al., "Vascular endothelial growth factor and its receptors," *Cytokine & Growth Factor Reviews* 7: 259-270 (1996).

Koch et al., "SH2 and SH3 domains: elements that control interactions of cytoplasmic signaling proteins," *Science* 252:668-678 (1991).

Kohn et al., "Cell cycle control and cance chemotherapy," *Journal of cellular Biochemistry*, 54:440-452 (1994).

Holch et al., "Regulation of the expression of the VEGF/VPS and ite receptors: role in tumor angiogenesis," *Breast Cancer Research and Treatment* 36: 139-155 (1995).

Korpelainen et al., "Signating angiogeniesis and lymphangiogenesis," *Curr. Opin. Cell Biol.*, 10:159-164 (1998).

Krek et al., "Mutations of p34cdc2 phosphorylation sites induce premature mitotic events in Hela cells: evedence for a double block to p43cdc2 kinase activation in vertabrates," *EMBO journal*, 10:3331-3341 (1991).

Lees, "Cyclin dependent kinase regulation," *Current opinion in Cell Biology*, 7:773-780 (1995).

Lymboussaki et al.,"Expression of the vascular endothefial growth factor C receptor VEGFR-3in lymphatic endothelium of the skin and in vascular tumors," *Am. J. Pathol.* 153(2):395-403 (1998).

Maglione et al., "Two alternative mRNAs coding for the angiogenic factor, placenta growth factor (PIGF), are transcribed from a single gene of chromosome 14," *Oncogen* 8:925-31 (1993).

Mariani, et al., "inhibition of angiogenesis by FCE 26806, a potent tyrosine kinase inhibitor," *Proc. Am. Assoc. Cencer Res.* 35:2268 (1994).

Matsushime et al., "D-type cyclin-dependent kinase activity in mammalian cells," *Molecular & Cellular Biology*, 14:2066-2076 (1994).

Gould et al., "Tyrosine phosphorylation of the fission yeast cdc2+ protein kinase regulates entry into mitosis," *Nature*, 342:39-45 (1989).

Matthews et al., "A receptor tyrosine kinase cDNA isolated from a population of enriched primitive hematopoietic cells and exhibiting close genetic linkage to c-kit," *PNAS USA*, 88; 9026-30 (1991).

Meyer et al., "A novel vascular endothelial growth factor encoded by Orf virus, VEGF-E, mediates angiogenesis via signalling through VEGFR-2 (KDR) but not VEGFR-1 (Flt-1) receptor tyrosine kinases," *EMBO J.* 18(2):363-374 (1999).

Myers et al., "The synthesis and sar of new 4-(N-alkyo-N-phenyl)amino-6, 7-dimethoxyquinazolines and 4-(N-alkyl-N-phenyl)amino-pyrazolo[3, 4-d]pyrimidines, inhibitors of CSF-1R tyrosine kinase activity," *Bioorganic & Medicinal Chemistry Letters*, 7:421-424 (1997).

Millauer et al., "High affinity VEGF binding and developmental expresion suggest Flk-1 as a major regulator of vasculogenesis," *Cell* 72:835-846 (1993).

Murray et al., "Cyclin synthesis drives the early embryonic cell cycle," *Nature*, 339:275-280 (1989).

Mustonen et al., "Endothelial receptor tyrosine kinases involved in angiogenesis," *J. Cell Biol.* 129:895-898 (1995).

Myers et al., "The preparation and sar of 4-(anilino). 4-(phenoxy), and 4-(thiophenosy)-quinazolines; inhibitors of p56$^{lck}$ and EGF-R tyrosine kinase activity," *Bioorg. med. chem. lett.* 7:417-420 (1997).

Oelrichs et al, "NYK/FLK-1: a putative receptor protein tyrosine kinase isolated from E10 embryonic neuroepithelium is expressed in endothelial cells of the developing embryo," *Oncogene* 8(1):11-15 (1993).

Ogawa et al, "A novel type of vascular endothelial growth factor, VEGF-E (NZ-7 VEGF), preferentially utilizes KDR/FIK-1 receptor and carries a potent mitotic activity without heparin-binding domain," *j. Biol. Chem.* 273(47):31273-31282 (1998).

Ohtsubo et al., "Cyclin-dependent regulationof G1 in mammalian fibroblast," *Science*, 259:1908-1912 (1993).

Osmani et al., "Parallel activation of the NIMA and p34cdc2 cell cycle-regulated protein kinases is required to initiate mitosis in A. nidulans," *Cell*, 67:283-291 (1991).

Osmani et al., "Activation of the mimA protein kinase plays a unique role during mitosis that cannot by by passed by absence of the bimE checkpoint," *EMBO journal*, 10:2669-2679 (1991).

Pagano et al., "Cyclin A is required at two points in the human cell cycle," *EMBO Journal*, 11:961-971 (1992).

Park et al., "Placenta growth factor. Potentiation of vascular endothelial growth factor bioactivity, in vitro and in vivo, and high affinity binding to Flt-1 but not to Flk-1/KDR." *J. Biol. Chem.* 269:25646-54 (1994).

Perkins et al., "Regulation of NF-kappaB by cyclin-dependent kinases associated with the p300 coactivator," *Science*, 275:523-527 (1997).

Migdal et, "Neuropilin-1 is a placenta growth factor-2 receptor," *J. Biol. Chem.* 273 (35): 22272-22278 (1998).

Pines, "Cell proliferation andcontrol," *Current Opinion in Cell Biology*, 4:144-148 (1992).

Pines, "Cyclins and cyclin-dependent kinases: take your partners," *Trends in Biochemical Sciences*, 18:195-197 (1993).

Powis, "Signalling pathways as targets for anticancer drug development," *Pharmacology & Therapeutics*, 62:57-95 (1994).

Quelle et al., "Overexpression of mouse D-type cyclins accelerates G1 phase in rodent fibroblasts," *Genes & Development*, 7:1559-1571 (1993).

Resnitzky et al., "Acceleration of the G1/S phase transition by expression of cyclins D1 and E with an inducible system," *Molecular & Cellular Biology*, 14:1669-1679 (1994).

Ristimaki et al, "Proinflammatory cytokines regulate expression of the lymphatic endothelial mitogen vascular endothelial growth factor-C," *J. Biol. Chem.* 273(14):8413-8418 (1998).

Rosenblatt et al., "Human cyclin-dependent kinase 2 is activated during the S and G2 phases of the cell cycle and associates with cyclin A," *Proc. Nat Acad. Sc. USA*, 89:2824-2828 (1992).

Schiessinger et al., "Growth factor signaling by receptor tyrosine kinases," *Neuron* 9:383-391 (1992).

Shawver et al., "Receptor tyrosine kinases as targets for inhibition of angiogenesis," *Drug Discovery Today*, 2:60-63 (1997).

Sherr, "Mammalian G1 cyclins," *Cell*,73:1059-1065 (1993).

Shibuya et al., "Nucleotide sequence and expression of a novel human receptor-type tyrosine kinase gene (ftt) closely related to the frns family," *Oncogene* 5:519-524 (1990).

Shoelson, "SH2 and PTB domain interactions in tyrosine kinase signal transduction," *Curr. Opin. Chem. Biol.* 1(2): 227-234 (1997).

Solomon et al., "Cyclin activation of p34cdc2," *Cell*, 63:1013-1024 (1990).

Solomon et al., "Role of phosphorylation in p34cdc2 activation: identification of an activation kinase," *Molecular biology of the Cell*, 3:13-27 (1992).

Songyang et al., "SH2 domains recognize specific phosphopeptide sequences," *Cell* 72:767-778 (1993).

Songyang et al., "Specific motifs recognized by the SH2 domains of Csk, 3BP2, fps/fes, GRB-2, HCP, SHC, Syk and Vav." *Mol. Cell. Biol.* 14:2777-2785 (1994).

Staunton et al., "The arrangement of the immunoglobulin-like domains of ICAM-1 and the binding sites for LFA-1 and Rhinovirus," *Cell* 61:243-254 (1990).

Stone et al., "Reversible, p16-mediated cell cycle arrest as protection from chemotherapy," *Cancer Research*, 56:3199-3202 (1996).

Takano, et al., "Inhibition of angiogenesis by a novel diaminoanthraquinone that inhibits protein kinase," *Mol. Bio. Cell* 4:358A (1993).

Tanaka et al., "c-CBL is downstream of c-Src in a signalling pathway necessary for bone resorption," *Nature*, 383:528-531 (1996).

Terman et al., "Identification of a new andothelial cell growth factor receptor tyrosine kinase," *Oncogene* 6:1677-1683 (1991).

Terman et al., "Identification of the KDR tyrosine kinase as a receptor for vascular endothelial cell growth factor," *Biochem. Biophys. Res. Comm.* 187:1579-1588 (1992).

Ullrich et al., "Signal transduction by receptors with tyrosine kinase activity," *Cell* 61:203-212 (1990).

Van Antwerp et al., "Suppression of TNF-alpha-induced apoptosis by NF-kappaB," *Science*, 274:787-789 (1996).

Vousden, "Interactions of human papillomavirus transforming proteins with the products of tumor suppressor genes," *FASEB Journal*, 7:872-879 (1993).

Walker et al., "Role for cyclin A in the dependence of mitosis on completion of DNA replication," *Nature*, 354:314-317 (1991).

Wang et al., "TNF-and cancer therapy-induced apoptosis: potentiation by inhibition of NF-kappaB," *Science*, 274:784-787 (1996).

Williams, "Factors regulating the expression of vascular permeability/vascular andothelial growth factor by human vascular tissues," *Diabetelogia* 40: S118-120 (1997).

Witzenbichler et al, "Vascular endothelial growth factor-C (VEGF-C/VEGF-2) promotes angiogenesis in the setting of tissue ischemia," *Am. J. Pathol.* 153(2):381-394 (1998).

Wright, et al., "Inhibition of angiogenesis in vitro and in ovo with an inhibitor of cellular protein kinases, MDL 27032," *J. Cellular Phys.* 152:448-57 (1992).

Yarden et al., "Growth factor receptor tyrosine kinases," *Ann. Rev. Biochem.* 57:443-478 (1988).

Zindy et al., "Cyclin A is required in S phase in normal Pepithelial cells," *Biochemical & Biophysical Research Communications*, 182:1144-1154 (1992).

Olofsson et al., "Vascular endothelial growth fator B (VEGF-B) binds to VEGF receptor-1 and regulates plasminogen activator activity in endothelial cells," *PNAS USA* 95:11709-11714 (1998).

* cited by examiner

BENZOTHIAZOLE DERIVATIVES

RELATED APPLICATION

This application claims the benefit of U.S. Provisional Application No. 60/180,841, filed on Feb. 7, 2000, the entire teachings of the above application(s) are incorporated herein by reference.

BACKGROUND OF THE INVENTION

The present invention is directed to benzothiazole derivatives of formula (I), as defined below, uses and pharmaceutical compositions thereof.

There are at least 400 enzymes identified as protein kinases. These enzymes catalyze the phosphorylation of target protein substrates. The phosphorylation is usually a transfer reaction of a phosphate group from ATP to the protein substrate. The specific structure in the target substrate to which the phosphate is transferred is a tyrosine, serine or threonine residue. Since these amino acid residues are the target structures for the phosphoryl transfer, these protein kinase enzymes are commonly referred to as tyrosine kinases or serine/threonine kinases.

The phosphorylation reactions, and counteracting phosphatase reactions, at the tyrosine, serine and threonine residues are involved in numerous cellular processes that underlie responses to diverse intracellular signals (typically mediated through cellular receptors), regulation of cellular functions, and activation or deactivation of cellular processes. A cascade of protein kinases often participate in intracellular signal transduction and are necessary for the realization of these cellular processes. Because of their ubiquity in these processes, the protein kinases can be found as an integral part of the plasma membrane or as cytoplasmic enzymes or localized in the nucleus, often as components of enzyme complexes. In many instances, these protein kinases are an essential element of enzyme and structural protein complexes that determine where and when a cellular process occurs within a cell.

Protein Tyrosine Kinases. Protein tyrosine kinases (PTKs) are enzymes which catalyze the phosphorylation of specific tyrosine residues in cellular proteins. This post-translational modification of these substrate proteins, often enzymes themselves, acts as a molecular switch regulating cell proliferation, activation or differentiation (for review, see Schlessinger and Ulrich, 1992, *Neuron* 9:383–391). Aberrant or excessive PTK activity has been observed in many disease states including benign and malignant proliferative disorders as well as diseases resulting from inappropriate activation of the immune system (e.g., autoimmune disorders), allograft rejection, and graft vs. host disease. In addition, endothelial-cell specific receptor PTKs such as KDR, Tie-2 and Tie-1 mediate the angiogenic process, and are thus involved in supporting the progression of cancers and other diseases involving inappropriate vascularization (e.g., diabetic retinopathy, choroidal neovascularization due to age-related macular degeneration, psoriasis, arthritis, retinopathy of prematurity, infantile hemangiomas).

Tyrosine kinases can be of the receptor-type (having extracellular, transmembrane and intracellular domains) or the non-receptor type (being wholly intracellular).

Receptor Tyrosine Kinases (RTKs). The RTKs comprise a large family of transmembrane receptors with diverse biological activities. At present, at least nineteen (19) distinct RTK subfamilies have been identified. The receptor tyrosine kinase (RTK) family includes receptors that are crucial for the growth and differentiation of a variety of cell types (Yarden and Ullrich, *Ann. Rev. Biochem.* 57:433–478, 1988; Ullrich and Schlessinger, *Cell* 61:243–254, 1990). The intrinsic function of RTKs is activated upon ligand binding, which results in phosphorylation of the receptor and multiple cellular substrates, and subsequently in a variety of cellular responses (Ullrich & Schlessinger, 1990, *Cell* 61:203–212). Thus, receptor tyrosine kinase mediated signal transduction is initiated by extracellular interaction with a specific growth factor (ligand), typically followed by receptor dimerization, stimulation of the intrinsic protein tyrosine kinase activity and receptor trans-phosphorylation. Binding sites are thereby created for intracellular signal transduction molecules and lead to the formation of complexes with a spectrum of cytoplasmic signaling molecules that facilitate the appropriate cellular response. (e.g., cell division, differentiation, metabolic effects, changes in the extracellular microenvironment) see Schlessinger and Ullrich, 1992, *Neuron* 9:1–20.

Proteins with SH2 (src homology-2) or phosphotyrosine binding (PTB) domains bind activated tyrosine kinase receptors and their substrates with high affinity to propagate signals into cell. Both of the domains recognize phosphotyrosine. (Fantl et al., 1992, *Cell* 69:413–423; Songyang et al., 1994, *Mol. Cell. Biol.* 14:2777–2785; Songyang et al., 1993, *Cell* 72:767–778; and Koch et al., 1991, *Science* 252:668–678; Shoelson, *Curr. Opin. Chem. Biol.* (1997), 1(2), 227–234; Cowburn, *Curr. Opin. Struct. Biol.* (1997), 7(6), 835–838). Several intracellular substrate proteins that associate with receptor tyrosine kinases (RTKs) have been identified. They may be divided into two principal groups: (1) substrates which have a catalytic domain; and (2) substrates which lack such a domain but serve as adapters and associate with catalytically active molecules (Songyang et al., 1993, *Cell* 72:767–778). The specificity of the interactions between receptors or proteins and SH2 or PTB domains of their substrates is determined by the amino acid residues immediately surrounding the phosphorylated tyrosine residue. For example, differences in the binding affinities between SH2 domains and the amino acid sequences surrounding the phosphotyrosine residues on particular receptors correlate with the observed differences in their substrate phosphorylation profiles (Songyang et al., 1993, *Cell* 72:767–778). Observations suggest that the function of each receptor tyrosine kinase is determined not only by its pattern of expression and ligand availability but also by the array of downstream signal transduction pathways that are activated by a particular receptor as well as the timing and duration of those stimuli. Thus, phosphorylation provides an important regulatory step which determines the selectivity of signaling pathways recruited by specific growth factor receptors, as well as differentiation factor receptors.

Several receptor tyrosine kinases such as FGFR-1, PDGFR, Tie-2, Tie-1 and c-Met, and growth factors that bind thereto, have been suggested to play a role in angiogenesis, although some may promote angiogenesis indirectly (Mustonen and Alitalo, *J. Cell Biol.* 129:895–898, 1995). One such receptor tyrosine kinase, known as "fetal liver kinase 1" (FLK-1), is a member of the type III subclass of RTKs. An alternative designation for human FLK-1 is "kinase insert domain-containing receptor" (KDR) (Terman et al., *Oncogene* 6:1677–83, 1991). Another alternative designation for FLK-1/KDR is "vascular endothelial cell growth factor receptor 2" (VEGFR-2) since it binds VEGF with high affinity. The murine version of FLK-1/VEGFR-2 has also been called NYK (Oelrichs et al, *Oncogene* 8(1):

11–15, 1993). DNAs encoding mouse, rat and human FLK-1 have been isolated, and the nucleotide and encoded amino acid sequences reported (Matthews et al., *Proc. Natl. Acad. Sci. USA,* 88:9026–30, 1991; Terman et al., 1991, supra; Terman et al., *Biochem. Biophys. Res. Comm.* 187:1579–86, 1992; Sarzani et al., supra; and Millauer et al., *Cell* 72:835–846, 1993). Numerous studies such as those reported in Millauer et al., supra, suggest that VEGF and FLK-1/KDR/VEGFR-2 are a ligand-receptor pair that play an important role in the proliferation of vascular endothelial cells, and formation and sprouting of blood vessels, termed vasculogenesis and angiogenesis, respectively.

Another type III subclass RTK designated "fms-like tyrosine kinase-1" (Flt-1) is related to FLK-1/KDR (DeVries et al. *Science* 255;989–991, 1992; Shibuya et al., *Oncogene* 5:519–524, 1990). An alternative designation for Flt-1 is "vascular endothelial cell growth factor receptor 1" (VEGFR-1). To date, members of the FLK-1/KDR/VEGFR-2 and Flt-1/VEGFR-1 subfamilies have been found expressed primarily on endothelial cells. These subclass members are specifically stimulated by members of the vascular endothelial cell growth factor (VEGF) family of ligands (Klagsburn and D'Amore, *Cytokine & Growth Factor Reviews* 7: 259–270, 1996). Vascular endothelial cell growth factor (VEGF) binds to Flt-1 with higher affinity than to FLK-1/KDR and is mitogenic toward vascular endothelial cells (Terman et al., 1992, supra; Mustonen et al. supra; DeVries et al., supra). Flt-1 is believed to be essential for endothelial organization during vascular development. Flt-1 expression is associated with early vascular development in mouse embryos, and with neovascularization during wound healing (Mustonen and Alitalo, supra). Expression of Flt-1 in monocytes, osteoclasts, and osteoblasts, as well as in adult tissues such as kidney glomeruli suggests an additional function for this receptor that is not related to cell growth (Mustonen and Alitalo, supra).

As previously stated, recent evidence suggests that VEGF plays a role in the stimulation of both normal and pathological angiogenesis (Jakeman et al., *Endocrinology* 133: 848–859, 1993; Kolch et al., *Breast Cancer Research and Treatment* 36: 139–155, 1995; Ferrara et al., *Endocrine Reviews* 18(1); 4–25, 1997; Ferrara et al., Regulation of Angiogenesis (ed. L. D. Goldberg and E. M. Rosen), 209–232, 1997). In addition, VEGF has been implicated in the control and enhancement of vascular permeability (Connolly, et al., *J. Biol. Chem.* 264: 20017–20024, 1989; Brown et al., *Regulation of Angiogenesis* (ed. L. D. Goldberg and E. M. Rosen), 233–269, 1997). Different forms of VEGF arising from alternative splicing of mRNA have been reported, including the four species described by Ferrara et al. (*J. Cell. Biochem.* 47:211–218, 1991). Both secreted and predominantly cell-associated species of VEGF have been identified by Ferrara et al. supra, and the protein is known to exist in the form of disulfide linked dimers.

Several related homologs of VEGF have recently been identified. However, their roles in normal physiological and disease processes have not yet been elucidated. In addition, the members of the VEGF family are often coexpressed with VEGF in a number of tissues and are, in general, capable of forming heterodimers with VEGF. This property likely alters the receptor specificity and biological effects of the heterodimers and further complicates the elucidation of their specific functions as illustrated below (Korpelainen and Alitalo, *Curr. Opin. Cell Biol.,* 159–164, 1998 and references cited therein).

Placenta growth factor (PlGF) has an amino acid sequence that exhibits significant homology to the VEGF sequence (Park et al., *J. Biol. Chem.* 269:25646–54, 1994; Maglione et al. *Oncogene* 8:925–31, 1993). As with VEGF, different species of PlGF arise from alternative splicing of mRNA, and the protein exists in dimeric form (Park et al., supra). PlGF-1 and PlGF-2 bind to Flt-1 with high affinity, and PlGF-2 also avidly binds to neuropilin-1 (Migdal et al, *J. Biol. Chem.* 273 (35): 22272–22278), but neither binds to FLK-1/KDR (Park et al., supra). PlGF has been reported to potentiate both the vascular permeability and mitogenic effect of VEGF on endothelial cells when VEGF is present at low concentrations (purportedly due to heterodimer formation) (Park et al., supra).

VEGF-B is produced as two isoforms (167 and 185 residues) that also appear to bind Flt-1/VEGFR-1. It may play a role in the regulation of extracellular matrix degradation, cell adhesion, and migration through modulation of the expression and activity of urokinase type plasminogen activator and plasminogen activator inhibitor 1 (Pepper et al, *Proc. Natl. Acad. Sci. U.S.A.* (1998), 95(20): 11709–11714).

VEGF-C was originally cloned as a ligand for VEGFR-3/Flt-4 which is primarily expressed by lymphatic endothelial cells. In its fully processed form, VEGF-C can also bind KDR/VEGFR-2 and stimulate proliferation and migration of endothelial cells in vitro and angiogenesis in in vivo models (Lymboussaki et al, *Am. J. Pathol.* (1998), 153(2): 395–403; Witzenbichler et al, *Am. J. Pathol.* (1998), 153(2), 381–394). The transgenic overexpression of VEGF-C causes proliferation and enlargement of only lymphatic vessels, while blood vessels are unaffected. Unlike VEGF, the expression of VEGF-C is not induced by hypoxia (Ristimaki et al, *J. Biol. Chem.* (1998), 273(14),8413–8418).

The most recently discovered VEGF-D is structurally very similar to VEGF-C. VEGF-D is reported to bind and activate at least two VEGFRs, VEGFR-3/Flt-4 and KDR/VEGFR-2. It was originally cloned as a c-fos inducible mitogen for fibroblasts and is most prominently expressed in the mesenchymal cells of the lung and skin (Achen et al, *Proc. Natl. Acad. Sci. U.S. A.* (1998), 95(2), 548–553 and references therein).

As for VEGF, VEGF-C and VEGF-D have been claimed to induce increases in vascular permeability in vivo in a Miles assay when injected into cutaneous tissue (PCT/US97/14696; WO98/07832, Witzenbichler et al., supra). The physiological role and significance of these ligands in modulating vascular hyperpermeability and endothelial responses in tissues where they are expressed remains uncertain.

There has been recently reported a virally encoded, novel type of vascular endothelial growth factor, VEGF-E (NZ-7 VEGF), which preferentially utilizes KDR/Flk-1 receptor and carries a potent mitotic activity without heparin-binding domain (Meyer et al, *EMBO J.* (1999), 18(2), 363–374; Ogawa et al, *J. Biol. Chem.* (1998), 273(47), 31273–31282). VEGF-E sequences possess 25% homology to mammalian VEGF and are encoded by the parapoxvirus Orf virus (OV). This parapoxvirus that affects sheep and goats and occasionally, humans, to generate lesions with angiogenesis. VEGF-E is a dimer of about 20 kDa with no basic domain nor affinity for heparin, but has the characteristic cysteine knot motif present in all mammalian VEGFs, and was surprisingly found to possess potency and bioactivities similar to the heparin-binding VEGF165 isoform of VEGF-A, i.e. both factors stimulate the release of tissue factor (TF), the proliferation, chemotaxis and sprouting of cultured vascular endothelial cells in vitro and angiogenesis in vivo. Like VEGF165, VEGF-E was found to bind with high affinity to VEGF receptor-2 (KDR) resulting in receptor autophosphorylation and a biphasic rise in free intracellular $Ca^{2+}$ concentrations, while in contrast to VEGF165, VEGF-E did not bind to VEGF receptor-1 (Flt-1).

Based upon emerging discoveries of other homologs of VEGF and VEGFRs and the precedents for ligand and receptor heterodimerization, the actions of such VEGF homologs may involve formation of VEGF ligand heterodimers, and/or heterodimerization of receptors, or binding to a yet undiscovered VEGFR (Witzenbichler et al., supra). Also, recent reports suggest neuropilin-1 (Migdal et al, supra) or VEGFR-3/Flt-4 (Witzenbichler et al., supra), or receptors other than KDR/VEGFR-2 may be involved in the induction of vascular permeability (Stacker, S. A., Vitali, A., Domagala, T., Nice, E., and Wilks, A. F., Angiogenesis and Cancer Conference, Amer. Assoc. Cancer Res., January 1998, Orlando, Fla.; Williams, *Diabetelogia* 40: S118–120 (1997)).

Tie-2 (TEK) is a member of a recently discovered family of endothelial cell specific receptor tyrosine kinases which is involved in critical angiogenic processes, such as vessel branching, sprouting, remodeling, maturation and stability. Tie-2 is the first mammalian receptor tyrosine kinase for which both agonist ligand(s) (e.g., Angiopoietin1 ("Ang1"), which stimulates receptor autophosphorylation and signal transduction), and antagonist ligand(s) (e.g., Angiopoietin2 ("Ang2")), have been identified. Knock-out and transgenic manipulation of the expression of Tie-2 and its ligands indicates tight spatial and temporal control of Tie-2 signaling is essential for the proper development of new vasculature. The current model suggests that stimulation of Tie-2 kinase by the Ang1 ligand is directly involved in the branching, sprouting and outgrowth of new vessels, and recruitment and interaction of periendothelial support cells important in maintaining vessel integrity and inducing quiescence. The absence of Ang1 stimulation of Tie-2 or the inhibition of Tie-2 autophosphorylation by Ang2, which is produced at high levels at sites of vascular regression, may cause a loss in vascular structure and matrix contacts resulting in endothelial cell death, especially in the absence of growth/survival stimuli. The situation is however more complex, since at least two additional Tie-2 ligands (Ang3 and Ang4) have recently been reported, and the capacity for heterooligomerization of the various agonistic and antagonistic angiopoietins, thereby modifying their activity, has been demonstrated. Targeting Tie-2 ligand-receptor interactions as an antiangiogenic therapeutic approach is thus less favored and a kinase inhibitory strategy preferred.

The soluble extracellular domain of Tie-2 ("ExTek") can act to disrupt the establishment of tumor vasculature in a breast tumor xenograft and lung metastasis models and in tumor-cell mediated ocular neovasculatization. By adenoviral infection, the in vivo production of mg/ml levels ExTek in rodents may be achieved for 7–10 days with no adverse side effects. These results suggest that disruption of Tie-2 signaling pathways in normal healthy animals may be well tolerated. These Tie-2 inhibitory responses to ExTek may be a consequence sequestration of ligand(s) and/or generation of a non-productive heterodimer with full-length Tie-2.

Recently, significant upregulation of Tie-2 expression has been found within the vascular synovial pannus of arthritic joints of humans, consistent with a role in the inappropriate neovascularization. This finding suggests that Tie-2 plays a role in the progression of rheumatoid arthritis. Point mutations producing constitutively activated forms of Tie-2 have been identified in association with human venous malformation disorders. Tie-2 inhibitors are, therefore, useful in treating such disorders, and in other situations of inappropriate neovascularization.

The Non-Receptor Tyrosine Kinases. The non-receptor tyrosine kinases represent a collection of cellular enzymes which lack extracellular and transmembrane sequences. At present, over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. At present, the Src subfamily of non-receptor tyrosine kinases is comprised of the largest number of PTKs and include Src, Yes, Fyn, Lyn, Lck, Blk, Hck, Fgr and Yrk. The Src subfamily of enzymes has been linked to oncogenesis and immune responses. A more detailed discussion of non-receptor tyrosine kinases is provided in Bolen, 1993, *Oncogene* 8:2025–2031, which is incorporated herein by reference.

Many of the tyrosine kinases, whether an RTK or non-receptor tyrosine kinase, have been found to be involved in cellular signaling pathways involved in numerous pathogenic conditions, including cancer, psoriasis, and other hyperproliferative disorders or hyper-immune responses.

Development of Compounds to Modulate the PTKs. In view of the surmised importance of PTKs to the control, regulation, and modulation of cell proliferation, the diseases and disorders associated with abnormal cell proliferation, many attempts have been made to identify receptor and non-receptor tyrosine kinase "inhibitors" using a variety of approaches, including the use of mutant ligands (U.S. Pat. No. 4,966,849), soluble receptors and antibodies (Application No. WO 94/10202; Kendall & Thomas, 1994, *Proc. Natl. Acad. Sci* 90:10705–09; Kim et al., 1993, *Nature* 362:841–844), RNA ligands (Jellinek, et al., *Biochemistry* 33:10450–56; Takano, et al., 1993, *Mol. Bio. Cell* 4:358A; Kinsella, et al. 1992, *Exp. Cell Res.* 199:56–62; Wright, et al., 1992, *J. Cellular Phys.* 152:448–57) and tyrosine kinase inhibitors (WO 94/03427; WO 92/21660; WO 91/15495; WO 94/14808; U.S. Pat. No. 5,330,992; Mariani, et al., 1994, *Proc. Am. Assoc. Cancer Res.* 35:2268).

More recently, attempts have been made to identify small molecules which act as tyrosine kinase inhibitors. For example, bis monocyclic, bicyclic or heterocyclic aryl compounds (PCT WO 92/20642) and vinylene-azaindole derivatives (PCT WO 94/14808) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0 566 266 A1; *Expert Opin. Ther. Pat.* (1998), 8(4): 475–478), selenoindoles and selenides (PCT WO 94/03427), tricyclic polyhydroxylic compounds (PCT WO 92/21660) and benzylphosphonic acid compounds (PCT WO 91/15495) have been described as compounds for use as tyrosine kinase inhibitors for use in the treatment of cancer. Anilinocinnolines (PCT WO97/34876) and quinazoline derivative compounds (PCT WO97/22596; PCT WO97/42187) have been described as inhibitors of angiogenesis and vascular permeability.

In addition, attempts have been made to identify small molecules which act as serine/threonine kinase inhibitors. For example, bis(indolylmaleimide) compounds have been described as inhibiting particular PKC serine/threonine kinase isoforms whose signal transducing function is associated with altered vascular permeability in VEGF-related diseases (PCT WO97/40830; PCT WO97/40831).

Plk-1 Kinase Inhibitors

Plk-1 is a serine/threonine kinase which is an important regulator of cell cycle progression. It plays critical roles in the assembly and the dynamic function of the mitotic spindle apparatus. Plk-1 and related kinases have also been shown to be closely involved in the activation and inactivation of other cell cycle regulators, such as cyclin-dependent kinases. High levels of Plk-1 expression are associated with cell proliferation activities. It is often found in malignant tumors of various origins. Inhibitors of Plk-1 are expected to block cancer cell proliferation by disrupting processes involving mitotic spindles and inappropriately activated cyclin-dependent kinases.

Cdc2/Cyclin B Kinase Inhibitors (Cdc2 is also known as cdk1)

Cdc2/cyclin B is another serine/threonine kinase enzyme which belongs to the cyclin-dependent kinase (cdk) family. These enzymes are involved in the critical transition between various phases of cell cycle progression. It is believed that uncontrolled cell proliferation, which is the hallmark of cancer is dependent upon elevated cdk activities in these cells. The inhibition of elevated cdk activities in cancer cells by cdc2/cyclin B kinase inhibitors can suppress proliferation and may restore the normal control of cell cycle progression.

The regulation of CDK activation is complex, but requires the association of the CDK with a member of the cyclin family of regulatory subunits (Draetta, *Trends in Cell Biology*, 3:287–289 (1993)); Murray and Kirschner, *Nature*, 339:275–280 (1989); Solomon et al., *Molecular Biology of the Cell*, 3:13–27 (1992)). A further level of regulation occurs through both activating and inactivating phosphorylations of the CDK subunit (Draetta, *Trends in Cell Biology*, 3:287–289 (1993)); Murray and Kirschner, *Nature*, 339: 275–280 (1989); Solomon et al., *Molecular Biology of the Cell*, 3:13–27 (1992); Ducommun et al., *EMBO Journal*, 10:3311–3319 (1991); Gautier et al., *Nature* 339:626–629 (1989); Gould and Nurse, *Nature*, 342:39–45 (1989); Krek and Nigg, *EMBO Journal*, 10:3331–3341 (1991); Solomon et al., *Cell*, 63:1013–1024 (1990)). The coordinate activation and inactivation of different cyclin/CDK complexes is necessary for normal progression through the cell cycle (Pines, *Trends in Biochemical Sciences*, 18:195–197 (1993); Sherr, *Cell*, 73:1059–1065 (1993)). Both the critical G1-S and G2-M transitions are controlled by the activation of different cyclin/CDK activities. In G1, both cyclin D/CDK4 and cyclin E/CDK2 are thought to mediate the onset of S-phase (Matsushima et al., *Molecular & Cellular Biology*, 14:2066–2076 (1994); Ohtsubo and Roberts, *Science*, 259: 1908–1912 (1993); Quelle et al., *Genes & Development*, 7:1559–1571 (1993); Resnitzky et al., *Molecular & Cellular Biology*, 14:1669–1679 (1994)). Progression through S-phase requires the activity of cyclin A/CDK2 (Girard et al., *Cell*, 67:1169–1179 (1991); Pagano et al., *EMBO Journal*, 11:961–971 (1992); Rosenblatt et al., *Proceedings of the National Academy of Science USA*, 89:2824–2828 (1992); Walker and Maller, *Nature*, 354:314–317 (1991); Zindy et al., *Biochemical & Biophysical Research Communications*, 182:1144–1154 (1992)) whereas the activation of cyclin A/cdc2 (CDK1) and cyclin B/cdc2 are required for the onset of metaphase (Draetta, *Trends in Cell Biology*, 3:287–289 (1993)); Murray and Kirschner, *Nature*, 339:275–280 (1989); Solomon et al., *Molecular Biology of the Cell*, 3:13–27 (1992); Girard et al., *Cell*, 67:1169–1179 (1991); Pagano et al., EMBO Journal, 11:961–971 (1992); Rosenblatt et al., *Proceedings of the National Academy of Science USA*, 89:2824–2828 (1992); Walker and Maller, *Nature*, 354:314–317 (1991); Zindy et al., *Biochemical & Biophysical Research Communications*, 182:1144–1154 (1992)). It is not surprising, therefore, that the loss of control of CDK regulation is a frequent event in hyperproliferative diseases and cancer. (Pines, *Current Opinion in Cell Biology*, 4:144–148 (1992); Lees, *Current Opinion in Cell Biology*, 7:773–780 (1995); Hunter and Pines, *Cell*, 79:573–582 (1994)).

Inhibitors of kinases involved in mediating or maintaining disease states represent novel therapies for these disorders. Examples of such kinases include, but are not limited to: (1) inhibition of c-Src (Brickell, *Critical Reviews in Oncogenesis*, 3:401–406 (1992); Courtneidge, *Seminars in Cancer Biology*, 5:236–246 (1994), raf (Powis, *Pharmacology & Therapeutics*, 62:57–95 (1994)) and the cyclin-dependent kinases (CDKs) 1, 2 and 4 in cancer (Pines, *Current Opinion in Cell Biology*, 4:144–148 (1992); Lees, *Current Opinion in Cell Biology*, 7:773–780 (1995); Hunter and Pines, *Cell*, 79:573–582 (1994)), (2) inhibition of CDK2 or PDGF-R kinase in restenosis (Buchdunger et al., *Proceedings of the National Academy of Science USA*, 92:2258–2262 (1995)), (3) inhibition of CDK5 and GSK3 kinases in Alzheimers (Hosoi et al., *Journal of Biochemistry* (Tokyo), 117:741–749 (1995); Aplin et al., *Journal of Neurochemistry*, 67:699–707 (1996), (4) inhibition of c-Src kinase in osteoporosis (Tanaka et al., *Nature*, 383:528–531 (1996), (5) inhibition of GSK-3 kinase in type-2 diabetes (Borthwick et al., *Biochemical & Biophysical Research Communications*, 210: 738–745 (1995), (6) inhibition of the p38 kinase in inflammation (Badger et al., *The Journal of Pharmacology and Experimental Therapeutics*, 279:1453–1461 (1996)), (7) inhibition of VEGF-R 1–3 and TIE-1 and -2 kinases in diseases which involve angiogenesis (Shawver et al., *Drug Discovery Today*, 2:50–63 (1997)), (8) inhibition of UL97 kinase in viral infections (He et al., *Journal of Virology*, 71:405411 (1997)), (9) inhibition of CSF-1R kinase in bone and hematopoetic diseases (Myers et al., *Bioorganic & Medicinal Chemistry Letters*, 7:421–424 (1997), and (10) inhibition of Lck kinase in autoimmune diseases and transplant rejection (Myers et al., *Bioorganic & Medicinal Chemistry Letters*, 7:417–420 (1997)).

It is additionally possible that inhibitors of certain kinases may have utility in the treatment of diseases when the kinase is not misregulated, but it nonetheless essential for maintenance of the disease state. In this case, inhibition of the kinase activity would act either as a cure or palliative for these diseases. For example, many viruses, such as human papilloma virus, disrupt the cell cycle and drive cells into the S-phase of the cell cycle (Vousden, *FASEB Journal*, 7:8720879 (1993)). Preventing cells from entering DNA synthesis after viral infection by inhibition of essential S-phase initiating activities such as CDK2, may disrupt the virus life cycle by preventing virus replication. This same principle may be used to protect normal cells of the body from toxicity of cycle-specific chemotherapeutic agents (Stone et al., *Cancer Research*, 56:3199–3202 (1996); Kohn et al., *Journal of Cellular Biochemistry*, 54:44452 (1994)). Inhibition of CDKs 2 or 4 will prevent progression into the cycle in normal cells and limit the toxicity of cytotoxics which act in S-phase, G2 or mitosis. Furthermore, CDK2/ cyclin E activity has also been shown to regulate NF-kB. Inhibition of CDK2 activity stimulates NF-kB-dependent gene expression, an event mediated through interactions with the p300 coactivator (Perkins et al., *Science*, 275: 523–527 (1997)). NF-kB regulates genes involved in inflammatory responses (such as hematopoetic growth factors, chemokines and leukocyte adhesion molecules) (Baeuerle and Henkel, *Annual Review of Immunology*, 12:141–179 (1994)) and may be involved in the suppression of apoptotic signals within the cell (Beg and Baltimore, *Science*, 274:782–784 (1996); Wang et al., *Science*, 274:

784–787 (1996); Van Antwerp et al., *Science,* 274:787–789 (1996)). Thus, inhibition of CDK2 may suppress apoptosis induced by cytotoxic drugs via a mechanism which involves NF-kB. This therefore suggests that inhibition of CDK2 activity may also have utility in other cases where regulation of NF-kB plays a role in etiology of disease. A further example may be take from fungal infections: Aspergillosis is a common infection in immune-compromised patients (Armstrong, *Clinical Infectious Diseases,* 16:1–7 (1993)). Inhibition of the *Aspergillus* kinases Cdc2/Cdc28 or Nim A (Osmani et al., *EMBO Journal,* 10:2669–2679 (1991); Osmani et al., *Cell,* 67:283–291 (1991)) may cause arrest or death in the fungi, improving the therapeutic outcome for patients with these infections.

The identification of effective small compounds which specifically inhibit signal transduction and/or cellular proliferation by modulating the activity of receptor and non-receptor tyrosine and serine/threonine kinases to regulate and modulate abnormal or inappropriate cell proliferation, differentiation, or metabolism is therefore desirable. In particular, the identification of methods and compounds that specifically inhibit the function of a tyrosine kinase which is essential for angiogenic processes or the formation of vascular hyperpermeability leading to edema, ascites, effusions, exudates, macromolecular extravasation and matrix deposition as well as associated disorders would be beneficial.

SUMMARY OF THE INVENTION

In one aspect, the present invention is directed to a compound of formula (I),

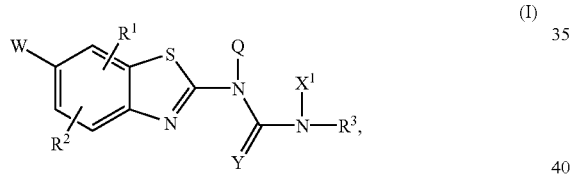

racemic-diastereomeric mixtures thereof, optical isomers thereof, prodrugs thereof, isotopes thereof or pharmaceutically-acceptable salts of said compound, isomers, prodrugs and isotopes, wherein, Q is H or represents a bond which is taken together with $X^1$ and the two nitrogen atoms to which Q and $X^1$ are attached and the C=Y group to which the two nitrogen atoms are attached to form

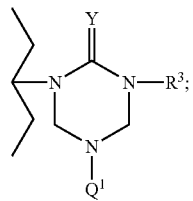

$Q^1$ is $(C_1-C_6)$alkyl;

Y is O or S;

W is H, Cl, Br, I, $NO_2$, CN, SCN, $OCF_3$, $-X_q-(C(R^{10})_2)_a$ $-Y^1_q-(C(R^{10})_2)_a-Z^1_q$, or an optionally substituted group selected from the group consisting of alkyl, alkenyl, alkynyl, heterocyclyl-alkenyl, and heterocyclyl-alkynyl;

$Y^1$ and X are each independently selected from the group consisting of phenyl, heterocyclyl, $NR^{10}$, O, S, SO, $SO_2$, $CF_2$, CFR, C=O, (C=O)$NR^{10}$, $SONR^{10}$, $SO_2NR^{10}$, $NR^{10}$(C=O), $NR^{10}SO$, $NR^{10}SO_2$, $NR^{10}SO_2NR^{10}$, $NR^{10}$(C=O)$NR^{10}$,

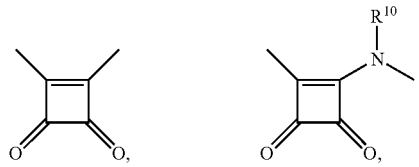

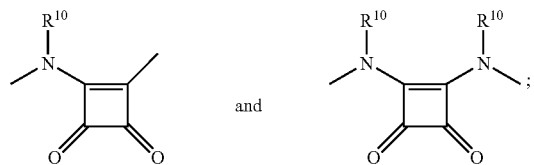 and 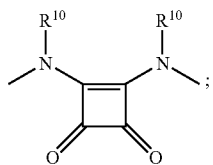

q for each occurrence is independently 0 or 1;
a for each occurrence is independently 0 or an integer from 1 to 5;
$R^{10}$ for each occurrence is independently selected from the group consisting of H, optionally substituted aryl, optionally substituted heterocyclyl and an optionally substituted alkyl group optionally substituted with one or more of the following: a $C_{1-6}$ alkyl group optionally substituted by one or more hydroxy, halo or optionally substituted amino; a $C_{1-6}$ alkoxy group optionally substituted by one or more hydroxy, halo or optionally substituted amino; hydroxy; halo; or optionally substituted amino;
$Z^1$ is H, optionally substituted alkyl, optionally substituted aryl or optionally substituted heterocyclyl;

$X^1$ is hydrogen, alkyl, hydroxyalkyl or represents a bond which is taken together with $R^3$ as described below or represents a bond which is taken together with Q as described above;

$R^1$ and $R^2$ are each independently hydrogen, halogen, hydroxy, nitro, cyano, COOH, $COOX^3$, $SX^3$, $SO_2X^3$, $SOX^3$, $C(O)X^3$, $NHC(O)X^3$, $C(O)NHX^3$, $NHSO_2X^3$ or selected from an optionally substituted group consisting of alkyl, alkenyl, alkynyl, alkoxy, amino, $NHX^3$, $NX^3X^3$, alkylamino, arylamino, heterocyclylamino, alkylthio, alkylsulfonato, aryl, aryloxy, arylalkyl, arylalkenyl, arylalkynyl, arylalkyloxy, heterocyclyl, heterocyclyloxy, heterocyclylalkyl, heterocyclyl-alkenyl, heterocyclyl-alkynyl, heterocyclyl-alkyloxy, heterocyclylthio, heterocyclylsulfinyl, heterocyclylsulfonyl, cycloalkyl, $-(CH_2)_m-(CHX^2)CN$, $-(CH_2)_m-(CHX^2)COOH$, $-(CH_2)_m-(CHX^2)COOX^3$, $-(CH_2)_m-(CHX^2)SO_2X^3$, $-(CH_2)_m-(CHX^2)C(O)X^3$, $-(CH_2)_m-(CHX^2)C(O)NHX^3$ and $-(CH_2)_m-(CHX^2)NHSO_2X^3$;

where m is 0 to 4;
$X^2$ for each occurrence is independently H or an optionally substituted moiety selected from the group consisting of alkyl, alkenyl, alkynyl, carbonyl, $S(O)_p$alkyl, $S(O)_p$aryl, $S(O)_p$heterocyclyl, amino, alkoxy, alkylthio, arylthio, perhaloalkyl, aryl, aryloxy, arylalkyl, arylalkyloxy, heterocyclyl and heterocyclyl-alkyl;

p is 0, 1 or 2;

$X^3$ for each occurrence is independently H or an optionally substituted moiety selected from the group consisting of mono- or di-alkylamino, alkyl, alkenyl, alkynyl, aryl, arylalkyl, heterocyclyl and heterocyclylalkyl;

or when $R^1$ is in the 7-position of the benzothiazole ring, $R^1$ and W can be taken together with the carbon atoms to which they are attached to form an optionally substituted 5- or 6-membered heterocyclyl ring;

$R^3$ is hydrogen, or an optionally substituted moiety selected from the group consisting of carbonyl, alkyl, alkenyl, alkynyl, cycloalkyl, aryl, arylalkyl, heterocyclyl, heterocyclylalkyl, heterocyclyl—heterocyclyl, heterocyclyl-cycloalkyl, amino, alkylamino, arylamino, alkoxy, thioalkoxy and acyl;

or $R^3$ and $X^1$ are taken together with the nitrogen atom to which they are attached to form

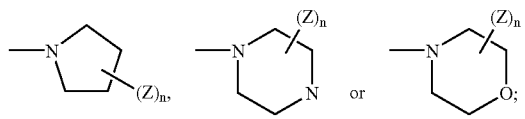

where Z for each occurrence is independently selected from the group consisting of oxo, or an optionally substituted moiety selected from the group consisting of —C(O)(C$_1$–C$_6$)alkyl, —C(O)aryl, —C(O)N(C$_1$–C$_6$)alkyl, —C(O)N-aryl, (C$_1$–C$_6$)alkyl, (C$_2$–C$_6$)alkenyl, (C$_2$–C$_6$)alkynyl, amino, mono- or di-(C$_1$–C$_6$)alkylamino, —COO(C$_1$–C$_6$)alkyl, pyridyl, phenyl, phenyl(C$_1$–C$_6$)alkyl and phenyl (C$_1$–C$_6$)alkenyl;

where each of the optionally substituted moieties described hereinabove is optionally substituted by one or more substituents each independently selected from the group consisting of oxo, amino, nitro, mono- or bi-(C$_1$–C$_6$)alkylamino, hydroxy, nitrile, chloro, fluoro, bromo, iodo, CF$_3$, (C$_1$–C$_6$)alkyl, —C(O)(C$_1$–C$_6$)alkyl, —COOH, —COO(C$_1$–C$_6$)alkyl, —S—(C$_1$–C$_6$)alkyl, —S-aryl, (C$_1$–C$_6$)alkoxy, —SO$_2$NH$_2$, phenyl, phenyl(C$_1$–C$_6$)alkyl, —O—(C$_1$–C$_6$)alkyl-OH, —O—(C$_1$–C$_6$)alkyl-O—(C$_1$–C$_6$)alkyl, —O—(C$_2$–C$_6$) alkyl-N—((C$_1$–C$_6$)alkyl)$_n$, —N—(C$_1$–C$_6$)alkyl-OH, —N—(C$_1$–C$_6$)alkyl-O—(C$_1$–C$_6$)alkyl, —C(O)NH$_2$, —C(O)N ((C$_1$–C$_6$)alkyl)$_n$, —S(O)$_n$(C$_1$–C$_6$)alkyl, —S(O)$_n$aryl, —S(O)$_n$heterocyclyl, and heterocyclyl, where the alkyl groups mentioned herein optionally have one or more unsaturated bonds in the alkyl portion;

n is 0, 1 or 2;

provided that 1) when Q is H; Y is O; $R^1$ and $R^2$ are each hydrogen, halogen, alkyl, alkoxy, alkylthio, carboxyalkyl or optionally substituted phenyl; and $X^1$ is hydrogen or alkyl; then $R^3$ is not alkyl, alkenyl, alkoxy, cycloalkyl or optionally substituted phenyl;

2) when Q is H; Y is O; $R^1$ and $R^2$ are each hydrogen, halogen, alkyl, alkoxy, alkylthio, carboxyalkyl or optionally substituted phenyl; then $X^1$ and $R^3$ are not taken together to form

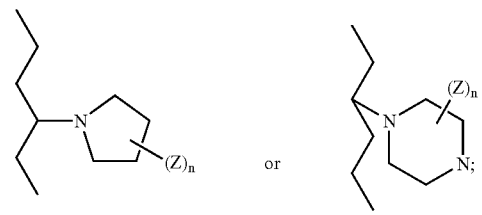

3) when W is Cl, Br or I; Q is hydrogen; Y is O; $X^1$ is H; then $R^3$ is not

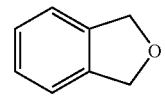

or phenyl optionally substituted by 1 to 3 substituents independently selected from the group consisting of amino, mono- or bi-(C$_1$–C$_6$)alkylamino, hydroxy, chloro, fluoro, bromo, iodo, (C$_1$–C$_6$)alkyl, (C$_1$–C$_6$)alkoxy and —SO$_2$NH$_2$;

4) when W is Cl, Br or I; Q is H; $R^1$ is 7-Cl; $R^2$ is H; and $X^1$ is alkyl; then $R^3$ is not alkyl, alkoxy or cycloalkyl;

5) when W is Cl, Br or I; Q is H; $R^1$ is 7-Cl; $R^2$ is H; and $X^1$ is H; then $R^3$ is not alkyl or cycloalkylamino;

6) when W is Cl, Br, I or NO$_2$; Q is H; Y is O; $X^1$ is H; $R^3$ is OH; $R^2$ is NO$_2$, amino, alkyl, alkoxy, hydroxy lower alkyl or dialkylamino; then $R^3$ is not H or alkyl;

7) when W is Cl, Br or I; Q is H; Y is O; $R^1$ is CF$_3$, CH$_2$F, NO$_2$, alkyl or alkoxy; $R^2$ is H; $X^1$ is H; then $R^3$ is not naphthyl or phenyl optionally substituted with halo, CF$_3$, alkyl or alkoxy;

8) when W is Cl, Br or I; Q is H; $R^1$ is alkyl; $R^2$ is H; $X^1$ is H or alkyl; then $R^3$ is not alkyl or alkoxy;

9) when W is Cl; Q is H; Y is S; $R^1$ and $R^2$ are each H; $X^1$ is H; then $R^3$ is not ethyl;

10) when W is Cl; Q is H; Y is O; $R^1$ and $R^2$ are each H; $X^1$ is H; then $R^3$ is not n-butyl; and 11) when W is H, then $R^1$ and $R^2$ are not H at the same time.

In a preferred embodiment, the present invention is directed to compounds of the formula

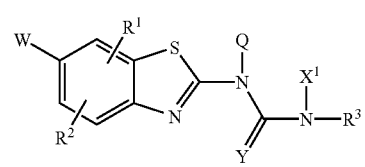

racemic-diastereomeric mixtures thereof, optical isomers thereof, prodrugs thereof, isotopes thereof or pharmaceutically-acceptable salts of said compound, isomers, prodrugs and isotopes, wherein, Q is H or represents a bond which is taken together with $X^1$ and the two nitrogen atoms to which Q and $X^1$ are attached and the C=Y group to which the two nitrogen atoms are attached to form

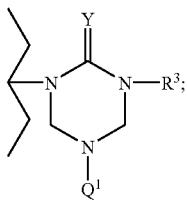

Q¹ is (C₁–C₆)alkyl;

Y is O or S;

W is Cl, Br, I, NO₂ or CN;

where X¹ is hydrogen, alkyl, hydroxyalkyl or represents a bond which is taken together with R³ as described below or represents a bond which is taken together with Q as described above;

R¹ and R² are each independently hydrogen, halogen, hydroxy, nitro, cyano, COOH, COOX³, SO₂X³, SOX³, C(O)X³, NHC(O)X³, C(O)NHX³, NHSO₂X³ or selected from an optionally substituted group consisting of alkyl, alkenyl, alkynyl, alkoxy, amino, NHX³, NX³X³, alkylamino, arylamino, heterocyclylamino, alkylthio, alkylsulfonato, aryl, aryloxy, arylalkyl, arylalkenyl, arylalkynyl, arylalkyloxy, heterocyclyl, heterocyclyloxy, heterocyclylalkyl, heterocyclyl-alkenyl, heterocyclyl-alkynyl, heterocyclyl-alkyloxy, heterocyclylthio, heterocyclylsulfinyl, heterocyclylsulfonyl, cycloalkyl, —(CH₂)ₘ—(CHX²)CN, —(CH₂)ₘ—(CHX²)COOH, —(CH₂)ₘ—(CHX²)COOX³, —(CH₂)ₘ—(CHX²)SO₂X³, —(CH₂)ₘ—(CHX²)C(O)X³, (CH²)ₘ—(CHX²)C(O)NHX³ and

—(CH₂)ₘ—(CHX²)NHSO₂X³;

where m is 0 to 4;

X² for each occurrence is independently H or an optionally substituted moiety selected from the group consisting of alkyl, alkenyl, alkynyl, carbonyl, S(O)ₚalkyl, S(O)ₚaryl, S(O)ₚheterocyclyl, amino, alkoxy, alkylthio, arylthio, perhaloalkyl, aryl, aryloxy, arylalkyl, arylalkyloxy, heterocyclyl and heterocyclyl-alkyl;

p is 0, 1 or 2;

X³ for each occurrence is independently H or an optionally substituted moiety selected from the group consisting of mono- or di-alkylamino, alkyl, alkenyl, alkynyl, aryl, arylalkyl, heterocyclyl and heterocyclylalkyl;

R³ is hydrogen, or an optionally substituted moiety selected from the group consisting of carbonyl, alkyl, alkenyl, alkynyl, cycloalkyl, aryl, arylalkyl, heterocyclyl, heterocyclylalkyl, amino, alkylamino, arylamino, alkoxy, thioalkoxy and acyl;

or R³ and X¹ are taken together with the nitrogen atom to which they are attached to form

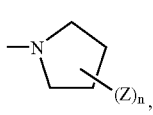 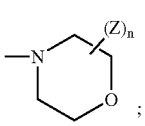 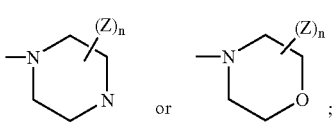

where Z for each occurrence is independently selected from the group consisting of oxo, or an optionally substituted moiety selected from the group consisting of —C(O)(C₁–C₆)alkyl, —C(O)aryl, —C(O)N(C₁–C₆)alkyl, —C(O)N-aryl, (C₁–C₆)alkyl, (C₂–C₆)alkenyl, (C₂–C₆)alkynyl, amino, mono- or di-(C₁–C₆)alkylamino, —COO(C₁–C₆)alkyl, pyridyl, phenyl, phenyl(C₁–C₆)alkyl and phenyl (C₁–C₆)alkenyl;

where each of the optionally substituted moieties described hereinabove is optionally substituted by one or more substituents each independently selected from the group consisting of oxo, amino, nitro, mono- or bi-(C₁–C₆)alkylamino, hydroxy, nitrile, chloro, fluoro, bromo, iodo, CF₃, (C₁–C₆)alkyl, —C(O)(C₁–C₆)alkyl, —COOH, —COO(C₁–C₆)alkyl, —S—(C₁–C₆)alkyl, —S-aryl, (C₁–C₆)alkoxy, —SO₂NH₂, phenyl, phenyl(C₁–C₆)alkyl, —O—(C₁–C₆)alkyl-OH, —O—(C₁–C₆)alkyl-O—(C₁–C₆)alkyl, —O—(C₂–C₆) alkyl-N—((C₁–C₆)alkyl)ₙ, —N—(C₁–C₆)alkyl-OH, —N—(C₁–C₆)alkyl-O—(C₁–C₆)alkyl, —C(O)NH₂, —C(O)N ((C₁–C₆)alkyl)ₙ, , —S(O)ₙ(C₁–C₆)alkyl, —S(O)ₙaryl, —S(O)ₙheterocyclyl, and heterocyclyl, where the alkyl groups mentioned herein optionally have one or more unsaturated bonds in the alkyl portion;

n is 0, or 2;

provided that 1) when Q is H; Y is O; R¹ and R² are each hydrogen, halogen, alkyl, alkoxy, alkylthio, carboxyalkyl or optionally substituted phenyl; and X¹ is hydrogen or alkyl; then R³ is not alkyl, alkenyl, alkoxy, cycloalkyl or optionally substituted phenyl;

2) when Q is H; Y is O; R¹ and R² are each hydrogen, halogen, alkyl, alkoxy, alkylthio, carboxyalkyl or optionally substituted phenyl; then X¹ and R³ are not taken together to form

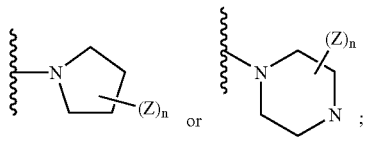

3) when W is Cl, Br or I; Q is hydrogen; Y is O; X¹ is H; then R³ is not

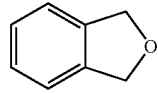

or phenyl optionally substituted by 1 to 3 substituents independently selected from the group consisting of amino, mono- or bi-(C₁–C₆)alkylamino, hydroxy, chloro, fluoro, bromo, iodo, (C₁–C₆)alkyl, (C₁–C₆)alkoxy and —SO₂NH₂;

4) when W is Cl, Br or I; Q is H; R¹ is 7-Cl; R² is H; and X¹ is alkyl; then R³ is not alkyl, alkoxy or cycloalkyl;

5) when W is Cl, Br or I; Q is H; R¹ is 7-Cl; R² is H; and X¹ is H; then R³ is not alkyl or cycloalkylamino;

6) when W is Cl, Br, I or NO₂; Q is H; Y is O; X¹ is H; R¹ is OH; R² is NO₂, amino, alkyl, alkoxy, hydroxy lower alkyl or dialkylamino; then R³ is not H or alkyl;

7) when W is Cl, Br or I; Q is H; Y is O; R¹ is CF₃, CH₂F, NO₂, alkyl or alkoxy; R² is H; X¹ is H; then R³ is not naphthyl or phenyl optionally substituted with halo, CF₃, alkyl or alkoxy;

8) when W is Cl, Br or I; Q is H; R¹ is alkyl; R² is H; X¹ is H or alkyl; then R³ is not alkyl or alkoxy;

9) when W is Cl; Q is H; Y is S; R¹ and R² are each H; X¹ is H; then R³ is not ethyl; and 10) when W is Cl; Q is H; Y is O; R¹ and R² are each H; X¹ is H; then R³ is not n-butyl.

A preferred group of compounds of formula (I), designated Group A, are those compounds wherein the alkyl, alkenyl and alkynyl moieties, and the alkyl portion of a moiety is an optionally substituted straight or branched chain having one to eight carbon atoms;

the aryl moiety and the aryl portion of a moiety is an optionally substituted phenyl,

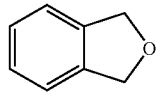

or naphthyl;

the heterocyclyl moiety and the heterocyclyl portion of a moiety are selected from the group consisting of an optionally substituted piperidinyl, pyridyl, pyrazinyl, pyrimidinyl, thienyl, pyrrolidinyl, piperazinyl, thiomorpholinyl, morpholinyl, 2,3,4,5-tetrahydrofuranyl, 1,3-dioxanyl, 1,4-dioxanyl, furanyl, and 1,2,4-triazolyl, tetrazolyl, imidazolyl, pyrazolyl, thiazolyl, oxazolyl, oxadiazolyl, thiadiazolyl, benzimidazolyl, 1,3-dioxolanyl, 2-imidazolinyl, imidazolidinyl, 2-pyrazolinyl, pyrazolidinyl, isothiazolyl, 1,2,3-triazolyl, 2H-pyranyl, 4H-pyranyl, 1,4-dithianyl, 1,3,5-triazinyl, 1,3,5-trithianyl, indolyl, isoindolyl, 3H-indolyl, indolinyl, purinyl, 4H-quinolizinyl, cinnolinyl, phthalazinyl, quinolinyl, isoquinolinyl, quinazolinyl, quinoxalinyl, 1,8-naphthpyridinyl, pteridinyl, quinuclidinyl, carbazolyl, acridinyl, phenazinyl, phenothiazinyl, phenoxazinyl, pyrrolyl, isoxazolyl, pyridazinyl, indazolyl, benzoxazolyl, benzofuranyl, benzothiazolyl, indolizinyl, imidazopyridinyl and benzothienyl.

A preferred group of compounds of Group A, designated Group B, are those compounds wherein R³ is an optionally substituted moiety selected from the group consisting of (C₁–C₈)alkyl, phenyl, phenyl(C₁–C₈)alkyl, thienyl, thienyl(C₁–C₈)alkyl, piperidinyl, piperidinyl(C₁–C₈)alkyl, pyrrolidinyl, pyrrolidinyl(C₁–C₈)alkyl, morpholinyl, morpholinyl(C₁–C₈)alkyl, 2,3,4,5-tetrahydrofuranyl, 2,3,4,5-tetrahydrofuranyl(C₁–C₈)alkyl, furanyl, furanyl(C₁–C₈) alkyl, cycloalkyl, cycloalkyl(C₁–C₈)alkyl, pyridyl, pyridyl(C₁–C₈)alkyl, 1,2,4-triazolyl, 1,2,4-triazolyl(C₁–C₈)alkyl,

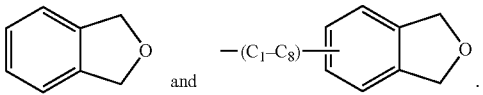

A preferred group of compounds of Group B, designated Group C, are those compounds wherein Q is H; is NO₂; Y is S; R¹ is in the 7-position and is hydrogen, —CH₂—SO₂-phenyl, —CH₂—CN, —CH(CH₃)(CN), or —CH(CN)(CH₂-phenyl); R² is hydrogen; X¹ is hydrogen, methyl or —(CH₂)₂—OH;

R³ is selected from the group consisting of ethyl, benzyl, EtOH, n-PrOH, n-BuOH, n-pentanol, n-hexanol, —(CH₂)₂—NH—(CH₂)₂—OH, —(CH₂)₂—O—(CH₂)₂—OH, —CH(CH₂CH₃)(CH₂OH), —CH(CH₂OH)(CH₂-i-Pr), 2,3-di-hydroxy-propyl, 2-hydroxypropyl, —CH(CH₃)(CH₂OH), —C(CH₃)₂(CH₂OH), —CH₂(CH₃)(CH₂OCH₃), 1,3-dihydroxyisopropyl, —CH(CH₂OH)(CH₂CH₂SCH₃), cyclopropyl, cyclopropylmethyl, 4-hydroxycyclohexyl, 3-chlorophenyl, 4-chlorophenyl, 2-methylphenyl, 3-methylphenyl, 4-aminobenzyl, (4-aminophenyl)ethyl, —(CH₂)₃—N(Et)₂, —(CH₂)₂—N(Me)₂, N-piperidinyl, 2,6-dimethylpiperidinyl,

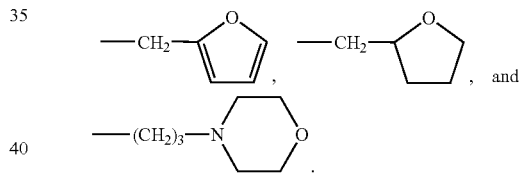

Another preferred group of compounds of Group B, designated Group D, are those compounds wherein Y is O; R¹ is in the 7-position and is hydrogen, —CH₂—SO₂-phenyl, —CH₂—CN, —CH(CH₃)(CN), or —CH(CN)(CH₂-phenyl); R² is hydrogen; X¹ is hydrogen, methyl or —(CH₂)₂—OH;

R³ is selected from the group consisting of benzyl, EtOH, n-PrOH, t-BuOH, n-hexanol, aminoethyl, aminopropyl, —(CH₂)₂—NH—(CH₂)₂—OH, —(CH₂)₂—O—(CH₂)₂—OH, —CH(CH₂CH₃)(CH₂OH), —CH(CH₂OH)(CH₂—i—Pr), 2,3-di-hydroxy-propyl, 2-hydroxypropyl, —CH(CH₃)(CH₂OH), 1,3-dihydroxyisopropyl, —CH(CH₂OH)(CH₂CH₂SCH₃), cyclobutyl, 4-hydroxycyclohexyl, —CH(COOEt)(CH₂)₂—SCH₃, —(CH₂)₂—COOEt, —(CH₂)₅—COOEt, (2-aminophenyl)methyl, 4-aminobenzyl, (4-aminophenyl)ethyl, —C(CH₃)₂(phenyl), —CH₂(2,4-difluorophenyl), 2-pyridylmethyl, 3-pyridylmethyl, 4-pyridylmethyl —(CH₂)₂-thien-2-yl, —CH(i—Pr)(COOEt), —CH(i—Pr)(CH₂OH), 3-(N-methylamino)propyl, —(CH₂)₃—N(Et)₂, —(CH₂)₄—N(Et)₂, —CH(Me)(CH₂)₄—CH₃, —CH(Me)(CH₂)₃—N(Et)₂, N-piperidinyl, —(CH₂)₂—(4-(SO₂NH₂)phenyl), 2,6-dimethylpiperidinyl,

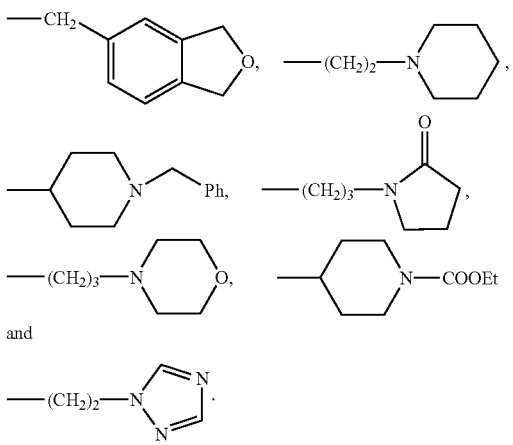

and

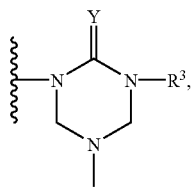

Another preferred group of compounds of Group B, designated Group E, are those compounds wherein W is $NO_2$; Q is hydrogen; $R^1$ is in the 7-position and is —$CH_2$—$CO_2$-t-Bu, allyl or benzyl; $R^2$ are each hydrogen; $X^1$ is hydrogen; and $R^3$ is ethyl.

Another preferred group of compounds of Group B, designated Group F, are those compounds wherein W is $NO_2$; $R^1$ is in the 7-position and is hydrogen, —$CH(CH_3)$(CN) or —$CH(CN)(CH_2$-phenyl); $R^2$ is hydrogen; and Q is taken together with $X^1$ and to form

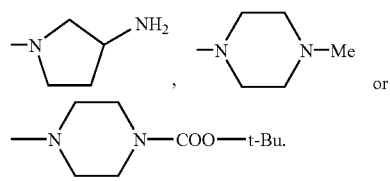

where Y is O and $R^3$ is ethyl.

Another preferred group of compounds of Group A, designated Group G, are those compounds wherein W is $NO_2$; Q is H; $R^1$ and $R^2$ are each hydrogen; and $R^3$ and $X^1$ are taken together with the nitrogen atom to which they are attached to form

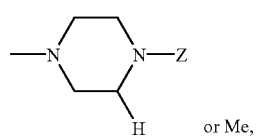

A preferred group of compounds of Group B, designated Group H, are those compounds wherein W is $NO_2$; $R^1$ is hydrogen or is in the 7-position and is —$CH_2$—CN, —$CH_2$—$CONH_2$ and —$CH_2$—COO-t-Bu; $R^2$ is hydrogen; $X^1$ is hydrogen or —$CH_2$—O—$CH_3$; $R^3$ is methyl, ethyl, n-BuOH, —$CH_2CF_3$, morpholino, —$(CH_2)_7$—$N(Me)_2$, 2-phenyl—phenyl, n-BuOH, —$CH_2CF_3$, morpholino, —$(CH_2)_4$—$N(Me)_2$, —$(CH_2)_2$—$N(Me)_2$, —$(CH_2)_3$—NHMe, benzyl or —$CH_2$—O—$CH_3$;

or Q is hydrogen or is taken together with $X^1$ to form

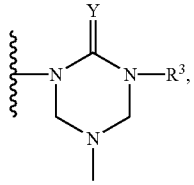

where Y is O and $R^3$ is ethyl;

or $R^3$ and $X^1$ are taken together with the nitrogen atom to which they are attached to form —N⟨⟩N—Z   H or Me, where Z is methyl, 4-fluorophenyl, 2-pyridyl, 2-methoxyphenyl, —$CH_2$—CH=CH-phenyl or 2,4-dimethoxyphenyl.

Another preferred group of compounds of formula (I), designated Group I, are those compounds wherein W is Cl or Br; Q is H; $R^3$ is an optionally substituted moiety selected from the group consisting of alkyl, alkenyl, phenyl, phenylalkyl, heterocyclyl, heterocyclyl-alkyl or aminoalkyl.

A preferred group of compounds of Group I, designated Group J, are those compounds wherein $R^3$ is alkyl, haloalkyl, esteralkyl, N,N-dialkylaminoalkyl, alkenyl, phenyl, phenylalkyl, halophenyl, alkoxyphenyl, aryloxyphenyl, thienyl-alkyl, halopyridyl, heterocyclyl, heterocyclyl-alkyl or aminoalkyl.

A preferred group of compounds of Group J, designated Group K, are those compounds wherein W is Cl; $R^3$ is ethyl, propyl, butyl, t-butyl, 2,4,6-trichlorophenyl, 2,4-dimethoxyphenyl, —$(CH_2)_2$-2-thienyl, allyl, 2-bromoethyl, 2-phenoxyphenyl, 2,6-dichloropyrid-4-yl, benzyl, —$(CH_2)_2$—COOEt, —$(CH_2)_3$—$N(Et)_2$, —$(CH_2)_4$—$N(Et)_2$, or —$(CH_2)_2$—$N(Me)_2$.

A preferred group of compounds of Group K, designated Group L, are those compounds wherein $R^3$ is —$(CH_2)_2$-2-thienyl, allyl, 2-bromoethyl, 2-phenoxyphenyl, 2,6-dichloropyrid-4-yl, benzyl, —$(CH_2)_2$—COOEt, —$(CH_2)_3$—$N(Et)_2$, —$(CH_2)_4$—$N(Et)_2$, or —$(CH_2)_2$—$N(Me)_2$.

Another preferred group of compounds of Group J, designated Group M, are those compounds wherein $R^1$ is hydroxy, nitro, or an optionally substituted moiety selected from the group consisting of alkyl, alkoxy, arylalkyloxy and sulfonato; $R^2$ is halo or nitro; and $R^3$ is alkyl or phenylalkyl.

A preferred group of compounds of Group M, designated Group N, are those compounds wherein $R^1$ is hydroxy, nitro, methyl, methoxy, isopropoxy, benzyloxy, 4-fluorobenzyloxy, —O—$C(CH_3)_2(C(O)NH_2)$, —O—$(CH_2)_2$—O—$(CH_2)_2$—OMe or —O—$SO_2$—$CF_3$; $R^2$ is Cl or nitro; and $R^3$ is ethyl or benzyl.

A preferred group of compounds of Group N, designated Group O, are those compounds wherein $X^1$ is H.

A preferred group of compounds of Group O, designated Group P, are those compounds wherein W is Cl; $R^1$ is in the 7-position; and $R^2$ is in the 4- or 5-position.

In another aspect, the present invention is directed to a compound of the formula

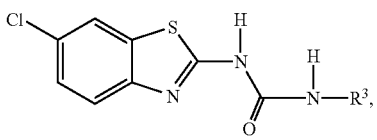

racemic-diastereomeric mixtures thereof, optical isomers thereof, prodrugs thereof, isotopes thereof or pharmaceutically-acceptable salts of said compound, isomers, prodrugs and isotopes, wherein $R^3$ is ethyl, propyl, t-butyl, 2,4,6-trichlorophenyl or 2,4-dimethoxyphenyl.

In another aspect, the present invention is directed to a compound of the formula

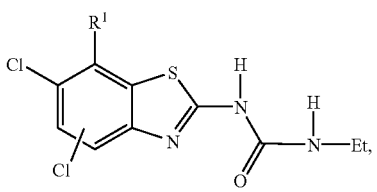

racemic-diastereomeric mixtures thereof, optical isomers thereof, prodrugs thereof, isotopes thereof or pharmaceutically-acceptable salts of said compound, isomers, prodrugs and isotopes, wherein $R^1$ is methyl, methoxy or isopropoxy.

In another aspect, the present invention is directed to a compound of the formula (IA),

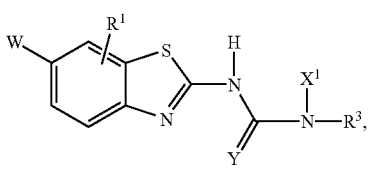

(IA)

racemic-diastereomeric mixtures thereof, optical isomers thereof, prodrugs thereof, isotopes thereof or pharmaceutically-acceptable salts of said compound, isomers, prodrugs and isotopes, wherein W is $NO_2$ or CN;

Y is O or S;

$R^1$ is in the 7-position and is hydrogen, methyl, ethyl, allyl, phenyl, benzyl, —$CH_2$—C(O)—$CH_3$, —$CH_2$—$CO_2$-t-Bu, —$CH_2$—$SO_2$-aryl, -alkyl-CN, or -alkyl(CN)($CH_2$-aryl);

$X^1$ is hydrogen, alkyl or hydroxyalkyl;

$R^3$ is selected from the group consisting of ethyl, n-butyl, t-butyl, n-propyl, allyl, hydroxyalkyl, aminoalkyl, -alkyl-NH-alkyl-OH, -alkyl-O-alkyl-OH, di-hydroxyalkyl, alkoxyalkyl, (alkylthio)hydroxyalkyl, cycloalkyl, cycloalkylalkyl, hydroxycycloalkyl, (alkylthio)(alkylester)alkyl, alkylesteralkyl, 2,4-dimethoxyphenyl, 3,5-trifluoromethylphenyl, 3-chlorophenyl, 4-chlorophenyl 2,6-dichlorophenyl, 2-methylphenyl, 3-methylphenyl, (substituted phenyl)alkyl, phenylalkyl, heterocyclylalkyl, N-alkylaminoalkyl, N,N-dialkylaminoalkyl, optionally substituted heterocyclyl, and optionally substituted heterocyclylalkyl.

A preferred group of compounds of formula (IA), designated Group Q, are those compounds wherein $R^1$ is hydrogen and $X^1$ is hydrogen.

Another preferred group of compounds of formula (IA), designated Group R, are those compounds wherein W is $NO_2$; Q is hydrogen; $R^1$ is in the 7-position and is hydrogen, methyl, ethyl or phenyl; $R^2$ are each hydrogen; $X^1$ is hydrogen; and $R^3$ is selected from the group consisting of ethyl, n-Bu, t-Bu, n-Pr, allyl, cyclopropyl, cyclobutyl, 2,4-dimethoxyphenyl, 3,5-bis-trifluoromethylphenyl, 3-chlorophenyl, 4-chlorophenyl, 2,6-dichlorophenyl, 2-methylphenyl and 3-methylphenyl.

Other preferred groups of compounds of the formula (I) are as follows:

wherein W is —$(CH_2)_2$—NH—C(O)—NH—$(C(R^{10})_2)_a$—$Z^1_q$ or an optionally substituted heterocyclyl;

$R_1$ and $R_2$ are each H; Q is H; Y is O; $X^1$ is H; and $R_3$ is an optionally substituted alkyl. A preferred group of compounds of the foregoing group is where W is:

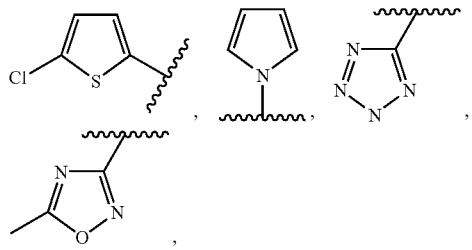

—$(CH_2)_2$—NH—C(O)—NH-Et, —$CH_2$—NH—C(O)—NH-ethyl, —$CH_2$—$NH_2$, —NH-phenyl, —C(O)—$NH_2$, —$CH_2$—NH—$S(O)_2$—Ph, —C(O)—NH-phenyl, —$CH_2$—NH—$S(O)_2$—$CF_3$, —$CH_2$—CN, —$CH_2$—NH—$CH_2$-5-methyl-furan-2-yl, —C(O)—NH—$(CH_2)_3$-(4-methylpiperazin-1-yl), —$(CH_2)_2$—NH—C(O)—NH-(phenyl), or —$(CH_2)_2$—NH—C(O)—NH-(p-toluyl). A preferred group of compounds of the immediately foregoing group is where $R^3$ is ethyl.

wherein W is CN; $R^1$ and $R^2$ are each H; Q is H; Y is O; $X^1$ is H; and $R^3$ is an optionally substituted heterocyclyl—heterocyclyl, or heterocyclyl-cycloalkyl. A preferred group of the foregoing compounds is where $R^3$ is 3-(4-methylpiperazino)propyl, 2-morpholinoethyl, 3-(9-benzyl-9-azabicyclo[3.3.1]nonyl, 6-(4-methylpiperazino)-3-pyridyl, 3-(8-benzyl-8-azabicyclo[3.2.1]octyl, methyl-3-(8-benzyl-8-azabicyclo[3.2.1]octyl, tert-butylcarboxylate-1-piperidinylmethyl, 4-piperidylmethyl, tert-butylcarboxylate-1-piperazinyl-ethyl, 2-piperazinoethyl, 4-(4-methylpiperazino)Cyclohexyl, 3-piperidinopropyl, 6-(4-methylpiperazino)-3-pyridyl.

wherein $R^1$ and W are taken together to form

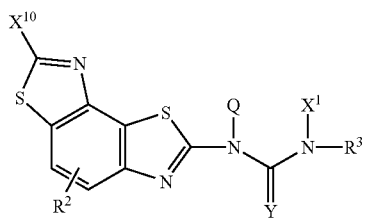

where $X^{10}$ is independently selected from the same group of substituents as $X^3$. A preferred group of the foregoing group of compounds is where $R^2$ is H; Q is H; Y is O; $X^1$ is H; $R^3$ is alkyl; and $X^{10}$ is ethyl, 3-pyridyl, N—(p-Br-phenyl)—NH—, 1-piperidyl or $CH_3$—NH—.

wherein W is H; and $R^1$ is —S—$X^3$, —S(O)$X^3$ or —S(O)$_2X^3$.

wherein W is Br, Cl or p-fluorophenoxy, $R^1$ and $R^2$ are each H; Q is H; Y is O; $X^1$ is H; and $R^3$ is alkyl-chloro,

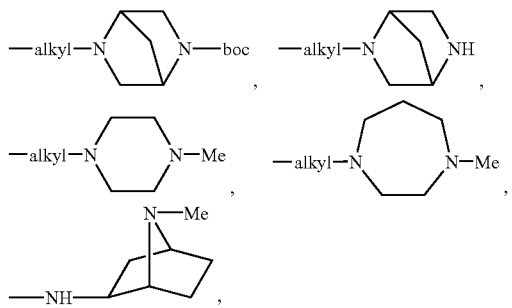

-alkyl-piperazin-1-yl, -alkyl-(2,5-dimethylpiperazin-1-yl), -alkyl-(3,5-dimethylpiperazin-1-yl), -alkyl-(3-aminocarbonylpiperidin-1-yl), -alkyl-(4-hydroxypiperidin-1-yl), -alkyl-(3-hydroxypiperidin-1-yl), -alkyl-COOEt, -alkyl-COOH, -alkyl-(4-methylpiperazin-1-yl), -alkyl-(N-morpholinoethylamino), -alkyl-(N-piperidinylethylamino), -alkyl-(N—(N,N-diethylaminoethyl)-N-(methyl)amino), -alkyl-((1-ethylpyrrolidin-2-yl)-methylamino), -alkyl-(N—(1-methylpiperidin-4-yl)—N—(methyl)amino), -alkylamino, -alkyl-piperidin-1-yl or -alkyl-(N,N-diethylaminoethylamino). A preferred group of the foregoing compounds is where the alkyl group is methylene, ethylene or propylene.

wherein $R^2$ is H; Q is H; Y is O; $X^1$ is H and $R^3$ is ethyl. Preferred groups of the foregoing group of compounds is where:

W is H or Br; and $R^1$ is in the 7-position of the benzothiazolyl ring and is —C≡CH, —C≡C—(2-pyridinyl), —C≡C—$CH_2$—$N(CH_3)_2$, —O—CH$(CH_3)_2$, phenyl or —CH=$CH_2$;

$R^1$ is —CH=$CH_2$ and W is —CH=$CH_2$;

$R^1$ is H and W is benzyl, p-fluorophenoxy or pyridin-4-ylmethyl;

W is F; $R^1$ is in the 7-position of the benzothiazolyl ring and is H or Cl; and $R^2$ is in the 5-position of the benzothiazolyl ring and is H or Cl; or $R^1$ is H and W is —CH=CH, —C≡C—Ph, —C≡C—$CH_2$—$N(CH_3)_2$, —C≡C—(4-fluorophenyl), —C≡C-(p-toluyl), —$(CH_2)_2$-Ph, —$(CH_2)_2$-(4-fluorophenyl), —CH=CH-phenyl, —CH=CH—$CH_2$—$N(CH_3)_2$, —CH=CH—(4-fluorophenyl), —CH=CH—(p-toluyl), or —CH=CH—(1-imidazolyl).

wherein W is p-fluorophenoxy, —$(CH_2)_3$—NHMe or —$(CH_2)_2$-1-piperazinyl; and $R^3$ is —$CH_2$—$C(Me)_2$—$CH_2$—$N(CH_3)_2$, —$(CH_2)_2$—(5-imidazolyl),

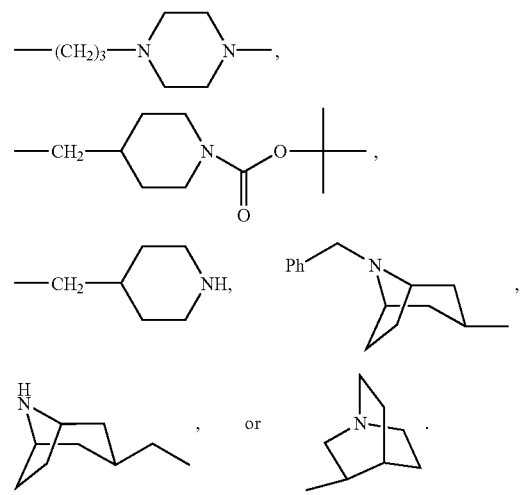

wherein $R^1$ is in the 7-position of the benzothiazolyl ring and is H or CN; $R^2$ is H; Y is O; Q and $X^1$ are each H; W is Cl, $NO_2$, —$CH_2$—OH, —$CH_2$—O—C(O)—NH-Et, —S-phenyl, —O-phenyl, —S—$CH_3$, —C(O)-phenyl, —S(O)-phenyl, —S-p-nitrophenyl, —S-p-methylphenyl, —S-p-chlorophenyl, —S-p-methoxyphenyl, —S-m-$CF_3$-phenyl, —S-o-chlorophenyl, —C(O)—$CH_3$, —NH—C(O)—NH-(—$(CH_2)_2$-2-thienyl, —NH—C(O)—NH-3-pyridyl, —S(O)$_2$-p-(carboxymethylamino)-phenyl, —N-morpholino, —NH—C(O)—NH—Et, —NH—C(O)—NH—$CH_2$-phenyl, —S-p-chlorophenyl, —S-p-bromophenyl, —S-m-$CF_3$-phenyl, or —S-p-fluorophenyl;

$R^3$ is

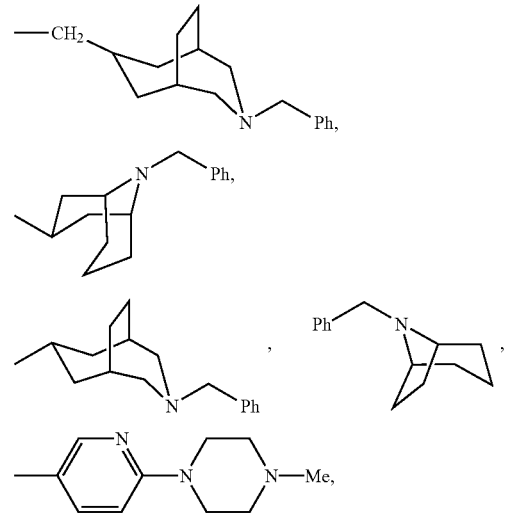

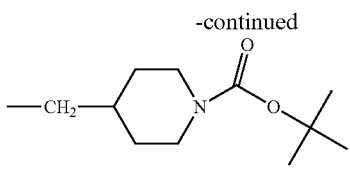

—(CH$_2$)$_2$—N-morpholino, or —CH$_2$-piperidin-4-yl.

wherein Q and X$^1$ are each H; Y is O; R$^3$ is ethyl; W is H, —OCF$_3$, —O-Et, F, CH$_3$, —OCH$_3$, —SO$_2$—Me, NH$_2$, —NH—C(O)—Me, —NH—CH$_2$-phenyl, —NH—S(O)$_2$-2-thienyl, —NH—S(O)$_2$—(3,5-dimethylisoxazol-4-yl), —NH—S(O)$_2$—Me, —NH—S(O)$_2$—CH$_2$-phenyl, —NH—C(O)—O—CH$_2$—CCl$_3$, —NH—C(O)—O—CH$_2$—Ph, —NH—C(O)—O-Me or NO$_2$;

R$^1$ is H, F or —CH$_2$—S(O)$_2$-phenyl; and

R$^2$ is H, 4-Cl, 4-methyl, 5-methyl, 5-Cl, 5-F or 5-OCH$_3$.

In another aspect, the present invention is directed to a method of using a compound of formula (IB) or a pharmaceutically acceptable salt thereof as a replacement therapy for anti-inflammatory glucocorticosteroid therapy in a patient undergoing anti-inflammatory glucocorticosteroid therapy comprising the step of replacing a glucocorticosteroid with a compound of formula (IB) or a pharmaceutically acceptable salt thereof.

Similarly, instead of a replacement therapy, a compound of the present invention can be used in conjunction with a glucocorticoid therapy as a means of "glucocorticoid sparing" to reduce deleterious side effects associated with glucocorticoid therapy.

In another aspect, the present invention is directed to a method of inhibiting protein kinase activity, which comprises administering to a patient a compound of formula (IB),

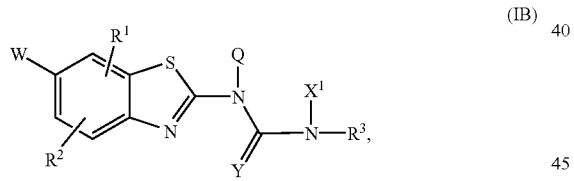

(IB)

racemic-diastereomeric mixtures thereof, optical isomers thereof, prodrugs thereof, isotopes thereof or pharmaceutically-acceptable salts of said compound, isomers, prodrugs and isotopes, wherein, Q is H or represents a bond which is taken together with X$^1$ and the two nitrogen atoms to which Q and X$^1$ are attached and the C=Y group to which the two nitrogen atoms are attached to form

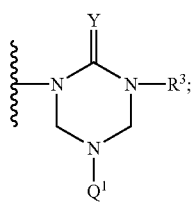

Q$^1$ is (C$_1$–C$_6$)alkyl;

Y is O or S;

W is H, Cl, Br, I, NO$_2$, CN, SCN, OCF$_3$, —X$_q$—(C(R$^{10}$)$_2$)$_a$—Y$^1_q$—(C(R$^{10}$)$_2$)$_a$—Z$^1_q$, or an optionally substituted group selected from the group consisting of alkyl, alkenyl, alkynyl, heterocyclyl-alkenyl, and heterocyclyl-alkynyl;

Y$^1$ and X are each independently selected from the group consisting of phenyl, heterocyclyl, NR$^{10}$, O, S, SO, SO$_2$, CF$_2$, CFR, C=O, (C=O)NR$^{10}$, SONR$^{10}$, SO$_2$NR$^{10}$, NR$^{10}$(C=O), NR$^{10}$SO, NR$^{10}$SO$_2$, NR$^{10}$SO$_2$NR$^{10}$, NR$^{10}$(C=O)NR$^{10}$,

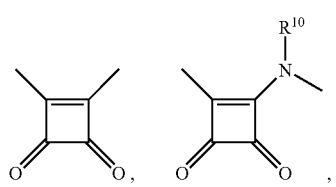

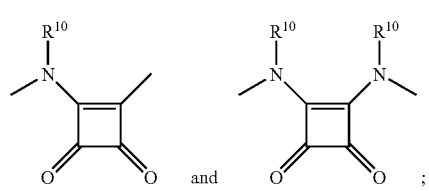

q for each occurrence is independently 0 or 1;

a for each occurrence is independently 0 or an integer from 1 to 5;

R$^{10}$ for each occurrence is independently selected from the group consisting of H, optionally substituted aryl, optionally substituted heterocyclyl and an optionally substituted alkyl group optionally substituted with one or more of the following: a C$_{1-6}$ alkyl group optionally substituted by one or more hydroxy, halo or optionally substituted amino; a C$_{1-6}$ alkoxy group optionally substituted by one or more hydroxy, halo or optionally substituted amino; hydroxy; halo; or optionally substituted amino;

Z$^1$ is H, optionally substituted alkyl, optionally substituted aryl or optionally substituted heterocyclyl;

X$^1$ is hydrogen, alkyl, hydroxyalkyl or represents a bond which is taken together with R$^3$ as described below or represents a bond which is taken together with Q as described above;

R$^1$ and R$^2$ are each independently hydrogen, halogen, hydroxy, nitro, cyano, COOH, COOX$^3$, SX$^3$, SO$_2$X$^3$, SOX$^3$, C(O)X$^3$, NHC(O)X$^3$, C(O)NHX$^3$, NHSO$_2$X$^3$ or selected from an optionally substituted group consisting of alkyl, alkenyl, alkynyl, alkoxy, amino, NHX$^3$, NX$^3$X$^3$, alkylamino, arylamino, heterocyclylamino, alkylthio, alkylsulfonato, aryl, aryloxy, arylalkyl, arylalkenyl, arylalkynyl, arylalkyloxy, heterocyclyl, heterocyclyloxy, heterocyclylalkyl, heterocyclyl-alkenyl, heterocyclyl-alkynyl, heterocyclyl-alkyloxy, heterocyclylthio, heterocyclylsulfinyl, heterocyclylsulfonyl, cycloalkyl, —(CH$_2$)$_m$—(CHX$^2$)CN, —(CH$_2$)$_m$—(CHX$^2$)COOH, —(CH$_2$)$_m$—(CHX$^2$)COOX$^3$, —(CH$_2$)$_m$—(CHX$^2$)SO$_2$X$^3$, —(CH$_2$)$_m$—(CHX$^2$)C(O)X$^3$ —(CH$_2$)$_n$—(CHX$^2$)C(O)NHX$^3$ and —(CH$_2$)$_m$—(CHX$^2$)NHSO$_2$X$^3$;

where m is 0 to 4;

$X^2$ for each occurrence is independently H or an optionally substituted moiety selected from the group consisting of alkyl, alkenyl, alkynyl, carbonyl, $S(O)_p$alkyl, $S(O)_p$aryl, $S(O)_p$heterocyclyl, amino, alkoxy, alkylthio, arylthio, perhaloalkyl, aryl, aryloxy, arylalkyl, arylalkyloxy, heterocyclyl and heterocyclyl-alkyl;

p is 0, 1 or 2;

$X^3$ for each occurrence is independently H or an optionally substituted moiety selected from the group consisting of mono- or di-alkylamino, alkyl, alkenyl, alkynyl, aryl, arylalkyl, heterocyclyl and heterocyclyl-alkyl;

or when $R^1$ is in the 7-position of the benzothiazole ring, $R^1$ and W can be taken together with the carbon atoms to which they are attached to form an optionally substituted 5- or 6-membered heterocyclyl ring;

$R^3$ is hydrogen, or an optionally substituted moiety selected from the group consisting of carbonyl, alkyl, alkenyl, alkynyl, cycloalkyl, aryl, arylalkyl, heterocyclyl, heterocyclyl-alkyl, heterocyclyl—heterocyclyl, heterocyclyl-cycloalkyl, amino, alkylamino, arylamino, alkoxy, thioalkoxy and acyl;

or $R^3$ and $X^1$ are taken together with the nitrogen atom to which they are attached to form

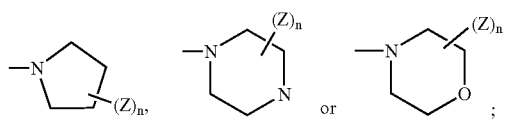

where Z for each occurrence is independently selected from the group consisting of oxo, or an optionally substituted moiety selected from the group consisting of —C(O)($C_1$–$C_6$)alkyl,
—C(O)aryl, —C(O)N($C_1$–$C_6$)alkyl, —C(O)N-aryl, ($C_1$–$C_6$)alkyl, ($C_2$–$C_6$)alkenyl, ($C_2$–$C_6$)alkynyl, amino, mono- or di-($C_1$–$C_6$)alkylamino, —COO($C_1$–$C_6$)alkyl, pyridyl, phenyl, phenyl($C_1$–$C_6$)alkyl and phenyl ($C_1$–$C_6$)alkenyl;

where each of the optionally substituted moieties described hereinabove is optionally substituted by one or more substituents each independently selected from the group consisting of oxo, amino, nitro, mono- or bi-($C_1$–$C_6$)alkylamino, hydroxy, nitrile, chloro, fluoro, bromo, iodo, $CF_3$, ($C_1$–$C_6$)alkyl, —C(O)($C_1$–$C_6$)alkyl, —COOH, —COO($C_1$–$C_6$)alkyl, —S—($C_1$–$C_6$)alkyl, —S-aryl, ($C_1$–$C_6$)alkoxy, —$SO_2NH_2$, phenyl, phenyl($C_1$–$C_6$)alkyl, —O—($C_1$–$C_6$)alkyl-OH, —O—($C_1$–$C_6$)alkyl-O—($C_1$–$C_6$)alkyl, —O—($C_2$–$C_6$) alkyl-N—(($C_1$–$C_6$)alkyl)$_n$, —N—($C_1$–$C_6$)alkyl-OH, —N—($C_1$–$C_6$)alkyl-O—($C_1$–$C_6$)alkyl, —C(O)$NH_2$, —C(O)N (($C_1$–$C_6$)alkyl)$_n$, , —S(O)$_n$($C_1$–$C_6$)alkyl, —S(O)$_n$aryl, —S(O)$_n$heterocyclyl, and heterocyclyl, where the alkyl groups mentioned herein optionally have one or more unsaturated bonds in the alkyl portion;

n is 0, 1 or 2.

A preferred embodiment of a compound of formula (IB) is

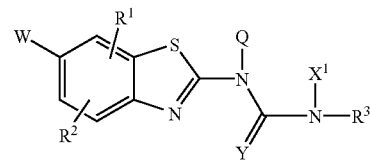

racemic-diastereomeric mixtures thereof, optical isomers thereof, prodrugs thereof, isotopes thereof or pharmaceutically-acceptable salts of said compound, isomers, prodrugs and isotopes, wherein, Q is H or represents a bond which is taken together with $X^1$ and the two nitrogen atoms to which Q and $X^1$ are attached and the C=Y group to which the two nitrogen atoms are attached to form

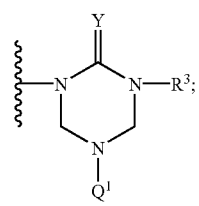

$Q^1$ is ($C_1$–$C_6$)alkyl;

Y is O or S;

W is Cl, Br, I, $NO_2$ or CN;

where $X^1$ is hydrogen, alkyl, hydroxyalkyl or represents a bond which is taken together with $R^3$ as described below or represents a bond which is taken together with Q as described above;

$R^1$ and $R^2$ are each independently hydrogen, halogen, hydroxy, nitro, cyano, COOH, COO$X^3$, $SO_2X^3$, SO$X^3$, C(O)$X^3$, NHC(O)$X^3$, C(O)NH$X^3$, NHSO$_2X^3$ or selected from an optionally substituted group consisting of alkyl, alkenyl, alkynyl, alkoxy, amino, NH$X^3$, N$X^3X^3$, alkylamino, arylamino, heterocyclylamino, alkylthio, alkylsulfonato, aryl, aryloxy, arylalkyl, arylalkenyl, arylalkynyl, arylalkyloxy, heterocyclyl, heterocyclyloxy, heterocyclyl-alkyl, heterocyclyl-alkenyl, heterocyclyl-alkynyl, heterocyclyl-alkyloxy, heterocyclylthio, heterocyclylsulfinyl, heterocyclylsulfonyl, cycloalkyl, —(CH$_2$)$_m$—(CH$X^2$)CN, (CH$_2$)$_m$(CH$X^2$)COOH, (CH$_2$)$_m$—(CH$X^2$)COO$X^3$, —(CH$_2$)$_m$—(CH$X^2$)SO$_2X^3$, (CH$_2$)$_m$—(CH$X^2$)C(O)$X^3$, (CH$^2$)$_m$—(CH$X^2$)C(O)NH$X^3$ and —(CH$_2$)$_m$—(CH$X^2$)NHSO$_2X^3$;

where m is 0 to 4;

$X^2$ for each occurrence is independently H or an optionally substituted moiety selected from the group consisting of alkyl, alkenyl, alkynyl, carbonyl, $S(O)_p$alkyl, $S(O)_p$aryl, $S(O)_p$heterocyclyl, amino, alkoxy, alkylthio, arylthio, perhaloalkyl, aryl, aryloxy, arylalkyl, arylalkyloxy, heterocyclyl and heterocyclyl-alkyl;

p is 0, 1 or 2;

$X^3$ for each occurrence is independently H or an optionally substituted moiety selected from the group consisting of mono- or di-alkylamino, alkyl, alkenyl, alkynyl, aryl, arylalkyl, heterocyclyl and heterocyclyl-alkyl;

R³ is hydrogen, or an optionally substituted moiety selected from the group consisting of carbonyl, alkyl, alkenyl, alkynyl, cycloalkyl, aryl, arylalkyl, heterocyclyl, heterocyclylalkyl, amino, alkylamino, arylamino, alkoxy, thioalkoxy and acyl;

or R³ and X¹ are taken together with the nitrogen atom to which they are attached to form

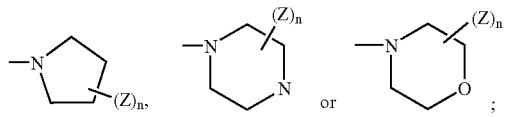

where Z for each occurrence is independently selected from the group consisting of oxo, or an optionally substituted moiety selected from the group consisting of —C(O)(C₁–C₆)alkyl, —C(O)aryl, —C(O)N(C₁–C₆)alkyl, —C(O)N-aryl, (C₁–C₆)alkyl, (C₂–C₆)alkenyl, (C₂–C₆)alkynyl, amino, mono- or di-(C₁–C₆)alkylamino, —COO(C₁–C₆)alkyl, pyridyl, phenyl, phenyl(C₁–C₆)alkyl and phenyl (C₁–C₆)alkenyl;

where each of the optionally substituted moieties described hereinabove is optionally substituted by one or more substituents each independently selected from the group consisting of oxo, amino, nitro, mono- or bi-(C₁–C₆)alkylamino, hydroxy, nitrile, chloro, fluoro, bromo, iodo, CF₃, (C₁–C₆)alkyl, —C(O)(C₁–C₆)alkyl, —COOH, —COO(C₁–C₆)alkyl, —S—(C₁–C₆)alkyl, —S-aryl, (C₁–C₆)alkoxy, —SO₂NH₂, phenyl, phenyl(C₁–C₆)alkyl, —O—(C₁–C₆)alkyl-OH, —O—(C₁–C₆)alkyl-O—(C₁–C₆)alkyl, —O—(C₂–C₆) alkyl-N—((C₁–C₆)alkyl)ₙ, —N—(C₁–C₆)alkyl-OH, —N—(C₁–C₆)alkyl-O—(C₁–C₆)alkyl, —C(O)NH₂, —C(O)N ((C₁–C₆)alkyl)ₙ, , —S(O)ₙ(C₁–C₆)alkyl, —S(O)ₙaryl, —S(O)ₙheterocyclyl, and heterocyclyl, where the alkyl groups mentioned herein optionally have one or more unsaturated bonds in the alkyl portion;

n is 0, 1 or 2.

A preferred method of the immediately foregoing method is where said protein kinase is a tyrosine kinase.

A preferred method of the immediately foregoing method is where said tyrosine kinase is a receptor tyrosine kinase or a non-receptor tyrosine kinase.

A preferred method of the immediately foregoing method is where tyrosine kinase is KDR or Lck.

Another preferred method of inhibiting a tyrosine kinase with a compound of formula (IB) is where the tyrosine kinase affects angiogenesis.

A preferred method of the immediately foregoing method is where the inhibition of said tyrosine kinase results in an anti-angiogenic effect.

In another aspect, the present invention is directed to a method of treating a condition, disorder or disease, which comprises administering to a patient a compound of formula (IB), as defined hereinabove, where said condition, disorder or disease is selected from the group consisting of hyperproliferative disorders, an ulcer, Lyme disease, sepsis, von Hippel Lindau disease, pemphigoid, psoriasis, Paget's disease, polycystic kidney disease, fibrosis, sarcoidosis, cirrhosis, thyroiditis, hyperviscosity syndrome, Osler-Weber-Rendu disease, chronic occlusive pulmonary disease, ovarian hyperstimulation syndrome, preeclampsia, menometrorrhagia, endometriosis, chronic inflammation, systemic lupus, glomerulonephritis, synovitis, inflammatory bowel disease, Crohn's disease, glomerulonephritis, rheumatoid arthritis, osteoarthritis, multiple sclerosis, graft rejection, sickle cell anaemia, an ocular condition, a cardiovascular condition, atherosclerosis, restenosis, ischemia/reperfusion injury, vascular occlusion, carotid obstructive disease, cancer, Crow-Fukase (POEMS) syndrome, a diabetic condition, anemia, ischemia, infarct, transplant rejection, a wound, gangrene, necrosis, asthma or edema following burns, trauma, radiation, stroke, hypoxia or ischemia, and infection by Herpes simplex, Herpes Zoster, human immunodeficiency virus, parapoxvirus, protozoa or toxoplasmosis.

A preferred method of the immediately foregoing method is where:
  the ocular condition is ocular or macular edema, ocular neovascular disease, scleritis, radial keratotomy, uveitis, vitritis, myopia, optic pits, chronic retinal detachment, post-laser treatment complications, conjunctivitis, Stargardt's disease, Eales disease, retinopathy or macular degeneration;
  the cancer is a solid tumor, a sarcoma, fibrosarcoma, osteoma, melanoma, retinoblastoma, a rhabdomyosarcoma, glioblastoma, neuroblastoma, teratocarcinoma, an hematopoietic malignancy, malignant ascites, Kaposi's sarcoma, Hodgkin's disease, lymphoma, myeloma or leukemia; and
  the diabetic condition is insulin-dependent diabetes mellitus glaucoma, diabetic retinopathy or microangiopathy.

In another aspect, the present invention is directed to a method of decreasing fertility in a patient, which comprises administering to a patient an effective amount of a compound of formula (IB), as defined hereinabove.

In another aspect, the present invention is directed to a method of promoting angiogenesis or vasculogenesis, which comprises administering to a patient a compound of formula (IB), as defined hereinabove.

A preferred method of the immediately foregoing method is where the compound of formula (IB) is administered in combination with a pro-angiogenic growth factor.

In another aspect, the present invention is directed to a method of treating a patient having a condition which is mediated by protein kinase activity, said method comprising the step of administering to the patient a therapeutically effective amount of a compound of formula (IB), as defined hereinabove.

A preferred method of the immediately foregoing method is where the protein kinase activity is involved in T cell activation, B cell activation, mast cell degranulation, monocyte activation, the potentiation of an inflammatory response or a combination thereof.

In another aspect, the present invention is directed to a pharmaceutical composition comprising a compound of formula (I), as defined hereinabove, and a pharmaceutically acceptable diluent or carrier.

In another aspect, the present invention is directed to a pharmaceutical composition comprising an effective amount of a compound of formula (IB) for inhibiting a protein kinase and a pharmaceutically acceptable carrier or diluent.

The compounds of this invention are useful as inhibitors of serine/threonine and tyrosine kinases. In particular, compounds of this invention are useful as inhibitors of tyrosine kinases that are important in hyperproliferative diseases, especially in cancer and in the process of angiogenesis. For example, certain of these compounds are inhibitors of such receptor kinases as KDR, Flt-1, VEGFR-3, FGFR, PDGFR, c-Met, Tie-2, Tie-1 or IGF-1-R. Since certain of these compounds are anti-angiogenic, they are important substances for inhibiting the progression of disease states, such as cancer, arthritis and ocular neovascularization, where angiogenesis is an important component. Since certain of these agents block the responses to VEGFs, and because VEGF is strongly upregulated under conditions of hypoxia, these compounds are useful in controlling the vascular leakage and neovascular events following ischemia and tissue damage. Certain compounds of the invention are effective as inhibitors of such serine/threonine kinases as PKCs, erk, MAP kinases, cdks, Plk-1 or Raf-1. These compounds are useful in the treatment of cancer, and hyperproliferative disorders. In addition, certain compounds are effective inhibitors of non-receptor kinases such as those of the Src (for example, Ick, blk and lyn), Tec, Csk, Jak, Map, Nik and Syk families. These compounds are useful in the treatment of cancer, hyperproliferative disorders and immunologic diseases.

The compounds of this invention, when administered to individuals in need of such compounds, inhibit vascular hyperpermeability and the formation of edema in these individuals. These compounds act, it is believed, by inhibiting the activity of KDR tyrosine kinase which is involved in the process of vascular hyperpermeability and edema formation. The KDR tyrosine kinase may also be referred to as FLK-1 tyrosine kinase, NYK tyrosine kinase or VEGFR-2 tyrosine kinase. KDR tyrosine kinase is activated when vascular endothelial cell growth factor (VEGF) or another activating ligand (such as VEGF-C, VEGF-D, VEGF-E or HIV Tat protein) binds to a KDR tyrosine kinase receptor which lies on the surface of vascular endothelial cells. Following such KDR tyrosine kinase activation, hyperpermeability of the blood vessels occurs and fluid moves from the blood stream past the blood vessel walls into the interstitial spaces, thereby forming an area of edema. Diapedesis also often accompanies this response. Similarly, excessive vascular hyperpermeability can disrupt normal molecular exchange across the endothelium in critical tissues and organs (e.g., lung and kidney), thereby causing macromolecular extravasation and deposition. Following this acute response to KDR stimulation which is believed to facilitate the subsequent angiogenic process, prolonged KDR tyrosine kinase stimulation results in the proliferation and chemotaxis of vascular endothelial cells and formation of new vessels. By inhibiting KDR tyrosine kinase activity, either by blocking the production of the activating ligand, by blocking the activating ligand binding to the KDR tyrosine kinase receptor, by preventing receptor dimerization and transphosphorylation, by inhibiting the enzyme activity of the KDR tyrosine kinase (inhibiting the phosphorylation function of the enzyme) or by some other mechanism that interrupts its downstream signaling (D. Mukhopedhyay et al., Cancer Res. 58:1278–1284 (1998) and references therein), hyperpermeability, as well as associated extravasation, subsequent edema formation and matrix deposition, and angiogenic responses, may be inhibited and minimized.

One group of preferred compounds of this invention have the property of inhibiting KDR tyrosine kinase activity without significantly inhibiting Flt-1 tyrosine kinase activity (Flt-1 tyrosine kinase is also referred to as VEGFR-1 tyrosine kinase). Both KDR tyrosine kinase and Flt-1 tyrosine kinase are activated by VEGF binding to KDR tyrosine kinase receptors and to Flt-1 tyrosine kinase receptors, respectively. Since Flt-1 tyrosine kinase activity may mediate important events in endothelial maintenance and vascular function, an inhibition of this enzyme activity may lead to toxic or adverse effects. At the very least, such inhibition is unnecessary for blocking the angiogenic responses, induction of vascular hyperpermeability and the formation of edema, so it is wasteful and of no value to the individual. Certain preferred compounds of this invention are unique because they inhibit the activity of one VEGF-receptor tyrosine kinase (KDR) that is activated by activating ligands but do not inhibit other receptor tyrosine kinases, such as Flt-1, that are also activated by certain activating ligands. The preferred compounds of this invention are, therefore, selective in their tyrosine kinase inhibitory activity.

The compounds of the present invention are also useful in the treatment of ulcers—bacterial, fungal, Mooren ulcers and ulcerative colitis.

Certain compounds of this invention are Tie-2 and/or Tie-1 kinase inhibitors which may be anti-angiogenic (especially in combination with inhibition of VEGFR), or pro-angiogenic, when employed in the presence of, or in conjunction with, a VEGF-related stimulus. In this manner such inhibitors can be used in the promotion of therapeutic angiogenesis to treat, for example, ischemia, infarct or occlusion, or to promote wound healing.

The present invention provides a method of inhibiting the kinase activity of tyrosine kinases and serine/threonine kinases comprising the administration of a compound represented by formula I to said kinase in sufficient concentration to inhibit the enzyme activity of said kinase.

The present invention further includes pharmaceutical compositions of the compounds described herein comprising a pharmaceutically effective amount of the compounds and a pharmaceutically acceptable carrier or excipient. These pharmaceutical compositions can be administered to individuals to slow or halt the process of angiogenesis in angiogenesis-aided diseases, or to treat edema, effusions, exudates or ascites and other conditions associated with vascular hyperpermeability. Certain pharmaceutical compositions can be administered to individuals to treat cancer and hyperproliferative disorders by inhibiting serine/threonine kinases such as cdk, Plk-1, erk, etc.

In the treatment of malignant disorders, combinations with antiproliferative or cytotoxic chemotherapies or radiation are anticipated.

DETAILED DESCRIPTION OF THE INVENTION

Certain of the compounds of this invention have antiangiogenic properties. These antiangiogenic properties are due at least in part to the inhibition of protein tyrosine kinases essential for angiogenic processes. For this reason, these compounds can be used as active agents against such disease states as arthritis, atherosclerosis, restenosis, psoriasis, hemangiomas, hemangioendothelioma, myocardial angiogenesis, coronary and cerebral collaterals, ischemic limb angiogenesis, ischemia/reperfusion injury, wound healing, peptic ulcer *Helicobacter* related diseases, virally-induced angiogenic disorders, fractures, Crow-Fukase syndrome (POEMS), preeclampsia, menometrorrhagia, cat scratch fever, rubeosis, neovascular glaucoma and retinopathies such as those associated with diabetic retinopathy, retinopathy of prematurity, or age-related macular degeneration. In addition, some of these compounds can be used as active agents against solid tumors, malignant ascites, von Hippel Lindau disease, hematopoietic cancers and hyperproliferative disorders such as thyroid hyperplasia (especially Grave's disease), and cysts (such as follicular cysts or hypervascularity of ovarian stroma characteristic of polycystic ovarian syndrome (Stein-Leventhal syndrome)) and polycystic kidney disease since such diseases require a proliferation of blood vessel cells for growth and/or metastasis.

Further, some of these compounds can be used as active agents against burns, chronic lung disease, stroke, polyps, asthma, anaphylaxis, chronic and allergic inflammation, delayed-type hypersensitivity, ovarian hyperstimulation syndrome, brain tumor-associated cerebral edema, or cerebral or pulmonary edema induced by high altitude trauma or hypoxia, ocular and macular edema, ascites, glomerulonephritis and other diseases where vascular hyperpermeability, effusions, exudates, protein extravasation, or edema is a manifestation of the disease. The compounds will also be useful in treating disorders in which protein extravasation leads to the deposition of fibrin and extracellular matrix, promoting stromal proliferation (e.g. keloid, fibrosis, cirrhosis and carpal tunnel syndrome). Increased VEGF production potentiates inflammatory processes such as monocyte recruitment and activation. The compounds of this invention will also be useful in treating inflammatory disorders such as inflammatory bowel disease (IBD) and Crohn's disease.

The compounds of the present invention are in particular applicable to the treatment of an inflammatory rheumatoid or rheumatic disease, especially of manifestations at the locomotor apparatus, such as various inflammatory rheumatoid diseases, especially chronic polyarthritis (=rheumatoid arthritis (very preferred)), including juvenile arthritis or psoriasis arthropathy; paraneoplastic syndrome or tumor-induced inflammatory diseases, turbid effusions, collagenosis, such as systemic Lupus erythematosus, poly-myositis, dermato-myositis, systemic sclerodermia or mixed collagenosis; postinfectious arthritis (where no living pathogenic organism can be found at or in the affected part of the body), or seronegative spondylarthritis, such as spondylitis ankylosans; vasculitis; sarcoidosis; peritoneal sclerosis (especially in dialysis patients); arthrosis; or further any combinations thereof.

From the foregoing it will be understood that the present invention is to be further understood as embracing the treatment, e.g. therapy of any disease or condition as set forth above, for example rheumatoid arthritis, arthroses, dermatomyositis etc., for example, for the alleviation or control of inflammatory processes or events and the sequelae associated therewith or consequential thereto, e.g. for the treatment of rheumatoid arthritis, e.g. to alleviate or control joint inflammation or effusion.

In a further aspect it has been found in accordance with the present invention that systemic administration of a compound of the present invention, or a salt thereof, is useful as replacement therapy for anti-inflammatory glucocorticosteroid, e.g. cortizone or the like, therapy or as glucocorticoid sparing therapy. For example for use in any means of treatment as hereinbefore set forth.

On the basis of their efficacy as inhibitors of VEGF-receptor tyrosine kinase activity, the compounds of the present invention primarily inhibit the growth of blood vessels and are thus, for example, effective against a number of diseases associated with deregulated angiogenesis, especially diseases caused by ocular neovascularisation, especially retinopathies, such as diabetic retinopathy or age-related macula degeneration, psoriasis, haemangioblastoma, such as haemangioma, mesangial cell proliferation disorders, such as chronic or acute renal diseases, e.g. diabetic nephropathy, malignant nephrosclerosis, thrombic microangiopathy syndromes or transplant rejection, or especially inflammatory renal disease, such as glomerulonephritis, especially mesangioproliferative glomerulonephritis, haemolytic-uraemic syndrome, diabetic nephropathy, hypertensive nephrosclerosis, atheroma, arterial restenosis, autoimmune diseases, acute inflammation, fibrotic disorders (e.g. hepatic cirrhosis), diabetes, neurodegenerative disorders and especially neoplastic diseases (solid tumors, but also leukemias and other hematopoietic malignancies, or "liquid tumours", those expressing c-kit, KDR or flt-1), such as especially breast cancer, cancer of the colon, lung cancer (especially small-cell lung cancer), cancer of the prostate or Kaposi's sarcoma. A compound of formula I (or an N-oxide thereof) inhibits the growth of tumours and is especially suited to preventing the metastatic spread of tumours and the growth of mircometastases.

VEGFs are unique in that they are the only angiogenic growth factors known to contribute to vascular hyperpermeability and the formation of edema. Indeed, vascular hyperpermeability and edema that is associated with the expression or administration of many other growth factors appears to be mediated via VEGF production. Inflammatory cytokines stimulate VEGF production. Hypoxia results in a marked upregulation of VEGF in numerous tissues, hence situations involving infarct, occlusion, ischemia, anemia, or circulatory impairment typically invoke VEGF/VPF mediated responses. Vascular hyperpermeability, associated edema, altered transendothelial exchange and macromolecular extravasation, which is often accompanied by diapedesis, can result in excessive matrix deposition, aberrant stromal proliferation, fibrosis, etc. Hence, VEGF-mediated hyperpermeability can significantly contribute to disorders with these etiologic features.

Because blastocyst implantation, placental development and embryogenesis are angiogenesis dependent, certain compounds of the invention are useful as contraceptive agents and antifertility agents.

It is envisaged that the disorders listed above are mediated to a significant extent by protein tyrosine kinase activity involving the KDR/VEGFR-2 and/or the Flt-1/VEGFR-1 and/or Flt-4/VEGFR-3 and/or Tie-2 and/or Tie-1 tyrosine kinases. By inhibiting the activity of these tyrosine kinases, the progression of the listed disorders is inhibited because the angiogenic or vascular hyperpermeability component of the disease state is severely curtailed. The action of certain compounds of this invention, by their selectivity for specific tyrosine kinases, result in a minimization of side effects that would occur if less selective tyrosine kinase inhibitors were used. Certain compounds of the invention are also effective inhibitors of FGFR, PDGFR, c-Met and IGF-1-R kinases. These receptor kinases can directly or indirectly potentiate angiogenic and hyperproliferative responses in various disorders, hence their inhibition can impede disease progression.

Progression through the eukaryotic cell cycle is controlled by a family of kinases called cyclin dependent kinases (CDKs) (Myerson et al., *EMBO Journal*, 11:2909–2917 (1992)). The regulation of CDK activation is complex, but requires the association of the CDK with a member of the cyclin family of regulatory subunits (Draetta, *Trends in Cell Biology*, 3:287–289 (1993)); Murray and Kirschner, *Nature*, 339:275–280 (1989); Solomon et al., *Molecular Biology of the Cell*, 3:13–27 (1992)). A further level of regulation occurs through both activating and inactivating phosphorylations of the CDK subunit (Draetta, *Trends in Cell Biology*, 3:287–289 (1993)); Murray and Kirschner, *Nature*, 339: 275–280 (1989); Solomon et al., *Molecular Biology of the*

Cell, 3:13–27 (1992); Ducommun et al., *EMBO Journal*, 10:3311–3319 (1991); Gautier et al., *Nature* 339:626–629 (1989); Gould and Nurse, *Nature*, 342:39–45 (1989); Krek and Nigg, *EMBO Journal*, 10:3331–3341 (1991); Solomon et al., *Cell*, 63:1013–1024 (1990)). The coordinate activation and inactivation of different cyclin/CDK complexes is necessary for normal progression through the cell cycle (Pines, *Trends in Biochemical Sciences*, 18:195–197 (1993); Sherr, *Cell*, 73:1059–1065 (1993)). Both the critical G1-S and G 2-M transitions are controlled by the activation of different cyclin/CDK activities. In G1, both cyclin D/CDK4 and cyclin E/CDK2 are thought to mediate the onset of S-phase (Matsushima et al., *Molecular & Cellular Biology*, 14:2066–2076 (1994); Ohtsubo and Roberts, *Science*, 259: 1908–1912 (1993); Quelle et al., *Genes & Development*, 7:1559–1571 (1993); Resnitzky et al., *Molecular & Cellular Biology*, 14:1669–1679 (1994)). Progression through S-phase requires the activity of cyclin A/CDK2 (Girard et al., *Cell*, 67:1169–1179 (1991); Pagano et al., *EMBO Journal*, 11:961–971 (1992); Rosenblatt et al., *Proceedings of the National Academy of Science USA*, 89:2824–2828 (1992); Walker and Maller, *Nature*, 354:314–317 (1991); Zindy et al., *Biochemical & Biophysical Research Communications*, 182:1144–1154 (1992)) whereas the activation of cyclin A/cdc2 (CDK1) and cyclin B/cdc2 are required for the onset of metaphase (Draetta, *Trends in Cell Biology*, 3:287–289 (1993)); Murray and Kirschner, *Nature*, 339:275–280 (1989); Solomon et al., *Molecular Biology of the Cell*, 3:13–27 (1992); Girard et al., *Cell*, 67:1169–1179 (1991); Pagano et al., *EMBO Journal*, 11:961–971 (1992); Rosenblatt et al., *Proceedings of the National Academy of Science USA*, 89:2824–2828 (1992); Walker and Maller, *Nature*, 354:314–317 (1991); Zindy et al., *Biochemical & Biophysical Research Communications*, 182:1144–1154 (1992)). It is not surprising, therefore, that the loss of control of CDK regulation is a frequent event in hyperproliferative diseases and cancer. (Pines, *Current Opinion in Cell Biology*, 4:144–148 (1992); Lees, *Current Opinion in Cell Biology*, 7:773–780 (1995); Hunter and Pines, *Cell*, 79:573–582 (1994)). The selective inhibition of CDKs is therefore an object of the present invention.

The method of the present invention is useful in the treatment of protein kinase-mediated conditions, such as any of the conditions described above. In one embodiment, the protein kinase-mediated condition is characterized by undesired angiogenesis, edema, or stromal deposition. For example, the condition can be one or more ulcers, such as ulcers caused by bacterial or fungal infections, Mooren ulcers and ulcerative colitis. The condition can also be due to a microbial infection, such as Lyme disease, sepsis, septic shock or infections by Herpes simplex, Herpes Zoster, human immunodeficiency virus, protozoa, toxoplasmosis or parapoxvirus; an angiogenic disorders, such as von Hippel Lindau disease, polycystic kidney disease, pemphigoid, Paget's disease and psoriasis; a reproductive condition, such as endometriosis, ovarian hyperstimulation syndrome, preeclampsia or menometrorrhagia; a fibrotic and edemic condition, such as sarcoidosis, fibrosis, cirrhosis, thyroiditis, hyperviscosity syndrome systemic, Osler-Weber-Rendu disease, chronic occlusive pulmonary disease, asthma, and edema following burns, trauma, radiation, stroke, hypoxia or ischemia; or an inflammatory/immunologic condition, such as systemic lupus, chronic inflammation, glomerulonephritis, synovitis, inflammatory bowel disease, Crohn's disease, rheumatoid arthritis, osteoarthritis, multiple sclerosis and graft rejection. Suitable protein kinase-mediated conditions also include sickle cell anaemia, osteoporosis, osteopetrosis, tumor-induced hypercalcemia and bone metastases. Additional protein kinase-mediated conditions which can be treated by the method of the present invention include ocular conditions such as ocular and macular edema, ocular neovascular disease, scleritis, radial keratotomy, uveitis, vitritis, myopia, optic pits, chronic retinal detachment, post-laser complications, conjunctivitis, Stargardt's disease and Eales disease, in addition to retinopathy and macular degeneration.

The compounds of the present invention are also useful in the treatment of cardiovascular conditions such as atherosclerosis, restenosis, vascular occlusion and carotid obstructive disease.

The compounds of the present invention are additionally useful in the treatment of one or more diseases afflicting mammals which are characterized by cellular proliferation in the areas of blood vessel proliferative disorders, vascular malformation, lymphoproliferative disorders lymphangiogenesis (especially Tie-2 & Flt-4/VEGFR-3 inhibitors), fibrotic disorders, mesangial cell proliferative disorders and metabolic diseases. Blood vessel proliferative disorders include inappropriate ocular neovascularization, arthritis and restenosis. Fibrotic disorders include hepatic cirrhosis and atherosclerosis. Mesangial cell proliferative disorders include glomerulonephritis, diabetic nephropathy, malignant nephrosclerosis, thrombotic microangiopathy syndromes, organ transplant rejection and glomerulopathies. Metabolic disorders include psoriasis, diabetes mellitus, chronic wound healing, inflammation, neurodegenerative diseases, macular degeneration, and diabetic retinopathy.

Inhibitors of kinases involved in mediating or maintaining these disease states represent novel therapies for these disorders. Examples of such kinases include, but are not limited to: (1) inhibition of c-Src (Brickell, *Critical Reviews in Oncogenesis*, 3:401–406 (1992); Courtneidge, *Seminars in Cancer Biology*, 5:236–246 (1994), raf (Powis, *Pharmacology & Therapeutics*, 62:57–95 (1994)) and the cyclin-dependent kinases (CDKs) 1, 2 and 4 in cancer (Pines, *Current Opinion in Cell Biology*, 4:144–148 (1992); Lees, *Current Opinion in Cell Biology*, 7:773–780 (1995); Hunter and Pines, *Cell*, 79:573–582 (1994)), (2) inhibition of CDK2 or PDGF-R kinase in restenosis (Buchdunger et al., *Proceedings of the National Academy of Science USA*, 92:2258–2262 (1995)), (3) inhibition of CDK5 and GSK3 kinases in Alzheimers (Hosoi et al., *Journal of Biochemistry (Tokyo)*, 117:741–749 (1995); Aplin et al., *Journal of Neurochemistry*, 67:699–707 (1996), (4) inhibition of c-Src kinase in osteoporosis (Tanaka et al., *Nature*, 383:528–531 (1996), (5) inhibition of GSK-3 kinase in type-2 diabetes (Borthwick et al., *Biochemical & Biophysical Research Communications*, 210:738–745 (1995), (6) inhibition of the p38 kinase in inflammation (Badger et al., *The Journal of Pharmacology and Experimental Therapeutics*, 279:1453–1461 (1996)), (7) inhibition of VEGF-R 1–3 and Tie-1 and -2 kinases in diseases which involve angiogenesis (Shawver et al., *Drug Discovery Today*, 2:50–63 (1997)), (8) inhibition of UL97 kinase in viral infections (He et al., *Journal of Virology*, 71:405–411 (1997)), (9) inhibition of CSF-1R kinase in bone and hematopoetic diseases (Myers et al., *Bioorganic & Medicinal Chemistry Letters*, 7:421–424 (1997), and (10) inhibition of Lck kinase in autoimmune diseases and transplant rejection (Myers et al., *Bioorganic & Medicinal Chemistry Letters*, 7:417–420 (1997)).

It is additionally possible that inhibitors of certain kinases may have utility in the treatment of diseases when the kinase is not misregulated, but it nonetheless essential for maintenance of the disease state. In this case, inhibition of the kinase activity would act either as a cure or palliative for these diseases. For example, many viruses, such as human papilloma virus, disrupt the cell cycle and drive cells into the S-phase of the cell cycle (Vousden, *FASEB Journal*, 7:8720879 (1993)). Preventing cells from entering DNA synthesis after viral infection by inhibition of essential S-phase initiating activities such as CDK2, may disrupt the virus life cycle by preventing virus replication. This same principle may be used to protect normal cells of the body from toxicity of cycle-specific chemotherapeutic agents (Stone et al., *Cancer Research*, 56:3199–3202 (1996); Kohn et al., *Journal of Cellular Biochemistry*, 54:44–452 (1994)). Inhibition of CDKs 2 or 4 will prevent progression into the cycle in normal cells and limit the toxicity of cytotoxics which act in S-phase, G2 or mitosis. Furthermore, CDK2/ cyclin E activity has also been shown to regulate NF-kB. Inhibition of CDK2 activity stimulates NF-kB-dependent gene expression, an event mediated through interactions with the p300 coactivator (Perkins et al., *Science*, 275: 523–527 (1997)). NF-kB regulates genes involved in inflammatory responses (such as hematopoetic growth factors, chemokines and leukocyte adhesion molecules) (Baeuerle and Henkel, *Annual Review of Immunology*, 12:141–179 (1994)) and may be involved in the suppression of apoptotic signals within the cell (Beg and Baltimore, *Science*, 274:782–784 (1996); Wang et al., Science, 274: 784–787 (1996); Van Antwerp et al., *Science*, 274:787–789 (1996)). Thus, inhibition of CDK2 may suppress apoptosis induced by cytotoxic drugs via a mechanism which involves NF-kB. This therefore suggests that inhibition of CDK2 activity may also have utility in other cases where regulation of NF-kB plays a role in etiology of disease. A further example may be take from fungal infections: Aspergillosis is a common infection in immune-compromised patients (Armstrong, *Clinical Infectious Diseases*, 16:1–7 (1993)). Inhibition of the *Aspergillus* kinases Cdc2/Cdc28 or Nim A (Osmani et al., *EMBO Journal*, 10:2669–2679 (1991); Osmani et al., *Cell*, 67:283–291 (1991)) may cause arrest or death in the fungi, improving the therapeutic outcome for patients with these infections.

In one embodiment, the present invention provides compounds of formulas (I), (IA) and (IB) as described above.

Compounds of formulas (I), (IA) and (IB) may exist as salts with pharmaceutically acceptable acids. The present invention includes such salts. Examples of such salts include but are not limited to hydrochlorides, hydrobromides, sulfates, methanesulfonates, nitrates, maleates, acetates, citrates, fumarates, tartrates [eg (+)-tartrates, (−)-tartrates or mixtures thereof including racemic mixtures], succinates, benzoates and salts with amino acids such as glutamic acid. These salts may be prepared by methods known to those skilled in the art.

Certain compounds of formulas (I), (IA) and (IB) which have acidic substituents may exist as salts with pharmaceutically acceptable bases. The present invention includes such salts. Example of such salts include sodium salts, potassium salts, lysine salts and arginine salts. These salts may be prepared by methods known to those skilled in the art.

Certain compounds of formulas (I), (IA) and (IB) and their salts may exist in more than one crystal form and the present invention includes each crystal form and mixtures thereof.

Certain compounds of formulas (I), (IA) and (IB) and their salts may also exist in the form of solvates, for example hydrates, and the present invention includes each solvate and mixtures thereof.

Certain compounds of formulas (I), (IA) and (IB) may contain one or more chiral centers, and exist in different optically active forms. When compounds of formulas (I), (IA) and (IB) contain one chiral center, the compounds exist in two enantiomeric forms and the present invention includes both enantiomers and mixtures of enantiomers, such as racemic mixtures. The enantiomers may be resolved by methods known to those skilled in the art, for example by formation of diastereoisomeric salts which may be separated, for example, by crystallization; formation of diastereoisomeric derivatives or complexes which may be separated, for example, by crystallization, gas-liquid or liquid chromatography; selective reaction of one enantiomer with an enantiomer-specific reagent, for example enzymatic esterification; or gas-liquid or liquid chromatography in a chiral environment, for example on a chiral support for example silica with a bound chiral ligand or in the presence of a chiral solvent. It will be appreciated that where the desired enantiomer is converted into another chemical entity by one of the separation procedures described above, a further step is required to liberate the desired enantiomeric form. Alternatively, specific enantiomers may be synthesized by asymmetric synthesis using optically active reagents, substrates, catalysts or solvents, or by converting one enantiomer into the other by asymmetric transformation.

When a compound of formulas (I), (IA) and (IB) contains more than one chiral center it may exist in diastereoisomeric forms. The diastereoisomeric pairs may be separated by methods known to those skilled in the art, for example chromatography or crystallization and the individual enantiomers within each pair may be separated as described above. The present invention includes each diastereoisomer of compounds of formulas (I), (IA) and (IB) and mixtures thereof.

Certain compounds of formulas (I), (IA) and (IB) may exist in different tautomeric forms or as different geometric isomers, and the present invention includes each tautomer and/or geometric isomer of compounds of formulas (I), (IA) and (IB) and mixtures thereof.

Certain compounds of formulas (I), (IA) and (IB) may exist in different stable conformational forms which may be separable. Torsional asymmetry due to restricted rotation about an asymmetric single bond, for example because of steric hindrance or ring strain, may permit separation of different conformers and atropisomers. The present invention includes each conformational isomer of compounds of formulas (I), (IA) and (IB) and mixtures thereof.

Certain compounds of formulas (I), (IA) and (IB) may exist in zwitterionic form and the present invention includes each zwitterionic form of compounds of formula (I), (IA) and (IB) and mixtures thereof.

Compounds of formulas (I), (IA) and (IB) include compounds identical to those depicted but for the fact that one or more hydrogen or carbon atoms are replaced by isotopes thereof. Such compounds are useful as research and diagnostic tools in metabolism pharmokinetic studies and in binding assays. For example, specific applications in research include radioligand binding assays, autoradiography studies and in vivo binding studies. Included among the radiolabelled forms of compounds of the formulas (I), (IA) and (IB) are the tritium and $C^{14}$ isotopes thereof.

The compounds of this invention have inhibitory activity against protein kinases. That is, these compounds modulate signal transduction by protein kinases. Compounds of this invention inhibit protein kinases from serine/threonine and tyrosine kinase classes. In particular, these compounds selectively inhibit the activity of the KDR/FLK-1/VEGFR-2 and Flt-4/VEGFR-3 tyrosine kinases. Certain compounds of this invention also inhibit the activity of additional tyrosine kinases such as Flt-1/VEGFR-1, Tie-2, Tie-1, FGFR, PDGFR, IGF-1R, c-Met, Src-subfamily kinases such as Lck, Src, fyn, blk, Lyn, yes, etc. Additionally, some compounds of this invention significantly inhibit serinelthreonine kinases such as PKC, MAP kinases, erk, CDKs, Plk-1, or Raf-1 which play an essential role in cell proliferation and cell-cycle progression. The potency and specificity of the generic compounds of this invention towards a particular protein kinase can often be altered and optimized by variations in the nature, number and arrangement of the substituents (i.e., W, $R^1$, $R^2$, $R^3$, Y, Q and $X^1$) and conformational restrictions. In addition the metabolites of certain compounds may also possess significant protein kinase inhibitory activity. These metabolite structures administered alone or generated in vivo may contribute to the observed efficacy.

The compounds of this invention, when administered to individuals in need of such compounds, inhibit vascular hyperpermeability and the formation of edema in these individuals. These compounds act, it is believed, at least in part by inhibiting the activity of KDR tyrosine kinase which is involved in the process of vascular hyperpermeability and edema formation. The KDR tyrosine kinase may also be referred to as FLK-1 tyrosine kinase, NYK tyrosine kinase or VEGFR-2 tyrosine kinase. KDR tyrosine kinase is activated when vascular endothelial cell growth factor (VEGF) or another activating ligand (such as VEGF-C, VEGF-D, VEGF-E or HIV Tat protein) binds to a KDR tyrosine kinase receptor which lies on the surface of vascular endothelial cells. Following such KDR tyrosine kinase activation, hyperpermeability of the blood vessels occurs and fluid moves from the blood stream past the blood vessel walls into the interstitial spaces, thereby forming an area of edema. Diapedesis also often accompanies this response. Similarly, excessive vascular hyperpermeability can disrupt normal molecular exchange across the endothelium in critical tissues and organs (e.g., brain, lung and kidney), thereby causing macromolecular extravasation and deposition. Following this acute response to KDR stimulation which is believed to facilitate the subsequent angiogenic process, prolonged KDR tyrosine kinase stimulation results in the proliferation and chemotaxis of vascular endothelial cells and formation of new vessels. By inhibiting KDR tyrosine kinase activity, either by blocking the production of the activating ligand, by blocking the activating ligand binding to the KDR tyrosine kinase receptor, by preventing receptor dimerization and transphosphorylation, by inhibiting the enzyme activity of the KDR tyrosine kinase (inhibiting the phosphorylation function of the enzyme) or by some other mechanism that interrupts its downstream signaling (D. Mukhopedhyay et al., *Cancer Res.* 58:1278–1284 (1998) and references therein), hyperpermeability, as well as associated extravasation, subsequent edema formation and matrix deposition, and angiogenic responses, may be inhibited and minimized.

The method of the present invention is useful in the treatment of protein kinase-mediated conditions, such as any of the conditions described above. In one embodiment, the protein kinase-mediated condition is characterized by undesired angiogenesis, edema, or stromal deposition. For example, the condition can be one or more ulcers, such as ulcers caused by bacterial or fungal infections, Mooren ulcers and ulcerative colitis. The condition can also be due to a microbial infection, such as Lyme disease, sepsis, septic shock or infections by Herpes simplex, Herpes Zoster, human immunodeficiency virus, protozoa, toxoplasmosis or parapoxvirus; an angiogenic disorders, such as von Hippel Lindau disease, polycystic kidney disease, pemphigoid, Paget's disease and psoriasis; a reproductive condition, such as endometriosis, ovarian hyperstimulation syndrome, preeclampsia or menometrorrhagia; a fibrotic and edemic condition, such as sarcoidosis, fibrosis, cirrhosis, thyroiditis, hyperviscosity syndrome systemic, Osler-Weber-Rendu disease, chronic occlusive pulmonary disease, asthma, and edema following burns, trauma, radiation, stroke, acute injury, hypoxia or ischemia; or an inflammatory/immunologic condition, such as systemic lupus, chronic inflammation, glomerulonephritis, synovitis, inflammatory bowel disease, Crohn's disease, rheumatoid arthritis, osteoarthritis, multiple sclerosis and graft rejection. Suitable protein kinase-mediated conditions also include sickle cell anaemia, osteoporosis, osteopetrosis, tumor-induced hypercalcemia and bone metastases. Additional protein kinase-mediated conditions which can be treated by the method of the present invention include ocular conditions such as ocular and macular edema, ocular neovascular disease, scleritis, radial keratotomy, uveitis, vitritis, myopia, optic pits, chronic retinal detachment, post-laser complications, conjunctivitis, Stargardt's disease and Eales disease, in addition to retinopathy and macular degeneration.

It has been noted that *Streptococcus pneumoniae* (pneumococcal infections) stimulate neutrophil production/secretion of VEGF (*Infection & Immunity*, 68 (8), 4792–4794 (2000)). VEGF is also noted to be elevated in cystic fibrosis and correlates with pulmonary exacerbation (*Am. J. Respir. Care Med.*, 161, 1877–1880 (2000)). Therefore, a compound of the present invention is useful in treating complications such as pulmonary exacerbation arising from the increased levels of VEGF associated with *S. pneumoniae* infection or onset of cystic fibrosis.

The compounds of the present invention are also useful in the treatment of cardiovascular conditions such as atherosclerosis, restenosis, vascular occlusion and carotid obstructive disease.

The compounds of the present invention are also useful in the treatment of cancer related indications such as various solid tumors, carcinomas, sarcomas (especially Ewing's sarcoma and osteosarcoma), retinoblastoma, rhabdomyosarcomas, neuroblastoma, hematopoietic malignancies, including leukaemia and lymphoma, tumor-induced pleural or pericardial effusions, and malignant ascites.

Castleman's disease is a lymphoproliferative disorder characterized by enlarged hyperplastic lymph nodes with marked vascular proliferation. Human IL-6 produced in the affected lymph nodes of Castleman's disease may be responsible for the increased VEGF-production by plasma cells and vascular proliferation in the lymph node, Nishi, J., and Maryuma, I., *Leuk. Lymphoma*, 38 387. Compounds of the present invention which antagonize VEGF-signaling are useful in the treatment of Castleman's disease.

The compounds of the present invention are also useful in the treatment of Crow-Fukase (POEMS) syndrome and diabetic conditions such as glaucoma, diabetic retinopathy and microangiopathy.

One group of preferred compounds of this invention have the property of inhibiting KDR tyrosine kinase activity without significantly inhibiting Flt-1 tyrosine kinase activity (Flt-1 tyrosine kinase is also referred to as VEGFR-1 tyrosine kinase). Both KDR tyrosine kinase and Flt-1 tyrosine kinase are activated by VEGF binding to KDR tyrosine kinase receptors and to Flt-1 tyrosine kinase receptors, respectively. Certain preferred compounds of this invention are unique because they inhibit the activity of one VEGF-receptor tyrosine kinase (KDR) that is activated by activating ligands but do not inhibit other receptor tyrosine kinases, such as Flt-1, that are also activated by certain activating ligands. In this manner, certain preferred compounds of this invention are, therefore, selective in their tyrosine kinase inhibitory activity.

In one embodiment, the present invention provides a method of treating a protein kinase-mediated condition in a patient, comprising administering to the patient a therapeutically or prophylactically effective amount of one or more compounds of Formula I. A "protein kinase-mediated condition" or a "condition mediated by protein kinase activity" is a medical condition, such as a disease or other undesirable physical condition, the genesis or progression of which depends, at least in part, on the activity of at least one protein kinase. The protein kinase can be, for example, a protein tyrosine kinase or a protein serine/threonine kinase.

The patient to be treated can be any animal, and is preferably a mammal, such as a domesticated animal or a livestock animal. More preferably, the patient is a human.

A "therapeutically effective amount" is an amount of a compound of Formula I or a combination of two or more such compounds, which inhibits, totally or partially, the progression of the condition or alleviates, at least partially, one or more symptoms of the condition. A therapeutically effective amount can also be an amount which is prophylactically effective. The amount which is therapeutically effective will depend upon the patient's size and gender, the condition to be treated, the severity of the condition and the result sought. For a given patient, a therapeutically effective amount can be determined by methods known to those of skill in the art.

The Src, Tec, Jak, Map, Csk, NFκB and Syk families of kinases play pivotal roles in the regulation of immune function. The Src family currently includes Fyn, Lck, Fgr, Fes, Lyn, Src, Yrk, Fyk, Yes, Hck, and Blk. The Syk family is currently understood to include only Zap and Syk. The TEC family includes Tec, Btk, Rlk and Itk. The Janus family of kinases is involved in the transduction of growth factor and proinflammatory cytokine signals through a number of receptors. Although BTK and ITK, members of the Tec family of kinases, play a less well understood role in immunobiology, their modulation by an inhibitor may prove therapeutically beneficial. The Csk family is currently understood to include Csk and Chk. The kinases RIP, IRAK-1, IRAK-2, NIK, p38 MAP kinases, Jnk, IKK-1 and IKK-2 are involved in the signal transduction pathways for key pro-inflammatory cytokines, such as TNF and IL-1. By virtue of their ability to inhibit one or more of these kinases, compounds of formula I may function as immunomodulatory agents useful for the maintenance of allografts, the treatment of autoimmune disorders and treatment of sepsis and septic shock. Through their ability to regulate the migration or activation of T cells, B-cells, mast cells, monocytes and neutrophils, these compounds could be used to treat such autoimmune diseases and sepsis. Prevention of transplant rejection, either host versus graft for solid organs or graft versus host for bone marrow, are limited by the toxicity of currently available immunosuppressive agents and would benefit from an efficacious drug with improved therapeutic index. Gene targeting experiments have demonstrated the essential role of Src in the biology of osteoclasts, the cells responsible for bone resorption. Compounds of formula I, through their ability to regulate Src, may also be useful in the treatment of osteoporosis, osteopetrosis, Paget's disease, tumor-induced hypercalcemia and in the treatment of bone metastases.

A number of protein kinases have been demonstrated to be protooncogenes. Chromosome breakage (at the ltk kinase break point on chromosome 5), translocation as in the case of the Abl gene with BCR (Philadelphia chromosome), truncation in instances such as c-Kit or EGFR, or mutation (e.g., Met) result in the creation of dysregulated proteins converting them from protooncogene to oncogene products. In other tumors, oncogenesis is driven by-an-autocrine or paracrine ligand/growth factor receptor interactions. Members of the src-family kinases are typically involved in downstream signal transduction thereby potentiating the proliferative response or oncogenesis and themselves may become oncogenic by over-expression or mutation. By inhibiting the protein kinase activity of these proteins the disease process may be disrupted. Vascular restenosis may involve FGF and/or PDGF—promoted smooth muscle and endothelial cell proliferation. The ligand stimulation of FGFR, PDGFR, IGF1-R and c-Met in vivo is proangiogenic, and potentiates angiogenesis dependent disorders. Inhibition of FGFr, PDGFr, c-Met, or IGF1-R kinase activities individually or in combination may be an efficacious strategy for inhibiting these phenomena. Thus compounds of formula I which inhibit the kinase activity of normal or aberrant c-kit, c-met, c-fms, src-family members, EGFr, erbB2, erbB4, BCR-Abl, PDGFr, FGFr, IGF1-R and other receptor or cytosolic tyrosine kinases may be of value in the treatment of benign and neoplastic proliferative diseases.

In many pathological conditions (for example, solid primary tumors and metastases, Kaposi's sarcoma, rheumatoid arthritis, blindness due to inappropriate ocular neovascularization, psoriasis and atherosclerosis) disease progression is contingent upon persistent angiogenesis. Polypeptide growth factors often produced by the disease tissue or associated inflammatory cells, and their corresponding endothelial cell specific receptor tyrosine kinases (e.g., KDR/VEGFR-2, Flt-1/VEGFR-1, Tie-2/Tek and Tie-1) are essential for the stimulation of endothelial cell growth, migration, organization, differentiation and the establishment of the requisite new functional vasculature. As a result of the vascular permeability factor activity of VEGF in mediating vascular hyperpermeability, VEGF-stimulation of a VEGFR kinase is also believed to play an important role in the formation of tumor ascites, cerebral and pulmonary edema, pleural and pericardial effusions, delayed-type hypersensitivity reactions, tissue edema and organ dysfunction following trauma, acute lung injury (ALI), burns, ischemia, diabetic complications, endometriosis, adult respiratory distress syndrome (ARDS), post-cardiopulmonary bypass-related hypotension and hyperpermeability, and ocular edema leading to glaucoma or blindness due to inappropriate neovascularization. In addition to VEGF, recently identified VEGF-C and VEGF-D, and virally-encoded VEGF-E or HIV-Tat protein can also cause a vascular hyperpermeability response through the stimulation of a VEGFR kinase. KDR/VEGFR-2 and/or Tie-2 and/or Tie-1 are expressed also in a select population of hematopoietic stem cells. Certain members of this population are pluripotent in nature and can be stimulated with growth factors to differentiate into endothelial cells and participate in vasculogenetic angiogenic processes. For this reason these have been called Endothelial Progenitor Cells (EPCs) (*J. Clin. Investig.* 103: 1231–1236 (1999)). In some progenitors, Tie-2 may play a role in their recruitment, adhesion, regulation and differentiation (*Blood,* 4317–4326 (1997)). Certain agents according to formula I capable of blocking the kinase activity of endothelial cell specific kinases could therefore inhibit disease progression involving these situations.

Vascular destabilization by the antagonist ligand of Tie-2 (Ang2) is believed to induce an unstable "plastic" state in the endothelium. In the presence of high VEGF levels a robust angiogenic response may result; however, in the absence of VEGF or a VEGF-related stimulus, frank vessel regression and endothelial apoptosis can occur (Genes and Devel. 13: 1055–1066 (1999)). In an analogous manner a Tie-2 kinase inhibitor can be proangiogenic or antiangiogenic in the presence or absence of a VEGF-related stimulus, respectively.

The compounds of formula I or a salt thereof or pharmaceutical compositions containing a therapeutically effective amount thereof may be used in the treatment of protein kinase-mediated conditions, such as benign and neoplastic proliferative diseases and disorders of the immune system, as described above. For example, such diseases include autoimmune diseases, such as rheumatoid arthritis, thyroiditis, type 1 diabetes, multiple sclerosis, sarcoidosis, inflammatory bowel disease, Crohn's disease, myasthenia gravis and systemic lupus erythematosus; psoriasis, organ transplant rejection (eg. kidney rejection, graft versus host disease), benign and neoplastic proliferative diseases, human cancers such as lung, breast, stomach, bladder, colon, pancreas, ovarian, prostate and rectal cancer and hematopoietic malignancies (leukemia and lymphoma), and diseases involving inappropriate vascularization for example diabetic retinopathy, retinopathy of prematurity, choroidal neovascularization due to age-related macular degeneration, and infantile hemangiomas in human beings. In addition, such inhibitors may be useful in the treatment of disorders involving VEGF mediated edema, ascites, effusions, and exudates, including for example macular edema, cerebral edema, acute lung injury and adult respiratory distress syndrome (ARDS).

The compounds of the present invention may also be useful in the prophylaxis of the above diseases.

It is envisaged that the disorders listed above are mediated to a significant extent by protein tyrosine kinase activity involving the VEGF receptors (e.g. KDR, Flt-1 and/or Tie-2 and/or Tie-1). By inhibiting the activity of these receptor tyrosine kinases, the progression of the listed disorders is inhibited because the angiogenic component of the disease state is severely curtailed. The action of the compounds of this invention, by their selectivity for specific tyrosine kinases, result in a minimization of side effects that would occur if less selective tyrosine kinase inhibitors were used.

In another aspect the present invention provides compounds of formula I as defined initially above for use as medicaments, particularly as inhibitors of protein kinase activity for example tyrosine kinase activity, serine kinase activity and threonine kinase activity. In yet another aspect the present invention provides the use of compounds of formula I as defined initially above in the manufacture of a medicament for use in the inhibition of protein kinase activity.

In this invention, the following definitions are applicable:

"Physiologically acceptable salts" refers to those salts which retain the biological effectiveness and properties of the free bases and which are obtained by reaction with inorganic acids such as hydrochloric acid, hydrobromic acid, sulfuric acid, nitric acid, phosphoric acid or organic acids such as sulfonic acid, carboxylic acid, organic phosphoric acid, methanesulfonic acid, ethanesulfonic acid, p-toluenesulfonic acid, salicylic acid, lactic acid, tartaric acid and the like.

"Alkyl" refers to a saturated aliphatic hydrocarbon, including straight-chain and branched-chain groups. Preferred straight chain and branched alkyl groups include $C_1$–$C_8$ alkyl groups.

"Alkenyl" refers to an aliphatic hydrocarbon having at least one double bond, including straight-chain and branched-chain groups. Preferred straight chain and branched alkenyl groups include $C_1$–$C_8$ alkyl groups.

"Alkynyl" refers to an aliphatic hydrocarbon having at least one triple bond, including straight-chain and branched-chain groups. Preferred straight chain and branched alkynyl groups include $C_1$–$C_8$ alkyl groups.

"Alkoxy" refers to an "O-alkyl" group, where "alkyl" is defined as described above.

"Cycloalkyl" refers to mono-, bi- and tri-carbocyclic groups having 3 to 12 carbon atoms, preferred cycloalkyl groups have 3 to 6 ring carbon atoms.

"Heterocyclyl" means an optionally substituted mono- or bi-cyclic aromatic or non-aromatic heterocycle in which the heterocycle contains 1, 2, 3 or 4 hetero atoms selected from nitrogen, sulphur or oxygen. The heterocyclyl group may be attached through a carbon atom or a hetero atom. Suitable heterocyclyl groups include but are not restricted to 1,3-dioxolanyl, 1,4-dioxolanyl, morpholinyl, piperidinyl, piperazinyl, thiomorpholinyl, 3H-indolyl, 4H-quinolizinyl, 2-imidazolinyl, imidazolidinyl, quinuclidinyl, 2-pyrazolinyl, pyrazolidinyl, 2H-pyranyl, 4H-pyranyl, 1,4-dithianyl, 1,3,5-trithianyl, tetrahydrofuranyl, pyrrolidinyl, pyrrolyl, imidazolyl, isothiazolyl, pyrazolyl, thiazolyl, oxazolyl, oxadiazolyl, thiadiazolyl, tetrazolyl, pyridyl, pyridazinyl, pyrimidinyl, pyrazinyl, benzimidazolyl, quinolinyl, isoquinolinyl, indazolyl, furanyl, 2,3,4,5-tetrahydrofuranyl, thienyl, benzofuranyl, indolizinyl, imidazopyridinyl, isoxazolyl, benzoxazolyl, indolyl, isoindolyl, indolinyl, benzothiazolyl, benzothienyl, purinyl, 1,2,3-triazolyl, 1,2,4-trizolyl, 1,3,5-triazinyl, cinnolinyl, phthalazinyl, quinazolinyl, quinoxalinyl, 1,8-naphthypyridinyl, pteridinyl, carbazolyl, acridinyl, phenazinyl, phenothiazinyl and phenoxazinyl.

"Aryl" means a mono-, bi- or tri-cyclic aromatic group. Suitable aryl groups include phenyl, indenyl, naphthyl, azulenyl, flourenyl and anthracenyl.

The term "optionally substituted" as used herein refers to substituents that can be attached to moieties to which the term refers. Particularly preferred substituents of phenyl, naphthyl and heterocyclyl groups, which can be substituted by one or more groups, are as follows: a) halo, b) $C_{1-6}$ alkyl optionally substituted by one or more of the following: hydroxy, halo, an optionally substituted amino group or a five, six or seven membered saturated heterocyclic ring containing a nitrogen atom which optionally contains an additional hetero atom selected from O, S or N and is optionally substituted by a $C_{1-6}$ alkyl group wherein said saturated ring is attached through a carbon atom c) $C_{1-6}$ alkoxy optionally substituted by one or more of the following: hydroxy, $C_{1-6}$ alkoxy, halo or optionally substituted amino group, or a five, six or seven membered saturated heterocyclic ring containing a nitrogen atom which optionally contains an additional hetero atom selected from O, S or N and is optionally substituted by a $C_{1-6}$ alkyl group wherein said saturated ring is attached through a carbon atom d) optionally substituted phenoxy, where the substituents are selected from the same group of preferred substituents as outlined in this paragraph, e) hydroxy, f)-$COR_a$ where $R_a$ is hydroxy, $C_{1-6}$ alkoxy or —$NR_bR_c$, where $R_b$ and $R_c$ independently are hydrogen, $C_{1-12}$ alkyl, $C_{3-12}$ cycloalkyl or phenyl wherein the $C_{1-12}$ alkyl group, the $C_{3-12}$ cycloalkyl group and phenyl are optionally substituted by one or more of the following: hydroxy, halo, $C_{3-12}$ cycloalkyl or —$NR_hR_j$, wherein $R_h$ and $R_j$ independently are hydrogen or $C_{1-6}$ alkyl or wherein $R_h$ and $R_j$ together with the nitrogen atom to which they are attached is a five, six or seven membered saturated heterocyclic ring which optionally contains an additional hetero atom selected from O, S or N and is optionally substituted by a $C_{1-6}$ alkyl group, g) —$NR_dR_e$ where $R_d$ and $R_e$ are each independently selected from the group consisting of hydrogen, $C_{1-12}$ alkyl, $C_{3-12}$ cycloalkyl or phenyl or —$COR_f$ wherein $R_f$ is hydrogen, $C_{1-12}$ alkyl, $C_{3-12}$ cycloalkyl, phenyl-$C_{1-6}$alkyl or phenyl wherein in each case the alkyl group, the cycloalkyl group, phenyl-$C_{1-6}$alkyl and phenyl are optionally substituted by one or more of the following: halo, hydroxy, nitro or —$NR_hR_j$ wherein $R_h$ and $R_j$ are independently selected from the same moieties as defined above, h) —$O(CH_2)_mR_g$ where m is 2, 3, 4 or 5 and $R_g$ is hydroxy or a group of formula —$NR_dR_e$ where $R_d$ and $R_e$ are independently selected from the same moieties as defined above; or $R_g$ is —$COR_a$ wherein $R_a$ is independently selected from the same moieties as defined above and, i) nitro, j) optionally substituted phenyl $C_{1-6}$ alkyl, k) optionally substituted phenyl-$C_{1-6}$alkoxy, l) cyano, m) $C_{3-6}$alkenyloxy, n) pyridyloxy or pyridylthio group wherein the pyridyl ring is optionally substituted by one or more of trifluoromethyl or nitro, o) hydroxyamidino, p) aminomethyl, q) formamidomethyl, r) $C_{1-6}$ alkythio, s) phenyl or t) $C_{2-4}$ alkenyl or $C_{2-4}$ alkynyl wherein each is optionally substituted by phenyl which in turn is optionally substituted by one or more of the following: $C_{1-6}$ alkyl, $C_{1-6}$ alkoxy or halo.

Pharmaceutical Formulations

The compounds of this invention can be administered to a human patient by themselves or in pharmaceutical compositions where they are mixed with suitable carriers or excipient(s) at doses to treat or ameliorate vascular hyperpermeability, edema, fibrosis, angiogenesis, tumor growth, psoriasis, arthritis, hyperproliferation and associated disorders. Mixtures of these compounds can also be administered to the patient as a simple mixture or in suitable formulated pharmaceutical compositions. A therapeutically effective dose further refers to that amount of the compound or compounds sufficient to result in the prevention or attenuation of inappropriate neovascularization, progression of hyperproliferative disorders, edema, VEGF-associated hyperpermeability and/or VEGF-related hypotension. Techniques for formulation and administration of the compounds of the instant application may be found in "Remington's Pharmaceutical Sciences," Mack Publishing Co., Easton, Pa., latest edition.

Routes of Administration

Suitable routes of administration may, for example, include oral, eyedrop, rectal, transmucosal, topical, or intestinal administration; parenteral delivery, including intramuscular, subcutaneous, intramedullary injections, as well as intrathecal, direct intraventricular, intravenous, intraperitoneal, intranasal, or intraocular injections.

Alternatively, one may administer the compound in a local rather than a systemic manner, for example, via injection of the compound directly into the diseased or an edematous site, often in a depot or sustained release formulation.

Furthermore, one may administer the drug in a targeted drug delivery system, for example, in a liposome coated with endothelial cell-specific antibody.

Composition/Formulation

The pharmaceutical compositions of the present invention may be manufactured in a manner that is itself known, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

For oral administration, the compounds can be formulated readily by combining the active compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining the active compound with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration.

For buccal administration, the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The compounds can be formulated for parenteral administration by injection, e.g. bolus injection or continuous infusion. Formulations for injection may be presented in unit dosage form, e.g. in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly or by intramuscular injection). Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

An example of a pharmaceutical carrier for the hydrophobic compounds of the invention is a cosolvent system comprising benzyl alcohol, a nonpolar surfactant, a water-miscible organic polymer, and an aqueous phase. The cosolvent system may be the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethysulfoxide also may be employed, although usually at the cost of greater toxicity. Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the compounds of the invention may be provided as salts with pharmaceutically compatible counterions. Pharmaceutically compatible salts may be formed with many acids, (including but not limited to hydrochloric, sulfuric, acetic, lactic, tartaric, malic, succinic, etc.) and with bases (including but not limited to sodium, potassium, lithium, tetralkylammonia, etc.). Salts tend to be more soluble in aqueous or other protonic solvents than are the corresponding free base forms.

Effective Dosage

Pharmaceutical compositions suitable for use in the present invention include compositions wherein the active ingredients are contained in an effective amount to achieve its intended purpose. More specifically, a therapeutically effective amount means an amount effective to prevent development of or to alleviate the existing symptoms of the subject being treated. Determination of the effective amounts is well within the capability of those skilled in the art.

For any compound used in the method of the invention, the therapeutically effective dose can be estimated initially from cellular assays. For example, a dose can be formulated in cellular and animal models to achieve a circulating concentration range that includes the $IC_{50}$ as determined in cellular assays (i.e., the concentration of the test compound which achieves a half-maximal inhibition of a given protein kinase activity). In some cases it is appropriate to determine the $IC_{50}$ in the presence of 3 to 5% serum albumin since such a determination approximates the binding effects of plasma protein on the compound. Such information can be used to more accurately determine useful doses in humans. Further, the most preferred compounds for systemic administration effectively inhibit protein kinase signaling in intact cells at levels that are safely achievable in plasma.

A therapeutically effective dose refers to that amount of the compound that results in amelioration of symptoms in a patient. Toxicity and therapeutic efficacy of such compounds can be determined by standard pharmaceutical procedures in cell cultures or experimental animals, e.g., for determining the maximum tolerated dose (MTD) and the $ED_{50}$ (effective dose for 50% maximal response). The dose ratio between toxic and therapeutic effects is the therapeutic index and it can be expressed as the ratio between MTD and $ED_{50}$. Compounds which exhibit high therapeutic indices are preferred. The data obtained from these cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. The exact formulation, route of administration and dosage can be chosen by the individual physician in view of the patient's condition. (See e.g. Fingl et al., 1975, in "The Pharmacological Basis of Therapeutics", Ch. 1 p1). In the treatment of crises, the administration of an acute bolus or an infusion approaching the MTD may be required to obtain a rapid response.

Dosage amount and interval may be adjusted individually to provide plasma levels of the active moiety which are sufficient to maintain the kinase modulating effects, or minimal effective concentration (MEC). The MEC will vary for each compound but can be estimated from in vitro data; e.g. the concentration necessary to achieve 50–90% inhibition of protein kinase using the assays described herein. Dosages necessary to achieve the MEC will depend on individual characteristics and route of administration. However, HPLC assays or bioassays can be used to determine plasma concentrations.

Dosage intervals can also be determined using the MEC value. Compounds should be administered using a regimen which maintains plasma levels above the MEC for 10–90% of the time, preferably between 30–90% and most preferably between 50–90% until the desired amelioration of symptoms is achieved. In cases of local administration or selective uptake, the effective local concentration of the drug may not be related to plasma concentration.

The amount of composition administered will, of course, be dependent on the subject being treated, on the subjects weight, the severity of the affliction, the manner of administration and the judgment of the prescribing physician.

Packaging

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

In some formulations it may be beneficial to use the compounds of the present invention in the form of particles of very small size, for example as obtained by fluid energy milling.

The use of compounds of the present invention in the manufacture of pharmaceutical compositions is illustrated by the following description. In this description the term "active compound" denotes any compound of the invention but particularly any compound which is the final product of one of the following Examples.

a) Capsules

In the preparation of capsules, for example, 10 parts by weight of active compound and 240 parts by weight of lactose can be de-aggregated and blended. The mixture can be filled into hard gelatin capsules, each capsule containing a unit dose or part of a unit dose of active compound.

b) Tablets

Tablets can be prepared from the following ingredients, for example:

| Parts by weight | |
|---|---|
| Active compound | 10 |
| Lactose | 190 |
| Maize starch | 22 |
| Polyvinylpyrrolidone | 10 |
| Magnesium stearate | 3 |

The active compound, the lactose and some of the starch can be de-aggregated, blended and the resulting mixture can be granulated with a solution of the polyvinyl- pyrrolidone in ethanol. The dry granulate can be blended with the magnesium stearate and the rest of the starch. The mixture is then compressed in a tabletting machine to give tablets each containing a unit dose or a part of a unit dose of active compound.

c) Enteric Coated Tablets

Tablets can be prepared by the method described in (b) above. The tablets can be enteric coated in a conventional manner using a solution of 20% cellulose acetate phthalate and 3% diethyl phthalate in ethanol:dichloromethane (1:1).

d) Suppositories

In the preparation of suppositories, for example, 100 parts by weight of active compound can be incorporated in 1300 parts by weight of triglyceride suppository base and the mixture formed into suppositories each containing a therapeutically effective amount of active ingredient.

In the compositions of the present invention the active compound may, if desired, be associated with other compatible pharmacologically active ingredients. For example, the compounds of this invention can be administered in combination with one or more additional pharmaceutical agents that inhibit or prevent the production of VEGF or angiopoietins, attenuate intracellular responses to VEGF or angiopoietins, block intracellular signal transduction, inhibit vascular hyperpermeability, reduce inflammation, or inhibit or prevent the formation of edema or neovascularization. A Tie-2 inhibitor would be useful in treating pyogenic granuloma of human gingiva (*J. Periodont. Res*, 2000: 35: 165–171). The compounds of the invention can be administered prior to, subsequent to or simultaneously with the additional pharmaceutical agent, whichever course of administration is appropriate. The additional pharmaceutical agents include but are not limited to anti-edemic steroids, NSAIDS, ras inhibitors, anti-TNF agents, anti-IL1 agents, antihistamines, PAF-antagonists, COX-1 inhibitors, COX-2 inhibitors, NO synthase inhibitors, Akt/PFB inhibitors, IGF-1R inhibitors, PKC inhibitors, chemotherapy agents such as mitomycin C or Paclitaxel, a vascular targeting agent such as combretastatin A4, a tubulin binding agent such as a dolastatin, and PI3 kinase inhibitors. The compounds of the invention and the additional pharmaceutical agents act either additively or synergistically. Thus, the administration of such a combination of substances that inhibit angiogenesis, vascular hyperpermeability and/or inhibit the formation of edema can provide greater relief from the deleterious effects of an inflammatory or hyperproliferative disorder, angiogenesis, vascular hyperpermeability or edema than the administration of either substance alone. In the treatment of malignant disorders combinations with antiproliferative or cytotoxic chemotherapies or radiation are anticipated.

The present invention also comprises the use of a compound of formula I as a medicament.

A further aspect of the present invention provides the use of a compound of formula I or a salt thereof in the manufacture of a medicament for treating vascular hyperpermeability, angiogenesis-dependent disorders, proliferative diseases and/or disorders of the immune system in mammals, particularly human beings.

The present invention also provides a method of treating vascular hyperpermeability, inappropriate neovascularization, proliferative diseases and/or disorders of the immune system which comprises the administration of a therapeutically effective amount of a compound of formula I to a mammal, particularly a human being, in need thereof.

The in vitro potency of compounds in inhibiting these protein kinases may be determined by the procedures detailed below.

The potency of compounds can be determined by the amount of inhibition of the phosphorylation of an exogenous substrate (e.g., synthetic peptide (Z. Songyang et al., *Nature*. 373:536–539) by a test compound relative to control.

KDR Tyrosine Kinase Production Using Baculovirus System:

The coding sequence for the human KDR intra-cellular domain (aa789–1354) was generated through PCR using cDNAs isolated from HUVEC cells. A poly-His6 sequence was introduced at the N-terminus of this protein as well. This fragment was cloned into transfection vector pVL1393 at the Xba 1 and Not 1 site. Recombinant baculovirus (BV) was generated through co-transfection using the BaculoGold Transfection reagent (PharMingen). Recombinant BV was plaque purified and verified through Western analysis. For protein production, SF-9 cells were grown in SF-900–1 µl medium at $2\times10^6$/ml, and were infected at 0.5 plaque forming units per cell (MOI). Cells were harvested at 48 hours post infection.

Purification of KDR

SF-9 cells expressing $(His)_6$ KDR(aa789–1354) were lysed by adding 50 ml of Triton X-100 lysis buffer (20 mM Tris, pH 8.0, 137 mM NaCl, 10% glycerol, 1% Triton X-100, 1 mM PMSF, 10 µg/ml aprotinin, 1 µg/ml leupeptin) to the cell pellet from 1L of cell culture. The lysate was centrifuged at 19,000 rpm in a Sorval SS-34 rotor for 30 min at 4E C. The cell lysate was applied to a 5 ml $NiCl_2$ chelating sepharose column, equilibrated with 50 mM HEPES, pH7.5, 0.3 M NaCl. KDR was eluted using the same buffer containing 0.25 M imidazole. Column fractions were analyzed using SDS-PAGE and an ELISA assay (below) which measures kinase activity. The purified KDR was exchanged into 25 mM HEPES, pH7.5, 25 mM NaCl, 5 mM DTT buffer and stored at –80E C.

Human Tie-2 Kinase Production and Purification

The coding sequence for the human Tie-2 intra-cellular domain (aa775–1124) was generated through PCR using cDNAs isolated from human placenta as a template. A poly-$HiS_6$ sequence was introduced at the N-terminus and this construct was cloned into transfection vector pVL 1939 at the Xba 1 and Not 1 site. Recombinant BV was generated through co-transfection using the BaculoGold Transfection reagent (PharMingen). Recombinant BV was plaque purified and verified through Western analysis. For protein production, SF-9 insect cells were grown in SF-900-II medium at 2×106/ml, and were infected at MOI of 0.5. Purification of the His-tagged kinase used in screening was analogous to that described for KDR.

Human Flt-1 Tyrosine Kinase Production and Purification

The baculoviral expression vector pVL1393 (Phar Mingen, Los Angeles, Calif.) was used. A nucleotide sequence encoding poly-His6 was placed 5' to the nucleotide region encoding the entire intracellular kinase domain of human Flt-1 (amino acids 786–1338). The nucleotide sequence encoding the kinase domain was generated through PCR using cDNA libraries isolated from HUVEC cells. The histidine residues enabled affinity purification of the protein as a manner analogous to that for KDR and ZAP70. SF-9 insect cells were infected at a 0.5 multiplicity and harvested 48 hours post infection.

Flt-4 VEGF3 Baculovirus Expression Vector

The cDNA corresponding to the intracellular kinase domain of human Flt-4/VEGF 3 was obtained by performing Polymerase Chain Reaction (PCR) with Flt-4 specific oligonucleotide primers on total cDNA from human placenta (Galland, F. et.al., Oncogene (1993), 8, 1233–1240). The cDNA sequence was compared and verified using the published GENBANK sequence (x69878.gb_prl). FLT-4 cDNA sequence corresponding to bp. 2413–3918 ie. aa. Cys798–Arg1298 was subcloned into the baculovirus expression vector pFastbacB (Life Technologies). The subcloning introduced 4 extra amino acids Ala-Met-Gly-Ser in front of Cys798. Therefore, the fusion protein produced would have Met-$(His)_6$, a spacer region, a Tev protease cleavage site followed by Flt-4 kinase domain including the 4 extra amino acids. The expression vector was introduced into SF9 cells to produce baculovirus which was then used to infect more SF9 cells and express Flt-4/VEGF3 kinase domain protein.

EGFR Tyrosine Kinase Source

EGFR was purchased from Sigma (Cat # E-3641; 500 units/50 µl) and the EGF ligand was acquired from Oncogene Research Products/Calbiochem (Cat # PF011-100).

Expression of ZAP70

The baculoviral expression vector used was pVL1393. (Pharmingen, Los Angeles, Calif.) The nucleotide sequence encoding amino acids $M(H)_6$ $LVPR_9S$ was placed 5' to the region encoding the entirety of ZAP70 (amino acids 1–619). The nucleotide sequence encoding the ZAP70 coding region was generated through PCR using cDNA libraries isolated from Jurkat immortalized T-cells. The histidine residues enabled affinity purification of the protein (vide infra). The $LVPR_9S$ bridge constitutes a recognition sequence for proteolytic cleavage by thrombin, enabling removal of the affinity tag from the enzyme. SF-9 insect cells were infected at a multiplicity of infection of 0.5 and harvested 48 hours post infection.

Extraction and Purification of ZAP70:

SF-9 cells were lysed in a buffer consisting of 20 mM Tris, pH 8.0, 137 mM NaCl, 10% glycerol, 1% Triton X-100, 1 mM PMSF, 1 µg/ml leupeptin, 10 µg/ml aprotinin and 1 mM sodium orthovanadate. The soluble lysate was applied to a chelating sepharose HiTrap column (Pharmacia) equilibrated in 50 mM HEPES, pH 7.5, 0.3 M NaCl. Fusion protein was eluted with 250 mM imidazole. The enzyme was stored in buffer containing 50 mM HEPES, pH 7.5, 50 mM NaCl and 5 mM DTT.

Protein Kinase Source:

Lck, Fyn, Src, Blk, Csk, and Lyn, and truncated forms thereof may be commercially obtained (e.g. from Upstate Biotechnology Inc., Saranac Lake, N.Y.; and Santa Cruz Biotechnology Inc., Santa Cruz, Calif.) or purified from known natural or recombinant sources using conventional methods.

Enzyme Linked Immunosorbent Assay (ELISA) For PTKs:

Enzyme linked immunosorbent assays (ELISA) were used to detect and measure the presence of tyrosine kinase activity. The ELISA were conducted according to known protocols which are described in, for example, Voller, et al., 1980, "Enzyme-Linked Immunosorbent Assay," In: *Manual of Clinical Immunology*, 2d ed., edited by Rose and Friedman, pp 359–371 Am. Soc. of Microbiology, Washington, D.C.

The disclosed protocol was adapted for determining activity with respect to a specific PTK. For example, preferred protocols for conducting the ELISA experiments is provided below. Adaptation of these protocols for determining a compound's activity for other members of the receptor PTK family, as well as non-receptor tyrosine kinases, are well within the abilities of those in the art. For purposes of determining inhibitor selectivity, a universal PTK substrate (e.g., random copolymer of poly(Glu$_4$ Tyr), 20,000–50,000 MW) was employed together with ATP (typically 5 μM) at concentrations approximately twice the apparent Km in the assay.

The following procedure was used or can be used to assay the inhibitory effect of compounds of this invention on KDR, VEGFR-3, Flt-1, Tie-2, Tie-1, EGFR, FGFR, PDGFR, IGF-1-R, Insulin receptor, c-Met, Lck, Blk, Csk, Src, Lyn, Fyn and ZAP70 tyrosine kinase activity:

Buffers and Solutions:

PGTPoly (Glu,Tyr) 4:1

Store powder at −20° C. Dissolve powder in phosphate buffered saline (PBS) for 50 mg/ml solution. Store 1 ml aliquots at −20° C. When making plates dilute to 250 μg/ml in Gibco PBS. Reaction Buffer: 100 mM Hepes, 20 mM MgCl$_2$, 4 mM MnCl$_2$, 5 mM DTT, 0.02% BSA, 200 μM NaVO$_4$, pH 7.10

ATP: Store aliquots of 100 mM at −20° C. Dilute to 201 μM in water

Washing Buffer: PBS with 0.1% Tween 20

Antibody Diluting Buffer: 0.1% bovine serum albumin (BSA) in PBS

TMB Substrate: mix TMB substrate and Peroxide solutions 9:1 just before use or use K-Blue Substrate from Neogen Stop Solution: 1M Phosphoric Acid Procedure 1. Plate Preparation:

Dilute PGT stock (50 mg/ml, frozen) in PBS to a 250 g/ml. Add 125 μg/ml per well of Corning modified flat bottom high affinity ELISA plates (Corning #25805-96). Add 125 μl PBS to blank wells. Cover with sealing tape and incubate overnight 37° C. Wash 1× with 250 μl washing buffer and dry for about 2 hrs in 37° C. dry incubator. Store coated plates in sealed bag at 4° C. until used.

2. Tyrosine Kinase Reaction:

Prepare inhibitor solutions at a 4× concentration in 20% DMSO in water.

Prepare reaction buffer

Prepare enzyme solution so that desired units are in 50 μl, e.g. for KDR make to 1 ng/μl for a total of 50 ng per well in the reactions. Store on ice.

Make 4× ATP solution to 20 μM from 100 mM stock in water. Store on ice

Add 50 μl of the enzyme solution per well (typically 5–50 ng enzyme/well depending on the specific activity of the kinase)

Add 25 μl 4× inhibitor

Add 25 μl 4× ATP for inhibitor assay

Incubate for 10 minutes at room temperature

Stop reaction by adding 50 μl 0.05N HCl per well

Wash plate

**Final Concentrations for Reaction: 5 μM ATP, 5% DMSO

3. Antibody Binding

Dilute 1 mg/ml aliquot of PY20-HRP (Pierce) antibody (a phosphotyrosine antibody) to 50 ng/ml in 0.1% BSA in PBS by a 2 step dilution (100×, then 200×)

Add 100 μl Ab per well. Incubate 1 hr at room temp. Incubate 1 hr at 4C.

Wash 4× plate

4. Color reaction

Prepare TMB substrate and add 100 μl per well

Monitor OD at 650 nm until 0.6 is reached

Stop with 1M Phosphoric acid. Shake on plate reader.

Read OD immediately at 450 nm

Optimal incubation times and enzyme reaction conditions vary slightly with enzyme preparations and are determined empirically for each lot.

For Lck, the Reaction Buffer utilized was 100 mM MOPSO, pH 6.5, 4 mM MnCl$_2$, 20 mM MgCl$_2$, 5 mM DTT, 0.2% BSA, 200 mM NaVO$_4$ under the analogous assay conditions.

Compounds of formula I may have therapeutic utility in the treatment of diseases involving both identified, including those not mentioned herein, and as yet unidentified protein tyrosine kinases which are inhibited by compounds of formula I. All compounds exemplified herein significantly inhibit either FGFR, PDGFR, KDR, VEGFR-3, Tie-2, Tie-1, Lck, Fyn, Blk, Lyn or Src at concentrations of 50 micromolar or below. Some compounds of this invention also significantly inhibit other tyrosine or serine/threonine kinases such as cdc2 (cdk1) or Plk-1 at concentrations of 50 micromolar or below.

Cdc2 Source

The human recombinant enzyme and assay buffer may be obtained commercially (New England Biolabs, Beverly, Mass. USA) or purified from known natural or recombinant sources using conventional methods.

Cdc2 Assay

The protocol used was that provided with the purchased reagents with minor modifications. In brief, the reaction was carried out in a buffer consisting of 50 mM Tris pH 7.5, 100 mM NaCl, 1 mM EGTA, 2 mM DTT, 0.01% Brij, 5% DMSO and 10 mM MgCl$_2$ (commercial buffer) supplemented with fresh 300 μM ATP (31 μCi/ml) and 30 μg/ml histone type IIIss final concentrations. A reaction volume of 80 µL, containing units of enzyme, was run for 20 minutes at 25 degrees C. in the presence or absence of inhibitor. The reaction was terminated by the addition of 120 µL of 10% acetic acid. The substrate was separated from unincorporated label by spotting the mixture on phosphocellulose paper, followed by 3 washes of 5 minutes each with 75 mM phosphoric acid. Counts were measured by a betacounter in the presence of liquid scintillant.

Certain compounds of this invention significantly inhibit cdc2 at concentrations below 50 uM.

PKC Kinase Source

The catalytic subunit of PKC may be obtained commercially (Calbiochem).

PKC Kinase Assay

A radioactive kinase assay was employed following a published procedure (Yasuda, I., Kirshimoto, A., Tanaka, S., Tominaga, M., Sakurai, A., Nishizuka, Y. *Biochemical and Biophysical Research Communication* 3:166, 1220–1227 (1990)). Briefly, all reactions were performed in a kinase buffer consisting of 50 mM Tris-HCl pH7.5, 10 mM $MgCl_2$, 2 mM DTT, 1 mM EGTA, 100 µM ATP, 8 µM peptide, 5% DMSO and $^{33}P$ ATP (8Ci/mM). Compound and enzyme were mixed in the reaction vessel and the reaction initiated by addition of the ATP and substrate mixture. Following termination of the reaction by the addition of 10 µL stop buffer (5 mM ATP in 75 mM phosphoric acid), a portion of the mixture was spotted on phosphocellulose filters. The spotted samples were washed 3 times in 75 mM phosphoric acid at room temperature for 5 to 15 minutes. Incorporation of radiolabel was quantified by liquid scintillation counting.

Erk2 Enzyme Source

The recombinant murine enzyme and assay buffer may be obtained commercially (New England Biolabs, Beverly Mass. USA) or purified from known natural or recombinant sources using conventional methods.

Erk2 Enzyme Assay

In brief, the reaction was carried out in a buffer consisting of 50 mM Tris pH 7.5, 1 nM EGTA, 2 mM DTT, 0.01% Brij, 5% DMSO and 10 mM $MgCl_2$ (commercial buffer) supplemented with fresh 100 µM ATP (31 µCi/ml) and 30 µM myelin basic protein under conditions recommended by the supplier. Reaction volumes and method of assaying incorporated radioactivity were as described for the PKC assay (vide supra).

In Vitro Models for T-cell Activation

Upon activation by mitogen or antigen, T-cells are induced to secrete IL-2, a growth factor that supports their subsequent proliferative phase. Therefore, one may measure either production of IL-2 from or cell proliferation of, primary T-cells or appropriate T-cell lines as a surrogate for T-cell activation. Both of these assays are well described in the literature and their parameters well documented (in Current Protocols in Immunology, Vol 2, 7.10.1–7.11.2).

In brief, T-cells may be activated by co-culture with allogenic stimulator cells, a process termed the one-way mixed lymphophocyte reaction. Responder and stimulator peripheral blood mononuclear cells are purified by Ficoll-Hypaque gradient (Pharmacia) per directions of the manufacturer. Stimulator cells are mitotically inactivated by treatment with mitomycin C (Sigma) or gamma irradiation. Responder and stimulator cells are co-cultured at a ratio of two to one in the presence or absence of the test compound. Typically $10^5$ responders are mixed with $5 \times 10^4$ stimulators and plated (200 µl volume) in a U bottom microtiter plate (Costar Scientific). The cells are cultured in RPMI 1640 supplemented with either heat inactivated fetal bovine serum (Hyclone Laboratories) or pooled human AB serum from male donors, $5 \times 10^{-5}$ M 2-mercaptoethanol and 0.5% DMSO, The cultures are pulsed with 0.5 µCi of $^3H$ thymidine (Amersham) one day prior to harvest (typically day three). The cultures are harvested (Betaplate harvester, Wallac) and isotope uptake assessed by liquid scintillation (Betaplate, Wallac).

The same culture system may be used for assessing T-cell activation by measurement of IL-2 production. Eighteen to twenty-four hours after culture initiation, the supernatants are removed and the IL-2 concentration is measured by ELISA (R and D Systems) following the directions of the manufacturer.

In-Vivo Models of T-Cell Activation

The in vivo efficacy of compounds can be tested in animal models known to directly measure T-cell activation or for which T-cells have been proven the effectors. T-cells can be activated in vivo by ligation of the constant portion of the T-cell receptor with a monoclonal anti-CD3 antibody (Ab). In this model, BALB/c mice are given 10 µg of anti-CD3 Ab intraperitoneally two hours prior to exsanguination. Animals to receive a test drug are pre-treated with a single dose of the compound one hour prior to anti-CD3 Ab administration. Serum levels of the proinflammatory cytokines interferon-γ (IFN-γ) and tumor necrosis factor-α(TNF-α), indicators of T-cell activation, are measured by ELISA. A similar model employs in vivo T-cell priming with a specific antigen such as keyhole limpet hemocyanin (KLH) followed by a secondary in vitro challenge of draining lymph node cells with the same antigen. As previously, measurement of cytokine production is used to assess the activation state of the cultured cells. Briefly, C57BL/6 mice are immunized subcutaneously with 100 µg KLH emulsified in complete Freund's adjuvant (CFA) on day zero. Animals are pre-treated with the compound one day prior to immunization and subsequently on days one, two and three post immunization. Draining lymph nodes are harvested on day 4 and their cells cultured at $6 \times 10^6$ per ml in tissue culture medium (RPMI 1640 supplemented with heat inactivated fetal bovine serum (Hyclone Laboratories) $5 \times 10^{-5}$ M 2-mercaptoethanol and 0.5% DMSO) for both twenty-four and forty-eight hours. Culture supernatants are then assessed for the autocrine T-cell growth factor Interleukin-2 (IL-2) and/or IFN-γ levels by ELISA.

Lead compounds can also be tested in animal models of human disease. These are exemplified by experimental autoimmune encephalomyelitis (EAE) and collagen-induced arthritis (CIA). EAE models which mimic aspects of human multiple sclerosis have been described in both rats and mice (reviewed FASEB J. 5:2560–2566, 1991; murine model: Lab. Invest. 4(3):278, 1981; rodent model:J. Immunol 146 (4):1163–8, 1991). Briefly, mice or rats are immunized with an emulsion of myelin basic protein (MBP), or neurogenic peptide derivatives thereof, and CFA. Acute disease can be induced with the addition of bacterial toxins such as *bordetella pertussis*. Relapsing/remitting disease is induced by adoptive transfer of T-cells from MBP/peptide immunized animals.

CIA may be induced in DBA/1 mice by immunization with type II collagen (J. Immunol:142(7):2237–2243). Mice will develop signs of arthritis as early as ten days following antigen challenge and may be scored for as long as ninety days after immunization. In both the EAE and CIA models, a compound may be administered either prophylactically or at the time of disease onset. Efficacious drugs should reduce severity and/or incidence.

Certain compounds of this invention which inhibit one or more angiogenic receptor PTK, and/or a protein kinase such as Ick involved in mediating inflammatory responses can reduce the severity and incidence of arthritis in these models.

Compounds can also be tested in mouse allograft models, either skin (reviewed in Ann. Rev. Immunol., 10:333–58, 1992; Transplantation: 57(12): 1701–17D6, 1994) or heart (Am.J.Anat.: 113:273, 1963). Briefly, full thickness skin grafts are transplanted from C57BL/6 mice to BALB/c mice. The grafts can be examined daily, beginning at day six, for evidence of rejection. In the mouse neonatal heart transplant model, neonatal hearts are ectopically transplanted from C57BL/6 mice into the ear pinnae of adult CBA/J mice. Hearts start to beat four to seven days post transplantation and rejection may be assessed visually using a dissecting microscope to look for cessation of beating.

Cellular Receptor PTK Assays

The following cellular assay was used to determine the level of activity and effect of the different compounds of the present invention on KDR/VEGFR2. Similar receptor PTK assays employing a specific ligand stimulus can be designed along the same lines for other tyrosine kinases using techniques well known in the art.

VEGF-Induced KDR Phosphorylation in Human Umbilical Vein Endothelial Cells (HUVEC) as Measured by Western Blots:

1. HUVEC cells (from pooled donors) were purchased from Clonetics (San Diego, Calif.) and cultured according to the manufacturer directions. Only early passages (3–8) were used for this assay. Cells were cultured in 100 mm dishes (Falcon for tissue culture; Becton Dickinson; Plymouth, England) using complete EBM media (Clonetics).

2. For evaluating a compound's inhibitory activity, cells were trypsinized and seeded at $0.5–1.0 \times 10^5$ cells/well in each well of 6-well cluster plates (Costar; Cambridge, Mass.).

3. 3–4 days after seeding, plates were 90–100% confluent. Medium was removed from all the wells, cells were rinsed with 5–10 ml of PBS and incubated 18–24 h with 5 ml of EBM base media with no supplements added (i.e., serum starvation).

4. Serial dilutions of inhibitors were added in 1 ml of EBM media (25 µM, 5 µM, or 1 µM final concentration to cells and incubated for one hour at 37 C. Human recombinant $VEGF_{165}$ (R & D Systems) was then added to all the wells in 2 ml of EBM medium at a final concentration of 50 ng/ml and incubated at 37 C for 10 minutes. Control cells untreated or treated with VEGF only were used to assess background phosphorylation and phosphorylation induction by VEGF.

All wells were then rinsed with 5–10 ml of cold PBS containing 1 mM Sodium Orthovanadate (Sigma) and cells were lysed and scraped in 200 µl of RIPA buffer (50 mM Tris-HCl) pH7, 150 mM NaCl, 1% NP-40, 0.25% sodium deoxycholate, 1 mM EDTA) containing protease inhibitors (PMSF 1 mM, aprotinin 1 µg/ml, pepstatin 1 µg/ml, leupeptin 1 µg/ml, Na vanadate 1 mM, Na fluoride 1 mM) and 1 µg/ml of Dnase (all chemicals from Sigma Chemical Company, St Louis, Mo.). The lysate was spun at 14,000 rpm for 30 min, to eliminate nuclei.

Equal amounts of proteins were then precipitated by addition of cold (–20 C) Ethanol (2 volumes) for a minimum of 1 hour or a maximum of overnight. Pellets were reconstituted in Laemli sample buffer containing 5%-mercaptoethanol (BioRad; Hercules, Calif.) and boiled for 5 min. The proteins were resolved by polyacrylamide gel electrophoresis (PAGE; 6%, 1.5 mm Novex, San Deigo, Calif.) and transferred onto a nitrocellulose membrane using the Novex system. After blocking with bovine serum albumin (3%), the proteins were probed overnight with anti-KDR polyclonal antibody (C20, Santa Cruz Biotechnology; Santa Cruz, Calif.) or with anti-phosphotyrosine monoclonal antibody (4G10, Upstate Biotechnology, Lake Placid, N.Y.) at 4° C. After washing and incubating for 1 hour with HRP-conjugated $F(ab)_2$ of goat anti-rabbit or goat-anti-mouse IgG the bands were visualized using the emission chemiluminescence (ECL) system (Amersham Life Sciences, Arlington Height, Ill.).

Certain examples of the present invention significantly inhibit cellular VEGF-induced KDR tyrosine kinase phosphorylation at concentrations of less than 50 µM.

The inhibition of VEGF-induced KDR-receptor autophosphorylation can be confirmed with a further in vitro experiment transfected CHO cells (CHO=Chinese hamster ovary), which permanently express human VEGF receptor (KDR). Cells are seeded in culture medium (with 10% fetal calf serum=FCS) in 6-well cell-culture plates and incubated at 37° C. under 5% $CO_2$ until they show about 80% confluency. The compounds to be tested are then diluted in culture medium (without FCS, with 0.1% bovine serum albumin) and added to the cells. (Controls compromise medium without test compounds). After two hours' incubation at 37° C., recombinant VEGF is added; the final VEGF concentration is 20 ng/ml.) After a further 5 minutes' incubation at 37° C., the cells are washed twice with ice-cold PBS (phosphate-buffered saline) and immediately lysed in 100 µl lysis buffer per well. The lysates are then centrifuged to remove the cell nuclei, and the protein concentrations of the supernatants are determined using a commercial protein assay (BIORAD). The lysates can then either be immediately used or, if necessary, stored at –20° C. before being assessed using PAGE and immunoblotting as described above.

In vivo Uterine Edema Model

This assay measures the capacity of compounds to inhibit the acute increase in uterine weight in mice which occurs in the first few hours following estrogen stimulation. This early onset of uterine weight increase is known to be due to edema caused by increased permeability of uterine vasculature. Cullinan-Bove and Koss (*Endocrinology* (1993), 133:829–837) demonstrated a close temporal relationship of estrogen-stimulated uterine edema with increased expression of VEGF mRNA in the rat uterus. These results have been confirmed by the use of neutralizing monoclonal antibody to VEGF which significantly reduced the acute increase in uterine weight following estrogen stimulation (WO 97/42187). Hence, this system can serve as a model for in vivo inhibition of VEGF signalling and the associated hyperpermeability and edema. Materials: All hormones were purchased from Sigma (St. Louis, Mo.) or Cal Biochem (La Jolla, Calif.) as lyophilized powders and prepared according to supplier instructions. Vehicle components (DMSO, Cremaphor EL) were purchased from Sigma (St. Louis, Mo.). Mice (Balb/c, 8–12 weeks old) were purchased from Taconic (Germantown, N.Y.) and housed in a pathogen-free animal facility in accordance with institutional Animal Care and Use Committee Guidelines.

Method:

Day 1: Balb/c mice were given an intraperitoneal (i.p.) injection of 12.5 units of pregnant mare's serum gonadotropin (PMSG).

Day 3: Mice received 15 units of human chorionic gonadotropin (hCG) i.p.

Day 4: Mice were randomized and divided into groups of 5–10. Test compounds were administered by i.p., i.v. or p.o. routes depending on solubility and vehicle at doses ranging from 1–100 mg/kg. Vehicle control group received vehicle only and two groups were left untreated.

Thirty minutes later, experimental, vehicle and 1 of the untreated groups were given an i.p. injection of 17-estradiol (500 mg/kg). After 2–3 hours, the animals were sacrificed by $CO_2$ inhalation. Following a midline incision, each uterus was isolated and removed by cutting just below the cervix and at the junctions of the uterus and oviducts. Fat and connective tissue were removed with care not to disturb the integrity of the uterus prior to weighing (wet weight). Uteri were blotted to remove fluid by pressing between two sheets of filter paper with a one liter glass bottle filled with water. Uteri were weighed following blotting (blotted weight). The difference between wet and blotted weights was taken as the fluid content of the uterus. Mean fluid content of treated groups was compared to untreated or vehicle treated groups. Significance was determined by Student's test. Non-stimulated control group was used to monitor estradiol response.

Results demonstrate that certain compounds of the present invention inhibit the formation of edema when administered systemically by various routes.

Certain compounds of this invention which are inhibitors of angiogenic receptor tyrosine kinases can also be shown active in a Matrigel implant model of neovascularization. The Matrigel neovascularization model involves the formation of new blood vessels within a clear marble of extracellular matrix implanted subcutaneously which is induced by the presence of proangiogenic factor producing tumor cells (for examples see: Passaniti, A., et al, Lab. Investig. (1992), 67(4), 519–528; Anat. Rec. (1997), 249(1), 63–73; Int. J. Cancer (1995), 63(5), 694–701; Vasc. Biol. (1995), 15(11), 1857–6). The model preferably runs over 3–4 days and endpoints include macroscopic visual/image scoring of neovascularization, microscopic microvessel density determinations, and hemoglobin quantitation (Drabkin method) following removal of the implant versus controls from animals untreated with inhibitors. The model may alternatively employ bFGF or HGF as the stimulus.

Certain compounds of this invention which inhibit one or more oncogenic, protooncogenic, or proliferation-dependent protein kinases, or angiogenic receptor PTK also inhibit the growth of primary murine, rat or human xenograft tumors in mice, or inhibit metastasis in murine models.

The antitumor efficacy of a compound of the present invention can be demonstrated in vivo as follows: in vivo activity in the nude mouse xenotransplant model: female BALB/c nude mice (8–12 weeks old, for example Novartis Animal Farm, Sisseln, Switzerland) are kept under sterile conditions with water and feed ad libitum. Tumours are induced by subcutaneous injection of tumour cells (e.g., human epithelial cell line A431; American Type Culture Collection (ATCC), Rockville, Md., USA, Catalogue Number ATCC CRL 1555; cell line from 85-year-old woman; epidermoid carcinoma cell line) into carrier mice. The resulting tumours pass through at least three consecutive transplantations before the start of treatment if tumor fragments are employed. Tumour fragments (about 25 mg) are implanted subcutaneously in the left flank of the animals using a 13-gauge trocar needle under Forene® anaesthesia (Abbott, Switzerland). Treatment with the test compound is started as soon as the tumour has reached a mean volume of 100 $mm^3$. Tumour growth is measured two to three times a week and 24 hours after the last treatment by determining the length of two perpendicular axes. The tumour volumes are calculated in accordance with published methods (see Evans et al., Brit. J. Cancer 45, 466–8 [1982]). The antitumour efficacy is determined as the mean increase in tumour volume of the treated animals divided by the mean increase in tumour volume of the untreated animals (controls) and, after multiplication by 100, is expressed as T/C %. Tumour regression (given in %) is reported as the smallest mean tumour volume in relation to the mean tumour volume at the start of treatment. The test compound is administered daily by gavage.

As an alternative to cell line A431, other cell lines may also be used in the same manner, for example:
- the MCF-7 breast adenocarcinoma cell line (ATCC No. HTB 22; see also J. Natl. Cancer Inst. (Bethesda) 51, 1409–16 [1973]);
- the MDA-MB 468 breast adenocarcinoma cell line (ATCC No. HTB 132; see also In Vitro 14, 911–15 [1978]);
- the MDA-MB 231 breast adenocarcinoma cell line (ATTC No. HTB 26; see also J. Natl. Cancer Inst. (Bethesda) 53, 661–71 [1974]);
- the colo 205 colon carcinoma cell line (ATCC No. CCL 222; see also Cancer Res. 38 1345–55 [1978]);
- the HCT 116 colon carcinoma cell line (ATCC No. 247; see also Cancer Res. 41, 1751–6 [1981];
- the DU145 prostate carcinoma cell line DU 145 (ATCC No. HTB 81; see also Cancer Res. 37, 4049–58 [1978]; or
- the PC-3 prostate carcinoma cell line PC-3 (ATCC No. CRL 1435; see also Cancer Res. 40, 524–34 [1980].

The activity of compounds of a compound of the present invention against pain can be shown in the following mode of nociception (pain). In this model, the hyperalgesia caused by an inter-planar yeast injection is measured by applying increased pressure to the foot until the animal vocalizes or withdraws its foot from the applied pressure pad. The model is sensitive to COX inhibitors, diclofenac at 3 mg/kg is used as a positive control.

Method: The baseline pressure required to induce vocalization or withdrawl of the paw of male Sprague Dawley rats (weighing approximately 180 g, supplied by Iffa Credo, France) is measured (2 hours before treatment), followed by an intra-planar injection of 100 μl of a 20% yeast suspension in water in the hind paw. The rats are treated orally with the test compound (3, 10 or 30 mg/kg), diclofenac (3 mg/kg) or vehicle (saline) p.o. 2 hours later (time point 0 hours), and the pressure test is repeated 1 and 2 hours after dosing. Using the standard apparatus supplied by Ugo Basile, Italy, the pressure required to induce vocalization or paw withdrawl of the compound-treated rats at these time points is compared to that of vehicle-treated animals.

A test compound of the formula 1 inhibits paw hyperalgesia both at 1 and 2 hours after dosing in the Randall-Selitto test preferably in the 20–75 mg/kg p.o. dose range, preferably by 10 to 100%, demonstrating that the compound has analgesic activity.

On the basis of these studies, a compound of the present invention surprisingly is appropriate for the treatment of inflammatory (especially rheumatic or rheumatoid) diseases and/or pain.

General Procedures. The compounds of the present invention can be and were synthesized according to the following description and examples. Unless otherwise specified, all starting materials and solvents were obtained from commercially available sources and were used without further purification. LCMS analyses and purification were performed using a Gilson HPLC system equipped with a 215 autosampler attached to a Micromass Platform Mass Spectrometer. Acetonitrile and aqueous 50 mM ammonium acetate (pH 4.5) were used to elute products from either a Pecosphere C18, 3 μm, 33×4.6 mm column or a Hypersil BDS-C18, 5 μm, 100×20 mm column for analytical or preparative work, respectively. A linear gradient from 0–100% acetonitrile over 4.5 min with a flow rate of 3.5 mL/min was used for analytical analysis. A linear gradient from 0–100% acetonitrile over 8.5 min with a flow rate of 25 mL/min was used for preparative separations. NMR spectra were recorded on a Bruker 400 MHz spectrometer with a deuterated solvent as the internal lock. $^1$H NMR data are reported as chemical shift (ppm), multiplicity, number of hydrogens, where the chemical shift is referenced to TMS.

Scheme I

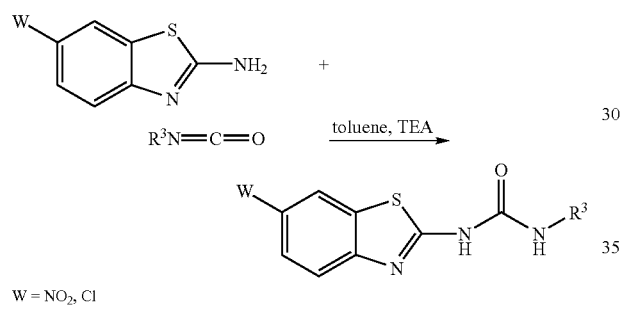

W = NO$_2$, Cl

Scheme II

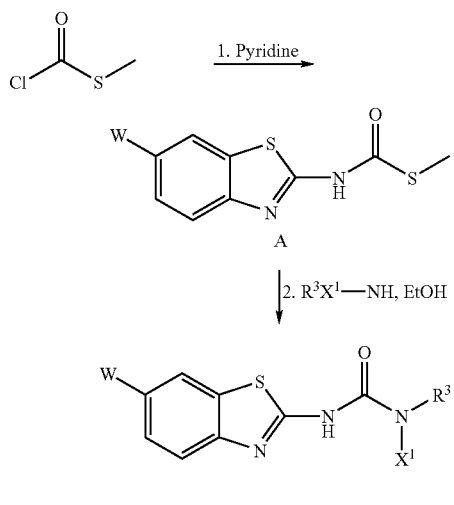

Scheme III

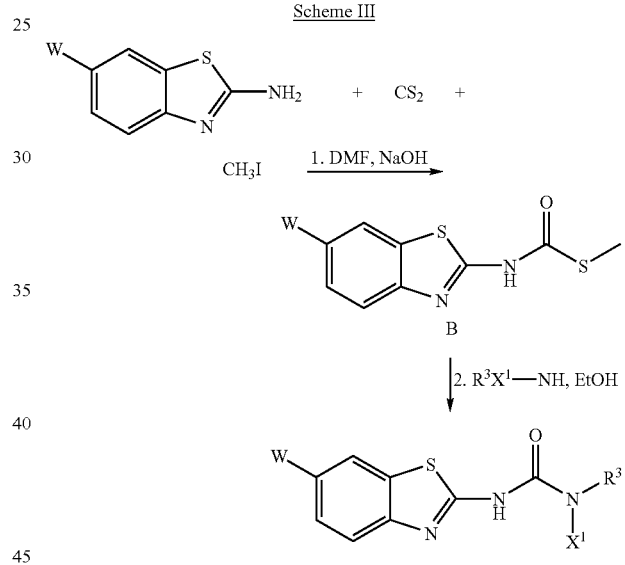

W = NO$_2$, Cl

Scheme IIIA

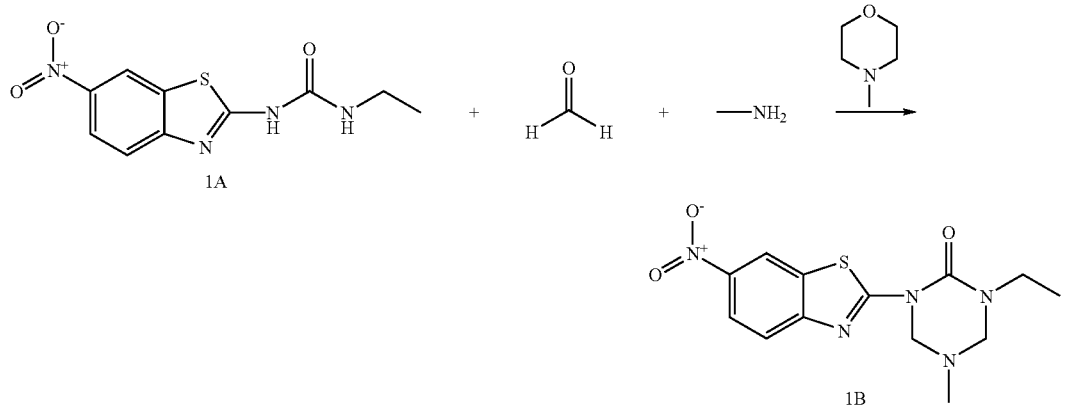

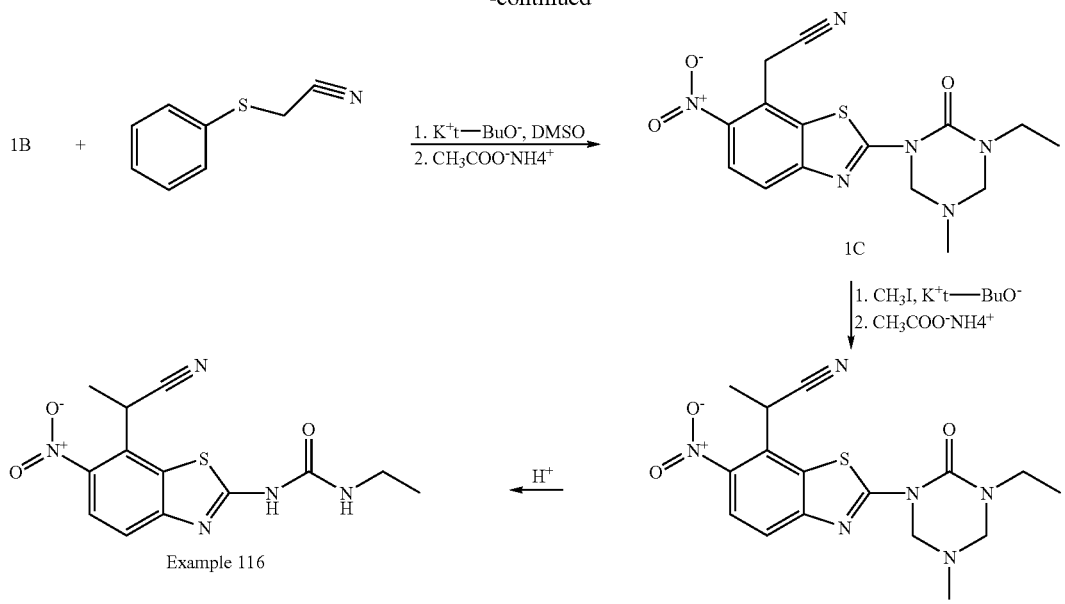

Example 116

General Description of Scheme I. A 1 dram vial is charged with either an aromatic or aliphatic isocyanate in an inert solvent such as toluene. An equal or excess molar ratio of 2-amino-6-nitrobenzothiazole or 2-amino-6-chlorobenzothiazole is added as a solid in one portion followed by addition of an equal molar ratio of a base such as triethylamine. The reaction mixture is heated with agitation in an incubator shaker at about 80° C. until the starting material is consumed. The precipitated product is collected by standard methods and washed with ether.

EXAMPLE 1

The following examples are representative of a synthesis in accordance with Scheme I.

EXAMPLE 1A

A 1 dram vial was charged with 3,5-dimethoxyphenylisocyanate (51 mg, 0.282 mmol) in 1 mL of toluene, and 2-amino-6-nitrobenzothiazole (50 mg, 0.256 mmol) was added as a solid in one portion followed by addition of triethylamine (36 µL, 0.256 mmol). The reaction mixture was heated with agitation in an incubator shaker at about 80° C. until the starting material was consumed. The product precipitated and was collected on a fritted funnel and washed with diethyl ether. (M–H) 373, HPLC RT 2.99 min, $^1$H NMR (δ-DMSO) 3.76 (s, 3H), 3.75 (s, 3H), 6.25 (s, 1H), 6.74 (s, 2H), 7.79 (d, 1H, J=8), 8.2 (dd, 1H, J=2 and J=8), 8.98 (s, 1H), 9.19 (br s, 1H), 11.20 (br s, 1H).

EXAMPLE 1B

A 1 dram vial was charged with ethyl isocyanate (2.1 mL, 24.5 mmol), 2-amino-6-chlorobenzothiazole (4.48 g, 24.3 mmol), and triethylamine (3.4 mL, 24.3 mmol) in 100 mL of toluene. The reaction mixture was heated to reflux and the reaction progress monitored until the starting material was consumed. The product was collected on a fritted funnel and washed with diethyl ether to yield 5.68 g, (92%) of pure material. HPLC RT 1.96 min; (M–H)253; $^1$H NMR (d-DMSO) δ 1.10 (t, 3H), 3.2 (q, 2H), 6.72 (br s, 1H), 7.38 (d, 1H), 7.61 (d, 1H), 8.01 (s, 1H), 10.77 (br s, 1H).

General Description of Scheme II. Synthesis of A of Scheme II. A round bottom flask is charged with 2-amino-6-nitro-benzothiazole or 2-amino-6-chloro-benzothiazole and methyl chlorothioformate in pyridine. The reaction mixture is heated at about 50° C. for about 8 hours and cooled to room temperature overnight. The off-white solid is collected on a fritted funnel, washed with diethyl ether, and dried in vacuo to yield the desired product.

A 1 dram vial is charged with A (1 eq) and the appropriate amine (about 1.2 eq or more) in absolute EtOH. The reaction mixture is heated to about 80° C. with agitation in an incubator shaker until all of the starting material is consumed. Products that precipitate are collected on a fritted funnel, washed with diethyl ether, and dried in vacuo. Products that do not precipitate are purified by preparative reversed-phase HPLC.

EXAMPLE 2

This example is representative of a synthesis in accordance with Scheme II. A 500 mL round bottom flask was charged with 2-amino-6-nitro-benzothiazole (7.0 g, 0.036 mol) and methyl chlorothioformate (6 g, 0.0543 mol) in 250 mL pyridine. The reaction mixture was heated at about 50° C. for about 8 hours and cooled to room temperature overnight. The off-white solid was collected on a fritted funnel, washed with diethyl ether, and dried in vacuo to yield 4.6 g, 47%, of product. (M–H) 267.1, HPLC RT 3.22 min, $^1$H NMR: (δ-DMSO) 2.42 (s, 3H), 7.87 (d, 1H, J=9), 8.27 (dd, 1H, J=2 and 9), 9.00 (s, 1H), 13.27 (br s, 1H).

A 1 dram vial is charged with A (50 mg, 0.186 mmol) and 2-amino-2-methyl-propanol (20 mg, 0.223 mmol) in 1 mL of absolute ethanol. The reaction mixture was heated at about 80° C. for about 14 hours or until the starting material was consumed. The product precipitated upon cooling and was collected on a fritted funnel, washed with diethyl ether and dried in vacuo. ((M–H)) 309.1; HPLC RT 2.06 min; $^1$H NMR (δ-DMSO) 1.43 (s, 6H), 3.41 (d, 2H), 5.07 (t, 1H), 6.67 (br s, 1H), 7.73 (d, 1H), 8.2 (d, 1H), 8.92 (s, 1H), 10.94 (br s, 1H).

General Description of Scheme III. Synthesis of B of Scheme II. The synthesis of B is achieved as described by Merchan et. al. Synthesis, 1982, 590. Recrystallization of the product is performed using DMF.

A 1 dram vial is charged with B (1 eq) and the appropriate amine (about 1.2 eq) in absolute EtOH. The reaction mixture is heated to about 80° C. with agitation in an incubator shaker until all of the starting materials are consumed. Products that precipitate are collected on a fritted funnel, washed with diethyl ether, and dried in vacuo. Products that do not precipitate are purified by preparative HPLC.

EXAMPLE 3

This example is representative of a synthesis in accordance with Scheme III. To a stirring solution of 2-amino-6-nitro-benzothiazole (7 g, 0.036 mol) in DMF at about 0° C. was added dropwise NaOH (2.58 mL, 20M, 0.043 mol). The base was added in 3 portions with each addition separated by about 20 min. A dark red color was observed. Carbon disulfide (4.33 mL, 0.072 mol) was added dropwise over a period of about 10 minutes. The reaction mixture was stirred at about 0° C. for about 30 min. before another equivalent of NaOH was added in portions. Methyl iodide (2.23 mL, 0.036 mol) was added neat and the ice bath was removed. The reaction mixture was stirred at room temperature for about 2 hours. The reaction mixture was poured into 200 mL of deionized water and neutralized with 2 N HCl. The resulting suspension was stirred at room temperature overnight and the precipitate collected on a fritted funnel. The product was isolated as long, yellow, crystals. (M–H) 284; HPLC RT 2.69 min; $^1$H NMR (δ-DMSO) 2.86 (s, 3H), 7.71 (d, 1H), 8.3 (d, 1H), 8.98 (s, 1H).

A 1 dram vial was charged with B (30 mg, 0.106 mmol) and ethylamine (63 uL (2M in methanol), 0.126 mmol) in 1 mL of absolute ethanol. The reaction mixture was heated at about 80° C. for about 16 hours or until the starting material was consumed. The product precipitated upon cooling and was collected on a fritted funnel, washed with diethyl ether and dried in vacuo. (M–H) 281; HPLC RT 2.74 min; $^1$H NMR (δ-DMSO) 1.1 (t, 3H), 3.5 (q, 2H), 7.7 (d, 1H), 8.2 (d, 1H), 8.9 (s, 1H), 9.1 (br s, 1H), 12.15 (br s, 1H). (M–H) 284, HPLC RT 2.71 min, $^1$H NMR (δ-DMSO) 2.61 (s, 3H), 7.72 (d, 1H, J=11), 8.34 (dd, 1H, J=2 and 9), 9.00 (d, 1H, J=2).

General Description of Scheme IIIA. To a stirring suspension of 1A, formaldehyde and methylamine in a solution of alcohol/water is added to N-methylmorpholine. The reaction mixture is heated to about 60 to 100° C., preferably 80° C., for about 18–20 hours. Reaction progress is monitored by LCMS. The reaction is heterogeneous throughout the reaction. The desired product 1B is collected using standard methods in the art.

A round bottom flask is charged with 1B and (phenylthio)acetonitrile in DMSO at room temperature. A 1 M solution of potassium tert-butoxide in THF is added in one portion. The reaction mixture is stirred at room temperature overnight. The crude reaction mixture is SLOWLY added to a vigorously stirring mixture of ethyl acetate and ammonium acetate. The layers are separated and the organic layer dried over anhydrous sodium sulfate and the desired product, 1C, isolated according to standard methods known in the art.

To a stirring solution of 1C in DMSO is added a solution of potassium tert-butoxide (about 1 eq) in THF. Upon addition of the base the reaction mixture turned deep purple in color. An equivalent of methyl iodide is added in one portion. The reaction mixture turned a deep red color. The reaction mixture is stirred at room temperature for 1–6 hours. An aqueous solution of ammonium acetate is added and the product extracted with methylene chloride. The crude product is purified according to standard methods known in the art.

The triazone protecting group is removed under acidic conditions to yield the desired free urea. Neat trifluoroacetic acid, 1 N aqueous hydrochloric acid, 4 M hydrochloric acid in dioxane and a solution of 1:1 acetic acid in methanol all remove the protecting group at room temperature within 4–24 h. The preferred conditions for deprotection are 4 M HCl in dioxane at room temperature until the reaction is complete.

EXAMPLE 4

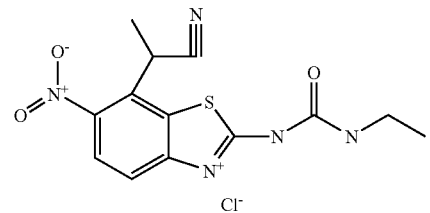

This example is representative of a synthesis in accordance with Scheme IIIA. To a stirring suspension of 1A (555 mg, 2.09 mmol), formaldehyde (1.02 g, 20.8 mmol), and methylamine (354 μL, 6.25 mmol) in a 1:1 (v/v) solution of ethanol/water was added N-methylmorpholine (583 μL, 4.17 mmol). The reaction mixture was heated to about 80° C. for about 18–20 hours. Reaction progress was monitored by LCMS. The reaction was heterogeneous throughout the reaction. The solid was collected on a fritted funnel to yield 575 mg (86%) of the desired product 1B as yellow needles. mp 193–194° C.; LCMS MH$^+$321.9 m/z; $^1$H NMR (d-DMSO) δ 8.9 (1H, s), 8.2 (1H, d), 7.8 (1H, d), 5.1 (2H, s), 4.3 (2H, s), 3.3 (2H, q), 2.6 (3H, s), 1.1 (3H, t); $^{13}$C NMR (d-DMSO) δ 164.6, 153.6, 151.0, 142.5, 133.5, 121.4, 120.0, 118.3, 69.1, 69.4, 38.5, 12.5.

A round bottom flask was charged with 1B (500 mg, 1.56 mmol) and (phenylthio)acetonitrile (279 μL, 1.87 mmol) in 10 mL of DMSO at room temperature. A 1 M solution of potassium tert-butoxide in THF (3.11 mL, 3.12 mmol) was added in one portion via syringe. Upon addition of the base the reaction mixture turned deep purple in color. The reaction mixture was stirred at room temperature overnight. The crude reaction mixture was SLOWLY added to a vigorously stirring mixture of ethyl acetate and 100 mM ammonium acetate. The layers were separated and the organic layer dried over anhydrous sodium sulfate. The solvent was removed in vacuo to yield 291 mg (52%) of product as a light brown solid. LCMS: 3.02 min; MH$^+$360 m/z.

To a stirring solution of 1C in DMSO was added a 1 M solution of potassium tert-butoxide (1 eq) in THF. Upon addition of the base the reaction mixture turned deep purple in color. An equivalent of methyl iodide was added in one portion. The reaction mixture turned a deep red color. The reaction mixture was stirred at room temperature for 1–6 hours. An aqueous solution of ammonium acetate (6M) was added and the product extracted with methylene chloride. The crude product was purified by preparative HPLC/MS. MH+375 m/z. The triazone protecting group was removed under acidic conditions, as described hereinabove, to yield the desired free urea title compound, LCMS: R.T. 2.66 min, MH-304 m/z.

EXAMPLE 5

N-(6-Chloro-1,3-benzothiazol-2-yl)-N'-ethylurea

Three grams of 6-chloro-1,3-benzothiazol-2-amine was dissolved in about 50 mL DMF. Next, about 2.5 mL of EtNCO was added followed by about 3.2 mL of triethylamine. The solution was allowed to react at about 80° C. for about 8 hours. The reaction solvent was then removed in vacuo and the crude oil was taken up in ether. The solids were isolated by filtration and washed with ether. The product was then dried in vacuo. $^1$H NMR 1.09 (t, 3H, J=7.2 Hz), 3.19 (m, 2H), 6.74 (br s, 1H), 7.37 (d, 1H, J=8.58 Hz), 7.60 (d, 1H, J=8.59 Hz), 8.01 (s, 1H), 10.8 (br s, 1H). LCMS: R.T. 2.3 min, MH-254 m/z.

EXAMPLE 6

N-(6-Chloro-5-nitro-1,3-benzothiazol-2-yl)-N'-ethylurea

Three grams of N-(6-chloro-1,3-benzothiazol-2-yl)-N'-ethylurea was dissolved in about 15 mL of concentrated sulfuric acid (about 92–94%). The solution was cooled to about 0–5° C. About 1.5 g of ice cooled nitric acid (70% concentration was used, though this is not necessary) was added dropwise. The reaction was held at 0–5° C. for about one hour then poured into water. The pH was then adjusted to about 7–8 with ammonia and the solids were isolated by filtration. The solids were washed with water then dried in vacuo. The product was further purified by chromatography then dried in vacuo. $^1$H NMR 1.08 (t, 3H, J=7.2 Hz), 3.19 (m, 2H), 6.92 (br s, 1H), 8.26 (s, 1H), 8.31 (s, 1H), LC/MS 3.72 min, 302 (M+1)

EXAMPLES 7–166

The following Examples were synthesized substantially according to the example indicated in the third column of the table using the appropriate starting material.

| Example # | Structure | Made according to example | Analytical RP-HPLC RT (min) | Mass Spec (m/z) |
|---|---|---|---|---|
| 7 | 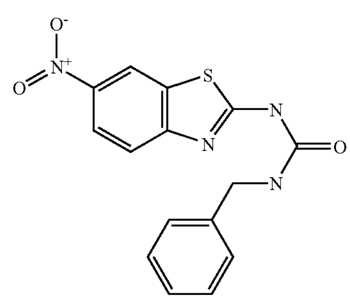 | 1 | 2.72 | 329 |
| 8 | 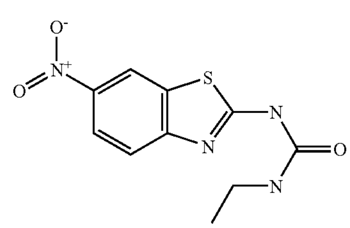 | 1 | 2.1 | 267 |
| 9 | 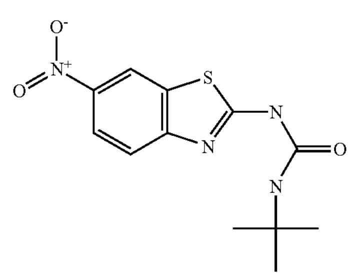 | 1 | 2.68 | 293 |

-continued

| Example # | Structure | Made according to example | Analytical RP-HPLC RT (min) | Mass Spec (m/z) |
|---|---|---|---|---|
| 10 | 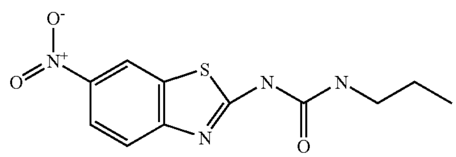 | 1 | 2.41 | 279 |
| 11 | 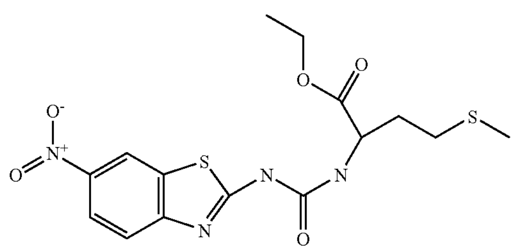 | 2 | 2.73 | 397 |
| 12 | 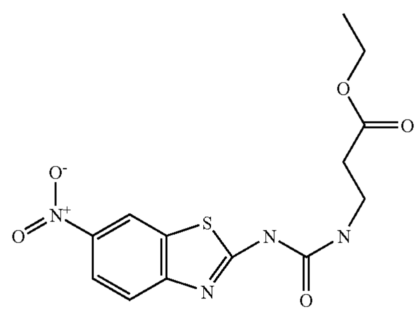 | 2 | 2.37 | 337 |
| 13 | 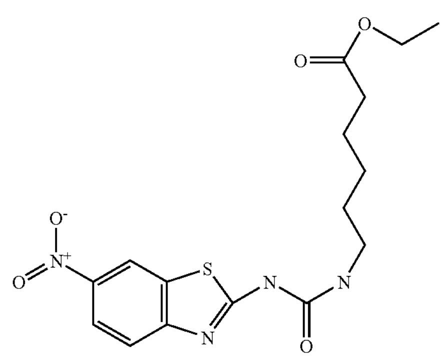 | 2 | 2.67 | 379 |
| 14 | 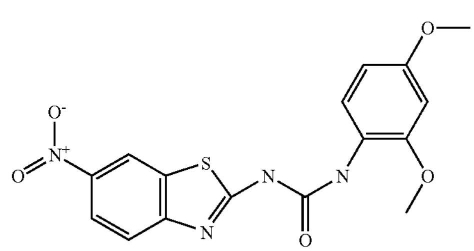 | 1 | 2.94 | 373 |

-continued

| Example # | Structure | Made according to example | Analytical RP-HPLC RT (min) | Mass Spec (m/z) |
|---|---|---|---|---|
| 15 | 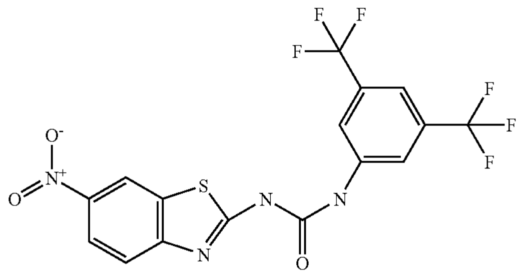 | 1 | 3.57 | 449 |
| 16 | 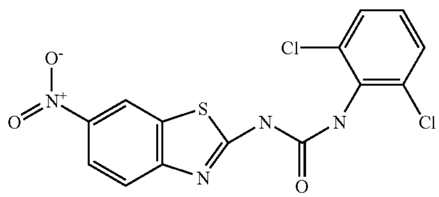 | 1 | 2.78 | 381 |
| 17 | 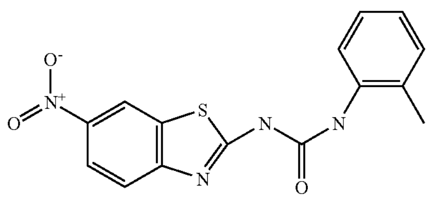 | 1 | 2.83 | 327 |
| 18 | 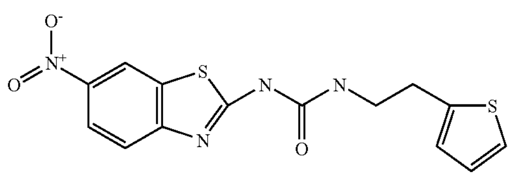 | 1 | 2.81 | 347 |
| 19 | 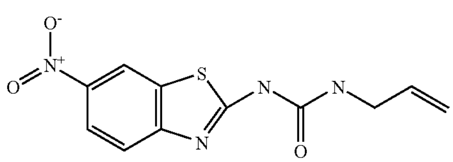 | 1 | 2.27 | 277 |
| 20 | 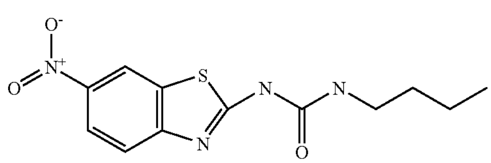 | 1 | 2.5 | 293 |
| 21 | 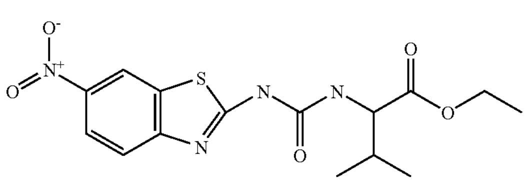 | 2 | 2.84 | 365 |

-continued
| Example # | Structure | Made according to example | Analytical RP-HPLC RT (min) | Mass Spec (m/z) |
|---|---|---|---|---|
| 22 | 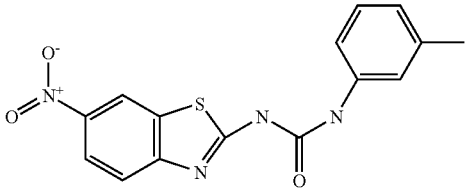 | 1 | 2.95 | 327 |
| 23 | 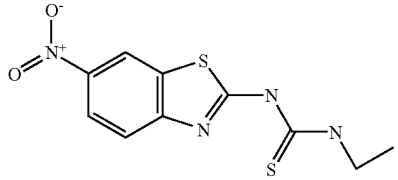 | 3 | 2.74 | 281 |
| 24 | 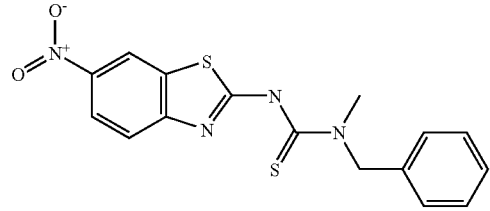 | 3 | 3.33 | 357 |
| 25 | 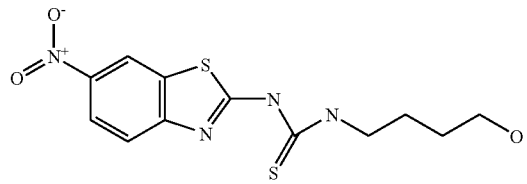 | 3 | 2.23 | 325 |
| 26 | 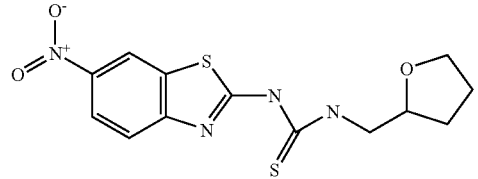 | 3 | 2.88 | 337 |
| 27 | 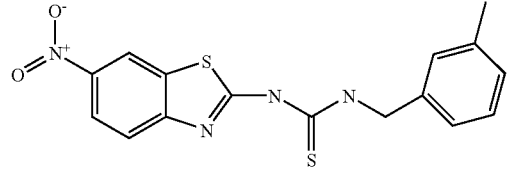 | 3 | 3.33 | 359 |
| 28 | 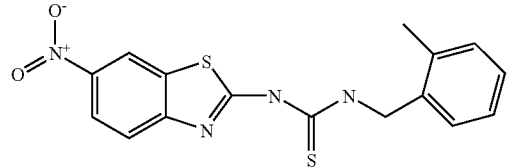 | 3 | 3.31 | 359 |

-continued

| Example # | Structure | Made according to example | Analytical RP-HPLC RT (min) | Mass Spec (m/z) |
|---|---|---|---|---|
| 29 | 6-nitrobenzothiazol-2-yl thiourea with 4-chlorobenzyl | 3 | 3.33 | 379* |
| 30 | 6-nitrobenzothiazol-2-yl thiourea with 3-chlorobenzyl | 3 | 3.33 | 379* |
| 31 | 6-nitrobenzothiazol-2-yl thiourea with furan-2-ylmethyl | 3 | 2.89 | 333 |
| 32 | 6-nitrobenzothiazol-2-yl urea with 4-(diethylamino)butyl, Cl⁻ | 2 | 1.79 | 366 |
| 33 | 6-nitrobenzothiazol-2-yl thiourea with 2-hydroxyethyl | 3 | 2.09 | 299 |
| 34 | 6-nitrobenzothiazol-2-yl thiourea with 3-(diethylamino)propyl | 3 | 1.73 | 366 |
| 35 | 6-nitrobenzothiazol-2-yl thiourea with 5-hydroxypentyl | 3 | 2.76 | 339 |

-continued

| Example # | Structure | Made according to example | Analytical RP-HPLC RT (min) | Mass Spec (m/z) |
|---|---|---|---|---|
| 36 | 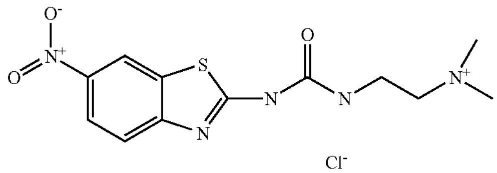 | 2 | 1.6 | 350 |
| 37 | 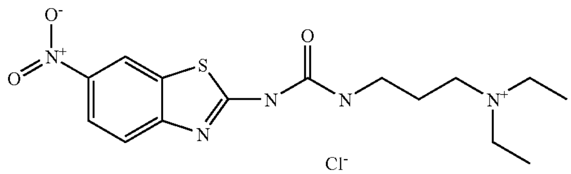 | 2 | 1.76 | 308 |
| 38 | 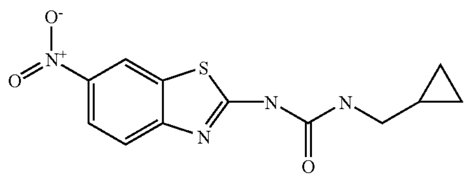 | 2 | 6.54 | 292 |
| 39 | 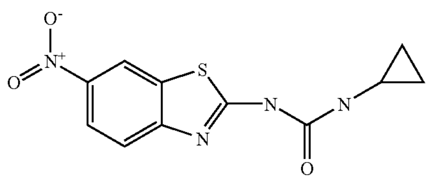 | 2 | 5.08 | 278 |
| 40 | 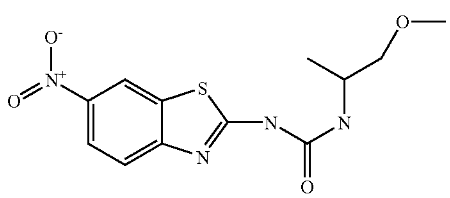 | 2 | 5.26 | 310 |
| 41 | 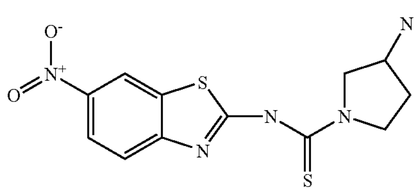 | 3 | 6.6 | 324 |
| 42 | 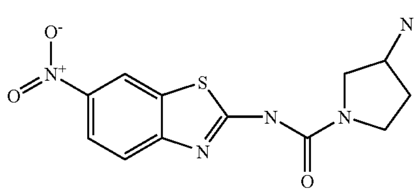 | 2 | 5.1 | 308 |
| 43 | 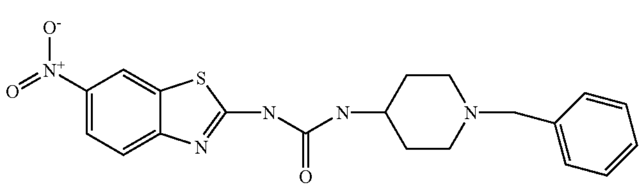 | 2 | 4 | 411 |

-continued

| Example # | Structure | Made according to example | Analytical RP-HPLC RT (min) | Mass Spec (m/z) |
|---|---|---|---|---|
| 44 | 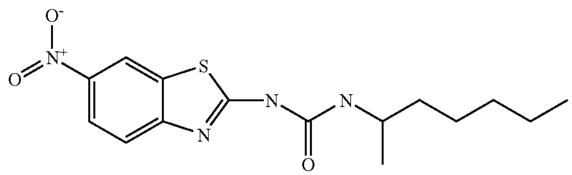 | 2 | 7.44 | 336 |
| 45 | 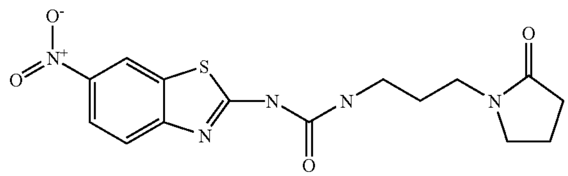 | 2 | 5.4 | 363 |
| 46 | 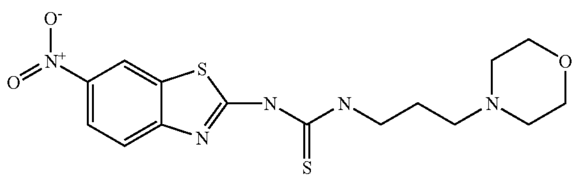 | 3 | 5.4 | 381 |
| 47 | 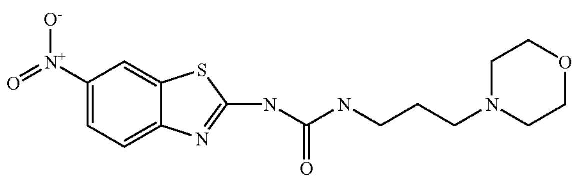 | 2 | 3.45 | 365 |
| 48 | 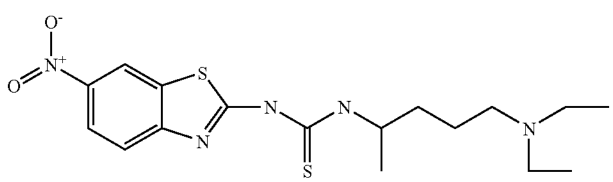 | 2 | 4.78 | 380 |
| 49 | 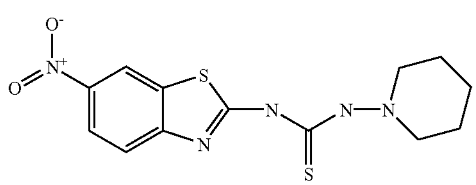 | 3 | 7.6 | 337 |
| 50 | 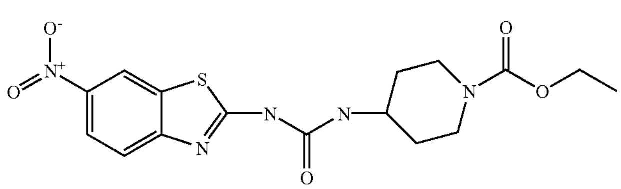 | 2 | 6.45 | 393 |
| 51 | 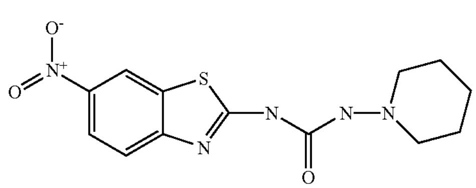 | 2 | 7.6 | 321 |

-continued

| Example # | Structure | Made according to example | Analytical RP-HPLC RT (min) | Mass Spec (m/z) |
|---|---|---|---|---|
| 52 | 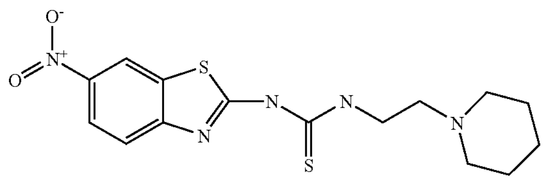 | 3 | 5 | 365 |
| 53 | 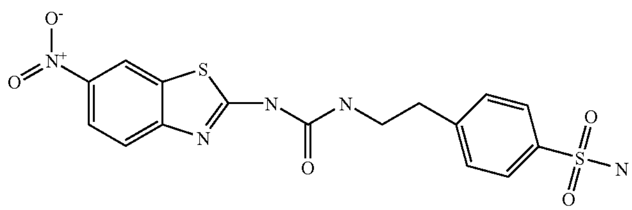 | 2 | 5.76 | 421 |
| 54 | 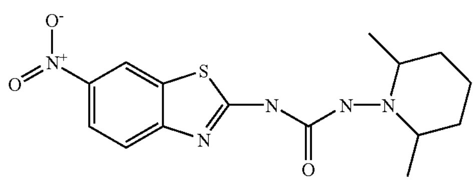 | 2 | 6.74 | 349 |
| 55 | 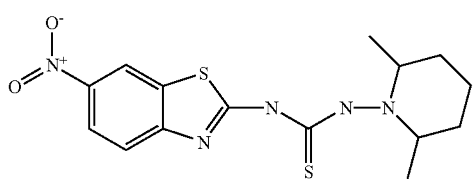 | 3 | 7.61 | 365 |
| 56 | 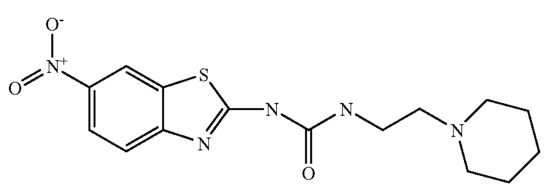 | 2 | 4.27 | 349 |
| 57 | 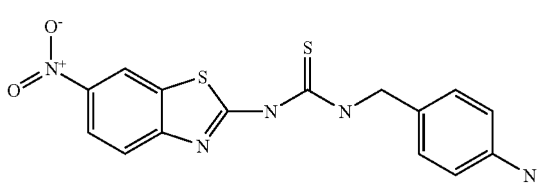 | 3 | 2.96 | 357.8 |
| 58 | 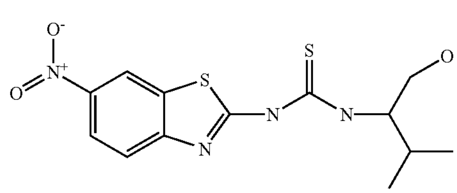 | 3 | 2.92 | 339 |

-continued

| Example # | Structure | Made according to example | Analytical RP-HPLC RT (min) | Mass Spec (m/z) |
|---|---|---|---|---|
| 59 | 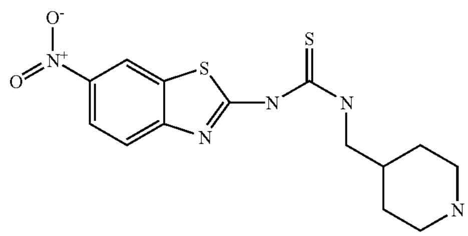 | 3 | 2.07 | 350 |
| 60 | 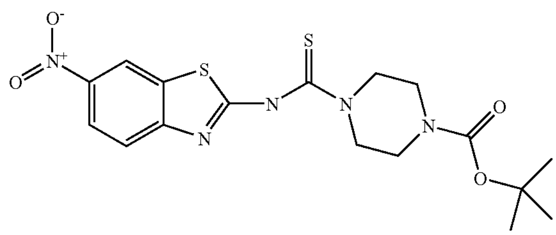 | 3 | 3.16 | 422 |
| 61 | 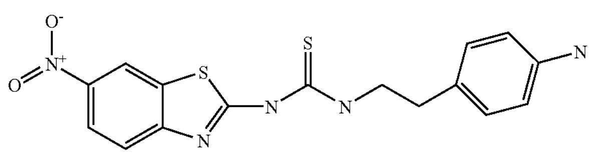 | 3 | 2.9 | 372 |
| 62 | 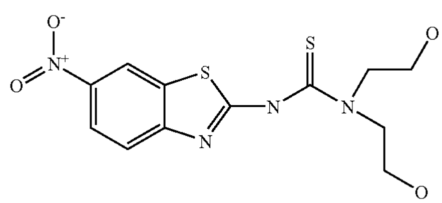 | 3 | 2.64 | 343* |
| 63 | 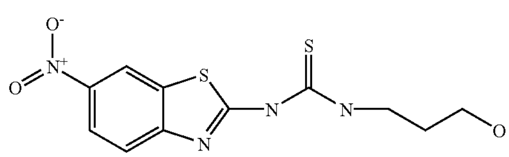 | 3 | 2.47 | 311 |
| 64 | Chiral | 3 | 2.59 | 311 |
| 65 | Chiral | 3 | 2.59 | 311 |

-continued

| Example # | Structure | Made according to example | Analytical RP-HPLC RT (min) | Mass Spec (m/z) |
|---|---|---|---|---|
| 66 | Chiral | 3 | 2.39 | 311 |
| 67 | 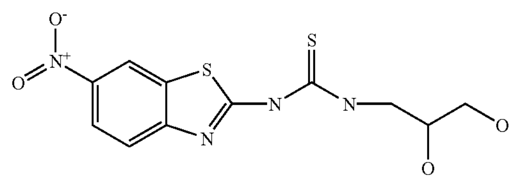 | 3 | 2.11 | 327 |
| 68 | 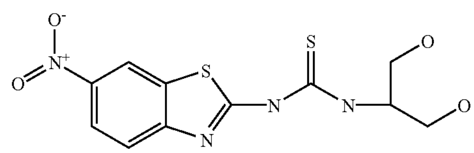 | 3 | 2.08 | 327 |
| 69 | 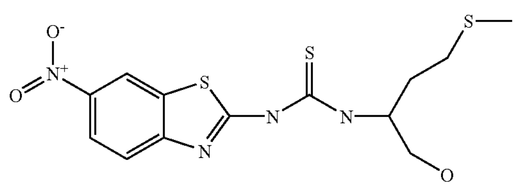 | 3 | 2.7 | 371 |
| 70 | 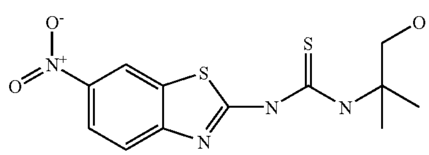 | 3 | 2.6 | 326 |
| 71 | Chiral | 3 | 3.16 | 353 |
| 72 | 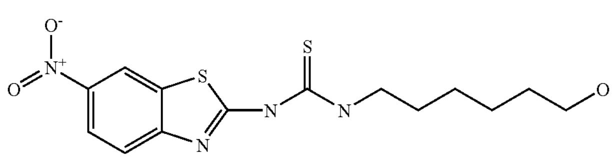 | 3 | 2.91 | 353 |
| 73 | 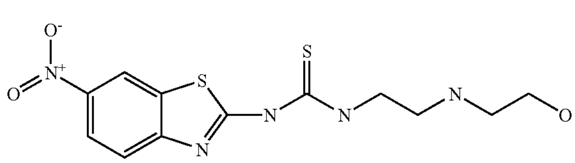 | 3 | 2.47 | 342* |

-continued

| Example # | Structure | Made according to example | Analytical RP-HPLC RT (min) | Mass Spec (m/z) |
|---|---|---|---|---|
| 74 | 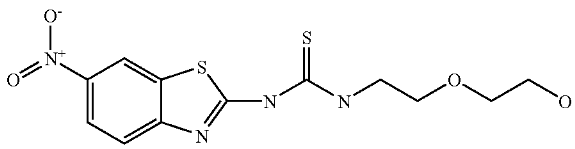 | 3 | 2.31 | 341 |
| 75 | 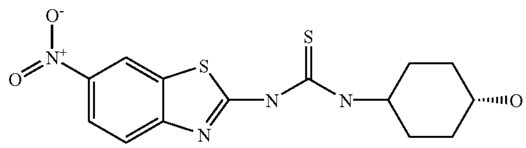 | 3 | 2.4 | 389* |
| 76 | 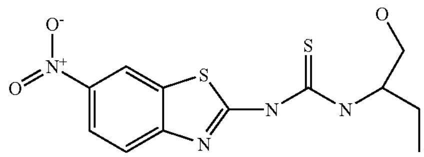 | 3 | 2.58 | 325 |
| 77 | 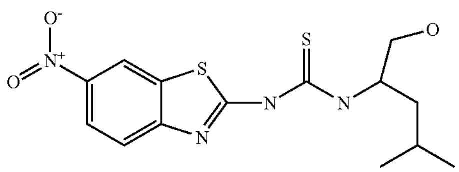 | 3 | 3.19 | 354 |
| 78 | Chiral | 3 | 2.34 | 312 |
| 79 | 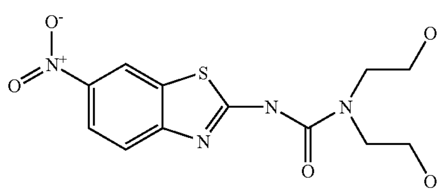 | 2 | 1.87 | 326 |
| 80 | Chiral | 2 | 2.42 | 324 |
| 81 | 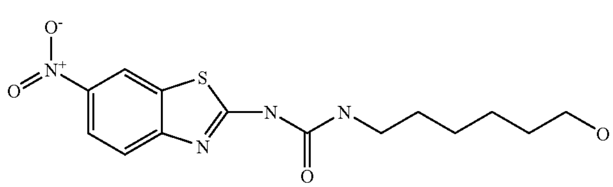 | 2 | 2.35 | 338 |

-continued

| Example # | Structure | Made according to example | Analytical RP-HPLC RT (min) | Mass Spec (m/z) |
|---|---|---|---|---|
| 82 | 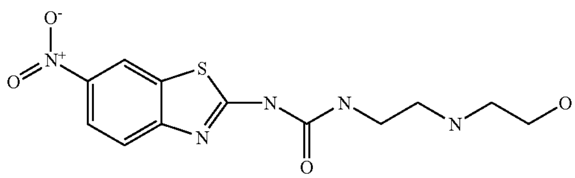 | 2 | 1.56 | 325 |
| 83 | 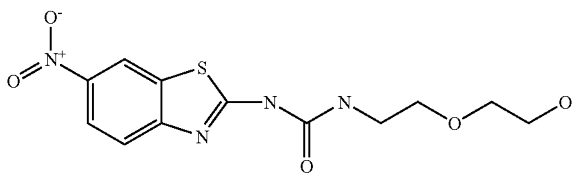 | 2 | 1.94 | 326 |
| 84 | Chiral | 2 | 2.18 | 310 |
| 85 | 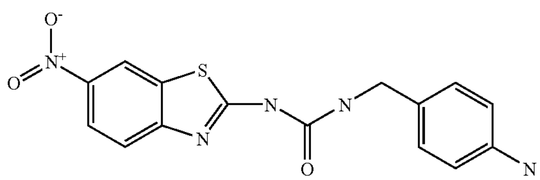 | 2 | 2.42 | 343 |
| 86 | Chiral | 2 | 2.62 | 338 |
| 87 | 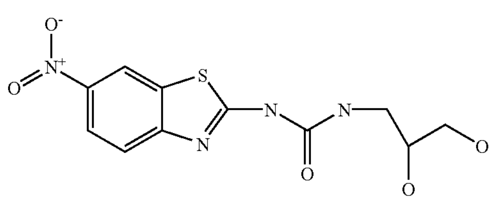 | 2 | 1.98 | 312 |
| 88 | Chiral | 2 | 2.04 | 296 |

-continued

| Example # | Structure | Made according to example | Analytical RP-HPLC RT (min) | Mass Spec (m/z) |
|---|---|---|---|---|
| 89 | Chiral | 2 | 2.04 | 296 |
| 90 | Chiral | 2 | 2.01 | 296 |
| 91 | 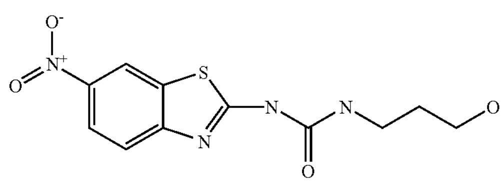 | 2 | 1.96 | 296 |
| 92 | 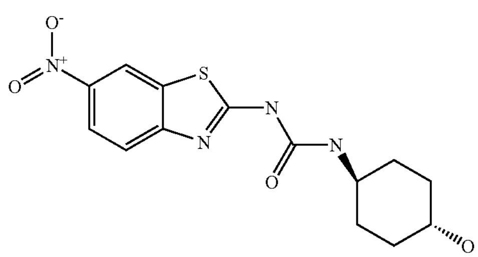 | 2 | NA | 372 |
| 93 | 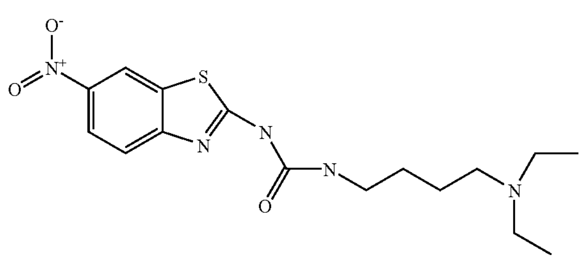 | 2 | 2.76 | 366 |
| 94 | 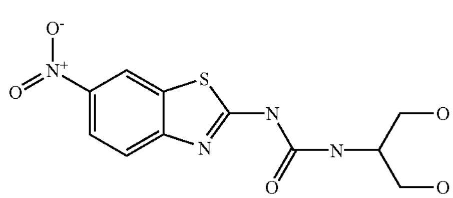 | 2 | 1.57 | 311 |
| 95 | 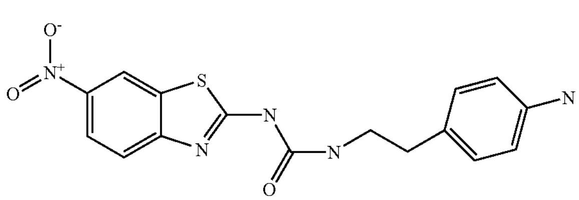 | 2 | 2.32 | 356 |

-continued

| Example # | Structure | Made according to example | Analytical RP-HPLC RT (min) | Mass Spec (m/z) |
|---|---|---|---|---|
| 96 | Chiral | 2 | 2.19 | 355 |
| 97 | 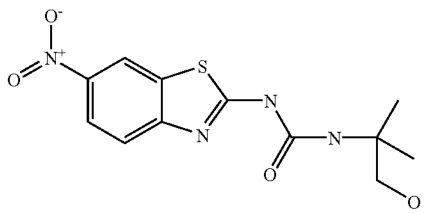 | 2 | 2.06 | 309 |
| 98 | 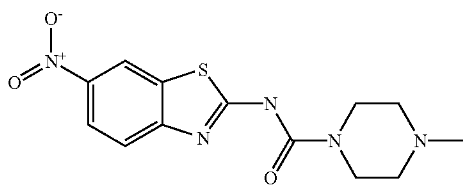 | 2 | 2.94 | 321 |
| 99 | 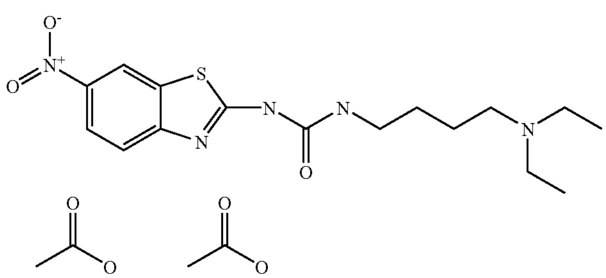 | 2 | 3.67 | 363.8 |
| 100 | 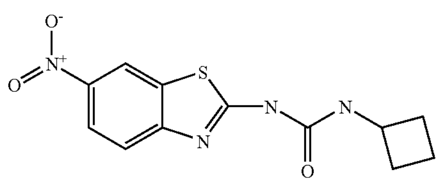 | 2 | 3.08 | 291 |
| 101 | 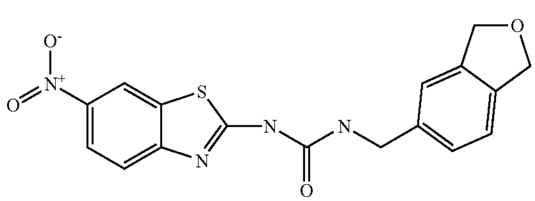 | 2 | 3.51 | 371 |
| 102 | 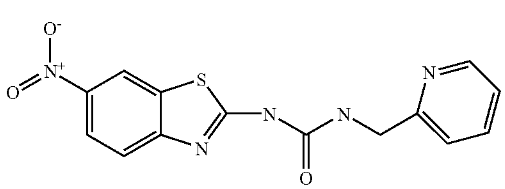 | 2 | 2.78 | 328 |

-continued

| Example # | Structure | Made according to example | Analytical RP-HPLC RT (min) | Mass Spec (m/z) |
| --- | --- | --- | --- | --- |
| 103 | 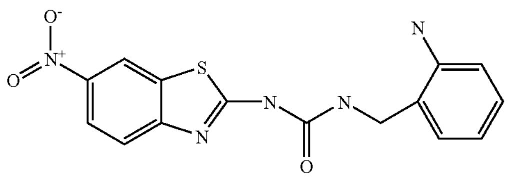 | 2 | 3.22 | 279 |
| 104 | 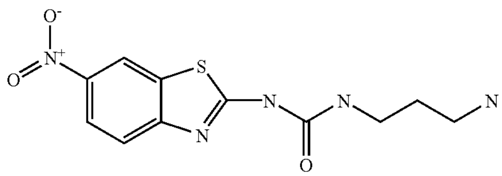 | 2 | 2.3 | 296 |
| 105 | 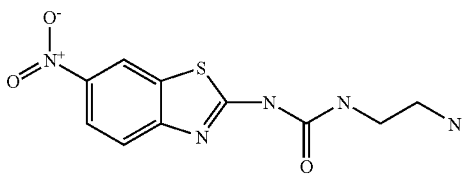 | 2 | 2.28 | 280 |
| 106 | 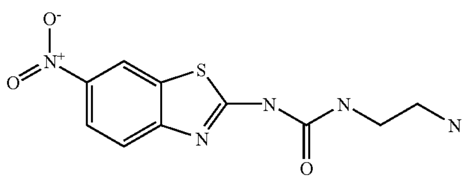 | 2 | 3.54 | 355 |
| 107 | 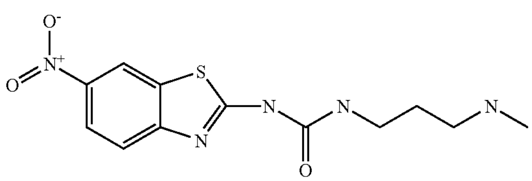 | 2 | 2.21 | 308 |
| 108 | 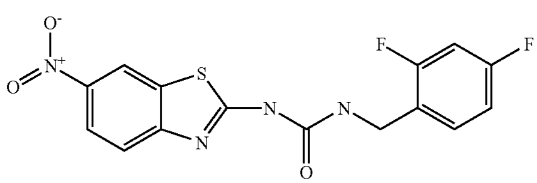 | 2 | 3.6 | 363 |
| 109 | 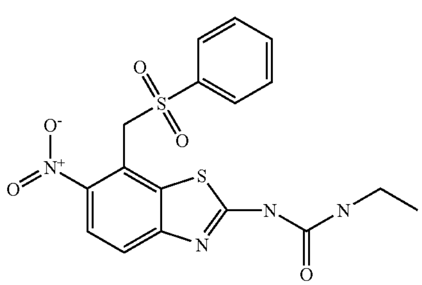 | 4 | 3.19 | 421 |

-continued

| Example # | Structure | Made according to example | Analytical RP-HPLC RT (min) | Mass Spec (m/z) |
|---|---|---|---|---|
| 110 | 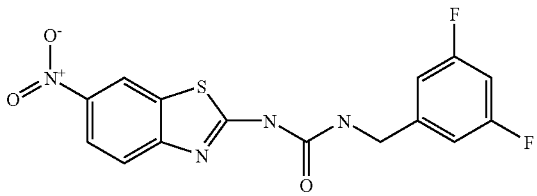 | 2 | 3.6 | 363 |
| 111 | 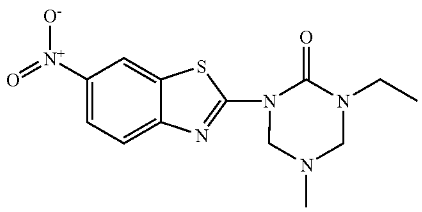 | 4 | 3.53 | 322 |
| 112 | 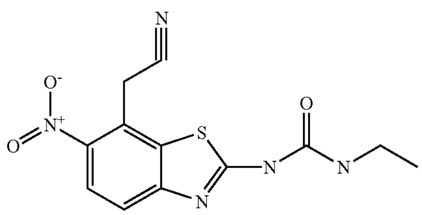 | 4 | 2.64 | 306 |
| 113 | 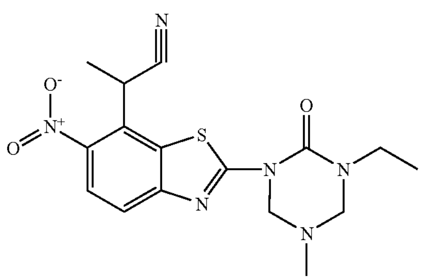 | 4 | 3.2 | 375 |
| 114 | 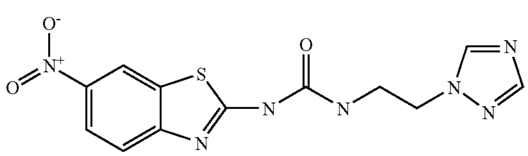 | 2 | 2.45 | 332 |
| 115 | 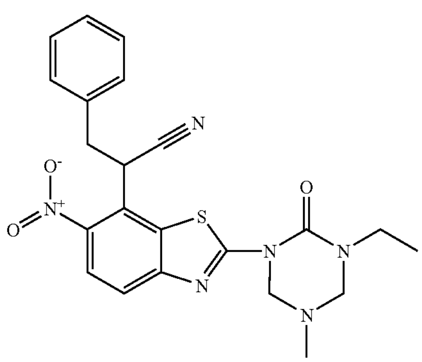 | 4 | 3.73 | 451 |

-continued

| Example # | Structure | Made according to example | Analytical RP-HPLC RT (min) | Mass Spec (m/z) |
|---|---|---|---|---|
| 116 | 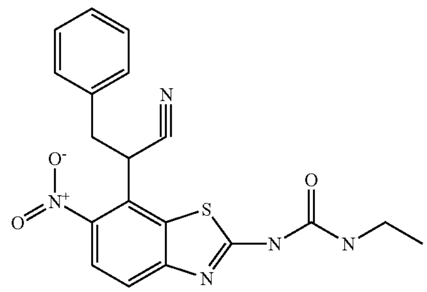 | 4 | 3.37 | 396 |
| 117 | 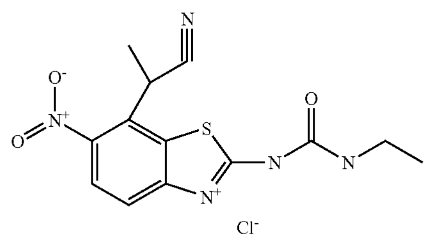 | 3A | 2.86 | 319 |
| 118 | 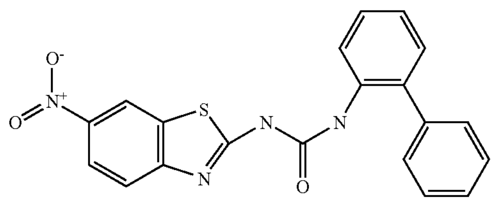 | 1 | 3.41 | 389 |
| 119 | 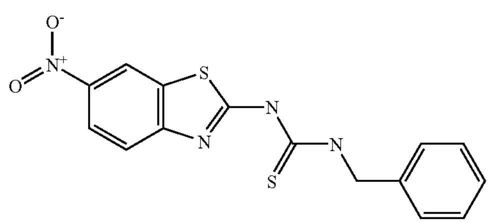 | 3 | 3.18 | 343 |
| 120 | 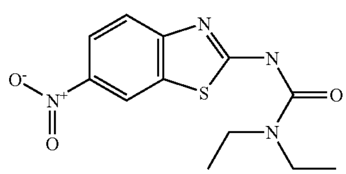 | 2 | 2.35 | 251 |
| 121 | 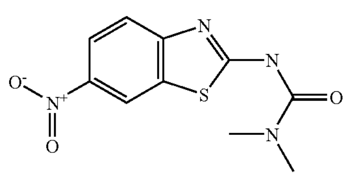 | 2 | 2.9 | 278 |
| 122 | 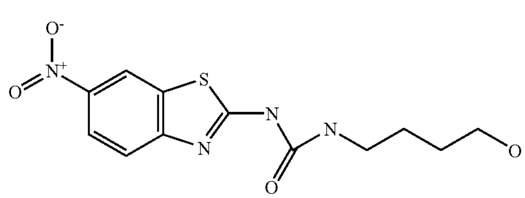 | 2 | 2.12 | 300 |

| Example # | Structure | Made according to example | Analytical RP-HPLC RT (min) | Mass Spec (m/z) |
|---|---|---|---|---|
| 123 | 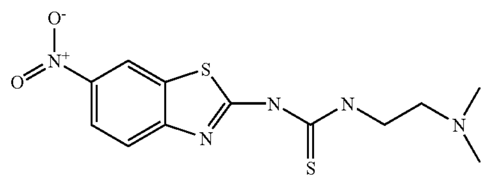 | 3 | 1.57 | 326 |
| 124 | 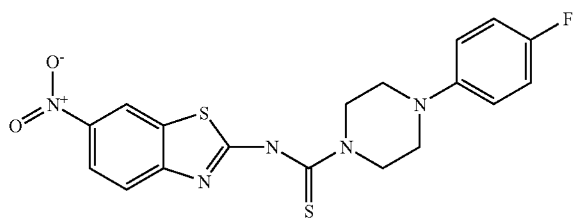 | 3 | 7.48 | 417 |
| 125 | 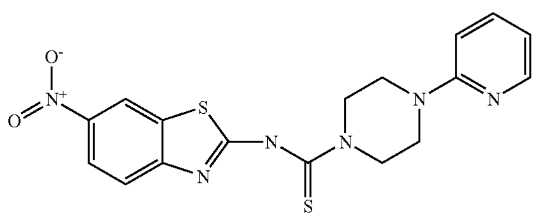 | 3 | 6.72 | 400 |
| 126 | 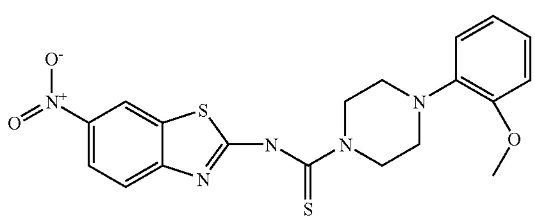 | 3 | 8.35 | 429 |
| 127 | 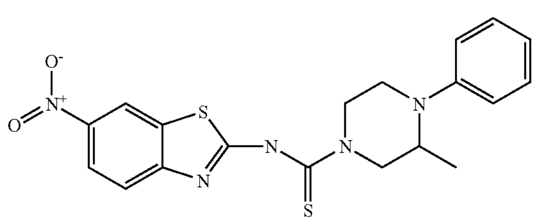 | 3 | 8.96 | 413 |
| 128 | 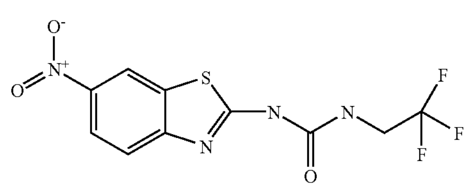 | 2 | 8.32 | 320 |
| 129 | 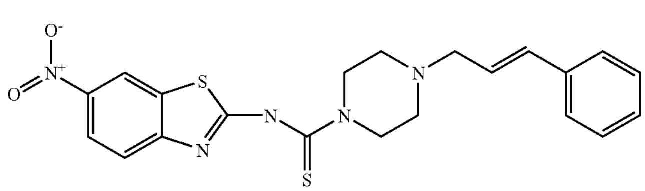 | 3 | 8.19 | 4.39 |

-continued

| Example # | Structure | Made according to example | Analytical RP-HPLC RT (min) | Mass Spec (m/z) |
|---|---|---|---|---|
| 130 | 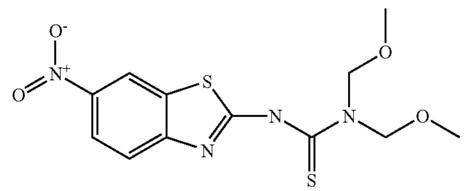 | 3 | 7.4 | 370 |
| 131 | 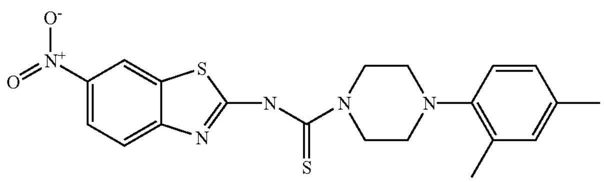 | 3 | 9.5 | 427 |
| 132 | 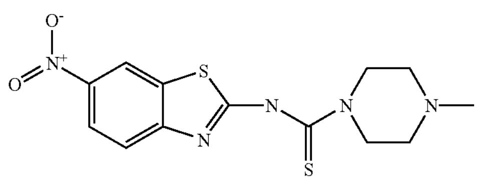 | 3 | 4.8 | 337 |
| 133 | 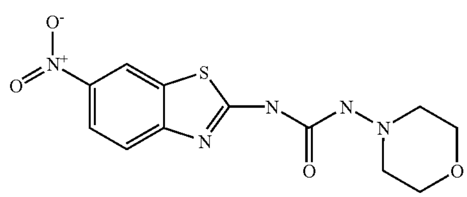 | 2 | 6.9 | 323 |
| 134 | 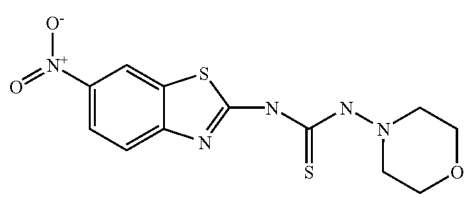 | 3 | 6.6 | 339 |
| 135 | 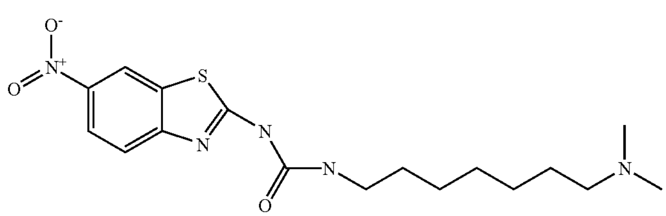 | 2 | 1.97 | 380 |
| 136 | 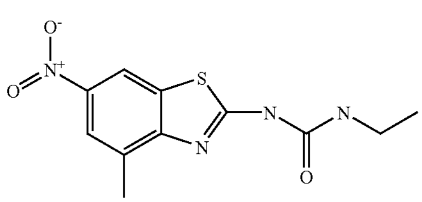 | 2 | 3.22 | 279 |

-continued

| Example # | Structure | Made according to example | Analytical RP-HPLC RT (min) | Mass Spec (m/z) |
|---|---|---|---|---|
| 137 | 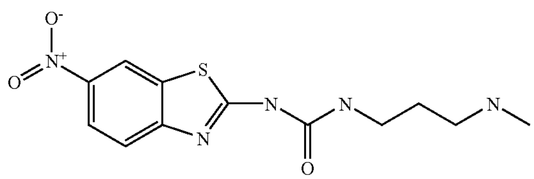 | 2 | 2.21 | 308 |
| 138 | 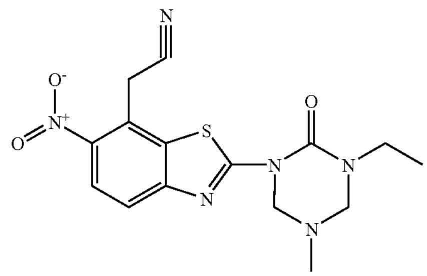 | 4 | 3.12 | 361 |
| 139 | 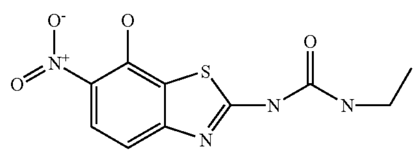 | 4 | 2.7 | 283 |
| 140 | 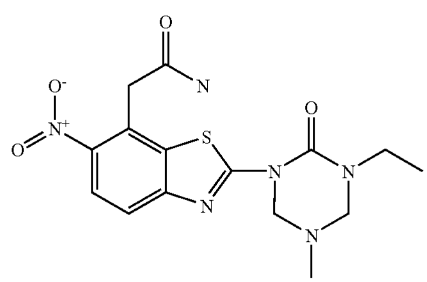 | 4 | 2.44 | 379 |
| 141 | 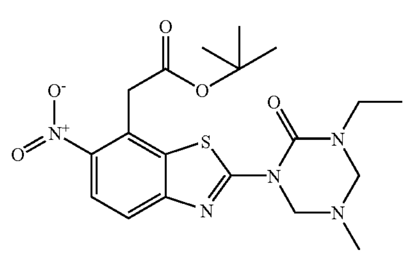 | 4 | 3.72 | 436 |
| 142 | 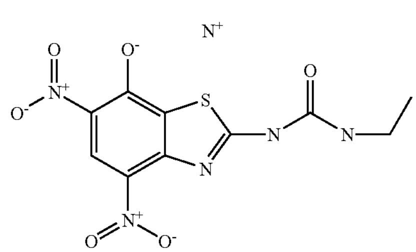 | 4 | 2.13 | 326 |

-continued

| Example # | Structure | Made according to example | Analytical RP-HPLC RT (min) | Mass Spec (m/z) |
|---|---|---|---|---|
| 143 | 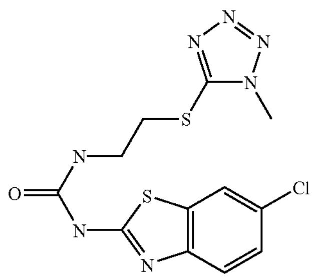 | 1 | 2.26<br>2.23 | 370<br>370 |
| 144 | 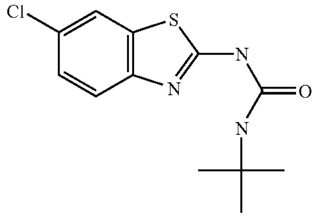 | 1 | 2.88 | 282 |
| 145 | 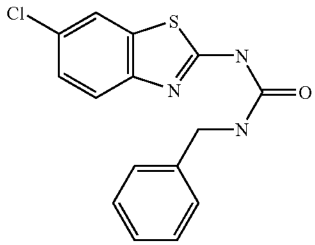 | 1 | 2.92 | 316 |
| 146 | 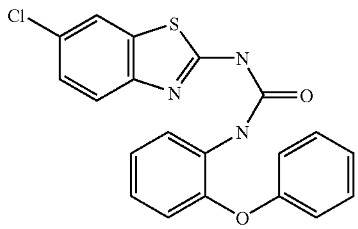 | 1 | 3.84 | 396 |
| 147 | 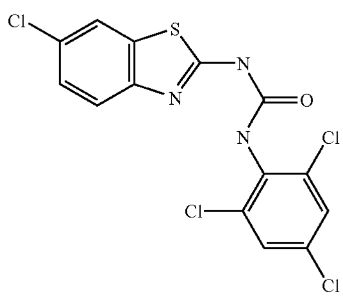 | 1 | 3.27 | 334 |
| 148 | 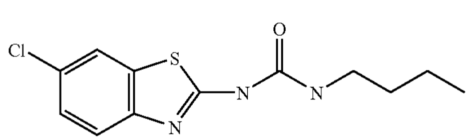 | 2 | 2.81 | 282 |

-continued

| Example # | Structure | Made according to example | Analytical RP-HPLC RT (min) | Mass Spec (m/z) |
|---|---|---|---|---|
| 149 | 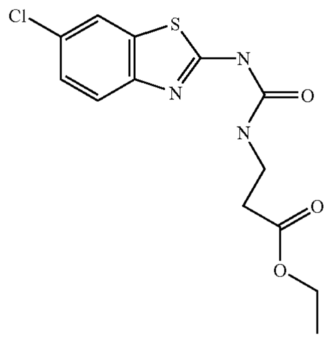 | 2 | 2.48 | 326 |
| 150 | 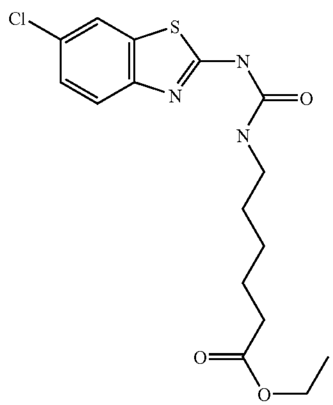 | 2 | 2.85 | 368 |
| 151 | 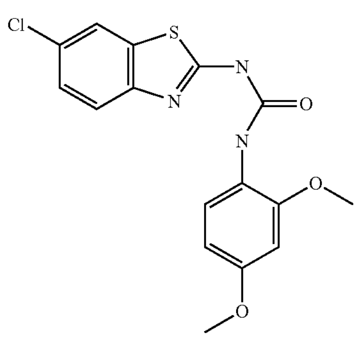 | 1 | 3.14 | 362 |
| 152 | 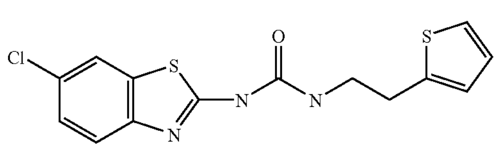 | 1 | 2.95 | 336 |
| 153 | 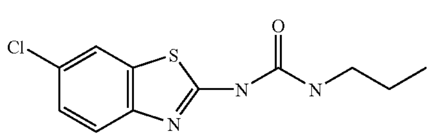 | 1 | 2.59 | 268 |
| 154 | 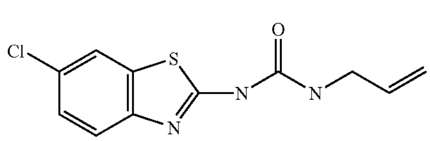 | 2 | 2.48 | 266 |

-continued

| Example # | Structure | Made according to example | Analytical RP-HPLC RT (min) | Mass Spec (m/z) |
|---|---|---|---|---|
| 155 | 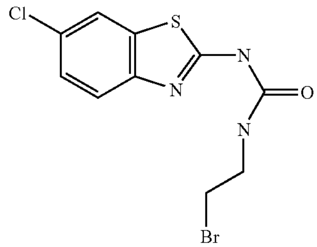 | 2 | 2.07 | 254 |
| 156 | 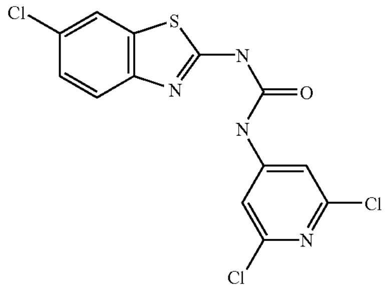 | 1 | 3.23 | 372 |
| 157 | 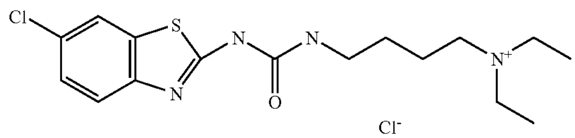 | 2 | 2 | 353 |
| 158 | 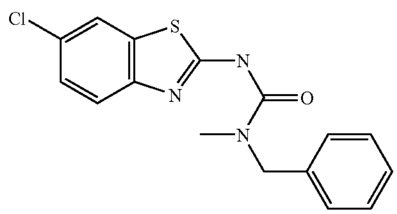 | 2 | 3.06 | 329 |
| 159 | 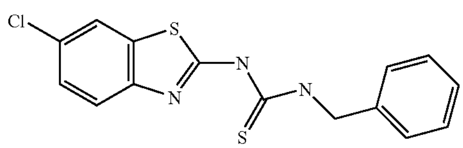 | 3 | 3.38 | 332 |
| 160 | 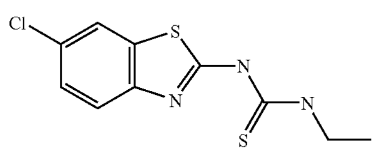 | 3 | 2.91 | 270 |
| 161 | 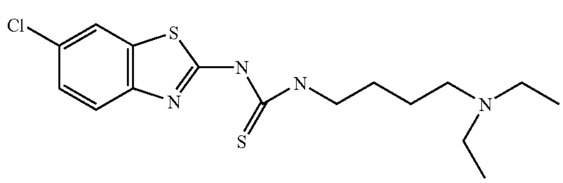 | 3 | 2.25 | 369 |

-continued

| Example # | Structure | Made according to example | Analytical RP-HPLC RT (min) | Mass Spec (m/z) |
|---|---|---|---|---|
| 162 | 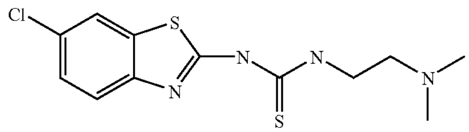 | 3 | 2.07 | 315 |
| 163 | 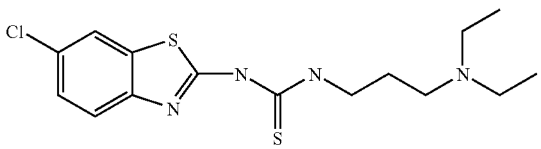 | 3 | 2.04 | 357 |
| 164 | 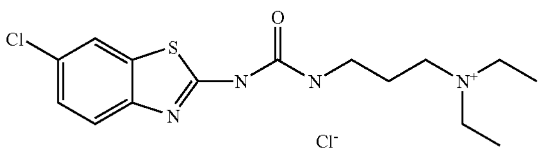 | 2 | 1.9 | 340 |
| 165 | 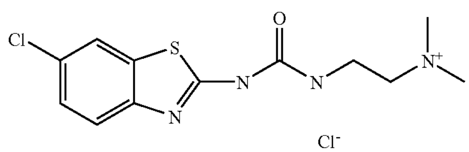 | 2 | 1.7 | 298 |
| 166 | 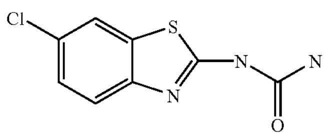 | 2 | 2.28 | 227 |

Note: NA = not available
The hydrogen(s) of hydroxy and amino groups are not shown in the above structural formulas but instead are assumed to be present.

Scheme IV

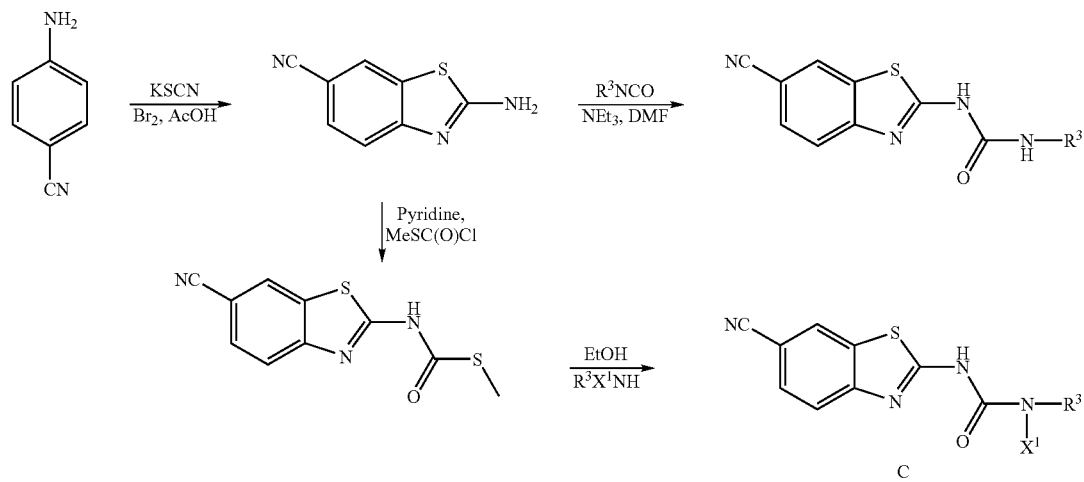

General Description of Scheme IV

2-Amino-1,3-benzothiazole-6-carbonitrile: 4-Aminobenzonitrile is dissolved in acetic acid (or a weak protic acid) and the solution is cooled to about 16–30° C., preferably 16–18° C. Potassium thiocyanate is added and the flask is then equipped with an addition funnel. The addition funnel is charged with bromine and acetic acid. This dark solution is then added to the benzonitrile solution in a dropwise fashion under good agitation and allowed to stir for about 12–20 hours, preferrably about 16 hours. The slurry is then drowned into water and filtered. The presscake is washed well with water, reslurried in dilute aqueous alkali and filtered. Again the presscake is washed well with water to obtain the title compound.

N-(6-Cyano-1,3-benzothiazol-2-yl)-N'-ethylurea: 2-Amino-1,3-benzothiazole-6-carbonitrile is dissolved in a polar aprotic solvent, preferrably dimethylformamide. $R^3$NCO is added, followed by an alkyl amine base, preferably triethylamine and the solution is heated to about 70–90° C., preferably about 80° C., under good agitation. The solution is allowed to stir for about 4–8 hours, preferably about 4 hours, then cooled to room temperature. The solvent is removed in vacuo and the solids are washed well with ether. The product is further purified by column chromatography and after drying in vacuo, the title product is isolated.

Methyl [(6-cyano-1,3-benzothiazol-2-yl)amino]methanethioate: 2-Amino-1,3-benzothiazole-6-carbonitrile is dissolved in pyridine. Methyl chlorothiolformate is added and the solution is heated to about 50–60° C., preferably about 50° C., under good agitation. The solution is allowed to stir for about 8–24 hours, preferably 8 hours, then cooled to room temperature. The slurry is filtered and the solids are washed well with water and dried in vacuo.

Synthesis of Compound C of Scheme IV: Methyl [(6-cyano-1,3-benzothiazol-2-yl)amino]methanethioate is dissolved in alkanol. An excess of the appropriate amine, $R^3X^1$NH is added, and the solution is heated to about 75–85° C., preferably 80° C., under good agitation. The solution is allowed to stir for about 8–24 hours, preferably 14 hours, then cooled to room temperature. The solvent is removed in vacuo. The product can be further purified by column chromatography to yield the desired product.

Preparation 1

2-Amino-1,3-benzothiazole-6-carbonitrile

Two grams of 4-aminobenzonitrile was dissolved in about 40 mL acetic acid and the solution was cooled to about 16° C. About 3.3 g of potassium thiocyanate was added and the flask was equipped with an addition funnel. The addition funnel was charged with about 2.7 g bromine and about 5 mL acetic acid. This dark solution was then added to the benzonitrile solution in a dropwise fashion under good agitation and allowed to stir for about 16 hours. The slurry was then drowned into water and filtered. The presscake was washed well with water, reslurried in dilute aqueous alkali and filtered. Again the presscake was washed well with water. After drying in vacuo, about 2 grams of the title compound was isolated. $^1$H NMR 6.8 (d, 1H, J=8.7 Hz), 6.9 (br s, 2H), 7.6 (dd, 1H, J=2 Hz, J=8.7 Hz), 8.0 (d, 1H, J=2 Hz), LC/MS 2.34 min, 174 (M–H$^-$), RP-HPLC RT 7.7 minutes.

Preparation 2

Methyl [(6-cyano-1,3-benzothiazol-2-yl)amino]methanethioate

2-Amino-1,3-benzothiazole-6-carbonitrile (1.4 g) was dissolved in about 50 mL pyridine. About 2 g of methylchlorothiolformate was added and the solution was heated to about 50° C. under good agitation. The solution was allowed to stir for about 8 hours then cooled to room temperature. The slurry was filtered and the solids were washed well with water. After drying in vacuo, about 1.2 grams of the title product was isolated. $^1$H NMR 2.4 (s, 3H), 7.8 (m, 2H), 8.5 (s, 1H), 13.2 (br s, 1H), LC/MS 2.92 min, 250 (MH$^+$), 248 (M–H—).

Instrumentation for Examples 166–197 were:

LC/MS purification conditions:

| | |
|---|---|
| Column: | Hypersil ®BDS, C18, 5 µ, 100 × 21.2 mm (Hypersil Inc., Needham, MA) |
| Gradient: | Generally from 100% pH 4.5 50 mM NH$_4$OAc/H$_2$O to 100% CH$_3$CN in 8.5 minutes but varies depending upon required separation |
| Flow rate: | 25 mL/min |

$^1$NMR spectrum

Recorded on a Bruker 400 MHz spectrometer in deuterated DMSO using tetramethylsilane (0.00 ppm) as internal standard.

LC conditions (analytical run):

| | |
|---|---|
| Column: | PECOSPHERE, C18, 3 µm, 33 × 4.6 mm (Perkin Elmer, Norwalk, CT) |
| Gradient: | From 100% pH 4.5 50 mM NH$_4$OAc/H$_2$O to 100% CH$_3$CN in 4.5 minutes |
| Flow rate: | 3.5 mL/min |

EXAMPLE 167–169

N-(6-Cyano-1,3-benzothiazol-2-yl)-N'-ethylurea

2-Amino-1,3-benzothiazole-6-carbonitrile (0.2 g) was dissolved in about 5 mL dimethylformamide. About 0.2 mL of ethylisocyanate was added, followed by about 0.3 mL triethylamine and the solution was heated to about 80° C. under good agitation. The solution was allowed to stir for about 4 hours then cooled to room temperature. The solvent was removed in vacuo and the solids were washed well with ether. The product was further purified by column chromatography and after drying in vacuo, about 0.14 grams was isolated. $^1$H NMR 1.1 (t, 3H, J=7.2 Hz), 3.2 (m, 2H), 6.8 (s, 1H), 7.7 (m, 2H), 8.4 (s, 1H), 11.0 (s, 1H), LC/MS 2.54 min, 247 (MH$^+$), 245 (M–H$^-$), lab RP-HPLC RT 7.8 minutes.

Examples 168 and 169 were synthesized according to the synthesis of Example 167 using the appropriate starting material.

EXAMPLE 168

N-(6-Cyano-1,3-benzothiazol-2-yl)-N'-[(1S)-1-phenylethyl]urea $^1$H NMR 1.4 (d, 3H, J=6.8 Hz), 4.9 (m, 1H), 7.3 (m, 6H), 7.7 (br s, 2H), 8.4 (s, 1H), 10.8 (br s, 1H), LC/MS 3.32 min, 323 (MH$^+$), 321 (M–H$^-$).

EXAMPLE 169

N-(6-Cyano-1,3-benzothiazol-2-yl)-N'-[(1R)-1-phenylethyl]urea $^1$H NMR 1.4 (d, 3H, J=6.9 Hz), 4.9 (m, 1H), 7.3 (m, 5H), 7.36 (d, 1H, J=4.5 Hz), 7.7 (m, 2H), 8.4 (s, 1H), 10.8 (br s, 1H), LC/MS 3.30 min, 321 (M–H$^-$).

EXAMPLES 170–171

The following examples were synthesized in accordance with the general procedure for making a compound C of Scheme IV, using the appropriate amine.

EXAMPLE 170

N-(6-Cyano-1,3-benzothiazol-2-yl)-N'-(4-pyridylmethyl)urea $^1$H NMR 4.4 (d, 2H, J=6 Hz), 7.31 (d, 2H, J=5.8 Hz), 7.4 (br s, 1H), 7.8 (m, 2H), 8.46 (s, 1H), 8.52 (d, 2H, J=5.8 Hz), 11.3 (br s, 1H), LC/MS 2.44 min 310 (MH$^+$), 308 (M−H$^-$).

EXAMPLE 171

N-(6-Cyano-1,3-benzothiazol-2-yl)-N'-(3-pyridylmethyl)urea $^1$H NMR 4.4 (d, 2H, J=5.9 Hz), 7.38 (m, 2H), 7.8 (m, 3H), 8.46 (m, 2H), 8.55 (s, 1H), 11.1 (br s, 1H), LC/MS 2.46 min, 310 (MH$^+$), 308 (M−H$^-$).

added followed by addition of a 2M solution of MeNH$_2$ in MeOH, then about 2 mole equivalents of N-methylmorpholine. The solution is warmed to about 70–85° C., preferably 80° C., then allowed to stir for about 4–24 hours, preferably 4 hours. The slurry is then cooled to room temperature, filtered and washed well with water, dried and the title product is isolated.

General Procedure for Grignard Addition:

The Grignard synthesis can be performed substantially according to the method of Bartoli, JOC, (1980), 45, 522–524. For example, 1-ethyl-5-methyl-3-(6-nitro-1,3-benzothiazol-2-yl)-1,3,5-triazinan-2-one is dissolved in an inert solvent such as an ether, preferably tetrahydrofuran. This slurry is cooled to about 0–5° C., preferably 0° C. About 2 molar equivalents of the appropriate Grignard reagent is added dropwise to the slurry. Once addition is complete the solution is stirred at about 0–30° C. for about 5 minutes. Next, about 0.66 mole equivalents of KMnO$_4$, dissolved in 1:1 acetone/water, is added dropwise at about 0–5° C., preferably 0° C. The solution is allowed to stir to room temperature. The reaction crude is then diluted with

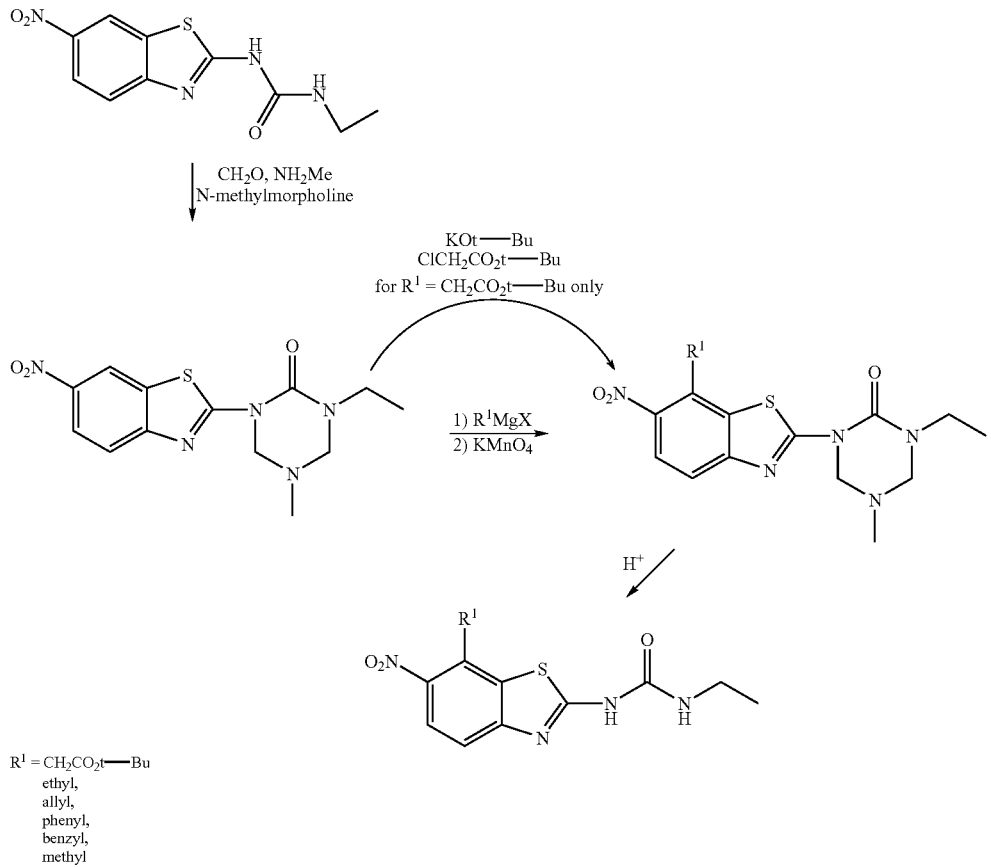

Scheme V

General procedure for synthesizing 1-ethyl-5-methyl-3-(6-nitro-1,3-benzothiazol-2-yl)-1,3,5-triazinan-2-one: N-Ethyl-N'-(6-nitro-1,3-benzothiazol-2-yl)urea is suspended in an alkanol/water mixture, preferably 1:1 EtOH/H$_2$O at room temperature. A 37% aqueous solution of formaldehyde is water and the desired product is extracted into methylene chloride. The combined organic layers are dried over magnesium sulfate, then the solvent is removed in vacuo. The product can be further purified by chromatography then dried in vacuo.

Preparation 3

1-Ethyl-5-methyl-3-(6-nitro-1,3-benzothiazol-2-yl)-1,3,5-triazinan-2-one

N-Ethyl-N'-(6-nitro-1,3-benzothiazol-2-yl)urea (2.8 g) was suspended in about 100 mL 1:1 EtOH/H$_2$O at room temperature. About 8 mL of a 37% aqueous solution of formaldehyde is added followed by addition of about 15 mL of a 2M solution of MeNH$_2$ in MeOH, then about 2.2 mL of N-methylmorpholine. The solution was warmed to about 80° C. then allowed to stir for about 16 hours. The slurry was then cooled to room temperature, filtered and washed well with water. After drying in vacuo, about 3.2 grams was isolated. $^1$H NMR 1.13 (t, 3H, J=7.1 Hz), 2.55 (s, 3H), 3.38 (q, 2H, J=7.1 Hz), 4.39 (s, 2H), 5.16 (s, 2H), 7.81 (d, 1H, J=8.9 Hz), 8.22 (dd, 1H, J=2.4 Hz, J=8.9 Hz), 8.95 (d, 1H, J=2.4 Hz) LC/MS=3.33 min, 322 (MH$^+$), 320(M−H$^-$).

EXAMPLES 172–177

The following examples were synthesized according to the foregoing synthetic description using the noted Grignard reagent.

EXAMPLE 172

1-Ethyl-3-(7-ethyl-6-nitro-1,3-benzothiazol-2-yl)-5-methyl-1,3,5-triazinan-2-one Grignard reagent=EtMgBr in Et$_2$O; $^1$H NMR 1.13 (t, 3H, J=7.1 Hz), 1.33 (t, 3H, J=7.5 Hz), 2.55 (s, 3H), 3.05 (m, 2H), 3.35 (m, 2H), 4.4 (s, 2H), 5.15 (s, 2H), 7.68 (d, 1H, J=8.84 Hz), 8.02 (d, 1H, J=8.83 Hz), LC/MS 3.61 min, 351 (MH$^+$), 349 (M−H$^-$).

EXAMPLE 173

1-(7-Allyl-6-nitro-1,3-benzothiazol-2-yl)-3-ethyl-5-methyl-1,3,5-triazinan-2-one Grignard reagent=Allyl-MgBr in THF; $^1$H NMR 1.12 (t, 3H, J=7.1 Hz), 2.54 (s, 3H), 3.38 (m, 2H), 3.82 (d, 2H, J=6.2 Hz), 4.4 (s, 2H), 5.02 (s, 1H), 5.06 (d, 1H, J=1.6 Hz), 5.1 (s, 2H), 6.02 (m, 2H), 7.72 (d, 1H, J=8.8 Hz), 8.06 (d, 1H, J=8.8 Hz), LC/MS 3.6 min, 362 (MH$^+$), 361 ((M−H)$^-$).

EXAMPLE 174

1-Ethyl-5-methyl-3-(6-nitro-7-pheny-1,3-benzothiazol-2-yl)-1,3,5-triazinan-2-one Grignard reagent=Phenyl-MgCl in THF; LC/MS 2.77 min., 398 (MH$^+$).

EXAMPLE 175

1-(7-benzyl-6-nitro-1,3-benzothiazol-2-yl)-3-ethyl-5-methyl-1,3,5-triazinan-2-one Grignard reagent=Benzyl-MgCl in THF; $^1$H NMR 1.09 (t, 3H, J=7.1 Hz), 2.52 (s, 3H). 3.3 (m, 2H), 4.36 (s, 2H), 4.49 (s, 2H), 5.12 (s, 2H), 7.12 (m, 2H), 7.19 (m, 1H), 7.28 (m, 2H), 7.76 (d, 1H, J=8.8 Hz), 8.09 (d, 1H, J=8.8 Hz), LC/MS 3.81 nm, 412 (MH$^+$).

EXAMPLE 176

1-Ethyl-3-(7-methyl-6-nitro-1,3-benzothiazol-2-yl)-5-methyl-1,3,5-triazinan-2-one Grignard reagent=MeMgCl in THF; $^1$H NMR 1.13 (m, 3H), 2.54 (s, 3H), 2.73 (s, 3H), 3.35 (m, 2H), 4.39 (s, 2H), 5.15 (s, 2H), 7.61 (d, 1H, J=8.4 Hz), 8.05 (d, 1H, J=8.8 Hz), LC/MS 3.36 min, 336 (MH$^+$), 335 (M−H$^-$).

EXAMPLE 177 tert-Butyl 2-(2-(3-ethyl-5-methyl-2-oxo-1,3,5-triazinan-1-yl)-6-nitro-1,3-benzothiazol-7-yl)-acetate 1-Ethyl-5-methyl-3-(6-nitro-1,3-benzothiazol-2-yl)-1,3,5-triazinan-2-one (0.05 g) was dissolved in about 25 mL dimethylformamide. The solution was cooled to about −40° C. About 0.24 mL of tert-butylchloroacetate was added dropwise. Next, about 1.5 mL of KOt-Bu in THF (1M) was introduced in a dropwise fashion. Once complete the solution was stirred at about −40 to −50° C. for about 3 hours. Next, about 2 mL of saturated ammonium chloride was added and the solution was warmed to room temperature. The reaction crude was then diluted with water and the product was extracted into ethyl acetate. The combined organic layers were dried over magnesium sulfate, then the solvent was removed in vacuo. The product was further purified by chromatography then dried in vacuo. $^1$H NMR 1.1 (t, 3H, J=7.0 Hz), 1.23 (s, 9H), 2.55 (s, 3H), 3.38 (m, 2H), 4.1 (s, 2H), 4.4 (s, 2H), 5.16 (s, 2H), 7.7 (d, 1H, J=8.8 Hz), 8.1 (d, 1H, J=8.8 Hz), LC/MS 3.72 min, 436 (MH$^+$).

General Procedure for Hydrolysis of Urea Protecting Group

The appropriate 7-substituted 1-ethyl-5-methyl-3-(6-nitro-1,3-benzothiazol-2-yl)-1,3,5-triazinan-2-one is dissolved in excess protic acid (such as trifluoroacetic acid or aqueous HCl) and stirred at room temperature until complete. Following neutralization, the products are either filtered and washed with water or extracted into methylene chloride then dried. Products are further purified by chromatography. The products are dried in vacuo.

EXAMPLES 178–183

The following examples were synthesized according the foregoing general description for hydrolysis.

EXAMPLE 178 tert-Butyl 2-(2-[(ethylamino)Carbonyl]amino-6-nitro-1,3-benzothiazol-7-yl)acetate $^1$H NMR 1.1 (t, 3H, J=7.2 Hz), 1.4 (s, 9H), 3.2 (m, 2H), 4.1 (s, 2H), 6.9 (br s, 1H), 7.69 (d, 1H, J=8.8 Hz), 8.14 (d, 1H, J=8.8 Hz), 11.25 (br s, 1H), LC/MS 3.32 min, 381 (MH$^+$).

EXAMPLE 179

N-Ethyl-N' (7-ethyl-6-nitro-1,3-benzothiazol-2-yl)urea $^1$H NMR, 1.1 (t, 3H, J=7.2 Hz), 1.3 (t, 3H, J=7.4 Hz), 3.0 (m, 2H), 3.2 (m, 2H), 7.0 (br s, 1H), 7.59 (d, 1H, J=8.8 Hz), 8.01 (d, 1H, J=8.8 Hz), 11.35 (br s, 1H), LC/MS 3.13 min., 295 (MH$^+$), 293 (M−1H).

EXAMPLE 180

N-(7-Allyl-6-nitro-1,3-benzothiazol-2-yl)-N'-ethylurea $^1$H NMR 1.1 (t, 3H, J=7.2 Hz), 3.2 (m, 2H), 3.82 (d, 2H, J=6 Hz), 5.06 (d, 1H, J=1.6 Hz), 5.12 (d, H, J=9.3 Hz), 6.0 (m, 1H), 6.8 (br s, 1H), 7.65 (d, 1H, J=8.8 Hz), 8.06 (d, 1H, J=8.8 Hz), 11.17 (br s, 1H), LC/MS 3.04 min., 307 (MH$^+$), 305 (M–H$^-$).

EXAMPLE 181

N-(7-Benzyl-6-nitro-1,3-benzothiazol-2-yl)-N'-ethylurea $^1$H NMR 1.07 (t, 3, J 7.2 Hz), 3.15 (m, 2H), 4.49 (s, 2H), 6.77 (br s, 1H), 7.11–7.29 (m, 5H), 7.69 (d, 1H, J=8.4 Hz), 8.09 (d, 1H, J=8.8 Hz), 11.15 (br s, 1H), LC/MS 3.44 min, 357 (MH$^+$), 355 (M–H$^-$).

EXAMPLE 182

N-Ethyl-N'-(6-nitro-7-phenyl-1,3-benzothiazol-2-yl)urea

LC/MS 2.51 min., 341 (MH$^+$), 343 (M–H$^-$).

EXAMPLE 183

N-Ethyl-N'-(7-methyl-6-nitro-1,3-benzothiazol-2-yl)urea $^1$H NMR, 1.1 (t, 3, J=7.1 Hz), 2.73 (s, 3H), 3.2 (m, 2H), 6.79 (br s, 1H), 7.61 (d, 1H, J=8.8 Hz), 8.05 (d, 1H, J=8.8 Hz), 11.15 (br s, 1H), LC/MS 2.85 min., 281 (MH$^+$), 279 (M–H$^-$).

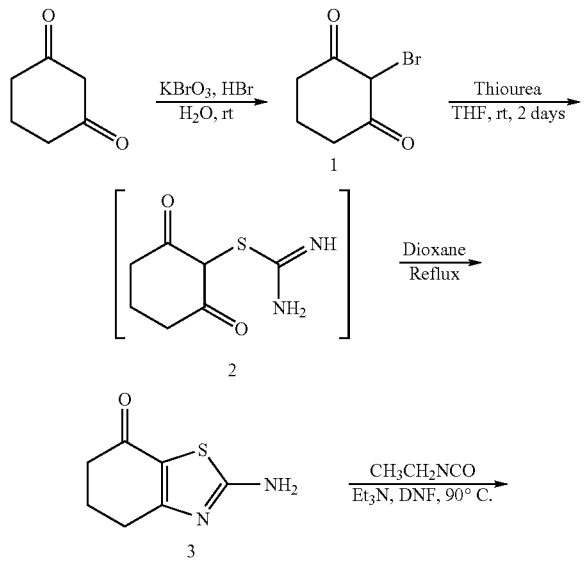

Scheme VI

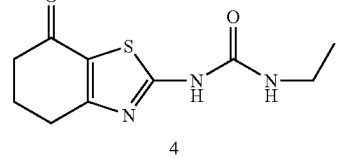

4

Preparation 4

2-Bromo-1,3-cyclohexadione (1). To a solution of 1,3-cyclohexadione (1.15 g, 10.0 mol, 97% pure) and 48% HBr (aq) (1.5 mL, 13.3 mmol, 1.33 eq) in H$_2$O (10 mL) at about 20° C., a warm solution of KBrO$_3$ (0.55 g, 3.30 mol, 0.33 eq) in H$_2$O (10 mL) was added dropwise over about 10 min. It was important to keep the solution of KBrO$_3$/H$_2$O around 35° C. in order to keep the potassium salt dissolved. The reaction mixture turned warm upon addition and was stirred at about 20° C. for about 15 min. The precipitation was filtered off and washed with H$_2$O (3×5 mL). The solid was dried under vacuum to give 1.68 g (88%) of 1. The material was used in the following synthesis without further purification. $^1$H NMR (CDCl$_3$) δ 6.52 (br s, 1H), 2.62 (m, 4H, CH$_2$), 2.03 (p, 2H, J=6.4 Hz, CH$_2$).

Preparation 5

2-Amino-7-oxo-4, 5, 6, 7-tetrahydro-benzothiazole (3). A suspension of 2-bromo-1,3-cyclohexadione 1 (15.44 g, 80.8 mmol) and thiourea (6.15 g, 80.8 mmol, 1.0 eq) in anhydrous THF (120 mL) was stirred at about 20° C. for about 2 days. The disappearance of 1 and the appearance of 2 could be seen on TLC. The mixture was concentrated and anhydrous dioxane (120 mL) was added. The reaction mixture was heated at about 110° C. for about 1 day. It was cooled down and the precipitation was filtered off and washed with THF (2×150 mL). The solid was dissolved in H$_2$O (100 mL) and neutralized with sat. NaHCO$_3$ solution whereupon a precipitate formed. The precipitate was collected and recrystallized from MeOH to give 7.93 g (58%) of 3. $^1$H NMR (DMSO) 68.10 (br s, 2H, NH$_2$), 2.67 (t, 2H, J=6.0 Hz, CH$_2$), 2.36 (t, 2H, J=6.0 Hz, CH$_2$), 1.99 (p, 2H, J=6.4 Hz, CH$_2$); Mp 259.3–262.5° C. (Decomposed).

Preparation 6

1-(7-Oxo-4,5,6,7-tetrahydro-2-benzothiazolyl)-3-ethyl-urea (4). A solution of 2-amino-7-oxo-4,5,6,7-tetrahydro-benzothiazole 3 (11.56 g, 68.7 mmol) in anhydrous DMF (200 mL) was treated with triethylamine (19.2 mL, 137 mmol, 2.0 eq) and ethyl isocyanate (10.9 nL, 137 mmol, 2.0 eq). The reaction mixture was heated at about 90° C. with stirring for about 3 hours. The DMF solvent was distilled off under reduced pressure. A sticky brown residue was obtained. Treatment with Et$_2$O (100 mL) gave a precipitate, which was filtered off and washed with more Et$_2$O (50 mL). The light brown colored solid was dried under vacuum to give 13.97 g (85%) of 4. The material was used in the following synthesis without further purification. $^1$H NMR (DMSO) δ 10.95 (br s, 1H, NH), 6.66 (br s, 1H, NH), 3.16 (p, 2H, J=7.2 Hz, CH$_2$), 2.79 (t, 2H, J=6.1 Hz, CH$_2$), 2.45 (t, 2H, J=6.5 Hz, CH$_2$), 2.05 (p, 2H, J=6.4 Hz, CH$_2$), 1.07 (t, 3H, J=7.2 Hz, CH$_3$); LC/MS 240 (MH$^+$); RP-HPLC RT 2.27 minutes.

Scheme VII

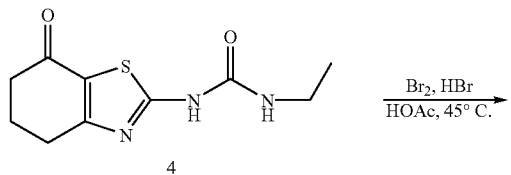

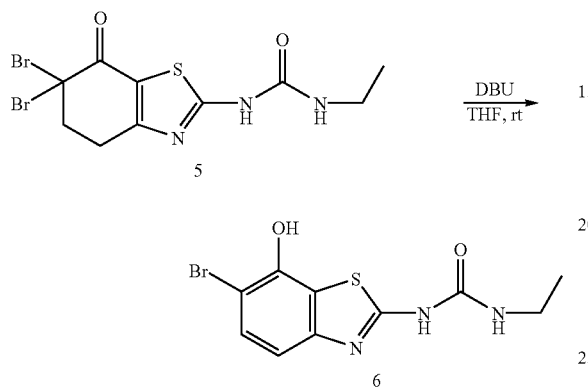

Scheme VIII

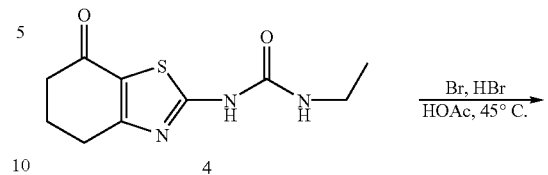

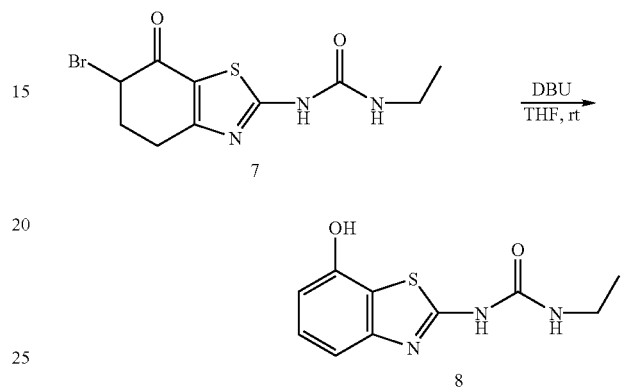

Preparation 7

1-(6,6-Dibromo-7-oxo-4,5,6,7-tetrahydro-2-benzothiazolyl)-3-ethyl-urea (5). A solution of 1-(7-oxo-4,5,6,7-tetrahydro-2-benzothiazolyl)-3-ethyl-urea 4 (5.00 g, 20.9 mmol), 48% HBr (aq) (1.20 mL, 2.09 mmol, 0.1 eq) and AcOH (451 mL) was treated dropwise with a solution of $Br_2$ (2.21 mL, 42.8 mmol, 2.05 eq) in AcOH (5 mL) with stirring. The reaction mixture was heated at about 45° C. with stirring for about 16 hours with a condensor on top of the reaction flask. An orange colored suspension was obtained. The solid was filtered off and washed with $Et_2O$ (20 mL), toluene (50 mL) and $Et_2O$ (3×30 mL). After drying under vacuum, 7.78 g (94%) of compound 5 was obtained. $^1$H NMR (DMSO) δ 11.35 (br s, 1H, NH), 6.78 (br s, 1H, NH), 3.18 (m, 2H, $CH_2$), 3.12 (t, 2H, J=5.6 Hz, $CH_2$), 2.91 (t, 2H, J=5.6 Hz, $CH_2$), 1.08 (t, 3H, J=7.2 Hz, $CH_3$); LC/MS 396 ($MH^+$); RP-HPLC RT 3.04 minutes.

EXAMPLE 184

1-(6-Bromo-7-hydroxy-2-benzothiazolyl)-3-ethyl-urea (6). A suspension of 1-(6,6-dibromo-7-oxo-4,5,6,7-tetrahydro-2-benzothiazolyl)-3-ethyl-urea 5 (7.78 g, 19.6 mmol) in THF (50 mL) was treated with DBU (8.79 mL, 58.8 mmol, 3.0 eq) dropwise at about 20° C. A dark green suspension was obtained while heat was generated upon addition of DBU. It was stirred at about 20° C. for about 18 hours. The reaction mixture was concentrated and the residue was treated with saturated $NH_4Cl$ (aq) solution to neutral. A light brown colored precipitate was obtained. It was filtered off and washed with $H_2O$ (2×50 mL), small amount of MeOH and $CH_2Cl_2$, and finally dried under vacuum to give 4.83 g (78%) of the desired compound 6. $^1$H NMR (DMSO) δ 10.68 (br s, 1H, NH), 7.43 (d, 1H, J=8.5 Hz, ArH), 7.08 (d, 1H, J=8.5 Hz, ArH), 6.70 (br s, 1H, NH), 3.18 (m, 2H, $CH_2$), 1.09 (t, 3H, J=7.2 Hz, $CH_3$). LC/MS 316 ($MH^+$); RP-HPLC RT 2.80 minutes.

Preparation 8

1-(6-Bromo-7-oxo-4,5,6,7-tetrahydro-2-benzothiazolyl)-3-ethyl-urea (7). A solution of 1-(7-oxo-4,5,6,7-tetrahydro-2-benzothiazolyl)-3-ethyl-urea 4 (1.00 g, 4.18 mmol) and 48% HBr (aq) (0.24 mL, 2.09 mmol, 0.5 eq) in AcOH (18 mL) was treated dropwise with a solution of $Br_2$ (0.23 mL, 4.39 mmol, 1.05 eq) in AcOH (1 mL) with stirring. The reaction mixture was heated at about 45° C. with stirring for about 16 hours with a condensor on top of the reaction flask. An orange colored suspension was obtained. The solid was filtered off and washed with AcOH (5 mL), toluene (2×3 mL) and $Et_2O$ (2×5 mL). After drying under vacuum, 1.11 g (83%) of the desired compound 7 was obtained. $^1$H NMR (DMSO) δ 11.15 (br s, 1H, NH), 6.73 (br s, 1H, NH), 4.87 (t, 1H, J=4.6 Hz, CH), 3.17 (m, 2H, $CH_2$), 2.87 (dd, 2H, J=7.2, 4.4 Hz, $CH_2$), 2.61–2.54 (m, 1H, $CH_2$), 2.39–2.33 (m, 1H, $CH_2$), 1.08 (t, 3H, J=7.2 Hz, $CH_3$); LC/MS 318 ($MH^+$); RP-HPLC RT 2.68 minutes.

Preparation 9

1-(7-Hydroxy-2-benzothiazolyl)-3-ethyl-urea (8). To a suspension of 1-(6-bromo-7-oxo-4,5,6,7-tetrahydro-2-benzothiazolyl)-3-ethyl-urea 5 (0.100 g, 0.314 mmol) in THF (1.0 mL) was added DBU (0.141 mL, 0.94 mmol, 3 eq) dropwise at about 20° C. A dark green suspension was obtained while heat was generated upon addition of DBU. It was stirred at about 20° C. for about 18 hours. The reaction mixture was concentrated and dissolved in DMF (2 mL). LC/MS purification gave 0.024 g (32%) of the desired compound 8. $^1$H NMR (DMSO) δ 10.54 (br s, 1H, NH), 7.17–7.07 (m, 2H, ArH), 6.63 (d, 1H, J=6.9 Hz, ArH), 6.70 (br s, 1H, NH), 3.18 (m, 2H, $CH_2$), 1.09 (t, 3H, J=7.2 Hz, $CH_3$). LC/MS 238 ($MH^+$); RP-HPLC RT 2.26 minutes.

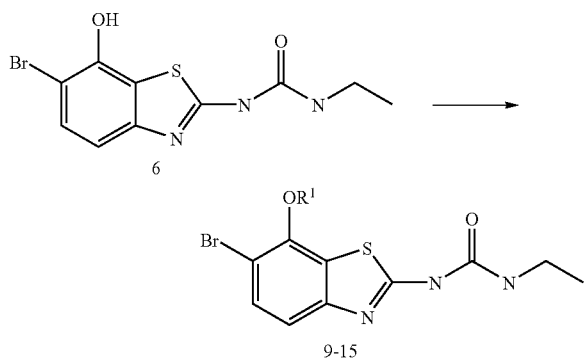

| | Compound | R¹ |
|---|---|---|
| Example 185 | 9 | C₆H₅CH₂— |
| Example 186 | 10 | CH₃— |
| Example 187 | 11 | (CH₃)₂CH— |
| Example 188 | 12 | CH₃O(CH₂)₂O(CH₂)₂— |
| Example 189 | 13 | p-F—C₆H₄CH₂— |
| Example 190 | 14 | CF₃SO₂— |
| Example 191 | 15 | NH₂COC(CH₃)₂— |

General Procedure for 1-(6-bromo-7-alkoxy-2-benzothiazolyl)-3-ethyl-urea compounds 9–13. A mixture of 1-(6-bromo-7-hydroxy-2-benzothiazolyl)-3-ethyl-urea 6 and potassium carbonate (1.05 eq) in anhydrous DMF was stirred at about 20° C. for about 0.5 hour, and was cooled down to about 0° C. The mixture was treated with an alkyl halide (1.0 eq), and was stirred at about 0–85° C. for about 16 hours. To the reaction mixture was added methanol. The solid was filtered off and washed with methanol. The solvent was evaporated and the residue was dissolved in DMF. The crude reaction solution was purified by preparature LC/MS to give pure desired product.

EXAMPLE 185

1-(6-Bromo-7-benzyloxy-2-benzothiazolyl)-3-ethyl-urea (9). A mixture of 1-(6-bromo-7-hydroxy-2-benzothiazolyl)-3-ethyl-urea 6 (0.050 g, 0.16 mmol) and potassium carbonate (0.023 g, 0.17 mmol, 1.05 eq) in anhydrous DMF (1.6 mL) was stirred at about 20° C. for about 0.5 hour, and was cooled down to about 0° C. The reaction mixture was treated with benzyl bromide (0.019 mL, 0.16 mmol, 1.0 eq), and was stirred at about 0° C. for about 16 hours. To the reaction mixture was added methanol (10 mL). The solid was filtered off and rinsed with methanol (3 mL). The solvent was evaporated and the residue was dissolved in DMF (2 mL). The crude reaction solution was purified by LC/MS to give 0.029 g (45%) of the desired compound 9. $^1$H NMR (DMSO) δ 10.86 (br s, 1H, NH), 7.59–7.34 (m, 7H, ArH), 6.72 (br s, 1H, NH), 5.17 (s, 2H, CH₂), 3.18 (m, 2H, CH₂), 1.09 (t, 3H, J=7.2 Hz, CH₃); LC/MS 406 (MH⁺); RP-HPLC RT 3.8 minutes.

EXAMPLE 186

1-(6-Bromo-7-methoxy-2-benzothiazolyl)-3-ethyl-urea (10). A mixture of 1-(6-bromo-7-hydroxy-2-benzothiazolyl)-3-ethyl-urea 6, potassium carbonate and iodomethane in DMF was reacted to give 0.0034 g (2%) of the desired compound 10. $^1$H NMR (DMSO) δ 10.88 (br s, 1H, NH), 7.55 (d, 1H, J=8.5 Hz, ArH), 7.33 (d, 1H, J=8.5 Hz, ArH), 6.82 (br s, 1H, NH), 3.93 (s, 3H, CH₃), 3.18 (m, 2H, CH₂), 1.09 (t, 3H, J=7.2 Hz, CH₃); LC/MS 330 (MH⁺); RP-HPLC RT 3.04 minutes.

EXAMPLE 187

1-(6-Bromo-7-isopropoxy-2-benzothiazolyl)-3-ethyl-urea (11). A mixture of 1-(6-bromo-7-hydroxy-2-benzothiazolyl)-3-ethyl-urea 6, potassium carbonate and 2-bromopropane in DMF was reacted to give 0.046 g (81%) of the desired compound 11. $^1$H NMR (DMSO) δ 10.83 (br s, 1H, NH), 7.55 (d, 1H, J=8.5 Hz, ArH), 7.31 (d, 1H, J=8.6 Hz, ArH), 6.71 (br s, 1H, NH), 4.69 (hept, 1H, J=6.0 Hz, CH), 3.18 (m, 2H, CH₂), 1.32 (d, 6H, J=6.1 Hz, CH₃), 1.09 (t, 3H, J=7.2 Hz, CH₃); LC/MS 358 (MH⁺); RP-HPLC RT 3.42 minutes.

EXAMPLE 188

1-(6-Bromo-7-(2-(2-methoxyethoxy)ethoxy)-2-benzothiazolyl)-3-ethyl-urea (12). A mixture of 1-(6-bromo-7-hydroxy-2-benzothiazolyl)-3-ethyl-urea 6, potassium carbonate and 2-(2-methoxyethoxy)ethyl bromide in DMF was reacted to give 0.026 g (39%) of the desired compound 12. $^1$H NMR (DMSO) δ 10.65 (br s, 1H, NH), 7.54 (d, 1H, J=8.5 Hz, ArH), 7.32 (d, 1H, J=8.6 Hz, ArH), 6.73 (br s, 1H, NH), 4.24 (d, 2H, J=4.4 Hz, CH₂), 3.76 (d, 2H, J=4.8 Hz, CH₂), 3.61 (dd, 2H, J=6.0, 5.2 Hz, CH₂), 3.48 (dd, 2H, J=6.0, 5.2 Hz, CH₂), 3.26 (s, 3H CH₃), 3.19 (m, 2H, CH₂), 1.09 (t, 3H, J=7.1 Hz, CH₃); LC/MS 418 (MH⁺); RP-HPLC RT 2.95 minutes.

EXAMPLE 189

1-(6-Bromo-7-(4-fluoro-benzyloxy)-2-benzothiazolyl)-3-ethyl-urea, (13): A mixture of 1-(6-bromo-7-hydroxy-2-benzothiazolyl)-3-ethyl-urea 6, potassium carbonate and p-fluoro-benzyl-bromide in DMF was reacted to give 0.013 g (19%) of the desired compound 13. $^1$H NMR (DMSO) δ 1.08 (t, 3H, J=8 Hz CH₂CH₃), 3.18 (m, 2H, CH₂), 5.16 (s, 2H, OCH₂Ar), 6.73 (br s, 1H, NH), 7.26 (dd, 2H, J=4, 4 Hz, ArH),7.36 (d, 1H, J=8 Hz, ArH), 7.56 (d, 1H, J=4 Hz, ArH), 7.58 (d, 2H, J=4 Hz, ArH), 10.89 (br s, 1H, NH). HPLC retention time 3.61 minutes.

EXAMPLE 190

1-(6-Bromo-7-trifluoromethanesulfonyl-2-benzthiazolyl)-3-ethyl-urea, (14): To a solution of 1-(6-bromo-7-hydroxy-2-benzothiazolyl)-3-ethyl-urea (50 mg, 0.158 mmol) in pyridine (1 mL) were added 3 portions of (CF₃SO₂)₂O (29 μL, 0.174 mmol) about 45 minutes apart. The reaction mixture was stirred for about 3 hours at about 35° C. The solvent was then evaporated. The crude material was purified by LC/MS to give 23 mg (32%) pure 14. $^1$H NMR (DMSO) δ 1.09 (t, 3H, J=8 Hz CH₃), 3.19 (m, 2H, CH₂), 6.79 (br s, 1H, NH), 7.67 (d, 1H, J=12 Hz, ArH), 7.80 (d, 1H, J=8 Hz, ArH), 11.20 (br s, 1H, NH). HPLC retention time 3.58 minutes.

EXAMPLE 191

1-(6-Bromo-7-(2-aminocarboxy)isopropoxy-2-benzothiazolyl)-3-ethyl-urea (15): A mixture of 1-(6-bromo-7- hydroxy-2-benzothiazolyl)-3-ethyl-urea 6 (0.050 g, 0.16 mmol), cesium carbonate (0.155 g, 0.48 mmol, 3.0 eq) and 60% sodium hydride (0.019 g, 0.48 mmol, 3.0 eq) in anhydrous dioxane (1.0 mL) was stirred at about 20° C. for about 0.5 hour, followed by the addition of 2-bromo-2-methylpropionyl amide (0.079 g, 0.48 mmol, 3.0 eq). It was heated at about 110° C. for about 18 hours. DMPU (2 mL) was added and it was heated at about 85° C. for about another 18 hours. An additional portion of 60% sodium hydride (0.013 g, 0.32 mmol, 2.0 eq. in minear oil) was added. After about 3.5 days, the reaction was quenched with H$_2$O (1 mL). The mixture was concentrated in vacuum, and EtOAc (25 mL) was added. The precipitation was filtered off and was rinsed with diethyl ether (2×5 mL) and methanol (2×5 mL). The organic solution was concentrated and residue was dissolved in DMF (2 mL). LC/MS purification gave 0.021 g (33%) of the desired compound 15. $^1$H NMR (DMSO) δ 10.81 (br s, 1H, NH), 7.73 (br s, 1H, NH$_2$), 7.57 (d, 1H, J=8.6 Hz, ArH), 7.44 (br s, 1H, NH$_2$), 7.34 (d, 1H, J=8.5 Hz, ArH), 6.71 (br, s, 1H, NH), 3.18 (m, 2H, CH$_2$), 1.46 (s, 6H, CH$_3$), 1.08 (t, 3H, J=7.2 Hz, CH$_3$); LC/MS 401 (MH$^+$); RP-HPLC RT 2.64 minutes.

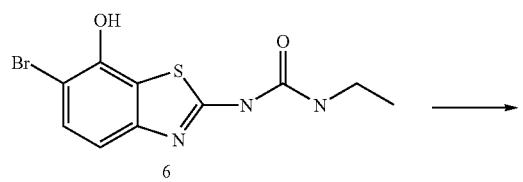

EXAMPLE 192

1-(6-Bromo-7-methoxy-2-benzothiazolyl)-1-methyl-3-ethyl-urea (16): Compound 16 was isolated in a small amount, as a side product in the formation of compound 10. 0.0030 g (2%) of the desired compound 16 was isolated. $^1$H NMR (DMSO) δ 7.73 (t, 1H, J=5.4 Hz, NH), 7.56 (d, 1H, J=8.5 Hz, ArH), 7.40 (d, 1H, J=8.5 Hz, ArH), 3.94 (s, 3H, CH$_3$), 3.59 (s, 3H, CH$_3$), 3.24 (m, 2H, CH$_2$), 1.09 (t, 3H, J=7.1 Hz, CH$_3$); LC/MS 344 (MH$^+$); RP-HPLC RT 3.58 minutes.

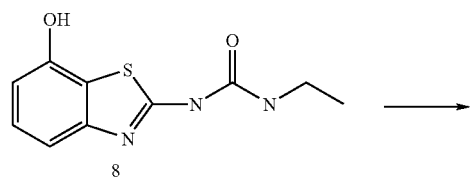

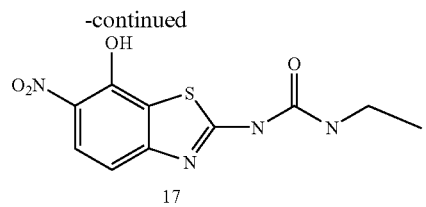

EXAMPLE 193

1-(7-Hydroxy-6-nitro-2-benzothiazolyl)-3-ethyl-urea (17): To a solution of 2-methylpyridone (0.020 mL, 0.20 mmol, 1.2 eq) in anhydrous acetonitrile (0.5 mL), nitronium tetrafluoroborate (0.045 g, 0.32 mmol, 1.9 eq) was added. The suspension was stirred at about 20° C. for about 5 minutes to get an orange solution. The solution was then transferred to a suspension of 1-(7-hydroxy-2-benzothiazolyl)-3-ethyl-urea 8 (0.040 g, 0.17 mmol) in acetonitrile (0.5 mL). The reaction mixture was stirred at about 20° C. for about 15 minutes, then taken up in diethyl ether (8 mL), and neutralized by washing with saturated sodium bicarbonate solution (1.5 mL). The organic extract was concentrated and dissolved in methanol (2 mL). LC/MS purification was followed by flash chromatography purification on silica (methylene chloride/methanol=40/1) to afford 0.005 g (10%) of the desired compound 17. $^1$H NMR (DMSO) δ 11.20 (br s, 1H, NH), 8.02 (d, 1H, J=9.0 Hz, ArH), 7.23 (d, 1H, J=7.5 Hz, ArH), 6.78 (br s, 1H, NH), 3.20 (m, 2H, CH$_2$), 1.10 (t, 3H, J=7.2 Hz, CH$_3$). LC/MS 283 (MH$^+$); RP-HPLC RT 2.74 minutes.

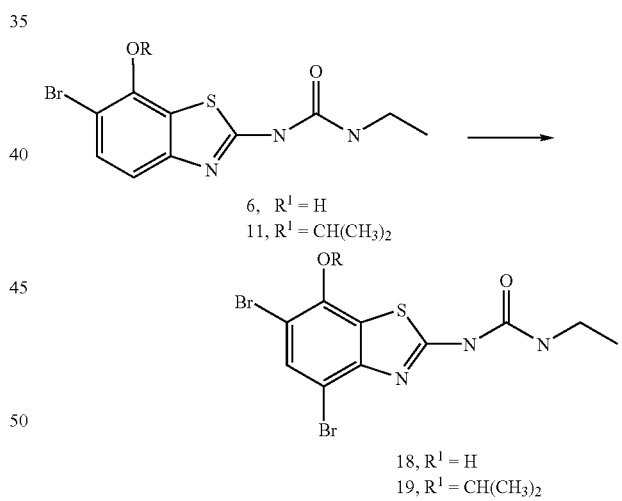

EXAMPLE 194

1-(4,6-Dibromo-7-hydroxy-2-benzothiazolyl)-3-ethyl-urea, (18): To a suspension of 1-(6-bromo-7-hydroxy-2-benzothiazolyl)-3-ethyl-urea (50 mg, 0.158 mmol) in AcOH (2 mL) at about 20° C. was added Br$_2$ (9 μl, 0.174 mmol). The reaction mixture was stirred at about 20° C. for about 15 minutes. Toluene (10 mL) was added and the solvents evaporated. The crude material was purified by preparative LC/MS to give 19 mg (30%) pure 18. $^1$H NMR (DMSO) δ 1.09 (t, 3H, J=6 Hz CH$_3$), 3.19 (m, 2H, CH$_2$), 6.55 (br s, 1H, NH), 7.68 (s, 1H, ArH), 10.51 (br s, 1H, NH or OH), 11.20 (br s, 1H, NH or OH). HPLC retention timer 2.90 minutes.

EXAMPLE 195

1-(4,6-Dibromo-7-isopropoxy-2-benzothiazolyl)-3-ethyl-urea, (19): Was prepared from 1-(6-bromo-7-isopropoxy-2-benzothiazolyl)-3-ethyl-urea as above. Purification by LC/MS gave 25 mg (41%) pure 19. $^1$H NMR (DMSO) δ 1.08 (t, 3H, J=8 Hz, CH$_2$CH$_3$), 1.32 (d, 6H, J=4 Hz, CH(CH$_3$)$_2$), 3.19 (m, 2H, CH$_2$), 4.68 (m, 1H, CH(CH$_3$)$_2$), 6.59 (br s, 1H, NH), 7.83 (s, 1H, ArH), 11.45 (br s, 1H, NH). HPLC retention time 4.01 minutes.

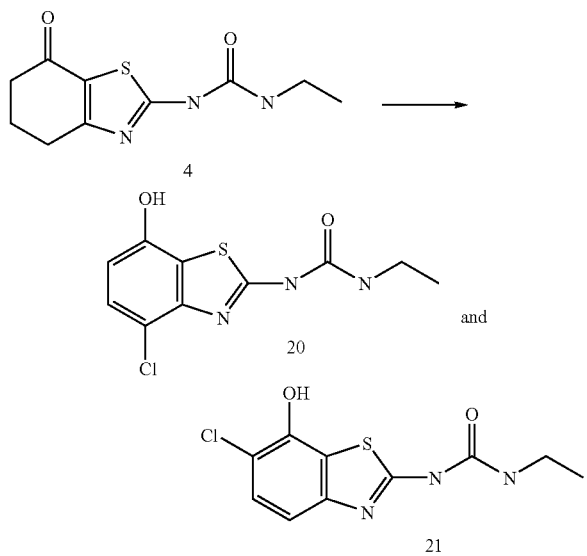

EXAMPLE 196–197

1-(4-Chloro-7-hydroxy-2-benzothiazolyl)-3-ethyl-urea, (20) and 1-(6-Chloro-7-hydroxy-2-benzothiazolyl)-3-ethyl-urea, (21): To a solution of 1-(7-oxo-4,5,6,7-tetrahydro-2-benzothiazolyl)-3-ethyl-urea (50 mg, 0.209 mmol) in DMF (1 mL) was added a freshly prepared solution of Cl$_2$ in DMF (3 mL) saturated at about 20° C. The reaction mixture was stirred at about 80° C. for about 24 hours. The solvent was evaporated and the crude material was purified by LC/MS. 6 mg (11%) of a mixture of pure 20 and 21 in a ratio of 1 to 1 was obtained. $^1$H NMR (DMSO) δ 1.08 (t, 3H, J=8 Hz CH$_2$CH$_3$), 3.16 (m, 2H, CH$_2$), 6.63 (d, 0.5H, J=8 Hz, ArH), 6.64 (br s, 0.5H, NH), 6.87 (br s, 0.5H, NH), 7.01 (d, 0.5H, J=8 Hz, ArH), 7.22 (d, 0.5H, J=8 Hz, ArH), 7.25 (d, 0.5H, J=8 Hz, ArH). HPLC retention time 2.54 minutes.

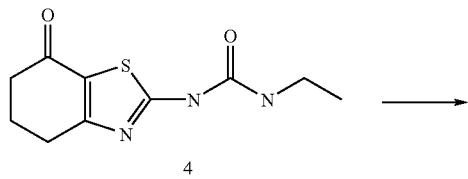

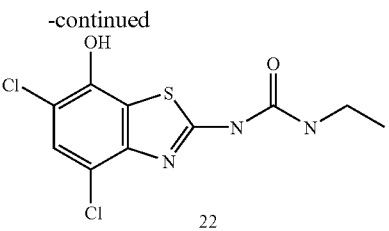

EXAMPLE 198

1-(4,6-Dichloro-7-hydroxy-2-benzothiazolyl)-3-ethyl-urea, (22): To a solution of 1-(7-oxo-4,5,6,7-tetrahydro-2-benzothiazolyl)-3-ethyl-urea (50 mg, 0.209 mmol) in AcOH (2 mL) was bubbled Cl$_2$ gas for about 1 minute at about 20° C. A white precipitate was formed that was filtered off. 5 mg (8%) pure 22 was obtained. $^1$H NMR (DMSO) δ 1.09 (t, 3H, J=6 Hz CH$_3$), 3.19 (m, 2H, CH$_2$), 6.59 (br s, 1H, NH), 7.47 (s, 1H, ArH), 10.58 (br s, 1H, NH or OH), 11.26 (br s, 1H, NH or OH). HPLC retention time 2.73 minutes.

General Procedure for Making 1-(7-Alkynyl-2-benzothiazolyl)-3-ethylurea Compounds.

Step A: 1-(7-Trinfluoromethylsulfonyl-2-benzothiazolyl)-3-ethylurea. To a solution of 1-(7-hydroxy-2-benzothiazolyl)-3-ethylurea (1.50 g, 6.32 mmol) in 15 mL pyridine at about 0° C., trifluoromethansulfonic anhydride (2.13 mL, 12.64 mmol) was added dropwise. It was stirred at about 0° C. for about 2 hours. The reaction was quenched with 15 mL MeOH and the solvent was evaporated. The crude mixture was purified by flash chromatography on SiO$_2$ with methylene chloride and methanol (90/1) to give 1.45 g (62%) of desired compound. LC/MS 369.9 (M+1); LC retention time 3.34 min.

Step B: A mixture of 1-(7-trifluoromethylsulfonyl-2-benzothiazolyl)-3-ethylurea, Pd(PPh$_3$)$_2$Cl$_2$ (0.08 eq), and triethylamine (4.3 eq) in anhydrous DMF is bubbled with nitrogen gas for about 5 minutes, followed by the addition of an alkyne of choice (5.0 eq). The mixture is heated at about 100° C. with stirring in a sealed tube for about 18 hours. The mixture is cooled down, taken up with MeOH, and evaporated to dryness. Purification by flash chromatography on SiO$_2$ with ethyl acetate and heptane to give pure desired products.

EXAMPLE 199

1-(7-Trimethylsilylacetylenyl-2-benzothiazolyl)-3-ethylurea

A mixture of 1-(7-trifluoromethylsulfonyl-2-benzothiazolyl)-3-ethylurea (0.080 g, 80% pure, 0.17 mmol), Pd(PPh$_3$)$_2$Cl$_2$ (0.010 g, 0.014 mmol, 0.08 eq), and triethylamine (0.102 mL, 0.73 mmol, 4.3 eq) in 1 mL of anhydrous DMF was bubbled with nitrogen gas for 5 minutes, followed by the addition of trimethylsilyl acetylene (0.12 mL, 0.85 mmol, 5.0 eq). The mixture was heated at about 100° C. with stirring in a sealed tube for about 18 hours. The mixture was cooled down, taken up in 10 mL MeOH, and evaporated to dryness. Purification by flash chromatography on SiO$_2$ with ethyl acetate and heptane (2/1) gave pure desired compound 0.050 g (93%). LC/MS 318 (M+1); LC retention time 9.25 min.

1-(7-Acetylenyl-2-benzothiazolyl)-3-ethylurea

A mixture of 1-(7-trimethylsilylacetylenyl-2-benzothiazolyl)-3-ethylurea 2 (0.050 g, 0.16 mmol) and 1M aqueous KOH solution (0.16 mL, 0.16 mmol, 1.0 eq) in 1.5 mL of 2/1 mixture of DMF/MeOH was stirred at room temperature for about 2 hours. The mixture was taken up in 10 mL MeOH and the precipitation was filtered off. The mother liquid was concentrated and purified by prep HPLC to give the desired compound 0.006 g (15%). LC/MS 246 (M+1); LC retention time 2.77 min.

EXAMPLE 200

1-(7-(N,N-Dimethylmethylacetylenyl)-2-benzothiazolyl)-3-ethylurea

According to the general procedure for making alkynyl compounds, a mixture of 1-(7-trifluoromethylsulfonyl-2-benzothiazolyl)-3-ethylurea, triethyl amine, Pd(PPh$_3$)$_2$Cl$_2$, and N,N-dimethylmethylacetylene in DMF was reacted to give 0.0025 g (8%) of the desired compound. LC/MS 303 (M+1); LC retention time 2.20 min.

EXAMPLE 201

1-(7-(2'-Pyridinylacetylenyl)-2-benzothiazolyl)-3-ethylurea

According to the general procedure for making alkynyl compounds, a mixture of 1-(7-trifluoromethylsulfonyl-2-benzothiazolyl)-3-ethylurea, triethyl amine, Pd(PPh$_3$)$_2$Cl$_2$, and 2-pyridinylacetylene in DMF was reacted to give 0.020 g (57%) of the desired compound. LC/MS 322.9 (M+1); LC retention time 3.18 min.

EXAMPLE 202

1-(7-Isopropoxy-2-benzothiazolyl)-3-ethylurea

A solution of 1-(6-bromo-7-isopropoxy-2-benzothiazolyl)-3-ethylurea (0.036 g, 0.10 mmol) in 0.5 mL DME was cooled down to about −78° C., and was treated with a solution of 1.6 M n-BuLi in hexanes (0.16 mL, 0.26 mmol, 2.6 eq). It was stirred at the temperature for about 20 min, then a solution of N-chlorosuccinimide (NCS) (0.015 g, 0.11 mmol, 1.1 eq) in 0.5 mL DME was added. It was warmed up to about 0° C. for about 0.5 hour. It was taken up in MeOH and purified by HPLC to give 0.007 g (25%) of the title compound. LC/MS 279.9 (M+1); LC retention time 3.10 min.

EXAMPLE 203

1-(7-Phenyl-2-benzothiazolyl)-3-ethylurea

A mixture of 1-(7-trifluoromethylsulfonyl-2-benzothiazolyl)-3-ethylurea (0.050 g, 80% pure, 0.11 mmol), lithium chloride (0.039 g, 0.92 mmol, 8.4 eq), triphenylphosphine (0.017 g, 0.066 mmol, 0.6 eq), Pd(PPh$_3$)$_2$Cl$_2$ (0.010 g, 0.013 mmol, 0.12 eq), tributylphenyltin (0.036 mL, 0.33 mmol, 3.0 eq), and a crystal of 2,6-di-tert-butyl-4-methylphenol in 1 mL anhydrous DMF was purged with nitrogen gas, and was heated at about 120° C. in a sealed tube for about 36 hours. More catalyst Pd(PPh$_3$)$_2$Cl$_2$ (0.010 g, 0.013 mmol, 0.12 eq) and tin reagent (0.024 mL, 0.22 mmol, 2.0 eq) were added to the mixture after the first 24 hours. The mixture was taken up in MeOH, filtered, and concentrated. Purification by HPLC gave 0.004 g (12%) of the desired compound. LC/MS 298.0 (M+1); LC retention time 3.37 min.

EXAMPLE 204

1-(7-Vinyl-2-benzothiazolyl)-3-ethylurea

Similar to the synthesis of Example 203, a mixture of 1-(7-trifluoromethylsulfonyl-2-benzothiazolyl)-3-ethylurea (0.050 g, 80% pure, 0.11 mmol), lithium chloride (0.039 g, 0.92 mmol, 8.4 eq), triphenylphosphine (0.017 g, 0.066 mmol, 0.6 eq), Pd(PPh$_3$)$_2$Cl$_2$ (0.009 g, 0.013 mmol, 0.12 eq), tetravinyltin (0.040 mL, 0.22 mmol, 2.0 eq), and a crystal of 2,6-di-tert-butyl-4-methylphenol was purged with nitrogen gas, and was heated at about 100° C. for about 1.5 hours. The mixture was taken up in MeOH, filtered, concentrated, and purified by HPLC and preparative TLC in ethyl acetate/heptane mixture to obtain 0.004 g (14%) of the desired compound. LC/MS 248 (M+1); LC retention time 2.96 min.

EXAMPLE 205

1-(6-Bromo-7-trifluoromethylsulfonyl-2-benzothiazolyl)-3-ethylurea

To a solution of 1-(6-bromo-7-hydroxy-2-benzothiazolyl)-3-ethylurea (3.35 g, 10.6 mmol) in 40 mL pyridine at about 0° C., trifluoromethansulfonic anhydride (2.67 mL, 15.9 mmol) was added dropwise. It was stirred at about 0° C. for about 4 hours. The reaction was taken up in 100 mL AcOEt, washed with 70 mL of 2M HCl and 70 mL of brine. The solution was dried (MgSO$_4$) and concentrated. The crude mixture was purified by flash chromatography on SiO$_2$ with AcOEt and heptane (1/3) to give 2.39 g (50%) of desired compound. LC/MS 445.9 (M−1); LC retention time 3.84 min.

1-(6,7-Di-vinyl-2-benzothiazolyl)-3-ethylurea

Similar to the synthesis of Example 203, a mixture of 1-(6-bromo-7-trifluoromethylsulfonyl-2-benzothiazolyl)-3-ethylurea (0.100 g, 0.22 mmol), lithium chloride (0.078 g, 1.84 mmol, 8.4 eq), triphenylphosphine (0.034 g, 0.13 mmol, 0.6 eq), Pd(PPh$_3$)$_2$Cl$_2$ (0.018 g, 0.026 mmol, 0.12 eq), tetravinyltin (0.080 mL, 0.44 mmol, 2.0 eq), and a crystal of 2,6-di-tert-butyl-4-methylphenol was purged with nitrogen gas, and was heated at about 100° C. for about 18 hours. Additional tin reagent (0.080 mL, 0.44 mmol, 2.0 eq) was added to the mixture after the first 2 hours. The mixture was taken up in MeOH, filtered, and concentrated. Purification by HPLC and flash chromatography on SiO$_2$ with ethyl acetate/methylene chloride (1/4) gave the desired compound 0.014 g (23%). LC/MS 274.3 (M+1); LC retention time 2.32 min.

General Procedure for Making 2-amino-6-Substituted benzothiazole Compounds.

A solution of 4-substituted aniline and KSCN (2.0 eq) in acetic acid is cooled at about 5° C., and is treated dropwise with a solution of bromine in acetic acid (1.0 eq). The mixture is stirred at room temperature for about 1 to 3 hours. The precipitate is filtered off and washed with Et$_2$O. The obtained solid is neutralized with saturated sodium carbonate solution, a new precipitate is formed. It is filtered off, washed with water, and dried under vacuum to give the desired compound.

EXAMPLE 206

2-Amino-6-benzyl-benzothiazole

A solution of 4-benzylaniline (0.916 g, 5.00 mmol) and KSCN (0.97 g, 10.0 mmol, 2.0 eq) in 10 mL acetic acid was cooled at about 5° C., and was treated dropwise with a solution of bromine (0.258 mL, 5.00 mmol, 1.0 eq) in 2 mL acetic acid. The mixture was stirred at room temperature for about 1 hour. The precipitate was filtered off and washed with Et$_2$O. The obtained solid was neutralized with saturated sodium carbonate solution, and a new precipitate was formed. It was filtered off, washed with water and MeOH, and dried under vacuum to give the desired compound 1.06 g (88%). LC/MS 241.2 (M+1); LC retention time 2.46 min.

1-(6-Benzyl-2-benzothiazolyl)-3-ethylurea

A suspension of 2-amino-6-benzyl-benzothiazole (0.040 g, 0.17 mmol), triethylamine (0.104 mL, 0.77 mmol, 4.5 eq), and ethyl isocyanate (0.049 mL, 0.64 mmol, 3.8 eq) in 1 mL toluene was heated at about 95° C. for about 16 hours. The precipitate was filtered off, washed with Et$_2$O and MeOH, and dried under vacuum to give the desired compound 0.029 g (56%). LC/MS 312.3 (M+1); LC retention time 2.62 min.

EXAMPLE 207

2-Amino-6-(4'-fluorophenoxy)-benzothiazole

A solution of 4-(4'-fluorophenoxy)aniline (0.305 g, 1.50 mmol) and KSCN (0.29 g, 3.00 mmol, 2.0 eq) in 3 mL acetic acid was cooled at about 5° C., and was treated dropwise with a solution of bromine (0.077 mL, 1.50 mmol, 1.0 eq) in 2 mL acetic acid. The mixture was stirred at room temperature for about 2 hours. The precipitate was filtered off and washed with Et$_2$O. The mother liquid from the filtration was concentrated, and the residue was combined with the precipitate. The obtained solid was neutralized with saturated sodium carbonate solution, and a new precipitate was formed. It was filtered off, washed with water, and dried under vacuum to give the desired compound 0.403 g (90%). LC/MS 261.2 (M+1); LC retention time 2.44 min.

EXAMPLE 208

2-Amino-6-(4'-pyridinylmethyl)-benzothiazole

A solution of 4-(4'-pyridinylmethyl)aniline (0.368 g, 2.00 mmol) and KSCN (0.388 g, 4.00 mmol, 2.0 eq) in 5 mL acetic acid was cooled at about 5° C., and was treated dropwise with a solution of bromine (0.103 mL, 2.00 mmol, 1.0 eq) in 2 mL acetic acid. The mixture was stirred at room temperature for 3 hours. The precipitate was filtered off and washed with Et$_2$O. The obtained solid was neutralized with saturated sodium carbonate solution, and a new precipitate was formed. It was filtered off, washed with water, and dried under vacuum to give the desired compound 0.41 g (85%). LC/MS 242.2 (M+1); LC retention time 1.61 min.

General Procedure for making 1-(6-substituted-2-benzothiazolyl)-3-ethylurea compounds. A suspension of 2-amino-6-substituted benzothiazole, triethylamine (3.0 eq) and ethyl isocyanate (2.5 eq) in toluene is heated at about 95° C. for about 3 to 20 hours. The precipitate is filtered off, washed with Et$_2$O and MeOH, and dried under vacuum to give the desired compound.

EXAMPLE 209

1-(6-(4'-Fluorophenoxy)-2-benzothiazolyl)-3-ethylurea

A mixture of 2-amino-6-(4'-fluorophenoxy)-benzothiazole, triethylamine, and ethyl isocyanate in toluene was reacted according to the general procedure described hereinabove to give 0.041 g (66%) desired compound. LC/MS 332.2 (M+1); LC retention time 2.66 min.

EXAMPLE 210

1-(6-(4'-Pyridinylmethyl)-2-benzothiazolyl)-3-ethylurea

A mixture of 2-amino-6-(4'-pyridinylmethyl)-benzothiazole, triethylamine, and ethyl isocyanate in toluene was reacted according to the general procedure described hereinabove to give 0.100 g (62%) of the desired compound. LC/MS 313.3 (M+1); LC retention time 1.96 min.

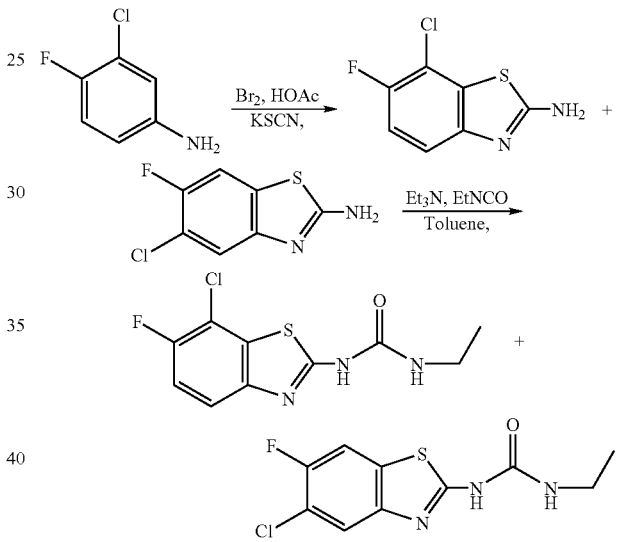

EXAMPLE 211

1-(6-Fluoro-7-chloro-2-benzothiazolyl)-3-ethylurea and 1-(5-Chloro-6-fluoro-2-benzothiazolyl)-3-ethylurea A solution of 3-chloro-4-fluoro-aniline (0.300 g, 2.06 mmol) and KSCN (0.412 g, 4.25 mmol, 2.06 eq) in 5 mL acetic acid was cooled to about 5° C., and was treated dropwise with a solution of bromine (0.159 mL, 3.09 mmol, 1.5 eq) in 5 mL acetic acid. The mixture was stirred at room temperature for about 3 hours. The mixture was concentrated and purified on SiO$_2$ with AcOEt and methylene chloride (1/8) to give 0.041 g (10%) a mixture of 6-fluoro-7-chloro-benzothiazole and 5-chloro-6-fluoro-benzothiazole. The mixture was mixed with triethylamine (0.055 mL, 0.40 mmol, 2.0 eq) and ethyl isocyanate (0.031 mL, 0.40 mmol, 2.0 eq) in 1 mL toluene. It was heated at about 110° C. for about one day. The residue was evaporated to dryness, and taken up in DMF. A precipitate was filtered off from the DMF solution, washed with Et$_2$O, and dried under vacuum to give 1-(5-chloro-6-fluoro-2-benzothiazolyl)-3-ethylurea 0.003 g. LC/MS 274.0 (M+1); LC retention time 3.10 min.

The DMF mother liquid was purified by HPLC and preparative TLC to give 1-(6-fluoro-7-chloro-2-benzothiazolyl)-3-ethylurea 0.002 g. LC/MS 274.0 (M+1); LC retention time 3.08 min.

EXAMPLE 212

1-(6-Bromo-2-benzothiazolyl)-3-ethylurea

A suspension of 2-amino-6-bromo-benzothiazole (6.12 g, 26.2 mmol), triethylamine (7.30 mL, 52.4 mmol, 2.0 eq), and ethyl isocyanate (4.15 mL, 52.4 mmol, 2.0 eq) in 50 mL toluene was heated at about 90° C. for about 15 hours. The precipitate was filtered off, washed with $Et_2O$, and dried under vacuum to give the desired compound 7.39 g (94%). LC/MS 300.0 (M−1); LC retention time 3.01 min.

General Procedure for making 1-(6-alkynyl-2-benzothiazolyl)-3-ethylurea compounds. A mixture of 1-(6-bromo-2-benzothiazolyl)-3-ethylurea, $Pd(PPh_3)_2Cl_2$ (0.05 eq), and triethylamine (4.3 eq) in anhydrous DMF is bubbled with nitrogen gas for about 5 minutes, followed by the addition of an alkyne of choice (5.0 eq). The mixture is heated at about 80° C. with stirring in a sealed tube for about 15 hours. The mixture is cooled down, taken up with MeOH, and evaporated to dryness. Purification by HPLC or by flash chromatography on $SiO_2$ with ethyl acetate and heptane to give pure desired product.

EXAMPLE 213

1-(6-Trimethylsilylacetylenyl-2-benzothiazolyl)-3-ethylurea

A mixture of 1-(6-bromo-2-benzothiazolyl)-3-ethylurea (0.100 g, 0.33 mmol), $Pd(PPh_3)_2Cl_2$ (0.012 g, 0.017 mmol, 0.05 eq), and triethylamine (0.20 mL, 1.42 mmol, 4.3 eq) in 1 mL of anhydrous DMF was bubbled with nitrogen gas for about 5 minutes, followed by the addition of trimethylsilyl acetylene (0.23 mL, 1.65 mmol, 5.0 eq). The mixture was heated at about 80° C. with stirring in a sealed tube for about 15 hours. The mixture was cooled down, taken up in 10 mL MeOH, and evaporated to dryness. Purification by HPLC gave pure desired compound 0.093 g (89%). LC/MS 318 (M+1); LC retention time 3.77 min.

EXAMPLE 214

1-(6-Phenylacetylenyl-2-benzothiazolyl)-3-ethylurea

A mixture of 1-(6-bromo-2-benzothiazolyl)-3-ethylurea, $Pd(PPh_3)_2Cl_2$, triethylamine, and phenylacetylene in 1 mL of anhydrous DMF was reacted according to the procedure of Example 213 to give 0.008 g (8%) of the desired compound. LC/MS 322 (M+1); LC retention time 3.65 min.

EXAMPLE 215

1-(6-(N,N-Dimethylaminomenthyl)acetylenyl-2-benzothiazolyl)-3-ethylurea

A mixture of 1-(6-bromo-2-benzothiazolyl)-3-ethylurea, $Pd(PPh_3)_2Cl_2$, triethylamine, and N,N-dimethylaminomethyl acetylene in 1 mL of anhydrous DMF was reacted according to the procedure of Example 213 to give 0.145 g (28%) of the desired compound. LC/MS 303 (M+1); LC retention time 1.40 min.

EXAMPLE 216

1-(6-(4'-Fluorophenyl)acetylenyl-2-benzothiazolyl)-3-ethylurea

A mixture of 1-(6-bromo-2-benzothiazolyl)-3-ethylurea, $Pd(PPh_3)_2Cl_2$, triethylamine, and 4-fluorophenylacetylene in 1 mL of anhydrous DMF was reacted according to the procedure of Example 213 to give 0.215 g (94%) of the desired compound. LC/MS 340.3 (M+1); LC retention time 2.92 min.

EXAMPLE 217

1-(6-(4'-Tolyl)acetylenyl-2-benzothiazolyl)-3-ethylurea

A mixture of 1-(6-bromo-2-benzothiazolyl)-3-ethylurea, $Pd(PPh_3)_2Cl_2$, triethylamine, and 4-tolylacetylene in 1 mL of anhydrous DMF was reacted according to the procedure of Example 213 to give 0.185 g (99%) of the desired compound. LC/MS 336.3 (M+1); LC retention time 3.07 min.

EXAMPLE 218

1-(6-Acetylenyl-2-benzothiazolyl)-3-ethylurea

A mixture of 1-(6-trimethylsilylacetylenyl-2-benzothiazolyl)-3-ethylurea (0.0710 g, 0.22 mmol) and 1M aqueous KOH solution (1.22 mL, 1.22 mmol, 5.5 eq) in 1.5 mL MeOH was stirred at room temperature for about 2 hours. The mixture acidified with 1 M HCl, then taken up in 20 mL AcOEt, and the aqueous phase was extracted with 10 mL AcOEt. The combined organic portions were dried ($MgSO_4$), concentrated, and purified by HPLC to give the desired compound 0.003 g (5%). LC/MS 246 (M+1); LC retention time 2.84 min.

EXAMPLE 219

1-(6-(2-Phenylethyl)-2-benzothiazolyl)-3-ethylurea

A suspension of 1-(6-phenylacetylenyl-2-benzothiazolyl)-3-ethylurea (0.048 g, 0.15 mmol) and 10% palladium on carbon (0.016 g, 10% weight purity, 0.015 mmol, 0.10 eq) in 2 mL ethanol was purged with nitrogen gas, followed by bubbling of hydrogen gas. It was stirred under hydrogen atmosphere for about 16 hours. The mixture was taken up in 8 mL MeOH, filtered, concentrated, and dried under vacuum to give 0.037 g (76%) of the desired compound. LC/MS 326.3 (M+1); LC retention time 2.84 min.

EXAMPLE 220

1-(6-(2-(4'-Fluoro-phenyl)ethyl)-2-benzothiazolyl)-3-ethylurea

A suspension of 1-(6-(4'-fluorophenyl)acetylenyl-2-benzothiazolyl)-3-ethylurea (0.144 g, 0.42 mmol) and Lindlar catalyst (0.090 g, 5% weight purity, 0.042 mmol, 0.10 eq) in 8 mL ethanol was purged with nitrogen gas, followed by bubbling of hydrogen gas. It was stirred under hydrogen atmosphere for about 16 hours. The resulting mixture consisted of compound having fully reduced triple bond and compound having partially reduced triple bond. A new catalyst, palladium on carbon (0.045 g, 0.042 mmol, 0.10 eq), was added. The reaction mixture was stirred under hydrogen gas for about another 1 hour. The mixture was taken up in 8 mL MeOH, filtered, concentrated, and recrystallized from MeOH to give 0.046 g (38%) of the desired compound. LC/MS 344.3 (M+1); LC retention time 2.81 min.

General procedure for the synthesis of 1-(6-(2(Z)-Substituted-vinyl)-2-benzothiazolyl)-3-ethylurea compounds. A suspension of 1-(6-substitued-acetylenyl-2-benzothiazolyl)-3-ethylurea compound and Lindlar catalyst (5% weight purity, 0.15 eq) in ethanol is purged with nitrogen gas, followed by bubbling of hydrogen gas. It is stirred under hydrogen atmosphere for about 36 hours. The mixture is taken up in MeOH, filtered, concentrated, and purified by preparative TLC to give the desired compound.

EXAMPLE 221

1-(6-(2(Z)-Phenylvinyl)-2-benzothiazolyl)-3-ethylurea

A suspension of 1-(6-phenylacetylenyl-2-benzothiazolyl)-3-ethylurea (0.032 g, 83% purity by weight, 0.083 mmol) and Lindlar catalyst (0.030 g, 5% weight purity, 0.012 mmol, 0.15 eq) in 2 mL ethanol was purged with nitrogen gas, followed by bubbling of hydrogen gas. It was stirred under hydrogen atmosphere for about 36 hours. The mixture was taken up in 10 mL MeOH, filtered, concentrated, and purified by preparative TLC to give 0.011 g (41%) of the desired compound. LC/MS 324 (M+1); LC retention time 2.84 min.

EXAMPLE 222

1-(6-(2(Z)-(N,N-Dimethylaminomethyl)vinyl)-benzothiazolyl)-3-ethylurea

A mixture of 1-(6-(N,N-dimethylaminomenthyl)acetylenyl-2-benzothiazolyl)-3-ethylurea and Lindlar catalyst under hydrogen was reacted according to the procedure of Example 221 to give the desired compound 0.013 g (21%). LC/MS 305.3 (M+1); LC retention time 1.51 min.

EXAMPLE 223

1-(6-(2(Z)-(4'-Fluorophenyl)vinyl)-2-benzothiazolyl)-3-ethylurea

A mixture of 1-(6-(4'-fluorophenyl)acetylenyl-2-benzothiazolyl)-3-ethylurea and Lindlar catalyst under hydrogen was reacted according to the procedure of Example 221 to give the desired compound 0.046 g (38%). LC/MS 344.3 (M+1); LC retention time 2.81 min.

EXAMPLE 224

1-(6-(2(Z)-(4'-Tolyl)vinyl)-2-benzothiazolyl)-3-ethylurea

A mixture of 1-(6-(4'-tolyl)acetylenyl-2-benzothiazolyl)-3-ethylurea and Lindlar catalyst under hydrogen was reacted according to the procedure of of Example 221 to give the desired compound 0.053 g (90%). LC/MS 338.3 (M+1); LC retention time 3.02 min.

General procedure for the synthesis of 1-(6-(2(E)-Substituted-vinyl)-2-benzothiazolyl)-3-ethylurea compounds. A mixture of 1-(6-bromo-2-benzothiazolyl)-3-ethylurea, Pd(PPh$_3$)$_2$Cl$_2$ (0.10 eq), 1,3-bis(diphenylphosphino)propane (dppp) (0.11 eq), triethylamine (1.2 eq), mono-substituted ethene (2.0 eq), and two crystals of BHT in anhydrous DMF is bubbled with nitrogen gas. The mixture is heated at about 105° C. with stirring in a sealed tube for about 15 hours. The mixture is cooled down, taken up in MeOH, and evaporated to dryness. Purification by flash chromatography on SiO$_2$ with MeOH and methylene chloride yields the desired compound.

EXAMPLE 225

1-(6-(2(E)-(4'-Fluorophenyl)vinyl)-2-benzothiazolyl)-3-ethylurea

A mixture of 1-(6-bromo-2-benzothiazolyl)-3-ethylurea (0.150 g, 0.50 mmol), Pd(PPh$_3$)$_2$Cl$_2$ (0.035 g, 0.05 mmol, 0.10 eq), dppp (0.023 g, 0.055 mmol, 0.11 eq), triethylamine (0.083 mL, 0.60 mmol, 1.2 eq), 4-fluorostyrene (0.120 mL, 1.00 mmol, 2.0 eq), and two crystals of BHT in 2 mL of anhydrous DMF was bubbled with nitrogen gas. The mixture was heated at about 105° C. with stirring in a sealed tube for about 15 hours. The mixture was cooled down, taken up in 5 mL MeOH, and evaporated to dryness. Purification by flash chromatography on SiO$_2$ with MeOH and methylene chloride (1.5/100) gave the desired compound 0.096 g (56%). It was further purified by precipitation from MeOH. LC/MS 342.3 (M+1); LC retention time 2.86 min.

EXAMPLE 226

1-(6-(2(E)-Phenylvinyl)-2-benzothiazolyl)-3-ethylurea

A mixture of 1-(6-bromo-2-benzothiazolyl)-3-ethylurea, Pd(PPh$_3$)$_2$Cl$_2$, dppp, triethylamine, styrene, and two crystals of BHT in anhydrous DMF was reacted according to the procedure of Example 225 to give the desired compound 0.201 g (62%). LC/MS 324.2 (M+1); LC retention time 2.87 min.

EXAMPLE 227

1-(6-(2(E)-(4'-Tolyl)vinyl)-2-benzothiazolyl)-3-ethylurea

A mixture of 1-(6-bromo-2-benzothiazolyl)-3-ethylurea, Pd(PPh$_3$)$_2$Cl$_2$, dppp, triethylamine, 4-methylstyrene, and two crystals of BHT in anhydrous DMF was reacted according to the procedure of Example 225 to give the desired compound 0.030 g (37%). LC/MS 338.0 (M+1); LC retention time 3.80 min.

EXAMPLE 228

1-(6-(2(E)-(1'-Imidazolyl)vinyl)-2-benzothiazolyl)-3-ethylurea

A mixture of 1-(6-bromo-2-benzothiazolyl)-3-ethylurea, Pd(PPh$_3$)$_2$Cl$_2$, dppp, triethylamine, 1-vinylimidazole, and two crystals of BHT in anhydrous DMF was reacted according to the procedure of Example 225 to give the desired compound 0.308 g (97%). LC/MS 314.1 (M+1); LC retention time 1.82 min.

EXAMPLE 229

Ethyl {[6-(4-Fluorophenoxy)-2-benzothiazolyl]amino}methanethioate

A suspension of 2-amino-6-(4'-fluorophenoxy)-benzothiazole (associated with 2.0 eq of KBr salt, 2.50 g, 5.02 mmol) in 10 mL pyridine was treated dropwise with methyl chlorothioformate (0.65 mL, 7.53 mmol, 01.5 eq). It was stirred at room temperature for about 1 hour, and was poured into 40 mL ice water. The mixture was acidified slowly with 1 M HCl solution. The result precipitate was filtered off, washed with water and MeOH, and dried under vacuum to give 1.18 g (65%) desired compound. LC/MS 334.9 (M+1); LC retention time 3.70 min.

General procedure for the synthesis of 1-(6-(4'-Fluorophenoxy)-2-benzothiazolyl)-3-optionally substituted-alkylurea compounds. A suspension of ethyl {[6-(4-fluorophenoxy)-2-benzothiazolyl]amino}methanethioate (Example 229) and an alkyl amine (1.2 eq) of choice in EtOH is heated at about 80° C. for about 2.5 hours to 3 days. The mixture is taken up in MeOH, concentrated, and purified by HPLC to give the desired compound.

EXAMPLE 230

1-(6-(4'-Fluorophenoxy)-2-benzothiazolyl)-3-(3-(4-methylpiperazinyl)propyl)urea

A suspension of ethyl {[6-(4-fluorophenoxy)-2-benzothiazolyl]amino}methanethioate (0.154 g, 0.46 mmol) and 4-methyl-1-(3-aminopropyl)piperazine (0.100 mL, 0.55 mmol, 1.2 eq) in 8 mL EtOH was heated at about 80° C. for about 3 days. A precipitate was filtered off, washed with MeOH, and dried under vacuum, giving compound N-(6-(4'-Fluorophenoxy)-2-benzothiazolyl)-ethylcarbamate as a side product. 0.004 g (3%). LC/MS 333.4 (M+1); LC retention time 3.66 min.

The mother liquid from the filtration was concentrated and purified by HPLC, it is the desired compound in the form of the acetic acid salt. LC/MS 444.1 (M+1); LC retention time 3.32 min.

A portion of the purified compound was dissolved in methylene chloride, and washed with 2 M NaOH solution. The organic portion was evaporated, dissolved in AcOEt, and treated with 1 mL solution of maleic acid in AcOEt. The white precipitation generated was filtered off, washed with AcOEt, and dried under vacuum to give 0.024 g (8%) of the desired compound in the form of maleic salt. LC/MS 444.1 (M+1); LC retention time 3.38 min.

In another run of the same reaction, the mixture was evaporated to dryness after the reaction was finished. The residue was recrystallized from Et$_2$O and heptane, giving 0.088 g (56%) of the desired product as the free base. LC/MS 444.1 (M+1); LC retention time 2.17 min.

EXAMPLE 231

1-(6-(4'-Fluorophenoxy)-2-benzothiazolyl)-3-(2-(4-imidazolyl)ethyl)urea

A mixture of ethyl {[6-(4-fluorophenoxy)-2-benzothiazolyl]amino}methanethioate and 4-(2-aminoethyl)imidazole in EtOH was reacted according to the procedure for obtaining the free base of Example 230 to give the desired compound 0.027 g (46%). LC/MS 398.2 (M+1); LC retention time 2.24 min.

EXAMPLE 232

1-(6-(4'-Fluorophenoxy)-2-benzothiazolyl)-3-(2,2-dimethyl-3-(N,N-dimethyl)aminopropyl)urea A mixture of ethyl {[6-(4-fluorophenoxy)-2-benzothiazolyl]amino}methanethioate and 2,2-dimethyl-3-(N,N-dimethyl)aminopropyl amine in EtOH was reacted to give the desired compound 0.047 g (38%). LC/MS 417.2 (M+1); LC retention time 2.46 min.

The following compounds were synthesized according to the procedure for Example 230 but using the appropriate amine:

| Structure | LC/MS (M + 1) | LC retention time (Min) |
|---|---|---|
| 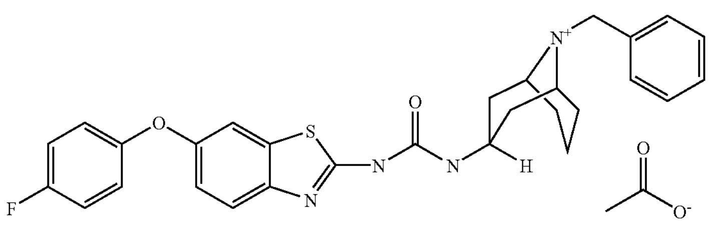 | 518.3 | 3.53 |
| 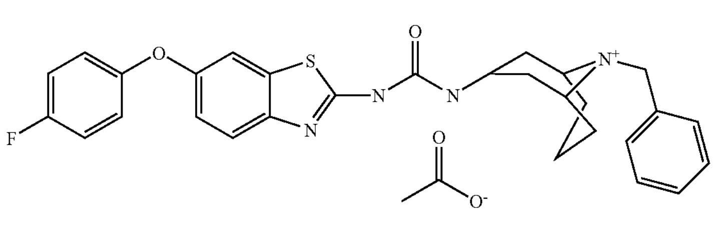 | 518.4 | 2.96 |

| Structure | LC/MS (M + 1) | LC retention time (Min) |
|---|---|---|
| 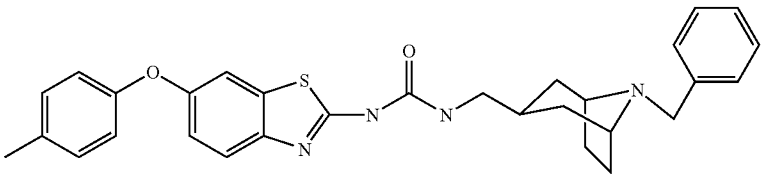 | 517.7 | 3.92 |
| 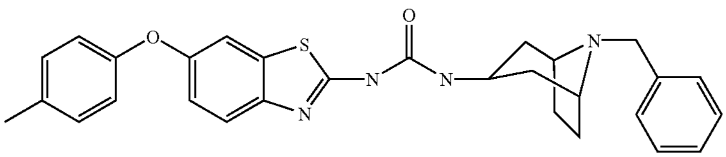 | 502.9 | 3.88 |
| 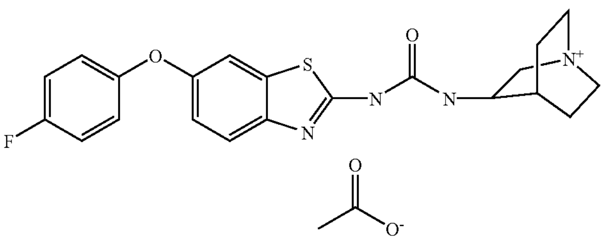 | 413.2 | 2.22 |

EXAMPLE 238

1-(6-(4'-Fluorophenoxy)-2-benzothiazolyl)-3-(4-piperidinylmethyl)urea

A mixture of ethyl {[6-(4-fluorophenoxy)-2-benzothiazolyl]amino}methanethioate and N-Boc-4-aminomethyl piperidine in EtOH was reacted to give the t-Boc protected analog of the title compound as an oil. The oil was dissolved in methylene chloride at about 0° C., and treated with 3 mL 30% TFA solution. It was warmed up and stirred at room temperature for about 4 hours. The mixture was concentrated, taken up in AcOEt, neutralized with NaHCO₃, and washed with water and brine. The organic portion was concentrated and purified by HPLC to give the desired compound 0.008 g (7% for two steps overall). LC/MS 401.2 (M+1); LC retention time 2.26 min.

EXAMPLE 239

1-(6-(4'-Fluorophenoxy)-2-benzothiazolyl)-3-(2-(1-piperazinyl)ethyl)urea

A mixture of ethyl {[6-(4-fluorophenoxy)-2-benzothiazolyl]amino}methanethioate 42 and 1-Boc-4-(2-aminoethyl) piperidine, and TFA was reacted according to the procedure of 48 to give the desired compound 0.040 g (32% for two steps overall). LC/MS 414.1 (M+1); LC retention time 2.84 min.

EXAMPLE 240

2-Amino-6-aceto-benzothiazole

According to the General Procedure for 2-amino-6-substituted benzothiazole compounds, a mixture of 4-acetoaniline, KSCN, and bromine in acetic acid was reacted to give 6.27 g (66%) of the desired compound. LC/MS 192.9 (M+1); LC retention time 2.25 min.

EXAMPLE 241

1-(6-Aceto-2-benzothiazolyl)-3-ethylurea

According to the General Procedure for 1-(6-substituted-2-benzothiazolyl)-3-ethylurea compounds, a mixture of 2-amino-6-aceto-benzothiazole, triethylamine and ethyl isocyanate in toluene was reacted to give the desired compound 2.08 g (83%).

EXAMPLE 242

N1-Phenyl-3-(2-{[(ethylamino)Carbonyl]amino}-1,3-benzothiazol-6-yl)-3-oxopropanamide To a suspension of 1-(6-aceto-2-benzothiazolyl)-3-ethylurea (0.100 g, 0.17 mmol) in 2 mL THF at about −78° C., a solution of 1 M LiHMDS in THF (0.51 mL, 0.51 mmol, 3.0 eq) was added. It was stirred at the temperature for about 15 min. The mixture was treated with phenyl isocyanate (0.022 mL, 0.20 mmol, 1.2 eq) and stirred at about −78° C. for about 10 min, then warmed up to room temperature over 5 hours. It was quenched with MeOH, slightly acidified with HCl, and concentrated. The residue was purified by flash chromatography on SiO₂ with MeOH and methylene chloride (1/100) to give the desired compound 0.002 g (3%). LC/MS 383.0 (M+1); LC retention time 4.10 min.

EXAMPLE 243

N1-(3-Methylphenyl)-3-(2-{[(ethylamino)Carbonyl]amino}-1,3-benzothiazol-6-yl)-3-oxopropanamide Similar to the synthesis of Example 242, a mixture of 1-(6-aceto-2-benzothiazolyl)-3-ethylurea, LiHMDS, and 3-methylphenyl isocyanate in THF was reacted to give 0.068 g (41%) of the desired compound. LC/MS 396.8 (M+1); LC retention time 3.12 min.

EXAMPLE 244

N1-[4-(Dimethylamino)phenyl]-3-(2-{[(ethylamino) Carbonyl]amino}-1,3-benzothiazol-6-yl)-3-oxopropanamide Similar to the synthesis of Example 242, a mixture of 1-(6-aceto-2-benzothiazolyl)-3-ethylurea, LiHMDS, and 4-dimethylaminophenyl isocyanate in THF was reacted to give 0.005 g (3%) of the desired compound. LC/MS 426.1 (M+1); LC retention time 2.00 min.

EXAMPLE 245

1-(6-Ethoxycarbonyl-2-benzothiazolyl)-3-ethylurea

According to the General Procedure for 1-(6-substituted-2-benzothiazolyl)-3-ethylurea compounds, and similar to the synthesis of 1-(6-benzyl-2-benzothiazolyl)-3-ethylurea, a mixture of 2-amino-6-ethoxycarbonyl-benzothiazole, triethylamine and ethyl isocyanate in toluene was reacted to give the desired compound 2.40 g (82%). LC/MS 294.0 (M+1); LC retention time 4.29 min.

EXAMPLE 246

1-(6-(2-Cyanoacetyl)-2-benzothiazolyl)-3-ethylurea

A solution of 1-(6-ethoxycarbonyl-2-benzothiazolyl)-3-ethylurea (1.20 g, 4.09 mmol) in 5 mL of anhydrous DMF was treated with 2 mL of acetonitrile, cooled down to about 0° C., followed by treatment with 1 M LiHMDS in THF (13.1 mL, 13.1 mmol, 3.2 eq). It was stirred at the temperature for about 0.5 hour, then warmed up to room temperature, and stirred for another 4 hours. More LiHMDS (4 mL, 4.0 mmol, 1.0 eq) was added after the first hour. The mixture was quenched with MeOH and water, concentrated, and purified by flash chromatography on SiO$_2$ with MeOH and methylene chloride (1/50) to give the desired compound 0.640 g (54%). LC/MS 288.9 (M+1); LC retention time 2.56 min.

EXAMPLE 247

1-(6-(3-Aminopropanoyl)-2-benzothiazolyl)-3-ethylurea

A suspension of 1-(6-(2-cyanoacetyl)-2-benzothiazolyl)-3-ethylurea (0.56 g, 1.94 mmol) and platinum (IV) oxide (0.176 g, 0.78 mmol, 0.40 eq) in 50 mL of 2/3 mixture of MeOH and chloroform was purged and bubbled with hydrogen gas. It was stirred under hydrogen gas for about 2 days. The mixture was filtered and concentrated to give 0.689 g (quantitative yield) desired compound. LC/MS 292.9 (M+1); LC retention time 1.80 min. HPLC purification gave corresponding acetic acid salt. LC/MS 292.9 (M+1); LC retention time 1.80 min. In a similar reaction, compound as an acetate salt form was obtained after HPLC purification.

EXAMPLE 248

N1-[3-(2-{[(Ethylamino)Carbonyl]amino}-1,3-benzothiazol-6-yl)-3-oxopropyl]benzamide A solution of 1-(6-(3-aminopropanoyl)-2-benzothiazolyl)-3-ethylurea (0.033 g, 0.10 mmol) in 1 mL anhydrous DMF was treated with triethylamine (0.028 mL, 0.20 mmol, 2.0 eq) at room temperature. It was stirred for about 5 min, followed by the addition of benzoyl chloride (0.014 mL, 0.12 mmol, 1.2 eq). It was stirred for about 2.5 hours, quenched with MeOH, filtered, concentrated, and purified by HPLC to give the desired compound 0.011 g (28%). LC/MS 396.7 (M+1); LC retention time 2.74 min.

EXAMPLE 249

1(6-(3-Phenylaminocarbonylamino-propanoyl)-2-benzothiazolyl)-3-ethylurea

A solution of 1-(6-(3-aminopropanoyl)-2-benzothiazolyl)-3-ethylurea (0.033 g, 0.10 mmol) in 1 mL anhydrous DMF was treated with triethylamine (0.028 mL, 0.20 mmol, 2.0 eq) at room temperature. It was stirred for about 5 min, followed by the addition of phenyl isocyanate (0.013 mL, 0.12 mmol, 1.2 eq). It was stirred for about 2.5 hours, quenched with MeOH, filtered, concentrated, and purified by HPLC to give the desired compound 0.009 g (22%). LC/MS 412.2 (M+1); LC retention time 2.80 min.

EXAMPLE 250

1 (6-(3-(3-Methylphenyl)aminocarbonylamino-propanoyl)-2-benzothiazolyl)-3-ethylurea Similar to the synthesis of Example 249, a mixture of 1-(6-(3-aminopropanoyl)-2-benzothiazolyl)-3-ethylurea, triethylamine and 3-methylphenhyl isocyanate in DMF was reacted to give the desired compound 0.021 g (25%). LC/MS 426.1 (M+1); LC retention time 2.94 min.

EXAMPLE 251

N1-[3-(2-{[(Ethylamino)Carbonyl]amino}-1,3-benzothiazol-6-yl)-3-oxopropyl]-4-(dimethylamino) benzamide Similar to the synthesis of Example 248, a mixture of 1-(6-(3-aminopropanoyl)-2-benzothiazolyl)-3-ethylurea, triethylamine and 4-dimethylaminobenzoyl chloride in DMF was reacted to give the desired compound 0.025 g (25%) as an acetic acid salt. LC/MS 440.1 (M+1); LC retention time 2.86 min.

EXAMPLE 252

N1-[3-(2-{[(Ethylamino)Carbonyl]amino-}1,3-benzothiazol-6-yl)-3-oxopropyl]-4-fluorobenzamide Similar to the synthesis of Example 248, a mixture of 1-(6-(3-aminopropanoyl)-2-benzothiazolyl)-3-ethylurea, triethylamine and 4-fluorobenzoyl chloride in DMF was reacted to give the desired compound 0.008 g (10%). LC/MS 415.1 (M+1); LC retention time 2.17 min.

EXAMPLE 253

N1-[3-(2-{[(Ethylamino)Carbonyl]amino}-1,3-benzothiazol-6-yl)-3-oxopropyl]-2,5-difluorobenzamide Similar to the synthesis of Example 249, a mixture of 1-(6-(3-aminopropanoyl)-2-benzothiazolyl)-3-ethylurea, triethylamine and 2,5-difluorobenzoyl chloride in DMF was reacted to give the desired compound 0.019 g (22%). LC/MS 433.0 (M+1); LC retention time 2.94 min.

EXAMPLE 254

1-(6-Bromo-1,3-benzothiazol-2-yl)-3-ethyl-5-methyl-1,3,5-triazinan-2-one

A mixture of 1-(6-bromo-2-benzothiazolyl)-3-ethylurea, methylamine, formaldehyde, and N-methyl morpholine in a mixed solvent of ethanol and water was reacted to give the desired compound 1.56 g (88%).

EXAMPLE 255

1-(6-(2(E)-(Ethoxycarbonyl)vinyl)-2-benzothiazolyl)-3-ethylurea

According to the general procedure described for the synthesis of 1-(6-(2(E)-substituted-vinyl)-2-benzothiazolyl)-3-ethylurea compounds, a mixture of 1-(6-bromo-1,3-benzothiazol-2-yl)-3-ethyl-5-methyl-1,3,5-triazinan-2-one, Pd(PPh$_3$)$_2$Cl$_2$, dppp, triethylamine, ethyl acrylate, and two crystals of BHT in anhydrous DMF was reacted to give the desired compound 65 0.022 g (29%). LC/MS 375.0 (M+1); LC retention time 3.63 min. A solution of compound (0.019 g, 0.051 mmol) in 1 mL 4 M HCl in dioxane was stirred at room temperature for about 4 hours. The mixture was filtered off, and the solid was washed with MeOH and dried under vacuum to give the desired compound 66 0.015 g (94%). LC/MS 320.2 (M+1); LC retention time 2.23 min.

EXAMPLE 256

1-(6-(3-Aminophenyl)-2-benzothiazolyl)-3-ethylurea

A suspension of 1-(6-bromo-2-benzothiazolyl)-3-ethylurea (0.300 g, 1.00 mmol), 3-aminophenyl boric acid (0.237 g, 1.50 mmol, 1.5 eq), and sodium bicarbonate (0.210 g, 2.50 mmol, 2.5 eq) in 8 mL of mixed solvent DMF/water (5/1) was purged with nitrogen gas. To the mixture, the catalyst Pd(PPh$_3$)$_4$ (0.058 g, 0.05 mmol, 0.05 eq) was added. It was purged with nitrogen gas again, and was heated at about 100° C. in a sealed tube for about 48 hours. More Pd(PPh$_3$)$_4$ (0.025 g, 0.02 mmol, 0.02 eq) and more boric acid (0.080 g, 0.50 mmol, 0.50 eq) were added after the first 24 hours. The mixture was taken up in MeOH, concentrated, dissolved in methylene chloride, washed with sodium bicarbonate solution, dried (MgSO$_4$), evaporated, and purified by flash chromatography on SiO$_2$ with MeOH and methylene chloride (1/50) to give the desired compound 0.073 g (23%). LC/MS 313.2 (M+1); LC retention time 2.11 min.

EXAMPLE 256

1-(6-(3-Phenylaminocarbonylaminophenyl)-2-benzothiazolyl)-3-ethylurea

A suspension of 1-(6-(3-aminophenyl)-2-benzothiazolyl)-3-ethylurea (0.062 g, 0.20 mmol), triethylamine (0.083 mL, 0.60 mmol, 3.0 eq), and phenyl isocyanate (0.055 mL, 0.50 mmol, 2.5 eq) in 2 mL toluene was stirred at room temperature for about 1 hour. The white precipitation was filtered off, washed with Et$_2$O and MeOH, and dried under vacuum to give the desired compound 0.038 g (44%). LC/MS 431.8 (M+1); LC retention time 3.49 min.

EXAMPLE 257

4-Pyrazolylboronic pinacolate

A mixture of 4-bromopyrazole (3.02 g, 20.3 mmol), bis(pinacolato) diborane (6.20 g, 24.4 mmol, 1.2 eq), KOAc (5.99 g, 60.9 mmol, 3.0 eq), and catalyst Pd(dppf)C12/CH$_2$Cl$_2$ (0.83 g, 1.02 mmol, 0.05 eq) in 40 DMF was purged with nitrogen gas. It was heated at about 95° C. in a sealed bottle for about 15 hours. It was taken up in AcOEt, concentrated, taken up again in AcOEt, filtered through a silica gel column, and concentrated. The residue was further purified by flash chromatography on SiO$_2$ with EtOAc and heptane (1/1) to give the desired compound 2.46 g (62%). LC/MS 195.1 (M+1); LC retention time 1.59 min.

EXAMPLE 258

1-(6-(4-Pyrazolyl)-2-benzothiazolyl)-3-ethylurea

Similar to the synthesis of 1-(6-(3-aminophenyl)-2-benzothiazolyl)-3-ethylurea, a mixture of 4-pyrazolylboronic pinacolate, 1-(6-bromo-2-benzothiazolyl)-3-ethylurea, sodium carbonate, and Pd(PPh$_3$)$_4$ in DMF/water mixed solvent was reacted to give the desired compound 0.543 g (30%). LC/MS 288.2 (M+1); LC retention time 2.61 min.

EXAMPLE 259

1-(6-(Pinacolatoborano)-2-benzothiazolyl)-3-ethylurea

Similar to the synthesis of 4-pyrrazolylboronic pinacolate, a mixture of 1-(6-bromo-2-benzothiazolyl)-3-ethylurea, bis(pinacolato) diborane, KOAc, and catalyst Pd(dppf)Cl$_2$/CH$_2$Cl$_2$ in DMF was reacted to give the desired compound 3.31 g (93%). LC/MS (M+1) 348.1; LC retention time 2.62 min.

EXAMPLE 260

Methyl 4-(2-{[(ethylamino)Carbonyl]amino}-1,3-benzothiazol-6-yl)-1H-2-pyrrolecarboxylate Similar to the synthesis of 1-(6-(4-pyrrazolyl)-2-benzothiazolyl)-3-ethylurea, a mixture of 1-(6-(pinacolatoborano)-2-benzothiazolyl)-3-ethylurea, methyl 4-bromopyrrole-2-carboxylate, sodium carbonate, and Pd(PPh$_3$)$_4$ in DMF/water mixed solvent was reacted to give the desired compound 0.001 g (1%). LC/MS 345.0 (M+1); LC retention time 3.04 min.

EXAMPLE 261

1-(6-(4-Chlorophenyl)-2-benzothiazolyl)-3-ethylurea

Similar to the synthesis of 1-(6-(4-pyrrazolyl)-2-benzothiazolyl)-3-ethylurea, a mixture of 1-(6-bromo-2-benzothiazolyl)-3-ethylurea, 4-chlorophenylboric acid, sodium bicarbonate, and Pd(PPh$_3$)$_4$ in DMF/water mixed solvent (5/1) was reacted to give the desired compound 0.020 g (18%). LC/MS 330 (M−1); LC retention time 2.70 min.

EXAMPLE 262

1-(6-(3-(3-Tolyl)aminocarbonylaminophenyl)-2-benzothiazolyl)-3-ethylurea

Similar to the synthesis of 1-(6-(3-phenylaminocarbonylaminophenyl)-2-benzothiazolyl)-3-ethylurea, a mixture of 1-(6-(3-aminophenyl)-2-benzothiazolyl)-3-ethylurea, triethylamine, and 3-tolyl isocyanate in toluene was reacted to give the desired compound 0.023 g (26%). LC/MS 446.2 (M+1); LC retention time 3.76 min.

EXAMPLE 263

1-(6-(1-Phenylaminocarbonylpyrrazol-4-yl)-2-benzothiazolyl)-3-ethylurea

Similar to the synthesis of 1-(6-(3-phenylaminocarbonylaminophenyl)-2-benzothiazolyl)-3-ethylurea, a mixture of 1-(6-(4-pyrrazolyl)-2-benzothiazolyl)-3-ethylurea, triethylamine, and phenyl isocyanate in toluene was reacted to give the desired compound 0.025 g (23%). LC/MS 407.1 (M+1); LC retention time 3.85 min.

EXAMPLE 264

1-(6-(3-(2-Fluorophenyl)aminocarbonylamino-propanoyl)-2-benzothiazolyl)-3-ethylurea Similar to the synthesis of Example 249, a mixture of 1-(6-(3-aminopropanoyl)-2-benzothiazolyl)-3-ethylurea, triethylamine and 2-fluorophenyl isocyanate in DMF was reacted to give the desired compound 0.022 g (26%). LC/MS 430.01 (M+1); LC retention time 2.89 min.

EXAMPLE 265

1-(6-(4'-Fluorophenoxy)-2-benzothiazolyl)-3-(2-(3-methylaminopropyl))urea

Similar to the synthesis of 1-(6-(4'-fluorophenoxy)-2-benzothiazolyl)-3-(4-piperidinylmethyl)urea, a mixture of ethyl {[6-(4-fluorophenoxy)-2-benzothiazolyl]amino}methanethioate, 3-Boc-3-methylpropylamine, and TFA was reacted to give the desired compound 0.044 g (39% for two steps overall). LC/MS 375.0 (M+1); LC retention time 3.17 min.

General Procedure for Making a Compound of the Formula

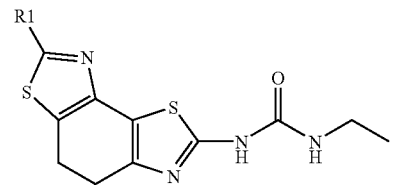

A suspension of N-(6-bromo-7-oxo-4,5,6,7-tetrahydro-1,3-benzothiazol-2-yl)-N'-ethylurea and a thioamide of choice (1 eq.) in n-propanol is heated to about 105° C. for about 16 hrs. The reaction mixture is concentrated in vacuo and the residual crude material is purified by preparative HPLC.

EXAMPLE 266

N-Ethyl-N'-[7-(3-pyridyl)-4,5-dihydro[1,3]thiazolo[4',5': 3,4]benzo[d][1,3]thiazol-2-yl]urea A suspension of N-(6-bromo-7-oxo-4,5,6,7-tetrahydro-1,3-benzothiazol-2-yl)-N'-ethylurea (25 mg, 0.079 mmol) and thionicotinamide (11 mg, 0.079 mmol) in n-propanol (0.4 mL) was heated to about 105° C. for about 16 hrs. The reaction mixture was concentrated in vacuo and the residual crude material was purified by preparative HPLC. 10 mg (36%) pure product was isolated.

EXAMPLE 267

N-Ethyl-N'-(7-ethyl-4,5-dihydro[1,3]thiazolo[4',5': 3,4]benzo[d][1,3]thiazol-2-yl)urea As above but using the appropriate starting material instead of thionicotinamide. 3 mg (20%) product was isolated.

General Procedure for Making a Compound of the Formula

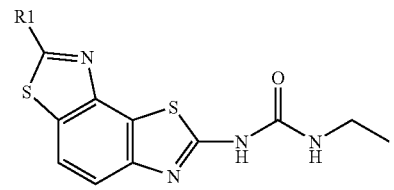

A suspension of N-ethyl-N'-[7-(3-R1)-4,5-dihydro[1,3]thiazolo[4',5': 3,4]-benzo[d][1,3]thiazol-2-yl]urea and DDQ (2 eq.) in toluene is heated to about 35° C. for about 3 hrs. The reaction mixture is concentrated in vacuo and purified by preparative HPLC.

EXAMPLE 268

N-Ethyl-N'-[7-(3-pyridyl)[1,3]thiazolo[4',5': 3,4]benzo[d][1,3]thiazol-2-yl]urea A suspension of N-ethyl-N'-[7-(3-pyridyl)-4,5-dihydro[1,3]thiazolo[4',5': 3,4]benzo[d]-[1,3]thiazol-2-yl]urea (10 mg, 0.028 mmol) and DDQ (13 mg, 0.056 mmol) in toluene (1 mL) was heated to about 35° C. for about 3 hrs. The reaction mixture was concentrated in vacuo and purified by preparative HPLC. 3 mg (30%) pure product was isolated. LC/MS 356 (MH⁺); RP-HPLC 14.25 min.

EXAMPLE 269

N-Ethyl-N'-(7-ethyl[1,3]thiazolo[4',5': 3,4]benzo[d][1,3]thiazol-2-yl)urea

As above but using N-ethyl-N'-(7-ethyl-4,5-dihydro[1,3]thiazolo[4',5': 3,4]benzo[d]-[1,3]thiazol-z-yl)urea as the starting material. 16 mg (23%) product was isolated. LC/MS 307 (MH⁺); RP-HPLC 2.88 min.

General Procedure for Making a Compound of the Formula

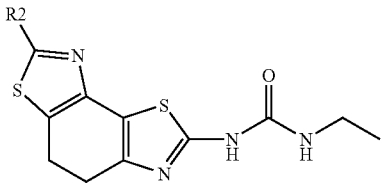

A suspension of N-(6-bromo-7-oxo-4,5,6,7-tetrahydro-1,3-benzothiazol-2-yl)-N'-ethylurea and a thioamide of choice (1 eq.) in THF is heated to about 65° C. for about 1.5 hrs. The reaction mixture is pumped down and used in the next step without further purification.

EXAMPLE 270

N-[7-(4-Bromoanilino)-4,5-dihydro[1,3]thiazolo[4',5': 3,4]benzo[d][1,3]thiazol-2-yl]-N'-ethylurea A suspension of N-(6-bromo-7-oxo-4,5,6,7-tetrahydro-1,3-benzothiazol-2-yl)-N'-ethylurea (50 mg, 0.16 mmol) and 4-bromo-phenyl-thiourea (36 mg, 0.16 mmol) in THF (1.0 mL) was heated to about 65° C. for about 1.5 hrs. The reaction mixture was pumped down and used in the next step without further purification.

EXAMPLE 271

N-Ethyl-N'-(7-piperidino-4,5-dihydro[1,3]thiazolo[4',5': 3,4]benzo[d][1,3]thiazol-2-yl)urea As above but using piperidylthiourea.

EXAMPLE 272

N-Ethyl-N'-[7-(methylamino)-4,5-dihydro[1,3]thiazolo[4',5': 3,4]benzo[d][1,3]thiazol-2-yl]urea As above but using methylthiourea.

General Procedure for Making a Compound of the Formula

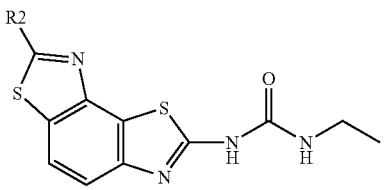

To a suspension of N-[7-(R2)-4,5-dihydro[1,3]thiazolo[4',5': 3,4]benzo[d] [1,3]thiazol-2-yl]-N'-ethylurea in toluene is added DDQ (2 eq.). The reaction mixture is stirred at about 20° C. for about 2 hrs. The reaction mixture is pumped down in vacuo and purified by preparative HPLC

EXAMPLE 273

N-[7-(4-Bromoanilino)[1,3]thiazolo[4',5': 3,4]benzo[d][1,3]thiazol-2-yl]-N'-ethylurea To a suspension of N-[7-(4-bromoanilino)-4,5-dihydro[1,3]thiazolo[4',5': 3,4]benzo[d][1,3]thiazol-2-yl]-N'-ethylurea (27 mg, 0.060 mmol) in toluene (2.0 mL) was added DDQ (28 mg, 0.125 mmol). The reaction mixture was stirred at about 20° C. for about 2 hrs. The reaction mixture was pumped down in vacuo and purified by preparative HPLC. 7 mg (26%, 2 steps) pure product was isolated. LC/MS 448 and 450 (MH⁺); RP-HPLC 18.09 min.

EXAMPLE 274

N-Ethyl-N'-(7-piperidino[1,3]thiazolo[4',5': 3,4]benzo[d][1,3]thiazol-2-yl)urea

As for Example 273 but using the appropriate starting material. 18 mg (21%, 2 steps). LC/MS 362 (MH⁺); RP-HPLC 16.97 min.

EXAMPLE 275

N-Ethyl-N'-[7-(1-methylammonio)[1,3]thiazolo[4',5': 3,4]benzo[d][1,3]thiazol-2-yl]urea acetate As for Example 273 but using the appropriate starting material. 5 mg (7%, 2 steps) of pure product was isolated. LC/MS 308 (MH⁺); RP-HPLC 8.75 min.

EXAMPLE 276

2-(3-Ethyl-5-methyl-2-oxo-1,3,5-triazinan-1-yl)-4,5,6,7-tetrahydro-1,3-benzothiazol-7-one To a suspension of N-ethyl-N'-(7-oxo-4,5,6,7-tetrahydro-1,3-benzothiazol-2-yl)urea (10.0 g, 41.79 mmol) in EtOH/H₂O (1/1, 300 mL) were added formaldehyde (37 wt % in H₂O, 20.4 g, 417.87 mmol), methylamine (40 wt % in H₂O, 10.8 mL, 125.37 mmol) and N-methylmorpholine (11.8 mL, 83.6 mmol). The suspension was heated to about 60° C. for about 5 hrs, then a solution had been formed. The reaction mixture was pumped down in vacuo to give 12.41 g (quantitative yield) pure product.

EXAMPLE 277

2-(3-Ethyl-5-methyl-2-oxo-1,3,5-triazinan-1-yl)-6-[(Z)-1-hydroxymethylidene]-4,5,6,7-tetrahydro-1,3-benzothiazol-7-one To a suspension of 2-(3-ethyl-5-methyl-2-oxo-1,3,5-triazinan-1-yl)-4,5,6,7-tetrahydro-1,3-benzothiazol-7-one (2.0 g, 6.79 mmol) and ethylformate (2.5 mL, 30.95 mmol) in toluene (60 mL) at about 0° C. was added solid NaH (60% in mineral oil, 2.5 g, 30.48 mmol). The reaction mixture was stirred at about 0° C. for about 7 hrs then poured into saturated NH₄Cl aq. The product was extracted into CH₂Cl₂ (3 times). The combined organic phases were filtered and the filtrate concentrated to give 2.5 g of crude product that was used in the next step without further purification.

General Procedure for Making a Compound of the Formula

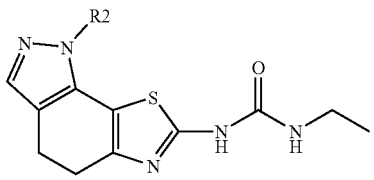

To a suspension of 2-(3-ethyl-5-methyl-2-oxo-1,3,5-triazinan-1-yl)-6-[(Z)-1-hydroxymethylidene]-4,5,6,7-tetrahydro-1,3-benzothiazol-7-one in EtOH is added $R_2HNNH_2$. $XH_2O$ (4 eq.). The reaction mixture is stirred at about 20° C. for about 16 hrs, additional $R_2HNNH_2.XH_2O$ (4 eq.) is added and the reaction mixture stirred at about 40° C. for about another 4 hrs, still some unprotected product present. A third portion of $R_2HNNH_2.XH_2O$ (8 eq.) is added and the reaction mixture stirred for about another 7 hrs at about 45° C. The reaction mixture is pumped down and carried on to the next step without further purification. An analytically pure sample is achieved by preparative HPLC.

EXAMPLE 278

N-(5,8-Dihydro-4H-[1,3]thiazolo[4,5-g]indol-2-yl)-N'-ethylurea

To a suspension of 2-(3-ethyl-5-methyl-2-oxo-1,3,5-triazinan-1-yl)-6-[(Z)-1-hydroxymethylidene]4,5,6,7-tetrahydro-1,3-benzothiazol-7-one (100 mg, 0.31 mmol) in EtOH (2.5 mL) was added $H_2NNH_2$. $XH_2O$ (0.040 mL, 1.24 mmol). The reaction mixture was stirred at about 20° C. for about 16 hrs, additional $H_2NNH_2.XH_2O$ (0.040 mL, 1.24 mmol) was added and the reaction mixture stirred at about 40° C. for another 4 hrs, still some unprotected product present. A third portion of $H_2NNH_2.XH_2O$ (0.080 mL, 2.48 mmol) was added and the reaction mixture stirred for about another 7 hrs at about 45° C. The reaction mixture was pumped down and carried on to the next step without further purification. An analytical pure sample was achieved by preparative HPLC. LC/MS 264 (MH$^+$); RP-HPLC 9.72 min.

EXAMPLE 279

N-Ethyl-N'-(8-methyl-5,8-dihydro-4H-[1,3]thiazolo[4,5-g]indol-2-yl)urea

As above but using $MeHNNH_2.XH_2O$ rather than $H_2NNH_2 XH_2O$. This product was carried on to the next step without extensive purification at this stage.

General Procedure for Making a Compound of the Formula

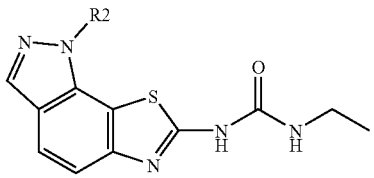

To a suspension of N-(5,8-dihydro-4H-[1,3]thiazolo[4,5-g]indol-2-yl)-N'-ethylurea in toluene is added DDQ (1.1 eq.). The reaction mixture is stirred at about 45° C. for about 4 hrs. The reaction mixture is pumped down and the crude material is purified by preparative HPLC.

EXAMPLE 280

N-Ethyl-N'-(8H-[1,3]thiazolo[4,5-g]indol-2-yl)urea

To a suspension of N-(5,8-dihydro-4H-[1,3]thiazolo[4,5-g]indol-2-yl)-N'-ethylurea (81 mg, 0.308 mmol) in toluene (3.5 mL) was added DDQ (78 mg, 0.34 mmol). The reaction mixture was stirred at about 45° C. for about 4 hrs. The reaction mixture was pumped down and the crude material was purified by preparative HPLC. 3 mg (4%, 2 steps) pure product was isolated. LC/MS 262 (MH$^+$); RP-BPLC RT 10.45 min.

EXAMPLE 281

7-[(Ethylamino)Carbonyl]amino-1-methyl-1H-[1,3]thiazolo[4,5-g]indazol-1-ium acetate As described for Example 280 but using the appropriate starting material. 6 mg (20%, 2 steps) of pure product was isolated. LC/MS 276 (MH$^+$); RP-HPLC 11.70 min.

EXAMPLE 282

N-[7,7-Di(phenylsulfanyl)-4,5,6,7-tetrahydro-1,3-benzothiazol-2-yl]-N'-ethylurea A suspension of N-ethyl-N'-(7-oxo-4,5,6,7-tetrahydro-1,3-benzothiazol-2-yl)urea (1.0 g, 4.18 mmol) and thiophenol (0.59 mL, 4.74 mmol) in EtOH (20 mL) was saturated with HCl (g) at about 0° C. The reaction mixture was stirred at about 20° C. for about 2 hrs then a second portion of thiophenol (0.59 mL, 4.74 mmol) was added and the reaction mixture stirred for about another 2 hrs. The ethanol was removed in vacuo and $H_2O$ was added. The aqueous phase was neutralized by addition of 2M NaOH and the product was extracted into $CH_2Cl_2$ (4 times). The combined organic phases were dried over $MgSO_4$. Evaporation of the solvent gave 1.85 g (quantitative yield) pure product.

EXAMPLE 283

N-Ethyl-N'-[7-(phenylsulfanyl)-4,5-dihydro-1,3-benzothiazol-2-yl]urea

To a suspension of N-[7,7-di(phenylsulfanyl)-4,5,6,7-tetrahydro-1,3-benzothiazol-2-yl]-N'-ethylurea (700 mg, 1.59 mmol) in THF (14.0 mL) was added DBU (0.36 mL, 2.38 mmol). The reaction mixture was stirred at about 20° C. for about 30 min. The reaction was concentrated in vacuo. The residual yellow oil was taken up in $CH_2Cl_2$, washed with $AcOH/H_2O$ 1/10 and dried over $MgSO_4$. The organic solvent was removed in vacuo and the residual oil (1.0 g) was used in the next step without further purification.

EXAMPLE 284

N-Ethyl-N'-[7-(phenylsulfanyl)-1,3-benzothiazol-2-yl]urea

To a mixture of N-ethyl-N'-[7-(phenylsulfanyl)-4,5-dihydro-1,3-benzothiazol-2-yl]urea (crude product from the previous reaction, 1.59 mmol) in toluene (35.0 mL) was added DDQ (500 mg, 2.17 mmol). The reaction mixture was stirred at about 20° C. for about 2 hrs. The toluene was removed in vacuo and the crude material was taken up in $CH_2Cl_2$. The organic phase was washed with 0.5 M NaOH (2 times) and dried over $MgSO_4$. The crude oil was purified by flash chromatography on $SiO_2$ (EtOAc/$CH_2Cl_2$ 5/95). 445 mg (85%, 2 steps) of pure product was isolated. LC/MS 330 ($MH^+$); RP-HPLC RT 17.56 min.

EXAMPLE 285

N-Ethyl-N'-[7-(phenylsulfinyl)-1,3-benzothiazol-2-yl]urea

To a suspension of N-ethyl-N'-[7-(phenylsulfanyl)-1,3-benzothiazol-2-yl]urea (107 mg, 0.32 mmol) in $CH_2Cl_2$ (5 mL) was added MCPBA (60 mg, 0.24 mmol, 70%). The reaction mixture was stirred at about 20° C. for about 1.5 hrs. The reaction mixture was then concentrated in vacuo. The crude reaction mixture was purified by flash chromatography on $SiO_2$ (EtOAc/$CH_2Cl_2$ 10/90). 32 mg (29%) of pure product was isolated. LC/MS 346 ($MH^+$); RP-HPLC RT 12.96 min.

EXAMPLE 286

N-Ethyl-N'-[7-(phenylsulfonyl)-1,3-benzothiazol-2-yl]urea

To a suspension of N-ethyl-N'-[7-(phenylsulfanyl)-1,3-benzothiazol-2-yl]urea (150 mg, 0.46 mmol) in $CH_2Cl_2$ (5 mL) was added MCPBA (125 mg, 0.50 mmol, 70%). The reaction mixture was stirred at about 20° C. for about 1.5 hrs then more MCPBA (60 mg, 0.24 mmol, 70%) was added. The reaction mixture was stirred for about 1 more hour then concentrated in vacuo. The crude reaction mixture was purified by flash chromatography on $SiO_2$ (EtOAc/$CH_2Cl_2$ 10/90). 45 mg (27%) of pure product was isolated. LC/MS 362 ($MH^+$); RP-HPLC RT 14.41 min.

EXAMPLE 287

N-(6-Bromo-1,3-benzothiazol-2-yl)-N'-(3-chloropropyl)urea

See general procedure below

General procedure for the preparation of a compound of the formula

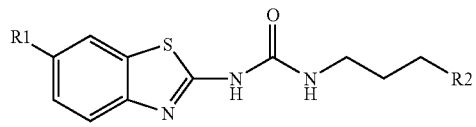

(See Table 1).

To a mixture of N-(6-bromo-1,3-benzothiazol-2-yl)-N'-(3-chloropropyl)urea in THF/EtOH is added an amine of choice (10 eq.). The reaction mixture is heated to about 55° C. for about 16 hrs. The crude reaction mixture is pumped down and purified by flash chromatography on $SiO_2$.

EXAMPLE 289

N-(6-Bromo-1,3-benzothiazol-2-yl)-N'-(3-piperazinopropyl)urea

To a mixture of N-(6-bromo-1,3-benzothiazol-2-yl)-N'-(3-chloropropyl)urea (100 mg, 0.287 mmol) in THF/EtOH (0.50/0.25 mL) was added piperazine (247 mg, 2.87 mmol). The reaction mixture was heated to about 55° C. for about 16 hrs. The crude reaction mixture was pumped down and purified by flash chromatography on $SiO_2$.

TABLE 1

| Example | R2 | RP-HPLC RT (min.) | LC/MS (MH+) |
|---|---|---|---|
| 287 | Cl | 16.78 | 349/351 |
| 288 | 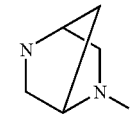 | 14.7 | 510/512 |
| 289 | 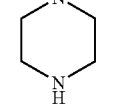 | 12.1 | 398/400 |
| 290 | 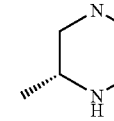 | 12.54 | 426/428 |
| 291 | 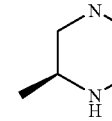 | 12.51 | 426/428 |
| 292 | 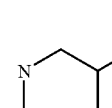 | 11.96 | 438/440 |
| 293 | 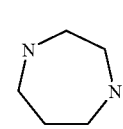 | 11.85 | 426/428 |
| 294 | 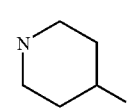 | 11.89 | 413/415 |
| 295 | 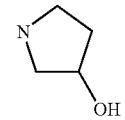 | 11.93 | 399/401 |

General Procedure for the Preparation of a Compound of the Formula

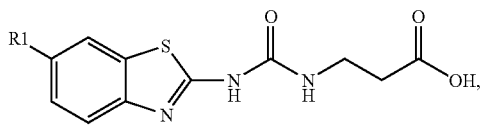

where R1 is Br (See Table 2).

To a solution of ethyl 4-([(6-bromo-1,3-benzothiazol-2-yl)amino]carbonylamino)-butanoate in THF/EtOH is added 2 M NaOH (10 eq.). The reaction mixture is stirred at about 20° C. for about 3 hrs then 2 M HCl is added until pH<6 and a white precipitate is formed. The precipitate is filtered off and washed with H$_2$O, pure product is isolated.

EXAMPLE 299

4-([(6-Bromo-1,3-benzothiazol-2-yl)amino]carbonylamino)butanoic acid

To a solution of ethyl 4-([(6-bromo-1,3-benzothiazol-2-yl)amino]carbonylamino)-butanoate (175 mg, 0.453 mmol) in THF/EtOH (1/1, 3 mL) was added 2 M NaOH (2.26 mL, 4.53 mmol). The reaction mixture was stirred at about 20° C. for about 3 hrs then 2 M HCl was added until pH<6 and a white precipitate was formed. The precipitate was filtered off and washed with H$_2$O. 25 mg (15%) pure product was isolated.

EXAMPLE 306

4-([(6-Chloro-1,3-benzothiazol-2-yl)amino]carbonylamino)butanamide

Gaseous ammonia was bubbled through a suspension of ethyl 4-([(6-chloro-1,3-benzothiazol-2-yl)amino]carbonylamino)butanoate (155 mg, 0.453 mmol) in MeOH (1.5 mL) for about 5 min the reaction mixture was then heated to about 85° C. for about 2 hrs. This procedure was repeated 4 times. The reaction mixture was cooled down and the white ppt was filtered off. 62 mg (44%) pure product was isolated.

General Procedure for the Preparation of a Compound of the Formula

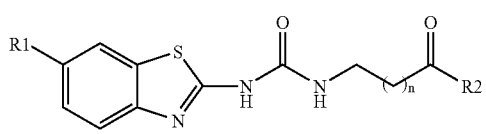

where R1 is Br and R2 is an Amine (see Table 2). Ethyl 4-([(6-bromo-1,3-benzothiazol-2-yl)amino]carbonylamino) butanoate is heated neat at about 80° C. with an amine of choice (10 eq.) for about 8 hrs. To the crude reaction mixture is added THF and the precipitate is filtered off and washed with THF

EXAMPLE 298

N-(6-Bromo-1,3-benzothiazol-2-yl)-N'-[4-(4-methylpiperazino)-4-oxobutyl]urea

Ethyl 4-([(6-bromo-1,3-benzothiazol-2-yl)amino]carbonylamino)butanoate (100 mg, 0.259 mmol) was heated neat at about 80° C. in N-methyl-piperazine (259 mg, 2.59 mmol) for about 8 hrs. To the crude reaction mixture was added THF (2 mL), the ppt was filtered off and washed with THF (1 mL). The product was dried in vacuo and gave 67 mg (53%) pure product.

| Example | R1 | n | Compound | R2 | RP-HPLC RT (min.) | LC/MS (MH+) |
|---|---|---|---|---|---|---|
| 296 | Br | 2 | 33 | piperazine-N-methyl | 12.14 | 440/442 |
| 297 | Br | 2 | 34 | OH | 13.02 | 358/360 |
| 298 | Br | 2 | 35 | HN-CH$_2$CH$_2$-morpholine | 12.27 | 470/472 |
| 299 | Br | 2 | 36 | HN-CH$_2$CH$_2$-piperidine | 12.76 | 468/470 |
| 300 | Br | 2 | 37 | 2,6-dimethylpiperazine | 12.18 | 454/456 |

-continued

| Example | R1 | n | Compound | R2 | RP-HPLC RT (min.) | LC/MS (MH+) |
|---|---|---|---|---|---|---|
| 301 | Cl | 2 | 38 | N-methyl-N-(2-(diethylamino)ethyl)amino | 8.59 | 426 |
| 302 | Cl | 2 | 39 | (S)-(1-ethylpyrrolidin-2-yl)methylamino | 8.45 | 424 |
| 303 | Cl | 2 | 40 | N-methyl-N-(1-methylpiperidin-4-yl)amino | | 424 |
| 304 | Cl | 2 | 41 | NH2 | 12.32 | 313 |
| 305 | Cl | 2 | 42 | (8-methyl-8-azabicyclo[3.2.1]oct-3-yl)amino | 17.25 | 436 |
| 306 | Cl | 1 | 43 | OH | 12.19 | 300 |
| 307 | Cl | 1 | 44 | piperidin-1-yl | 15.57 | 367 |
| 308 | Cl | 1 | 45 | 2-(diethylamino)ethylamino | 11.83 | 398 |
| 309 | Cl | 1 | 46 | 2-morpholinoethylamino | 11.73 | 412 |
| 310 | Cl | 1 | 47 | 2-(piperidin-1-yl)ethylamino | 12.2 | 410 |
| 311 | Cl | 1 | 48 | 4-methylpiperazin-1-yl | 11.73 | 382 |
| 312 | Cl | 1 | 49 | (8-methyl-8-azabicyclo[3.2.1]oct-3-yl)amino | 16.57 | 422 |

| Example | R1 | n | Compound R2 | RP-HPLC RT (min.) | LC/MS (MH+) |
|---|---|---|---|---|---|
| 313 | p-F—PhO | 2 | 50 (piperazine ring with N-CH3) | 14.03 | 472 |

EXAMPLE 314

N-[6-(5-Chloro-2-thienyl)-1,3-benzothiazol-2-yl]-N'-ethylurea

A 40 ml pressure tube was charged with about 100 mg N-(6-bromo-1,3-benzothiazol-2-yl)-N'-ethylurea, and about 2 ml ethylene glycol dimethyl ether. The slurry was stirred via magnetic stirbar followed by evacuation then release to nitrogen atmosphere (3 times). Next about 6 mol percent Pd(PPh$_3$)$_4$ was added, followed by about 1.1 eq of 5-chlorothiophene-2-boronic acid. Following addition of about 3 equivalents sodium carbonate in about 0.5 ml water, the suspension was evacuated and released to nitrogen atmosphere 3 times. The pressure tube was then sealed tightly and heated to about 85–90° C. for about 12–20 hours. The reaction was cooled to room temperature then purified by preparative HPLC to yield 16% of N-[6-(5-chloro-2-thienyl)-1,3-benzothiazol-2-yl]-N'-ethylurea. $^1$H NMR 1.1 (t, 3H), 3.2 (m, 2H), 6.75 (m, 1H), 7.18 (d, 1H), 7.38 (m, 1H), 7.6 (m, 2H), 8.19 (d, 1H), 10.75 (br s, 1H); LC/MS 3.86 min, 338 (M+1), 336 (M−1).

EXAMPLE 315

N-[6-(5-Chloro-2-thienyl)-1,3-benzothiazol-2-yl]-N'-ethylurea

This is an alternative procedure for making the compound of Example 314. A 40 ml pressure tube was charged with about 32 mg 5-chlorothiophene-2-boronic acid, about 50 mg N-(6-bromo-1,3-benzothiazol-2-yl)-N'-ethylurea and about 30 mg potassium fluoride as base. About 3 ml ethylene glycol dimethyl ether was added and the suspension was vacuum purged and released to nitrogen three times. The catalyst solution was prepared in a separate flask as follows: about 31 mg of Pd(OAc)$_2$ and about 110 mg of 2-dicyclohexylphosphino-2'-(N,N-dimethylamino)biphenyl were charged followed by about 6 ml ethylene glycol dimethyl ether. The flask was vacuum purged and released to nitrogen 3 times followed by stirring to complete solution. An appropriate amount of catalyst solution (about 10–50 mol percent catalyst) was then transferred to the pressure tube. The pressure tube was then evacuated then released to nitrogen atmosphere three times, sealed tightly and heated to about 85–90° C. for about 12–20 hours. Upon cooling to room temperature the now clear solution was purified by preparative HPLC to yield about 33% of N-[6-(5-chloro-2-thienyl)-1,3-benzothiazol-2-yl]-N'-ethylurea. $^1$H NMR 1.1 (t, 3H), 3.2 (m, 2H), 6.75 (m, 1H), 7.18 (d, 1H), 7.38 (m, 1H), 7.6 (m, 2H), 8.19 (d, 1H), 10.75 (br s, 1H); LC/MS 3.86 min, 338 (M+1), 336 (M−1).

EXAMPLE 316

N-[6-(5-Chloro-2-thienyl)-1,3-benzothiazol-2-yl]-N'-ethylurea

This is another alternative method of making the compound of Example 314. A 40 ml pressure tube was charged with about 100 mg of N-(6-bromo-1,3-benzothiazol-2-yl)-N'-ethylurea, about 1.2 equivalents pinacoldiborane, about 3 equivalents potassium acetate and about 1.5 ml dimethylformamide. The reaction mixture was evacuated and released to nitrogen 3 times. About 5 mole percent of PdCl$_2$dppf was added and the reaction flask was again evacuated and released to nitrogen 3 times. The tube was tightly sealed and the mixture was heated to about 85–90° C. overnight. Following cooling to room temperature, the mixture was purified on silica gel to give about 90% yield of N-ethyl-N'-[6-(4,4,5,5-tetramethyl-1,3,2-dioxaborolan-2-yl)-1,3-benzothiazol-2-yl]urea. LC/MS 3.5 min, 348 (M+1), 346 (M−1).

A 40 ml pressure tube was charged with about 1.5 ml ethylene glycol dimethyl ether, about 10 mg Pd(PPh$_3$)$_4$ and about 0.016 ml 2-bromo-5-chlorothiophene. The slurry was evacuated then released to nitrogen atmosphere three times. Next 52 mg N-ethyl-N'-[6-(4,4,5,5-tetramethyl-1,3,2-dioxaborolan-2-yl)-1,3-benzothiazol-2-yl]urea was added and the slurry was again evacuated and released to nitrogen three times. Following addition of sodium carbonate solution (about 46 mg in about 0.5 ml water), the suspension was evacuated and released to nitrogen atmosphere 3 times. The reaction tube was then sealed tightly and heated to about 85–90° C. overnight. Upon cooling to room temperature the now clear solution was purified by preparative HPLC to yield 43% of N-[6-(5-chloro-2-thienyl)-1,3-benzothiazol-2-yl]-N'-ethylurea.

$^1$H NMR 1.1 (t, 3H), 3.2 (m, 2H), 6.75 (m, 1H), 7.18 (d, 1H), 7.38 (m, 1H), 7.6 (m, 2H), 8.19 (d, 1H), 10.75 (br s, 1H); LC/MS 3.86 min, 338 (M+1), 336 (M−1).

EXAMPLE 317

N-Ethyl-N'-[6-(1H-1-pyrrolyl)-1,3-benzothiazol-2-yl]urea

Charged about 500 mg N-ethyl-N'-(6-nitro-1,3-benzothiazol-2-yl)urea into about 75 ml ethanol. Added about 20 mg platinum oxide then evacuated and released to hydrogen three times. The system was then put under hydrogen pressure (about 20–40 psi) for about 5–20 hours. The reaction was stopped and the entire mass was filtered through diatomaceous earth and washed with methanol. The solvent was removed in vacuo and the crude N-(6-amino-1,3-benzothiazol-2-yl)-N'-ethylurea was used for the next step without further purification. Charged about 0.44 g N-(6-amino-1,3-benzothiazol-2-yl)-N'-ethylurea into about 15 ml acetic acid then added about 0.23 ml 2,5-dimethoxytetrahydrofuran. Refluxed for about 1 hour then cooled to room temperature. The solvent was removed in vacuo and the product was purified by preparative HPLC. $^1$H NMR 1.1 (t, 3H), 3.2 (m, 2H), 6.26 (m, 2H), 6.71 (m, 1H), 7.35 (m, 2H), 7.55 (m, 1H), 7.7 (m, 1H), 8.1 (m, 1H), 10.69 (br s, 1H); LC/MS 3.1 min, 285 (M−1).

EXAMPLE 318

(2-Amino-1,3-benzothiazol-6-yl)methyl cyanide 2 grams of 4-aminobenzonitrile is dissolved in about 40 mL acetic acid and the solution is cooled to about 16° C. About 3.3 g of potassium thiocyanate is added and the flask is equipped with an addition funnel. The addition funnel is charged with about 2.7 g bromine and about 5 ml acetic acid. This dark solution is then added to the benzonitrile solution in a dropwise fashion under good agitation and allowed to stir for about 16 hours. The slurry is then drowned into water and filtered. The presscake is washed well with water, reslurried in dilute aqueous alkali and filtered. Again the presscake is washed well with water. After drying in vacuo, about 2 grams is isolated.

$^1$H NMR 6.8 (d, 1H, J=8.7 Hz), 6.9 (br s, 2H), 7.6 (dd, 1H, J=2 Hz, J=8.7 Hz), 8.0 (d, 1H, J=2 Hz), LC/MS 2.34 min, 174 (M−1), lab LC retention time 7.7 minutes.

EXAMPLE 319

N-(6-Cyano-1,3-benzothiazol-2-yl)-N'-ethylurea 0.2 grams of 2-amino-1,3-benzothiazole-6-carbonitrile is dissolved in about 5 ml dimethylformamide. About 0.2 ml of ethylisocyanate is added followed by about 0.3 ml triethylamine and the solution is heated to about 80° C. under good agitation. The solution is allowed to stir for about 4 hours then cooled to RT. The solvent is removed in vacuo and the solids are washed well with ether. The product is further purified by column chromatography and after drying in vacuo, about 0.14 grams is isolated.

$^1$H NMR 1.1 (t, 3H, J=7.2 Hz), 3.2 (m, 2H), 6.8 (s, 1H), 7.7 (m, 2H), 8.4 (s, 1H), 11.0 (s, 1H), LC/MS 2.54 min, 247 (M+1), 245 (M−1), lab LC retention time 7.8 minutes.

EXAMPLE 320

N-[6-(2-Aminoethyl)-1,3-benzothiazol-2-yl]-N'-ethylurea

Charged about 500 mg N-(6-cyano-1,3-benzothiazol-2-yl)-N'-ethylurea into about 50 ml ethanol and about 1 ml chloroform. Add about 0.1 grams platinum oxide then stir under 20–40 psi hydrogen for about 8 hours. The solution is then basified with sodium bicarbonate to pH>7, filtered through a bed of Celite® and washed well with ethyl acetate. The resulting crude product is purified by preparative HPLC to yield unreacted N-(6-cyano-1,3-benzothiazol-2-yl)-N'-ethylurea and N-[6-(2-aminoethyl)-1,3-benzothiazol-2-yl]-N'-ethylurea (20%).

$^1$H NMR 1.08 (t, 3H), 2.7 (m, 2H), 2.9 (m, 2H), 3.16 (m 2H), 6.8 (br s, 1H), 7.2 (m, 1H), 7.25 (br s, 1H), 7.5 (m, 1H), 7.95 (m, 1H), LC/MS 2.09 min, 263 (M−1), 265 (M+1).

General Procedure for the Reaction of N-[6-(2-aminoethyl)-1,3-benzothiazol-2-yl]-N'-ethylurea with an isocyanate 0.02 grams of N-[6-(2-aminoethyl)-1,3-benzothiazol-2-yl]-N'-ethylurea is dissolved in about 1 ml dimethylformamide. About 2 equivalents of the appropriate isocyanate is added followed by about 0.02 ml triethylamine and the solution is heated to about 80° C. under good agitation. The solution is allowed to stir for about 10–24 hours then cooled to RT. The solvent is removed in vacuo and the solids are washed well with ether. The product is further purified by preparative HPLC and dried in vacuo.

EXAMPLE 321

N-[6-(ethylureido)methyl)-1,3-benzothiazol-2-yl]-N'-ethylurea

LC/MS 2.65 min, 336 (M+1), 334 (M−1).

EXAMPLE 322

N-[6-(phenylureido)methyl)-1,3-benzothiazol-2-yl]-N'-ethylurea $^1$H NMR 1.08 (m, 3H), 2.85 (m, 2H), 3.25 (m, 2H), 3.45 (m, 2H), 6.1 (m, 1H), 6.75 (m, 1H), 6.8–7.3 (m, 5H), 7.35 (m, 1H), 7.45 (m, 1H), 7.75 (s, 1H), 8.43 (s, 1H), 10.58 (br s, 1H), LC/MS 3.4 min, 384 (M+1).

EXAMPLE 323

N-[6-(Ethyl-2-amino-m-tolylurea)-1,3-benzothiazol-2-yl]-N'-ethylurea $^1$H NMR 1.09 (m, 3H), 2.23 (s, 3H), 2.8 (m, 2H), 3.17 (m, 2H), 3.35 (m, 2H), 6.07 (m, 1H), 6.7 (m, 2H), 7.0–7.5 (m, 5H), 7.7 (s, 1H), 8.35 (s, 1H), 10.57 (br s, 1H), LC/MS 3.27 min, 398 (M+1).

EXAMPLE 324

N-(8-Cyano[1,3]thiazolo[5',4': 3,4]benzo[c]isoxazol-2-yl)-N'-ethylurea 0.2 g of [2-(3-ethyl-5-methyl-2-oxo-1,3,5-triazinan-1-yl)-6-nitro-1,3-benzothiazol-7-yl]methyl cyanide was charged into about 2 ml dimethylformamide. About 15 equivalents of triethylamine were then added followed by about 15 equivalents of trimethylsilyl chloride. The solution was stirred at room temperature for about 4–20 hours. The reaction was quenched by pouring into dilute aqueous hydrochloric acid then extracted well with ethyl acetate. The combined organics were back extracted with dilute sodium bicarbonate then dried over magnesium sulfate and concentrated. The dark oil was further purified by preparative HPLC to yield 2-(3-ethyl-5-methyl-2-oxo-1,3,5-triazinan-1-yl) [1,3]thiazolo[5',4': 3,4]benzo[c]isoxazol-8-yl cyanide.

$^1$H NMR 1.12 (m, 3H), 2.55 (s, 3H), 3.4 (m, 2H), 4.39 (s, 2H), 5.16 (s, 2H), 7.9 (d, 1H), 7.95 (d, 1H), LC/MS 2.6 min, 343 (M+1).

The foregoing product was then deprotected with NHCl in dioxane. Thus, the product was dissolved in about 2 ml 4 NHCl in dioxane. After stirring for about 2–8 hours, the crude reaction mixture is poured onto ice and separated between water and ether. Following further extraction with ether, the combined organic layers are dried with magnesium sulfate and concentrated. The product is further purified by preparative HPLC.

¹H NMR 1.11 (t, 3H), 3.22 (m, 2H), 6.8 (br s, 1H), 7.9 (d, 2H), 11.25 (br s, 1H), LC/MS 2.24 min, 288 (M+1).

General Procedure for Preparation of Ureas 0.2 grams of methyl [(6-cyano-1,3-benzothiazol-2-yl)amino]methanethioate is dissolved in about 5 ml of an alkanol. About 0.04 ml of pyridine is added followed by an excess of the appropriate amine and the solution is heated to about 80° C. under good agitation. The solution is allowed to stir for about 14 hours then cooled to RT. The solvent is removed in vacuo. The product is further purified by preparative HPLC then dried in vacuo. If necessary, maleate salts were prepared by dissolving in an alkanol, then adding to this solution a solution of the appropriate amount of maleic acid in alkanol solvent. Upon cooling, the maleate products were collected as a precipitate.

EXAMPLE 325

N-(6-Cyano-1,3-benzothiazol-2-yl)-N'-[3-(4-methylpiperazino)propyl]urea

¹H NMR 1.6 (m, 2H), 2.1 (s, 3H), 2.3 (m, 2H), 2.7 (br s, 4H), 2.9 (br s, 4H), 3.1 (m, 2H), 7.65 (m, 1H), 7.95 (m, 2H), 8.35 (br s, 1H), 8.45 (br s, 1H), LC/MS 1.50 min, 359 (M+1).

EXAMPLE 326

N-(6-Cyano-1,3-benzothiazol-2-yl)-N'-(2-morpholinoethyl)urea

¹H NMR 1.9 (s, 3H), 2.42 (m, 6H), 3.58 (m, 4H), 6.85 (br s, 1H), 7.73 (m, 2H), 8.43 (s, 1H), 9.8 (br s, 1H), LC/MS 1.54 min, 332 (M+1).

EXAMPLE 327

N-(6-Cyano-1,3-benzothiazol-2-yl)-N'-(3-(9-benzyl-9-azabicyclo[3.3.1]nonyl))urea ¹H NMR 1.48 (m, 2H), 1.6–2.0 (m, 8H), 2.85 (br s, 2H), 3.82 (br s, 2H), 4.45 (m, 1H), 6.7 (br s, 1H), 7.22 (m, 1H), 7.35 (m, 4H), 7.75 (m, 2H), 8.46 (s, 1H), 10.9 (br s, 1H). LC/MS 2.16 min, 432 (M+1).

EXAMPLE 328

N-(6-Cyano-1,3-benzothiazol-2-yl)-N'-[6-(4-methylpiperazino)-3-pyridyl]urea

¹H NMR 2.84 (s, 3H), 3.1 (br s, 4H), 3.49 (br s, 2H), 4.32 (br s, 2H), 6.125 (s, 2H), 6.99 (d, 1H), 7.8 (m, 3H), 8.28 (s, 1H), 8.48 (s, 1H), 9.17 (s, 1H), 9.76 (br s, 1H). LC/MS 2.62 min, 394 (M+1), 392 (M−1).

EXAMPLE 329

N-(6-Cyano-1,3-benzothiazol-2-yl)-N'-(3-(8-benzyl-8-azabicyclo[3.2.1]octyl))urea ¹H NMR 1.5–1.8 (m, 6H), 2.05 (m, 2H), 3.15 (m, 2H), 3.36 (br s, 2H), 3.95 (m, 1H), 6.7 (br s, 1H), 7.35 (m, 5H), 7.74 (m, 2H), 8.46 (s, 1H), 10.9 (br s, 1H). LC/MS 2.86 min, 418 (M+1), 416 (M−1).

EXAMPLE 330

N-(6-Cyano-1,3-benzothiazol-2-yl)-N'-(methyl-3-(8-benzyl-8-azabicyclo[3.2.1]octyl))urea ¹H NMR 1.3–1.6 (m, 6H), 1.8 (br s, 1H), 1.9 (br s, 2H), 3.1 (m, 2H), 3.2 (m, 2H), 3.5 (br s, 2H), 6.8 (br s, 1H), 7.35 (m, 5H), 7.74 (m, 2H), 8.45 (s, 1H), 11.8 (br s, 1H). LC/MS 3.09 min, 432 (M+1), 430 (M−1).

EXAMPLE 331 tert-Butyl 4-[([(6-cyano-1,3-benzothiazol-2-yl)amino]carbonylamino)methyl]-1-piperidinecarboxylate ¹H NMR 1.1 (m, 2H), 1.38 (s, 9H), 1.62 (m, 3H), 2.7 (m, 2H), 3.1 (m, 2H), 3.95 (m, 2H), 6.9 (br s, 1H), 7.74 (m, 2H), 8.45 (s, 1H), 11.0 (br s, 1H). LC/MS 2.61 min, 414 (M−1).

EXAMPLE 332

N-(6-Cyano-1,3-benzothiazol-2-yl)-N'-(4-piperidylmethyl)urea

¹H NMR 1.1 (m, 2H), 1.6 (m, 3H), 3.1 (m, 4H), 3.4 (m, 4H), 7.32 (br s, 1H), 7.6 (d, 1H), 7.67 (d, 1H), 7.95 (s, 1H), 8.31 (br s, 1H). LC/MS 1.54 min, 316 (M+1).

EXAMPLE 333 tert-Butyl 4-[2-([(6-cyano-1,3-benzothiazol-2-yl)amino]carbonylamino)ethyl]-1-piperazinecarboxylate ¹H NMR 1.4 (s, 9H), 1.9 (s, 3H), 2.4 (m, 6H), 3.3 (m, 4H), 6.85 (br s, 1H), 7.74 (m, 2H), 8.45 (s, 1H), 11.2 (br s, 1H), other signals under DMSO or water peaks. LC/MS 2.81 min, 431 (M+1), 429 (M−1).

EXAMPLE 334

N-(6-Cyano-1,3-benzothiazol-2-yl)-N'-(2-piperazinoethyl)urea

¹H NMR 1.9 (s, 6H), 2.4 (m, 6H), 2.75 (m, 4H), 3.3 (m, 2H), 3.5 (br s, 1H), 7.15 (br s, 1H), 7.7 (m, 2H), 7.95 (s, 1H), 8.4 (s, 1H). LC/MS 2.58 min, 331 (M+1), 329 (M−1).

EXAMPLE 335

N-(6-Cyano-1,3-benzothiazol-2-yl)-N'-[4-(4-methylpiperazino)Cyclohexyl]urea More polar (trans)

¹H NMR 1.2 (m, 4H), 1.8 (m, 21), 1.91 (s, 3H), 1.93 (m, 2H), 2.33 (m, overlapping with DMSO), 3.36 (m, overlapping with water), 6.7 (m, 1H), 7.7 (m, 2H), 8.45 (s, 1H), 10.8 (m, 1H), other signals under DMSO or water. LC/MS 1.64 min, 399 (M+1).

EXAMPLE 336

N-(6-Cyano-1,3-benzothiazol-2-yl)-N'-[4-(4-methylpiperazino)Cyclohexyl]urea Less polar (cis)

¹H NMR 1.55–1.75 (m, 4H), 2.2 (m, overlapping with DMSO), 3.85 (m, 1H), 6.95 (m, 1H), 7.7 (m, 2H), 8.46 (s, 1H), 10.65 (m, 1H), other signals under DMSO or water. LC/MS 1.75 min, 399 (M+1).

EXAMPLE 337

N-(6-Cyano-1,3-benzothiazol-2-yl)-N'-(3-piperidino-propyl)urea $^1$H NMR 1.35 (m, 2H), 1.6 (m, 4H), 1.75 (m, 2H), 1.9 (s, 3H), 2.3 (m, 6H), 3.25 (m, 2H), 6.9 (m, 1H), 7.7 (m, 2H), 8.4 (s, 1H), 10.8 (br s, 1H), LC/MS 1.69 min, 344 (M+1).

EXAMPLE 338

2-[(Ethylamino)Carbonyl]amino-1,3-benzothiazole-6-carboxylic acid

About 60 mg N-(6-cyano-1,3-benzothiazol-2-yl)-N'-ethylurea was charged into about 5 mL of about a 1:1 mixture of about 2N aq KOH and dioxane. The reaction mixture was then brought to reflux for about 12–24 hours. Upon cooling, the reaction mixture was poured into about 25 mL of dilute aqueous acid. The white precipitate was collected by filtration and was washed well with water. $^1$H NMR 1.09 (t, 3H), 3.19 (m, 2H), 6.79 (br s, 1H), 7.65 (d, 1H), 7.92 (m, 1H), 8.48 (d, 1H), 11.0 (br s, 1H), 12.8 (br s, 1H); LC/MS 2.12 min, 266 (M+1), 264 (M−1), lab LC retention time 4.7 minutes.

EXAMPLE 339

N-(6-Bromo-1,3-benzothiazol-2-yl)-N'-ethylurea

About 5 g of 4-bromoaniline is dissolved in about 100 mL acetic acid and the solution is cooled to about 16° C. About 5.6 g of potassiumthiocyanate is added and the flask is equipped with an addition funnel. The addition funnel is charged with about 4.7 g bromine and about 20 mL acetic acid. This dark solution is then added to the benzonitrile solution in a dropwise fashion under good agitation and allowed to stir for about 6–20 hours. The slurry is then drowned into water and filtered. The presscake is washed well with water, dilute alkali, and then water and filtered. LC/MS confirms product is a mixture of 6-bromo-1,3-benzothiazol-2-amine and 2-amino-1,3-benzothiazol-6-yl thiocyanate which was carried on to the next step without further purification.

About 0.75 g of 6-bromo-1,3-benzothiazol-2-amine (crude) is dissolved in about 15 mL DMF. About 0.5 mL of ethylisocyanate is added followed by about 0.9 mL triethylamine and the solution is heated to about 80° C. under good agitation. The solution is allowed to stir for about 4 hours then cooled to RT. The solvent is removed in vacuo and the solids are washed well with ether. The product is further purified by column chromatography.

$^1$H NMR 1.08 (t, 3H), 3.19 (m, 2H), 6.71 (s, 1H), 7.48 (m, 1H), 7.54 (d, 1H), 8.13 (d, 1H), 10.75 (br s, 1H); LC/MS 3.78 min, 301 (M+1), lab LC retention time 8.9 minutes.

EXAMPLE 340

2-(((Ethylamino)Carbonyl)amino)-1,3-benzothiazol-6-yl thiocyanate

Also islated the title compound from the reaction mixture of Example $^1$H NMR 1.09 (t, 3H), 3.19 (m, 2H), 6.75 (s, 1H), 7.62 (m, 1H), 7.71 (d, 1H), 8.3 (d, 1H), 10.9 (br s, 1H); LC/MS 3.0 min, 279 (M+1), lab LC retention time 7.8 minutes.

EXAMPLE 341

2-[(Ethylamino)Carbonyl]amino-1,3-benzothiazole-6-carboxamide

About 1 g of N-(6-cyano-1,3-benzothiazol-2-yl)-N'-ethylurea was charged into about 30 mL of aqueous alkanol. Added about 0.6 g hydroxylamine hydrochloride and about 0.45 g sodium carbonate then heated to reflux. The solution was refluxed for about 4–8 hours then cooled to room temperature. The precipitate was recovered by filtration and washed well with water. LC/MS indicated a mixture of two products identified as the following after further purification by preparative HPLC:

$^1$H NMR 1.09 (t, 3H), 3.16 (m, 2H), 5.8 (s, 2H), 7.1 (br s, 1H), 7.55 (d, 1H), 7.67 (m, 1H), 8.1 (d, 1H); LC/MS 2.1 min, 265 (M+1), 263 (M−1).

2-[(Ethylamino)Carbonyl]amino-1,3-benzothiazole-6-carboxamideoxime

Also isolated this title product from the reaction mixture of Example $^1$H NMR 1.09 (t, 3H), 3.19 (m, 2H), 5.81 (br s, 2H), 6.72 (br s, 1H), 7.57 (d, 1H), 7.68 (m, 1H), 8.13 (d, 1H), 9.58 (s, 1H), 10.7 (br s, 1H); LC/MS 2.04 min, 278 (M−1).

EXAMPLE 342

N-Ethyl-N'-[6-(5-methyl-1,2,4-oxadiazol-3-yl)-1,3-benzothiazol-2-yl]urea

About 50 mg of 2-[(ethylamino)Carbonyl]amino-1,3-benzothiazole-6-carboxamideoxime was charged into about 1 mL of glacial acetic acid. The mixture was heated to about 110° C. then stirred at this temperature for about 12–20 hours. The solution was cooled to room temperature and the solvent was removed under reduced pressure. The residue was then further purified by preparative HPLC. $^1$H NMR 1.10 (t, 3H), 2.67 (s, 3H), 3.17 (m, 2H), 6.74 (s, 1H), 7.73 (d, 1H), 7.97 (d, 1H), 8.53 (s, 1H), 10.9 (s, 1H); LC/MS 2.69 min, 304 (M+1), 302 (M−1).

EXAMPLE 343

N-(6-Anilino-1,3-benzothiazol-2-yl)-N'-ethylurea

About 150 mg of N-(6-amino-1,3-benzothiazol-2-yl)-N'-ethylurea, and about 285 mg triphenyl bismuthane were charged into about 15 mL dichloromethane. Introduced about 0.1 mL triethylamine and then about 120 mg of copper(II) acetate. The mixture was stirred at RT for about 12–24 hours. The solution was poured into about 60 mL of dilute aqueous acid then stirred for about 1 hour at room temperature. The crude mixture was extracted with dichloromethane and the combined organics were washed with dilute aqueous acid, then water, then dilute aqueous potassium carbonate then dried. The solvent was removed under reduced pressure. The crude mixture was further purified by preparative HPLC. $^1$H NMR 1.09 (t, 3H), 3.18 (m, 2H), 6.69 (s, 1H), 6.78 (m, 2H), 7.04 (d, 2H), 7.09 (m, 1H), 7.21 (m, 2H), 7.49 (d, 1H), 7.55 (d, 1H), 8.13 (s, 1H), 10.46 (br s, 1H); LC/MS 3.06 min, 313 (M+1), 311 (M−1).

EXAMPLE 344

N-[6-(Aminomethyl)-1,3-benzothiazol-2-yl]-N'-ethylurea

About 0.05 g of N-(6-cyano-1,3-benzothiazol-2-yl)-N'-ethylurea was charged into about 10 mL of ethyleneglycol dimethylether. Introduced about 50 mg lithium aluminum hydride in several portions over about 12–24 hours. The slurry was quenched with about 5–10 mL ethyl acetate then about 1–2 mL of saturated aqueous sodium sulfate. The slurry was then diluted with water and extracted with ethyl acetate. Following drying and removal of solvents under reduced pressure, the product was isolated by preparative HPLC. $^1$H NMR 1.08 (t, 3H), 1.88 (s, 3H), 3.17 (m, 2H), 3.83 (s, 2H), 7.07 (m, 1H), 7.32 (m, 1H), 7.54 (d, 1H), 7.8 (s, 1H); LC/MS 1.86 min, 251 (M+1), 249 (M−1).

EXAMPLE 345

N-[6-(Ethylureido)methyl)-1,3-benzothiazol-2-yl]-N'-ethylurea

About 0.025 g of N-[6-(aminomethyl)-1,3-benzothiazol-2-yl]-N'-ethylurea was dissolved in about 1 mL dimethylformamide. About 0.015 mL of ethylisocyanate was added followed by about 0.029 mL triethylamine and the solution was heated to about 80° C. under good agitation. The solution was allowed to stir for about 4 hours then cooled to RT. The solvent was removed in vacuo and the solids were washed well with ether. $^1$H NMR 1.0 (t, 3H), 1.09 (t, 3H), 3.0 (m, 2H), 3.2 (m, 2H), 4.25 (d, 2H), 5.86 (m, 1H), 5.33 (br s, 1H), 6.3 (m, 1H), 6.7 (m, 1H), 7.23 (m, 1H), 7.53 (d, 1H), 7.69 (d, 1H), 10.6 (br s, 1H); LC/MS 1.43 min, 322 (M+1).

EXAMPLE 346

N-Ethyl-N'-[6-(2H-1,2,3,4-tetraazol-5-yl)-1,3-benzothiazol-2-yl]urea

About 30 mg N-(6-cyano-1,3-benzothiazol-2-yl)-N'-ethylurea was charged into about 5 mL dry tetrahydrofuran. Added about 2 g of azidotributylstannane then refluxed for about 48–72 hours. The solvent was removed under reduced pressure then the crude oil was taken up in dichloromethane. About 0.5 mL of dilute aqueous hydrochloric acid was added and a white precipitate formed. This was allowed to sit for about 30 minutes then the precipitate was collected by filtration, washed with warm THF then dried under vacuum. $^1$H NMR 1.10 (t, 3H), 3.2 (m, 2H), 6.76 (br s, 1H), 7.78 (d, 1H), 8.0 (d, 1H), 8.58 (s, 1H), 10.91 (s, 1H); LC/MS 1.37 min, 290 (M+1).

EXAMPLE 347

N1-[(2-[(Ethylamino)Carbonyl]amino-1,3-benzothiazol-6-yl)methyl]-1-benzenesulfonamide About 0.015 g of N-[6-(aminomethyl)-1,3-benzothiazol-2-yl]-N-ethylurea is dissolved into about 1 mL dichloromethane. Cooled to about 0–5° C. then added about 0.01 mL of triethylamine followed by about 1.2 equivalents of the appropriate sulfonylchloride. The reaction is warmed to room temperature then stirred for about 12–24 hours. The solvent is removed under reduced pressure and the reaction crude is further pruified by preparative HPLC. $^1$H NMR 1.08 (t, 3H), 3.19 (m, 2H), 4.05 (d, 2H), 6.71 (br s, 1H), 7.20 (m, 1H), 7.5 (d, 1H), 7.54–7.65 (m, 4H), 7.8 (d, 1H), 8.16 (m, 1H), 10.6 (br s, 1H); LC/MS 1.98 min, 391 (M+1).

EXAMPLE 348

N-[(2-[(Ethylamino)Carbonyl]amino-1,3-benzothiazol-6-yl)methyl]trifluoromethanesulfonamide Also isolated the title compound from the reaction mixture of Example 347 $^1$H NMR 1.09 (t, 3H), 3.18 (m, 2H), 4.4 (s, 2H), 6.71 (m, 1H), 6.6 (d, 1H), 7.32 (m, 1H), 7.81 (s, 1H), 9.93 (br s, 1H), 10.68 (br s, 1H); LC/MS 2.15 min, 383 (M+1).

EXAMPLE 349

N6-Phenyl-2-[(ethylamino)Carbonyl]amino-1,3-benzothiazole-6-carboxamide

About 0.2 g of 2-[(ethylamino)Carbonyl]amino-1,3-benzothiazole-6-carboxylic acid was dissolved into about 20 mL dichloromethane and about 0.2 mL triethylamine. Added about 1 eq of the appropriate amine followed by about 0.3 g of 1-ethyl-3-(3-dimethylaminopropyl)Carbodiimide hydrochloride then stirred at room temperature for about 12–24 hours. The solvent was removed under reduced pressure then the crude reaction mixture was purified by preparative HPLC. $^1$H NMR 1.10 (t, 3H), 3.2 (m, 2H), 6.76 (br s, 11), 7.10 (m, 1H), 7.36 (m, 2H), 7.70 (d, 1H), 7.79 (d, 2H), 7.97 (m, 1H), 8.5 (s, 1H), 10.23 (s, 1H), 10.9 (br s, 1H); LC/MS 2.86 min, 341 (M+1);

EXAMPLE 350

N6-[3-(4-Methylpiperazino)propyl]-2-[(ethylamino)Carbonyl]amino-1,3-benzothiazole-6-carboxamide Also isolated the title compound from the reaction mixture of Example $^1$H NMR 1.09 (t, 3H), 1.76 (m, 2H), 2.6–2.7 (m, 4H), 3.2 (m, 4H), 3.3 (m, 4H), 3.42 (m, 2H), 6.12 (s, 4H), 6.75 (m, 1H), 7.64 (d, 1H), 7.84 (m, 1H), 8.34 (d, 1H), 8.49 (m, 1H), 10.9 (br s, 1H), one methyl group under solvent peaks; LC/MS 1.34 min, 405 (M+1).

General Procedure for Preparation of Ureas 0.2 grams of methyl [((6-cyano-1,3-benzothiazol-2-yl)amino]methanethioate is dissolved in about 5 ml of an alkanol. About 0.04 ml of pyridine is added followed by an excess of the appropriate amine and the solution is heated to about 80° C. under good agitation. The solution is allowed to stir for about 14 hours then cooled to RT. The solvent is removed in vacuo. The product is further purified by preparative HPLC then dried in vacuo. If necessary, maleate salts were prepared by dissolving in an alkanol, then adding to it a solution of the appropriate amount of maleic acid in the same alkanol solvent. Upon cooling, the maleate products were collected as a precipitate.

EXAMPLE 351

N-(6-Cyano-1,3-benzothiazol-2-yl)-N'-[6-(4-methylpiperazino)-3-pyridyl]urea $^1$H NMR 2.84 (s, 3H), 3.1 (br s, 4H), 3.49 (br s, 2H), 4.32 (br s, 2H), 6.125 (s, 2H), 6.99 (d, 1H), 7.8 (m, 3H), 8.28 (s, 1H), 8.48 (s, 1H), 9.17 (s, 1H), 9.76 (br s, 1H). LC/MS 2.62 min, 394 (M+1), 392 (M−1).

EXAMPLE 352

N-(6-Methylcyano-1,3-benzothiazol-2-yl)-N'-ethylurea

About 1 g of (2-amino-1,3-benzothiazol-6-yl)methyl cyanide is dissolved in about 10 ml dimethylformamide. About 0.8 ml of ethylisocyanate is added followed by about 1.4 ml triethylamine and the solution is heated to about 80° C. under good agitation. The solution is allowed to stir for about 4–6 hours then cooled to RT. The solvent is removed in vacuo and the solids are washed well with ether. The product is recrystallized from hot EtOAc. $^1$H NMR 1.09 (t, 3H), 3.1 (m, 2H), 4.1 (s, 2H), 6.72 (m, 1H), 7.32 (m, 1H), 7.61 (d, 1H), 7.85 (s, 1H), 10.7 (s, 1H); LC/MS 2.73 min, 261 (M+1), 259 (M−1).

EXAMPLE 353

N-[6-(Di[(5-methyl-2-furyl)methyl]aminomethyl)-1,3-benzothiazol-2-yl]-N'-ethylurea About 10 mg of N-(6-aminomethyl-1,3-benzothiazol-2-yl)-N'-ethylurea was dissolved in about 1 mL dichloromethane, 3 μL acetic acid, and 4 μL 5-methyl-2furfural. Stirred for about 1 hour at room temperature then about 0.013 g of sodiumtriacetoxyborohydride was added. The mixture was stirred at room temperature for about 12–20 hours. The reaction was drowned into about 5 mL water then extracted well with dichloromethane. The combined organics were dried over magnesium sulfate and solvent was removed under reduced pressure. The crude mixture was further purified by preparative HPLC. $^1$H NMR 1.10 (t, 31), 1.8 (s, 3H), 2.2 (s, 6H), 3.1 (m, 2H), 3.5 (s, 4H), 3.6 (s, 2H), 6.0 (m, 2H), 6.2 (m, 2H), 7.29 (m, 1H), 7.4 (br s, 1H), 7.5 (m, 1H), 7.7 (s, 1H); LC/MS 2.87 min, 439 (M+1).

General Procedure for Making Compounds of the Formula

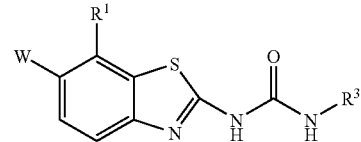

Starting from a substituted aniline.

To a stirring solution of a substituted aniline, such as 4-(p-flourophenylthio)aniline and potassium thiocyanate (~2 eq.) in glacial acetic acid at room temperature was added dropwise a solution of bromine (~1 eq.) in glacial acetic acid. The reaction mixture was stirred for about 24 hours. The solid (KBr) was removed by filtration and the resulting solution concentrated in vacuo to give the corresponding benzothiazolyl as the HBr salt. HPLC RT=3.3 min, MH+ 277.

To a stirring solution of the benzothiazolyl from the preceding step and triethylamine (~2 eq.) in toluene was added ethylisocyanate (~1.5 eq.). The reaction mixture was heated to about 80 degrees for about 2 days. The precipitated product was collected on a fritted funnel, washed with diethyl ether and dried in vacuo. HPLC RT=3.61 min, MH+ 349.

The following examples were synthesized according to the procedures described hereinabove.

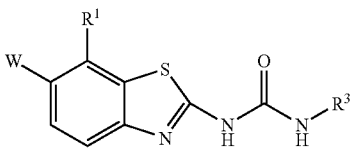

| Ex. # | W | $R^1$ | $R^3$ | HPLC (min.) | MH+ |
|---|---|---|---|---|---|
| 354 | —CH$_2$—OH | H | ethyl | 2.22 | 434 |
| 355 | —CH$_2$—O—C(O)—NH—Et | H | ethyl | 2.47 | 307 |
| 356 | —S-phenyl | H | ethyl | 2.22 | 308 |
| 357 | —O-phenyl | H | ethyl | 2.70 | 370 |
| 358 | —S—CH$_3$ | H | ethyl | 3.82 | 363 |
| 359 | —C(O)-phenyl | H | ethyl | 3.86 | 409 |
| 360 | —S(O)-phenyl | H | ethyl | 3.73 | 399 |
| 361 | —S-p-nitrophenyl | H | ethyl | 3.42 | 452 |
| 362 | —S-p-methylphenyl | H | ethyl | 3.14 | 452 |
| 363 | —S-p-chlorophenyl | CN | ethyl | 3.20 | 439 |
| 364 | —S-p-methoxyphenyl | CN | ethyl | 2.77 | 368 |
| 365 | —S-m-CF$_3$-phenyl | CN | ethyl | 2.97 | 427 |
| 366 | —S-o-chlorophenyl | H | ethyl | 3.53 | 441 |
| 367 | —C(O)—CH$_3$ | H | ethyl | 3.40 | 441 |
| 368 | —NH—C(O)—NH—(—CH$_2$)$_2$-2-thienyl | H | ethyl | 1.71 | 352 |
| 369 | —NH—C(O)—NH-3-pyridyl | H | ethyl | 1.91 | 414 |
| 370 | —S(O)$_2$-p-(carboxymethylamino)-phenyl | H | ethyl | 3.13 | 403 |
| 371 | —N-morpholino | H | ethyl | 3.1 | 403 |
| 372 | —NH—C(O)—NH—Et | H | ethyl | 3.52 | 436 |
| 373 | —NH—C(O)—NH—CH$_2$-phenyl | H | ethyl | 1.81 | 425 |
| 374 | S-p-chlorophenyl | H | ethyl | 2.29 | 252 |
| 375 | —S-p-bromophenyl | H | ethyl | 2.65 | 323 |
| 376 | —S-m-CF$_3$-phenyl | H | ethyl | 3.53 | 330 |

-continued
| | | | | | |
|---|---|---|---|---|---|
| 377 | NO₂ | H | 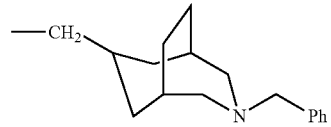 | 3.29 | 314 |
| 378 | NO₂ | H | 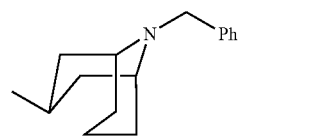 | 3.02 | 268 |
| 379 | NO₂ | H | 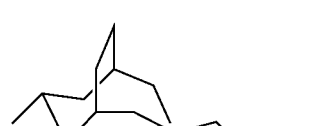 | 3.44 | 255 |
| 380 | Cl | H | —(CH₂)₃-4-methylpiperazin-1-yl | 2.53 | 346 |
| 381 | Cl | H | 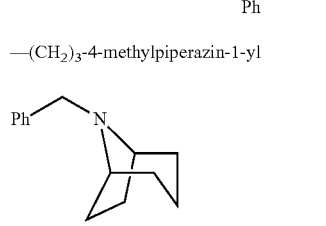 | 3.56 | 375 |
| 382 | Cl | H | 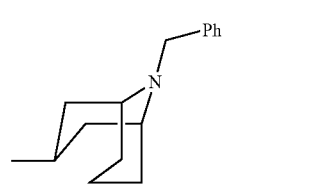 | 3.73 | 344 |
| 383 | Cl | H |  | 3.72 | 389 |
| 384 | NO₂ | H | —(CH₂)₂—N-morpholino | 3.37 | 385 |
| 385 | NO₂ | H | 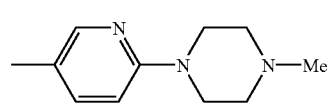 | 3.80 | 423 |
| 386 | Cl | H | 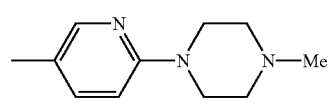 | 3.69 | 364 |
| 387 | Cl | H | —(CH₂)₂—N-morpholino | 1.79 | 264 |
| 389 | Cl | H | 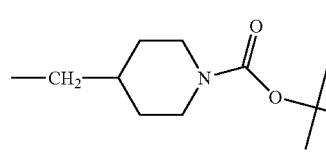 | 2.72 | 390 |
| 390 | Cl | H | —CH₂-piperidin-4-yl | 2.30 | 357 |
| 391 | —S-p-fluorophenyl | H | —(CH₂)₃-4-methylpiperazin-1-yl | 2.32 | 461 |

-continued

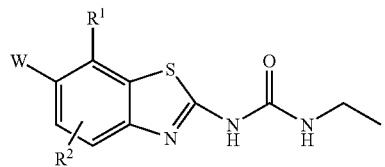

| Ex # | W | R¹ | R² | HPLC (min) | MH⁺ |
|---|---|---|---|---|---|
| 392 | —OCF₃ | H | H | 2.43 | 306 |
| 393 | —OEt | H | H | 2.12 | 266 |
| 394 | F | H | H | 2.03 | 240 |
| 395 | H | H | 4-Cl | 2.30 | 256 |
| 396 | H | H | 4-CH₃ | 2.25 | 236 |
| 397 | CH₃ | H | H | 2.17 | 236 |
| 398 | CH₃ | H | 5-CH₃ | 2.71 | 276 |
| 399 | —OCH₃ | H | H | 2.37 | 250 |
| 400 | —SO₂—Me | H | H | 1.95 | 252 |
| 401 | NH₂ | H | H | 1.75 | 300 |
| 402 | —NH—C(O)—Me | H | H | 2.51 | 237 |
| 403 | —NH—CH₂-phenyl | H | H | 2.58 | 279 |
| 404 | H | H | 5-CH₃ | 3.28 | 327 |
| 405 | H | F | 5-F | 3.12 | 266 |
| 406 | H | H | 5-Cl | 3.21 | 258 |
| 407 | —NH—S(O)₂-2-thienyl | H | H | 3.38 | 256 |
| 408 | —NH—S(O)₂-(3,5-dimethylisoxazol-4-yl) | H | H | 3.17 | 383 |
| 409 | —NH—S(O)₂—Me | H | H | 3.10 | 396 |
| 410 | —NH—S(O)₂—CH₂-phenyl | H | H | 2.81 | 315 |
| 411 | —NH—C(O)—O—CH₂—CCl₃ | H | H | 2.77 | 391 |
| 412 | —NH—C(O)—O—CH₂—Ph | H | H | 2.16 | 412 |
| 413 | —NH—C(O)—O—Me | H | H | 3.47 | 371 |
| 414 | NO₂ | H | 4-CH₃ | 2.87 | 295 |
| 415 | NO₂ | —CH₂—S(O)₂-phenyl | H | 3.22 | 281 |
| 416 | —OCH₃ | H | 5-OCH₃ | 2.56 | 282 |

The invention claimed is:

1. A compound of formula (I),

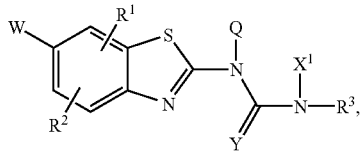

racemic-diastereomeric mixtures thereof, optical isomers thereof, isotopes thereof or pharmaceutically-acceptable salts of said compound, isomers, and isotopes, wherein, Q is H Y is O or S;

W is H, Cl, Br, I, NO₂, CN, SCN, OCF₃, —X$_q$—(C(R¹⁰)₂)$_a$—Y¹$_q$—(C(R¹⁰)₂)$_a$—Z¹$_q$, or an optionally substituted group selected from the group consisting of alkyl, alkenyl and alkynyl;

Y¹ and X are each independently selected from the group consisting of phenyl, NR¹⁰, O, S, SO, SO₂, CF₂, CFR, C=O, (C=O)NR¹⁰, SONR¹⁰, SO₂NR¹⁰, NR¹⁰(C=O), NR¹⁰SO, NR¹⁰SO₂, NR¹⁰SO₂NR¹⁰, NR¹⁰(C=O)NR¹⁰,

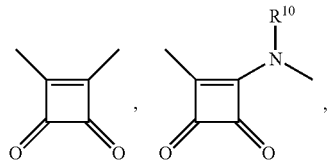

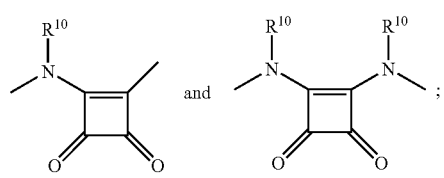

q for each occurrence is independently 0 or 1;

a for each occurrence is independently 0 or an integer from 1 to 5;

R¹⁰ for each occurrence is independently selected from the group consisting of H, optionally substituted aryl, and an optionally substituted alkyl group optionally substituted with one or more of the following: a C₁₋₆ alkyl group optionally substituted by one or more hydroxy, halo or optionally substituted amino; a C₁₋₆ alkoxy group optionally substituted by one or more hydroxy, halo or optionally substituted amino; hydroxy; halo; or optionally substituted amino;

$Z^1$ is H, optionally substituted alkyl or optionally substituted aryl $X^1$ is hydrogen, alkyl or hydroxyalkyl;

$R^1$ and $R^2$ are each independently hydrogen, halogen, hydroxy, nitro, cyano, COOH, COOX$^3$, SX$^3$, SO$_2$X$^3$, SOX$^3$, C(O)X$^3$, NHC(O)X$^3$, C(O)NHX$^3$, NHSO$_2$X$^3$ or selected from an optionally substituted group consisting of alkyl, alkenyl, alkynyl, alkoxy, amino, —NHX$^3$, —NX$^3$X$^3$, alkylamino, arylamino, alkylthio, alkylsulfonato, aryl, aryloxy, arylalkyl, arylalkenyl, arylalkynyl, arylalkyloxy, cycloalkyl, —(CH$_2$)$_m$—(CHX$^2$)CN, —(CH$_2$)$_m$—(CHX$^2$)COOH, —(CH$_2$)$_m$—(CHX$^2$)COOX$^3$, —(CH$_2$)$_m$—(CHX$^2$)SO$_2$X$^3$, —(CH$_2$)$_m$—(CHX$^2$)C(O)X$^3$, —(CH$^2$)$_m$—(CHX$^2$)C(O)NHX$^3$ and —(CH$_2$)$_m$—(CHX$^2$)NHSO$_2$X$^3$ provided that the alkylamino and arylamino are attached to the phenyl ring via the nitrogen of the amino group;

where m is 0 to 4;

X for each occurrence is independently H or an optionally substituted moiety selected from the group consisting of alkyl, alkenyl, alkynyl, carbonyl, S(O)$_p$alkyl, S(O)$_p$aryl, S(O)$_p$heterocyclyl, amino, alkoxy, alkylthio, arylthio, perhaloalkyl, aryl, aryloxy, arylalkyl, and arylalkyloxy;

p is 0, 1 or 2;

$X^3$ for each occurrence is independently H or an optionally substituted moiety selected from the group consisting of mono- or di-alkylamino, alkyl, alkenyl, alkynyl, aryl; and arylalkyl;

$R^3$ is hydrogen, or an optionally substituted moiety selected from the group consisting of carbonyl, alkyl, alkenyl, alkynyl, cycloalkyl, aryl, arylalkyl, amino, alkylamino, arylamino, alkoxy; and acyl;

where each of the optionally substituted moieties described hereinabove is optionally substituted by one or more substituents each independently selected from the group consisting of oxo, amino, nitro, mono- or bi-(C$_1$–C$_6$)alkylamino, hydroxy, nitrile, chloro, fluoro, bromo, iodo, CF$_3$, (C$_1$–C$_6$)alkyl, —C(O)(C$_1$–C$_6$)alkyl, —COOH, —COO (C$_1$–C$_6$)alkyl, —S—(C$_1$–C$_6$)alkyl, —S-aryl, (C$_1$–C$_6$) alkoxy, —SO$_2$NH$_2$, phenyl, phenyl(C$_1$–C$_6$)alkyl, —O—(C$_1$–C$_6$)alkyl-OH, —O—(C$_1$–C$_6$)alkyl-O—(C$_1$—C$_6$)alkyl, —O—(C$_2$–C$_6$)alkyl-N—((C$_1$–C$_6$)alkyl)$_n$, —N—(C$_1$–C$_6$) alkyl-OH, —N—(C$_1$–C$_6$)alkyl-O—(C$_1$–C$_6$)alkyl, —C(O) NH$_2$, —C(O)N((C$_1$–C$_6$)alkyl)$_n$, , —S(O)$_n$(C$_1$–C$_6$)alkyl; and —S(O)$_n$aryl—where the alkyl groups mentioned herein optionally have one or more unsaturated bonds in the alkyl portion;

n is 0, 1 or 2;

provided that 1) when Q is H; Y is O; $R^1$ and $R^2$ are each hydrogen, halogen, alkyl, alkoxy, alkylthio, carboxyalkyl or optionally substituted phenyl; and $X^1$ is hydrogen or alkyl; then $R^3$ is not alkyl, alkenyl, alkoxy, cycloalkyl or optionally substituted phenyl;

2) when Q is H; Y is O; $R^1$ and $R^2$ are each hydrogen, halogen, alkyl, alkoxy, alkylthio, carboxyalkyl or optionally substituted phenyl; then $X^1$ and $R^3$ are not taken together to form

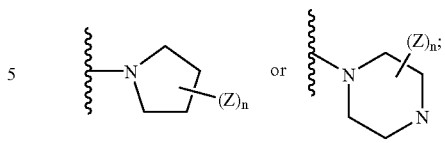

3) when W is Cl, Br or I; Q is hydrogen; Y is O; $X^1$ is H; then $R^3$ is not

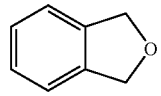

or phenyl optionally substituted by 1 to 3 substituents independently selected from the group consisting of amino, mono- or bi-(C$_1$–C$_6$)alkylamino, hydroxy, chloro, fluoro, bromo, iodo, (C$_1$–C$_6$)alkyl, (C$_1$–C$_6$)alkoxy and —SO$_2$NH$_2$;

4) when W is Cl, Br or I; Q is H; $R^1$ is 7-Cl; $R^2$ is H; and $X^1$ is alkyl; then $R^3$ is not alkyl, alkoxy or cycloalkyl;

5) when W is Cl, Br or I; Q is H; $R^1$ is 7-Cl; $R^2$ is H; and $X^1$ is H; then $R^3$ is not alkyl or cycloalkylamino;

6) when W is Cl, Br, I or NO$_2$; Q is H; Y is O; $X^1$ is H; $R^1$ is OH; $R^2$ is NO$_2$, amino, alkyl, alkoxy, hydroxy lower alkyl or dialkylamino; then $R^3$ is not H or alkyl;

7) when W is Cl, Br or I; Q is H; Y is O; $R^1$ is CF$_3$, CH$_2$F, NO$_2$, alkyl or alkoxy; $R^2$ is H; $X^1$ is H; then $R^3$ is not naphthyl or phenyl optionally substituted with halo, CF$_3$, alkyl or alkoxy;

8) when W is Cl, Br or I; Q is H; $R^1$ is alkyl; $R^2$ is H; $X^1$ is H or alkyl; then $R^3$ is not alkyl or alkoxy;

9) when W is Cl; Q is H; Y is S; $R^1$ and $R^2$ are each H; $X^1$ is H; then $R^3$ is not ethyl;

10) when W is Cl; Q is H; Y is O; $R^1$ and $R^2$ are each H; $X^1$ is H; then $R^3$ is not n-butyl;

11) when W is H, then $R^1$ and $R^2$ are not H at the same time.

12) the compound is not

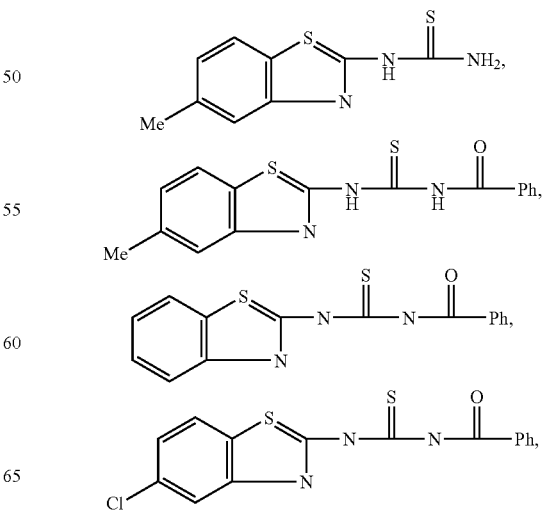

-continued

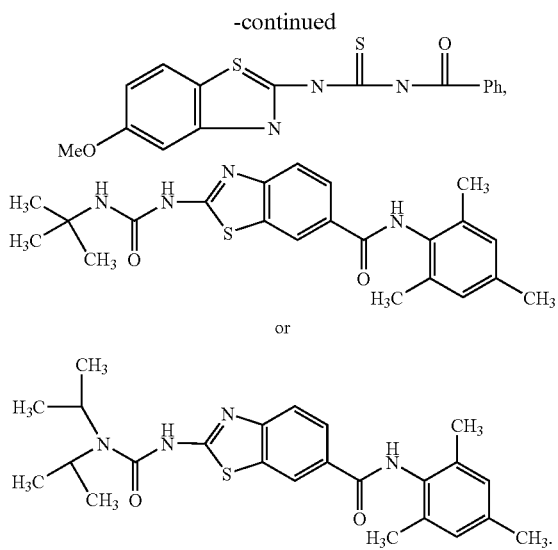

or naphthyl.

3. A compound according to claim 2, racemic-diastereomeric mixtures thereof, optical isomers thereof, isotopes thereof or pharmaceutically-acceptable salts of said compound, isomers, and isotopes, wherein
$R^3$ is an optionally substituted moiety selected from the group consisting of $(C_1–C_8)$alkyl, phenyl, phenyl$(C_1–C_8)$alkyl, cycloalkyl and cycloalkyl$(C_1–C_8)$alkyl.

4. A compound of formula (IA),

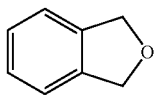
(IA)

racemic-diastereomeric mixtures thereof, optical isomers thereof, isotopes thereof or pharmaceutically-acceptable salts of said compound, isomers, and isotopes, wherein
W is $NO_2$ or CN;
Y is O or S;
$R^1$ is in the 7-position and is hydrogen, methyl, ethyl, allyl, phenyl, benzyl, —$CH_2$—C(O)—$CH_3$, —$CH_2$—$CO_2$-t-Bu, —$CH_2$—$SO_2$-aryl, -alkyl-CN, or -alkyl(CN)($CH_2$-aryl);
$X^1$ is hydrogen, alkyl or hydroxyalkyl;

2. A compound according to claim 1, racemic-diastereomeric mixtures thereof, optical isomers thereof, isotopes thereof or pharmaceutically-acceptable salts of said compound, isomers, and isotopes, wherein
the alkyl, alkenyl and alkynyl moieties, and the alkyl portion of a moiety is an optionally substituted straight or branched chain having one to eight carbon atoms;
the aryl moiety and the aryl portion of a moiety is an optionally substituted phenyl,

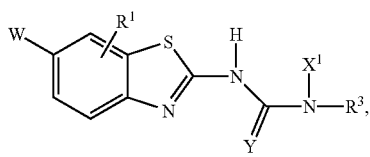

$R^3$ is selected from the group consisting of ethyl, n-butyl, t-butyl, n-propyl, allyl, hydroxyalkyl, aminoalkyl, -alkyl-NH-alkyl-OH, -alkyl-O-alkyl-OH, di-hydroxyalkyl, alkoxyalkyl, cycloalkyl, cycloalkylalkyl, hydroxycycloalkyl, alkylesteralkyl, 2,4-dimethoxyphenyl, 3,5-trifluoromethylphenyl, 3-chlorophenyl, 4-chlorophenyl 2,6-dichlorophenyl, 2-methylphenyl, 3-methylphenyl, (substituted phenyl)alkyl, phenylalkyl, heterocyclylalkyl, N-alkylaminoalkyl and N,N-dialkylaminoalkyl.

5. A compound according to claim 4, racemic-diastereomeric mixtures thereof, optical isomers thereof, isotopes thereof or pharmaceutically-acceptable salts of said compound, isomers, and isotopes, wherein $R^1$ is hydrogen and $X^1$ is hydrogen.

6. A compound according to claim 4, racemic-diastereomeric mixtures thereof, optical isomers thereof, isotopes thereof or pharmaceutically-acceptable salts of said compound, isomers, and isotopes, wherein
W is $NO_2$;
Q is hydrogen;
$R^1$ is in the 7-position and is hydrogen, methyl, ethyl or phenyl;
$R^2$ are each hydrogen;
$X^1$ is hydrogen; and
$R^3$ is selected from the group consisting of ethyl, n-Bu, t-Bu, n-Pr, allyl, cyclopropyl, cyclobutyl, 2,4-dimethoxyphenyl, 3,5-bis-trifluoromethylphenyl, 3-chlorophenyl, 4-chlorophenyl, 2,6-dichlorophenyl, 2-methylphenyl and 3-methylphenyl.

7. A compound according to claim 3, racemic-diastereomeric mixtures thereof, optical isomers thereof, isotopes thereof or pharmaceutically-acceptable salts of said compound, isomers, and isotopes, wherein
Q is H;
W is $NO_2$;
Y is S;
$R^1$ is in the 7-position and is hydrogen, —$CH_2$—$SO_2$-phenyl, —$CH_2$—CN, —CH($CH_3$)(CN), or —CH(CN)($CH_2$-phenyl);
$R^2$ is hydrogen;
$X^1$ is hydrogen, methyl or —$(CH_2)_2$—OH;
$R^3$ is selected from the group consisting of ethyl, benzyl, EtOH, n-PrOH, n-BuOH, n-pentanol, n-hexanol, —$(CH_2)_2$—NH—$(CH_2)_2$—OH, —$(CH_2)_2$—O—$(CH_2)_2$—OH, —CH($CH_2CH_3$)($CH_2OH$), —CH($CH_2OH$)($CH_2$-i-Pr), 2,3-di-hydroxy-propyl, 2-hydroxypropyl, —CH($CH_3$)($CH_2OH$), —C($CH_3$)$_2$($CH_2OH$), —$CH_2$($CH_3$)($CH_2OCH_3$), 1,3-dihydroxyisopropyl, —CH($CH_2OH$)($CH_2CH_2SCH_3$), cyclopropyl, cyclopropylmethyl, 4-hydroxycyclohexyl, 3-chlorophenyl, 4-chlorophenyl, 2-methylphenyl, 3-methylphenyl, 4-aminobenzyl, (4-aminophenyl)ethyl, —$(CH_2)_3$—N(Et)$_2$, and —$(CH_2)_2$—N(Me).

8. A compound according to claim 3, racemic-diastereomeric mixtures thereof, optical isomers thereof, isotopes thereof or pharmaceutically-acceptable salts of said compound, isomers, and isotopes, wherein
Y is O;
$R^1$ is in the 7-position and is hydrogen, —$CH_2$—$SO_2$-phenyl, —$CH_2$—CN, —CH($CH_3$)(CN), or —CH(CN)($CH_2$-phenyl);
$R^2$ is hydrogen;
$X^1$ is hydrogen, methyl or —$(CH_2)_2$—OH;
$R^3$ is selected from the group consisting of benzyl, EtOH, n-PrOH, t-BuOH, n-hexanol, aminoethyl, aminopropyl, —$(CH_2)_2$—NH—$(CH_2)_2$—OH, —$(CH_2)_2$—O—$(CH_2)_2$—OH, —CH($CH_2CH_3$)($CH_2OH$), —CH(CH$_2$OH)(CH$_2$-i-Pr), 2,3-di-hydroxy-propyl, 2-hydroxypropyl, —CH(CH$_3$)(CH$_2$OH), 1,3-dihydroxyisopropyl, —CH(CH$_2$OH)(CH$_2$CH$_2$SCH$_3$), cyclobutyl, 4-hydroxycyclohexyl, —CH(COOEt)(CH$_2$)$_2$—SCH$_3$, —(CH$_2$)$_2$—COOEt, —(CH$_2$)$_5$—COOEt, (2-aminophenyl)methyl, 4-aminobenzyl, (4-aminophenyl)ethyl, —C(CH$_3$)$_2$(phenyl), —CH$_2$(2,4-difluorophenyl), —CH(i-Pr)(COOEt), —CH(i-Pr)(CH$_2$OH), 3-(N-methylamino)propyl, —(CH$_2$)$_3$—N(Et)$_2$, —(CH$_2$)$_4$—N(Et)$_2$, —CH(Me)(CH$_2$)$_4$—CH$_3$, —CH(Me)(CH$_2$)$_3$—N(Et)$_2$, and —(CH$_2$)$_2$—(4—(SO$_2$NH$_2$)phenyl).

9. A compound according to claim 3, racemic-diastereomeric mixtures thereof, optical isomers thereof, isotopes thereof or pharmaceutically-acceptable salts of said compound, isomers, and isotopes, wherein
W is NO$_2$;
Q is hydrogen;
R$^1$ is in the 7-position and is —CH$_2$—CO$_2$-t-Bu, allyl or benzyl;
R are each hydrogen;
X$^1$ is hydrogen; and
R$^3$ is ethyl.

10. A compound according to claim 3, racemic-diastereomeric mixtures thereof, optical isomers thereof, isotopes thereof or pharmaceutically-acceptable salts of said compound, isomers, and isotopes, wherein
W is NO$_2$;
R$^1$ is in the 7-position and is hydrogen, —CH(CH$_3$)(CN) or —CH(CN)(CH$_2$-phenyl); and
R$^2$ is hydrogen.

11. A compound according to claim 2, racemic-diastereomeric mixtures thereof, optical isomers thereof, isotopes thereof or pharmaceutically-acceptable salts of said compound, isomers, and isotopes, wherein
W is NO$_2$;
Q is H;
R$^1$ and R$^2$ are each hydrogen.

12. A compound according to claim 3, racemic-diastereomeric mixtures thereof, optical isomers thereof, isotopes thereof or pharmaceutically-acceptable salts of said compound, isomers, and isotopes, wherein
W is NO$_2$;
R$^1$ is hydrogen or is in the 7-position and is —CH$_2$—CN, —CH$_2$—CONH$_2$ and —CH$_2$—COO-t-Bu;
R$^2$ is hydrogen;
X$^1$ is hydrogen or —CH$_2$—O—CH$_3$;
R$^3$ is methyl, ethyl, n-BuOH, —CH$_2$CF$_3$, —(CH$_2$)$_7$—N(Me)$_2$, 2-phenyl—phenyl, n-BuOH, —CH$_2$CF$_3$, —(CH$_2$)$_4$—N(Me)$_2$, —(CH$_2$)$_2$—N(Me)$_2$, —(CH$_2$)$_3$—NHMe, benzyl or —CH$_2$—O—CH$_3$.

13. A compound according to claim 1, racemic-diastereomeric mixtures thereof, optical isomers thereof, isotopes thereof or pharmaceutically-acceptable salts of said compound, isomers, and isotopes, wherein
W is Cl or Br;
Q is H;
R$^3$ is an optionally substituted moiety selected from the group consisting of alkyl, alkenyl, phenyl, phenylalkyl, or aminoalkyl.

14. A compound according to claim 13, racemic-diastereomeric mixtures thereof, optical isomers thereof, isotopes thereof or pharmaceutically-acceptable salts of said compound, isomers, and isotopes, wherein
R$^3$ is alkyl, haloalkyl, esteralkyl, N,N-dialkylaminoalkyl, alkenyl, phenyl, phenylalkyl, halophenyl, alkoxyphenyl, aryloxyphenyl or aminoalkyl.

15. A compound according to claim 14, racemic-diastereomeric mixtures thereof, optical isomers thereof, isotopes thereof or pharmaceutically-acceptable salts of said compound, isomers, and isotopes, wherein
W is Cl;
R$^3$ is ethyl, propyl, butyl, t-butyl, 2,4,6-trichlorophenyl, 2,4-dimethoxyphenyl, allyl, 2-bromoethyl, 2-phenoxyphenyl, benzyl, —(CH$_2$)$_2$—COOEt, —(CH$_2$)$_3$—N(Et)$_2$, —(CH$_2$)$_4$—N(Et)$_2$, or —(CH$_2$)$_2$—N(Me)$_2$.

16. A compound according to claim 15, racemic-diastereomeric mixtures thereof, optical isomers thereof, isotopes thereof or pharmaceutically-acceptable salts of said compound, isomers, and isotopes, wherein R$^3$ is allyl, 2-bromoethyl, 2-phenoxyphenyl, benzyl, —(CH$_2$)$_2$—COOEt, —(CH$_2$)$_3$—N(Et)$_2$, —(CH$_2$)$_4$—N(Et)$_2$, or —(CH$_2$)$_2$—N(Me)$_2$.

17. A compound of the formula

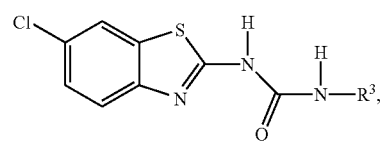

racemic-diastereomeric mixtures thereof, optical isomers thereof, isotopes thereof or pharmaceutically-acceptable salts of said compound, isomers, and isotopes, wherein
R$^3$ is ethyl, propyl, t-butyl, 2,4,6-trichlorophenyl or 2,4-dimethoxyphenyl.

18. A compound according to claim 14, racemic-diastereomeric mixtures thereof, optical isomers thereof, isotopes thereof or pharmaceutically-acceptable salts of said compound, isomers, and isotopes, wherein
R$^1$ is hydroxy, nitro, or an optionally substituted moiety selected from the group consisting of alkyl, alkoxy, arylalkyloxy and sulfonato;
R is halo or nitro; and
R$^3$ is alkyl or phenylalkyl.

19. A compound according to claim 18, racemic-diastereomeric mixtures thereof, optical isomers thereof, isotopes thereof or pharmaceutically-acceptable salts of said compound, isomers, and isotopes, wherein
R$^1$ is hydroxy, nitro, methyl, methoxy, isopropoxy, benzyloxy, 4-fluorobenzyloxy, —O—C(CH$_3$)$_2$(C(O)NH$_2$), —O—(CH$_2$)$_2$—O—(CH$_2$)$_2$—OMe or —O—SO$_2$—CF$_3$;
R$^2$ is Cl or nitro; and
R$^3$ is ethyl or benzyl.

20. A compound according to claim 19, racemic-diastereomeric mixtures thereof, optical isomers thereof, isotopes thereof or pharmaceutically-acceptable salts of said compound, isomers, and isotopes, wherein X$^1$ is H.

21. A compound according to claim 20, racemic-diastereomeric mixtures thereof, optical isomers thereof, isotopes thereof or pharmaceutically-acceptable salts of said compound, isomers, and isotopes, wherein W is Cl; R$^1$ is in the 7-position; and R$^2$ is in the 4- or 5-position.

22. A compound of the formula

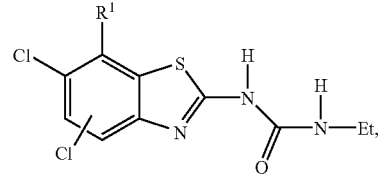

racemic-diastereomeric mixtures thereof, optical isomers thereof, isotopes thereof or pharmaceutically-acceptable salts of said compound, isomers, and isotopes, wherein $R^1$ is methyl, methoxy or isopropoxy.

23. A pharmaceutical composition comprising a compound according to claim 1 and a pharmaceutically acceptable diluent or carrier.

24. A pharmaceutical composition, which composition comprises a pharmaceutically acceptable carrier or diluent and an effective amount of a compound of formula (I) of claim 1 as defined hereinabove, racemic-diastereomeric mixtures thereof, optical isomers thereof, isotopes thereof or pharmaceutically-acceptable salts of said compound, isomers, and isotopes.

25. A compound according to claim 1, wherein W is —$(CH_2)_2$—NH—C(O)—NH—$(C(R^{10})_2)_a$—$Z^1_q$; $R_1$ and $R_2$ are each H; Q is H; Y is O; $X^1$ is H; and $R_3$ is an optionally substituted alkyl.

26. A compound according to claim 25 wherein W is: —$(CH_2)_2$—NH—C(O)—NH—Et, —$CH_2$—NH—C(O)—NH-ethyl, —$CH_2$—$NH_2$, —NH-phenyl, —C(O)—$NH_2$, —$CH_2$—NH—$S(O)_2$—Ph, —C(O)—NH-phenyl, —$CH_2$—NH—$S(O)_2$—$CF_3$, —$CH_2$—CN, —$(CH_2)_2$—NH—C(O)—NH-(phenyl), or —$(CH_2)_2$—NH—C(O)—NH-(p-toluyl).

27. A compound according to claim 26, wherein $R^3$ is ethyl.

28. A compound according to claim 1, wherein W is CN; $R^1$ and $R^2$ are each H; Q is H; Y is O; and $X^1$ is H.

29. A compound according to claim 1, wherein W is H; and $R^1$ is —S—$X^3$, —$S(O)X^3$ or —$S(O)_2X^3$.

30. A compound according to claim 1, wherein W is Br, Cl or p-fluorophenoxy, $R^1$ and $R^2$ are each H; Q is H; Y is O; $X^1$ is H; and $R^3$ is alkyl-chloro, -alkyl-COOEt, -alkyl-COOH, -alkyl-(N—(N,N-diethylaminoethyl)-N-(methyl)amino), -alkylamino, or -alkyl-(N,N-diethylaminoethylamino).

31. A compound according to claim 30, wherein the alkyl group is methylene, ethylene or propylene.

32. A compound according to claim 1, wherein $R^2$ is H; Q is H; Y is O; $X^1$ is H and $R^3$ is ethyl.

33. A compound according to claim 32, wherein W is H or Br; and $R^1$ is in the 7-position of the benzothiazolyl ring and is —C≡CH, —C≡C—$CH_2$—$N(CH_3)_2$, —O—CH$(CH_3)_2$, phenyl or —CH═$CH_2$.

34. A compound according to claim 32, wherein $R^1$ is —CH═$CH_2$ and W is —CH═$CH_2$.

35. A compound according to claim 32, wherein $R^1$ is H and W is benzyl or p-fluorophenoxy.

36. A compound according to claim 32, wherein W is F; $R^1$ is in the 7-position of the benzothiazolyl ring and is H or Cl; and R is in the 5-position of the benzothiazolyl ring and is H or Cl.

37. A compound according to claim 32, wherein $R^1$ is H and W is —CH═CH, —C≡C—Ph, —C≡C—$CH_2$—N$(CH_3)_2$, —C≡C-(4-fluorophenyl), —C≡C-(p-toluyl), —$(CH_2)_2$—Ph, —$(CH_2)_2$-(4-fluorophenyl), —CH═CH-phenyl, —CH═CH—$CH_2$—$N(CH_3)_2$, —CH═CH-(4-fluorophenyl) or —CH═CH-(p-toluyl).

38. A compound according to claim 1, wherein W is p-fluorophenoxy or —$(CH_2)_3$—NHMe; and $R^3$ is —$CH_2$—$C(Me)_2$—$CH_2$—$N(CH_3)_2$.

39. A compound according to claim 1, wherein $R^1$ is in the 7-position of the benzothiazolyl ring and is H or CN; $R^2$ is H; Y is O; Q and $X^1$ are each H; W is $C_1$, $NO_2$, —$CH_2$—OH, —$CH_2$—O—C(O)—NH-Et, —S-phenyl, —O-phenyl, —S—$CH_3$, —C(O)-phenyl, —S(O)-phenyl, —S-p-nitrophenyl, —S-p-methylphenyl, —S-p-chlorophenyl, —S-p-methoxyphenyl, —S-m-$CF_3$-phenyl, —S-o-chlorophenyl, —C(O)—$CH_3$, —$S(O)_2$-p-(carboxymethylamino)-phenyl, —NH—C(O)—NH-Et, —NH—C(O)—NH—$CH_2$-phenyl, —S-p-chlorophenyl, —S-p-bromophenyl, —S-m-$CF_3$-phenyl, or —S-p-fluorophenyl;

$R^3$ is ethyl.

40. A compound of the formula

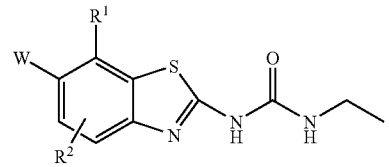

wherein W is H, —$OCF_3$, —O-Et, F, $CH_3$, —$OCH_3$, —$SO_2$—Me, $NH_2$, —NH—C(O)—Me, —NH—$CH_2$-phenyl, —NH—$S(O)_2$—Me, —NH—$S(O)_2$—$CH_2$-phenyl, —NH—C(O)—O—$CH_2$—$CCl_3$, —NH—C(O)—O—$CH_2$—Ph, —NH—C(O)—O—Me or $NO_2$;

$R^1$ is H, F or —$CH_2$—$S(O)_2$-phenyl; and $R^2$ is H, 4-Cl, 4-methyl, 5-methyl, 5-Cl, 5-F or 5-$OCH_3$ provided that the compound is not

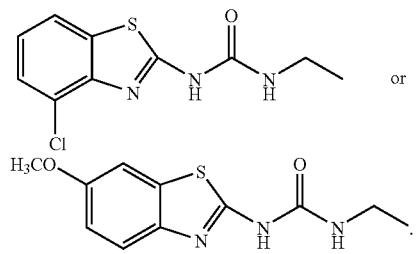

* * * * *

UNITED STATES PATENT AND TRADEMARK OFFICE
CERTIFICATE OF CORRECTION

PATENT NO. : 7,091,227 B2
APPLICATION NO. : 09/777554
DATED : August 15, 2006
INVENTOR(S) : Barbara Scott et al.

It is certified that error appears in the above-identified patent and that said Letters Patent is hereby corrected as shown below:

Column 173, line 21 -   replace "X" with "$X^2$"

Column 173, line 47 -   delete "," after "-C(O)N(($C_1$-$C_6$)alkyl)$_n$,"

Column 173, line 47 -   delete ";" after "-S(O),($C_1$-$C_6$)alkyl)"

Column 176, line 53 -   add (subscript) "2" after "-(CH$_2$)$_2$-N(Me)"

Column 177, line 20 -   add (superscript) "2" after "R"

Column 178, line 37 -   add (superscript) "2" after "R"

Column 180, line 10 -   replace "$C_1$" with "C1"

Signed and Sealed this

Fourteenth Day of November, 2006

JON W. DUDAS
*Director of the United States Patent and Trademark Office*